US008969345B2

(12) United States Patent
Yamamoto et al.

(10) Patent No.: US 8,969,345 B2
(45) Date of Patent: Mar. 3, 2015

(54) DIBENZOOXEPIN DERIVATIVE

(75) Inventors: Keisuke Yamamoto, Tokyo (JP); Tomohiro Tamura, Tokyo (JP); Rina Nakamura, Tokyo (JP); Kimihisa Ueno, Tokyo (JP); Shintaro Hosoe, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 14/236,545

(22) PCT Filed: Aug. 3, 2012

(86) PCT No.: PCT/JP2012/069876
§ 371 (c)(1),
(2), (4) Date: Jan. 31, 2014

(87) PCT Pub. No.: WO2013/018899
PCT Pub. Date: Feb. 7, 2013

(65) Prior Publication Data

US 2014/0163008 A1 Jun. 12, 2014

(30) Foreign Application Priority Data

Aug. 3, 2011 (JP) ................................ 2011-169701

(51) Int. Cl.

| | |
|---|---|
| ***C07D 413/14*** | (2006.01) |
| ***C07D 471/04*** | (2006.01) |
| ***C07D 487/04*** | (2006.01) |
| ***C07D 495/04*** | (2006.01) |
| ***A61K 31/4245*** | (2006.01) |
| ***A61K 31/437*** | (2006.01) |
| ***A61K 31/4439*** | (2006.01) |
| ***A61K 31/454*** | (2006.01) |
| ***A61K 31/4985*** | (2006.01) |
| ***A61K 31/5025*** | (2006.01) |
| ***A61K 31/519*** | (2006.01) |

(52) U.S. Cl.
CPC ............ *C07D 495/04* (2013.01); *C07D 413/14* (2013.01); *C07D 471/04* (2013.01); *C07D 487/04* (2013.01)
USPC ........... 514/244; 514/248; 514/300; 514/303; 514/337; 514/340; 514/364; 544/236; 544/350; 546/118; 546/121; 546/196; 546/269.1; 548/132; 548/302.7; 548/305.1

(58) Field of Classification Search
USPC ......... 514/364, 337, 340, 303, 300, 244, 248; 548/132, 302.7, 305.1; 544/236, 350; 546/269.1, 118, 196, 121
See application file for complete search history.

(56) References Cited

U.S. PATENT DOCUMENTS

| | | | |
|---|---|---|---|
| 4,687,777 | A | 8/1987 | Meguro et al. |
| 5,378,701 | A | 1/1995 | Ohshima et al. |
| 5,756,525 | A | 5/1998 | Hindley et al. |

(Continued)

FOREIGN PATENT DOCUMENTS

| | | | |
|---|---|---|---|
| JP | 61-267580 | A | 11/1986 |
| JP | 01-131169 | A | 5/1989 |

(Continued)

OTHER PUBLICATIONS

Berger et al.,*Molecular Endocrinology*, 17(4): 662-676 (2003).

(Continued)

*Primary Examiner* — Bruck Kifle
(74) *Attorney, Agent, or Firm* — Leydig, Voit & Mayer, Ltd.

(57) ABSTRACT

A dibenzoxepin derivative represented by the following general formula (I) wherein Y is a hydrogen atom and the like, $R^A$ is a hydrogen atom and the like, X is the formula (b3) wherein $R^B$ is a hydrogen atom and the like, and the like, A is the formula (a18) wherein $R^1$ is a hydrogen atom and the like, and $R^C$ and $R^D$ are the same or different and each is a hydrogen atom and the like, and the like, which has a PPARγ agonist activity and the like, and useful as a therapeutic agent and/or prophylaxis agent and the like for type 2 diabetes and the like, or a pharmaceutically acceptable salt thereof and the like is provided.

(I)

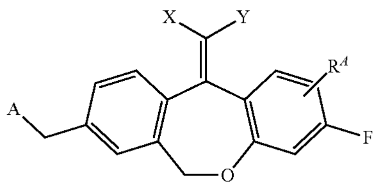

(b3)

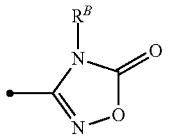

(a18)

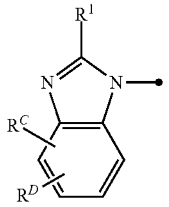

17 Claims, No Drawings

(56) References Cited

U.S. PATENT DOCUMENTS

| | | | |
|---|---|---|---|
| 8,053,598 | B2 | 11/2011 | Polivka |
| 2009/0012171 | A1 | 1/2009 | Polivka |
| 2009/0176760 | A1 | 7/2009 | Yanagisawa et al. |
| 2011/0201640 | A1 | 8/2011 | Yanagisawa et al. |

FOREIGN PATENT DOCUMENTS

| | | | |
|---|---|---|---|
| JP | 06-228065 | A | 8/1994 |
| WO | WO 2005/105736 | A1 | 11/2005 |
| WO | WO 2008/096829 | A1 | 8/2008 |
| WO | WO 2010/016549 | A1 | 2/2010 |
| WO | WO 2010/047369 | A1 | 4/2010 |

OTHER PUBLICATIONS

Lehmann et al., *The Journal of Biological Chemistry*, 270(22): 12953-12956 (1995).

Willson et al., *Journal of Medicinal Chemistry*, 39: 665-668 (1996).

Japanese Patent Office, International Search Report in International Patent Application No. PCT/JP2012/069876 (Oct. 30, 2012), English translation.

DIBENZOOXEPIN DERIVATIVE

CROSS-REFERENCE TO RELATED APPLICATIONS

This patent application is a U.S. national phase of International Patent Application PCT/JP2012/069876, filed on Aug. 3, 2012, which claims the benefit of Japanese Patent Application No. 2011-169701, filed on Aug. 3, 2011, which is incorporated by reference in its entirety herein.

TECHNICAL FIELD

The present invention relates to a dibenzoxepin derivative having a peroxisome proliferator-activated receptor (PPAR) γ agonist activity, which is useful as an agent for treating and/or preventing, for example, type 2 diabetes, impaired glucose tolerance, insulin resistance syndrome, hypertension, hyperlipidemia, metabolic syndrome, visceral obesity, obesity, hypertriglyceridemia, inflammatory skin diseases, inflammatory diseases, inflammatory neuropsychiatric diseases, neurodegenerative neuropsychiatric diseases and the like.

BACKGROUND ART

Peroxisome proliferator-activated receptor (PPAR) is a member of the nuclear receptor superfamily of ligand activated transcription factor. Three subtypes of PPAR, i.e., PPAR α, PPAR γ, and PPAR δ, have been cloned from mouse and human. PPAR is known as an important nuclear hormone receptor for the metabolism of carbohydrate and lipid, immunoregulation, and inflammatory reaction. It has been reported that compounds that activate PPAR are useful for the treatment and prophylaxis of various clinical diseases such as metabolic syndrome, obesity, prediabetes, type 2 diabetes and the other insulin resistance syndrome, hypertension, atherosclerosis, lipemia, inflammatory skin diseases such as psoriasis, inflammatory bowel disease, and inflammatory neurodegenerative diseases such as multiple sclerosis, Alzheimer's disease etc., and the like. PPAR γ specifically is said to play an important role in adipocyte differentiation. Hypertrophic adipocytes secrete large amounts of cytokines, namely TNF-α and free fatty acid which induce insulin resistance. On the other hand, it has been reported that thiazolidinedione derivatives such as pioglitazone, rosiglitazone and the like improve insulin resistance by activating PPAR γ to decrease hypertrophic adipocytes by apoptosis, and promoting differentiation of preadipocytes into small adipocytes having normal function (non-patent documents 1 and 2). Pioglitazone and rosiglitazone, which are PPAR γ agonists, have already been clinically used as therapeutic drugs for diabetes (patent documents 1 and 2).

PPAR γ agonists are also useful as agents for treating and/or preventing diseases besides diabetes, such as metabolic syndrome, obesity, impaired glucose tolerance and other insulin resistance syndrome, which are prediabetic conditions, hypertension, atherosclerosis, hyperlipidemia, inflammatory diseases such as psoriasis and the like, inflammatory bowel disease, and the like.

It has been reported that selective partial agonists for PPAR γ do not accompany side effects such as body weight increase, adipocyte accumulation and the like, as compared to the existing full agonists (thiazolidinedione derivative or the like) (non-patent document 3).

A tricyclic compound represented by the following formula (A) and a derivative thereof are known as PPAR agonists/antagonists/regulators (patent document 3).

(A)

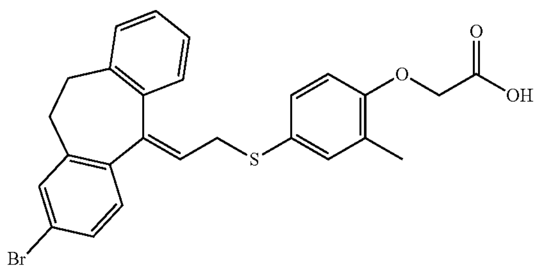

It is known that a compound represented by the following formula (B), which is a tricyclic compound, and a derivative thereof have a superior hypotensive action based on an angiotensin II receptor antagonistic action (see patent document 4).

(B)

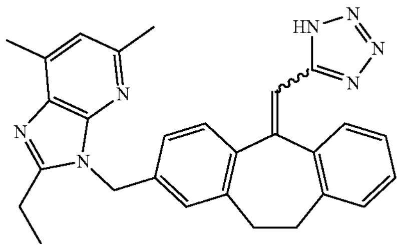

A compound represented by the following formula (C), which is a tricyclic compound, and a derivative thereof are known as PPARγ agonists (see patent document 5).

(C)

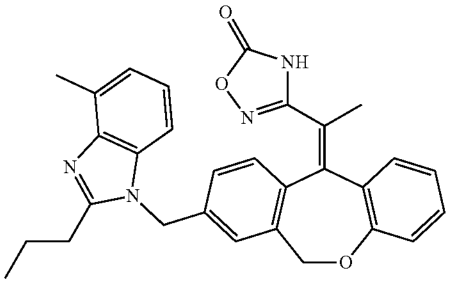

DOCUMENT LIST

Patent Documents patent document 1: JP-A-61-267580
patent document 2: JP-A-1-131169
patent document 3: WO2005/105736
patent document 4: JP-A-6-228065
patent document 5: WO2010/016549

Non-Patent Documents non-patent document 1: J. Biol. Chem., 1995, vol. 270, p. 12953
non-patent document 2: J. Med. Chem., 1996, vol. 39, p. 665
non-patent document 3: Molecular Endocrinology, 2003, vol. 17, No. 4, p. 662

SUMMARY OF THE INVENTION

Problems to be Solved by the Invention

An object of the present invention is to provide a novel dibenzoxepin derivative or a pharmaceutically acceptable salt thereof having a peroxisome proliferator-activated receptor γ (PPARγ) agonist activity, or the like. The dibenzoxepin derivative provided by the present invention or a pharmaceutically acceptable salt thereof is useful as a therapeutic and/or prophylactic agent for type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), inflammatory neuropsychiatric diseases (e.g., multiple sclerosis etc.), neurodegenerative neuropsychiatric diseases (e.g., Alzheimer's disease, Parkinson's disease etc.), cardiovascular diseases such as arteriosclerosis, cardiac disease, cerebral apoplexy, renal diseases, or the like.

Another object of the present invention is to provide a PPAR γ agonist containing a dibenzoxepin derivative as an active ingredient.

Means of Solving the Problems

The present invention relates to the following (1)-(30).

(1) A tricyclic compound represented by the general formula (I)

(I)

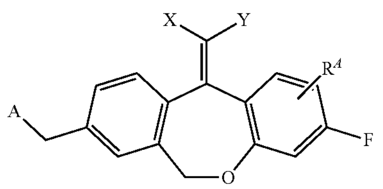

[wherein Y is a hydrogen atom, lower alkyl optionally having substituent(s), lower alkoxy optionally having substituent(s), cycloalkyl optionally having substituent(s) or halogen, $R^A$ is a hydrogen atom, halogen, hydroxy, lower alkoxy, or lower alkyl, X is the formula (b1)-(b16)

(b1)

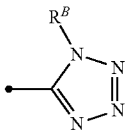

(b2)

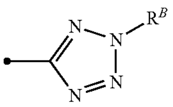

(b3)

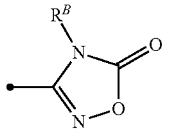

-continued (b4)

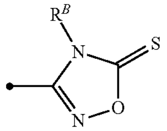

(b5)

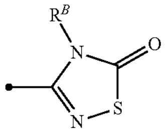

(b6)

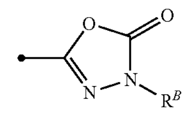

(b7)

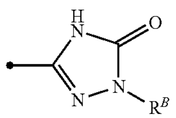

(b8)

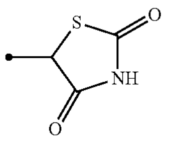

(b9)

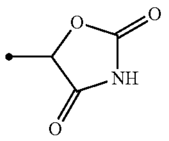

(b10)

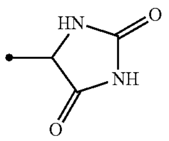

(b11)

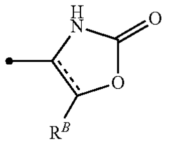

(b12)

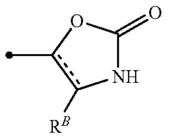

(b13)

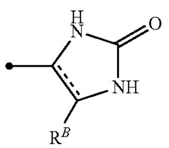

(b14)

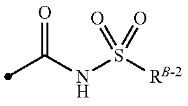

-continued
(b15)
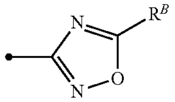
(b16)
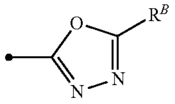
(wherein $R^{B-2}$ is lower alkyl optionally having substituent(s) or cycloalkyl optionally having substituent(s), $R^B$ is a hydrogen atom, lower alkyl optionally having substituent(s) or cycloalkyl optionally having substituent(s), and the broken line shows absent or a single bond),
A is the formula (a1)-(a29)
(a1)
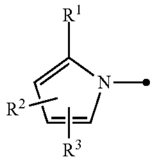
(a2)
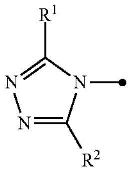
(a3)
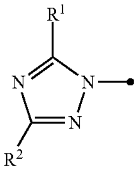
(a4)
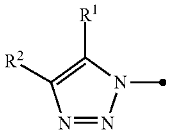
(a5)
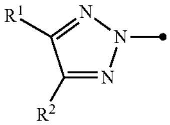
(a6)
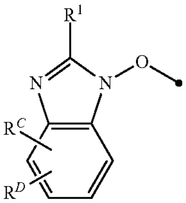
-continued
(a7)
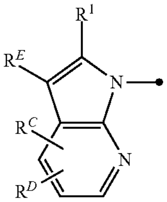
(a8)
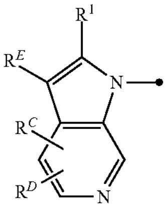
(a9)
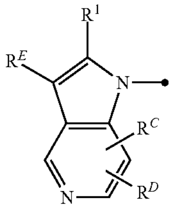
(a10)
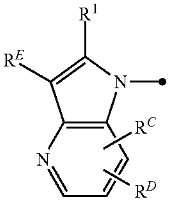
(a11)
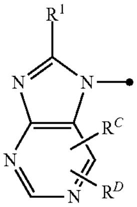
(a12)
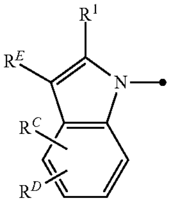
(a13)
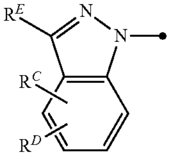

-continued
(a14)
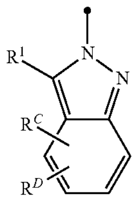
(a15)
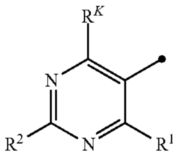
(a16)
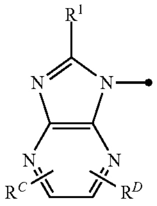
(a17)
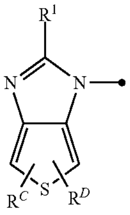
(a18)
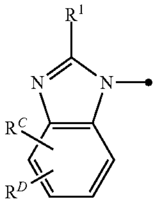
(a19)
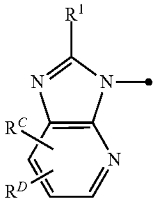
(a20)
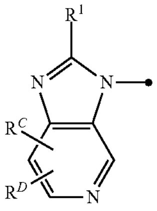
-continued
(a21)
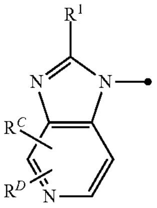
(a22)
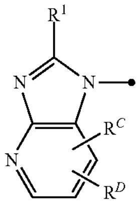
(a23)
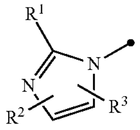
(a24)
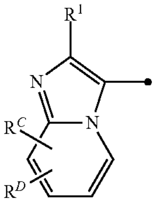
(a25)
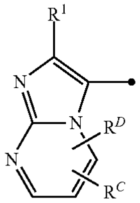
(a26)
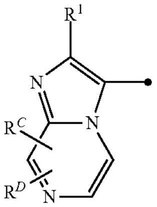
(a27)
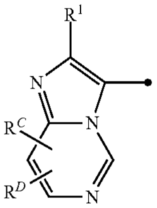
(a28)
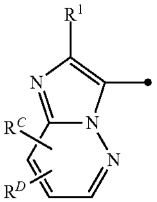

-continued (a29)

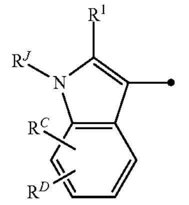

(wherein $R^1$, $R^2$ and $R^3$ are the same or different and each is a hydrogen atom, cyano, lower alkyl optionally having substituent(s), cycloalkyl optionally having substituent(s), halogen, lower alkoxy optionally having substituent(s), —$NR^FR^G$ (wherein $R^F$ and $R^G$ are the same or different and each is a hydrogen atom, lower alkyl optionally having substituent(s), lower alkanoyl optionally having substituent(s), lower alkoxycarbonyl optionally having substituent(s) or aralkyl optionally having substituent(s), or $R^F$ and $R^G$ form, together with the adjacent nitrogen atom, a nitrogen-containing heterocyclic group optionally having substituent(s)), lower alkylsulfanyl optionally having substituent(s), lower alkenyl optionally having substituent(s), lower alkanoyl optionally having substituent(s), lower alkoxycarbonyl optionally having substituent(s), carbamoyl, lower alkylcarbamoyl optionally having substituent(s), di-lower alkylcarbamoyl optionally having substituent(s), aliphatic heterocyclylcarbonyl optionally having substituent(s), aryloxy optionally having substituent(s), aryl optionally having substituent(s), aromatic heterocyclic group optionally having substituent(s), aliphatic heterocyclic group optionally having substituent(s), aralkyl optionally having substituent(s) or aralkyloxy optionally having substituent(s), $R^C$, $R^D$ and $R^E$ are the same or different and each is a hydrogen atom, halogen, nitro, cyano, formyl, oxo, hydroxy, lower alkoxy optionally having substituent(s), —$NR^{Fa}R^{Ga}$ (wherein $R^{Fa}$ and $R^{Ga}$ are as defined for the aforementioned $R^F$ and $R^G$, respectively), lower alkanoyloxy optionally having substituent(s), lower alkyl optionally having substituent(s), lower alkenyl optionally having substituent(s), lower alkynyl optionally having substituent(s), lower alkanoyl optionally having substituent(s), lower alkoxycarbonyl optionally having substituent(s), lower alkylsulfonyl optionally having substituent(s), lower alkylsulfanyl optionally having substituent(s), cycloalkyl optionally having substituent(s) or —$CONR^HR^I$ (wherein $R^H$ and $R^I$ are the same or different and each is a hydrogen atom, lower alkyl optionally having substituent(s), lower alkanoyl optionally having substituent(s), lower alkoxycarbonyl optionally having substituent(s) or aralkyl optionally having substituent(s), or $R^H$ and $R^I$ form, together with the adjacent nitrogen atom, a nitrogen-containing heterocyclic group optionally having substituent(s)), $R^J$ is a hydrogen atom, lower alkyl optionally having substituent(s), lower alkanoyl optionally having substituent(s), lower alkoxycarbonyl optionally having substituent(s), aryl optionally having substituent(s), lower alkylsulfonyl optionally having substituent(s), aralkyl optionally having substituent(s) or cycloalkyl optionally having substituent(s), and $R^K$ is a hydrogen atom, halogen, hydroxy, lower alkoxy, lower alkyl or —$NR^{Fb}R^{Gb}$ (wherein $R^{Fb}$ and $R^{Gb}$ are as defined for the aforementioned $R^F$ and $R^G$, respectively)], or a pharmaceutically acceptable salt thereof.

(2) The tricyclic compound according to (1), wherein Y is halogen, lower alkyl or cycloalkyl, or a pharmaceutically acceptable salt thereof.

(3) The tricyclic compound according to (1), wherein Y is lower alkyl, or a pharmaceutically acceptable salt thereof.

(4) The tricyclic compound according to (1), wherein Y is cycloalkyl, or a pharmaceutically acceptable salt thereof.

(5) The tricyclic compound according to any of (1), (2), (3) or (4), wherein X is the formula (b1-1), (b3-1), (b4-1) or (b5-1)

(b1-1)

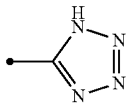

(b3-1)

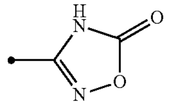

(b4-1)

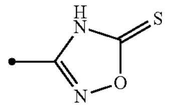

(b5-1)

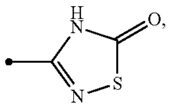

or a pharmaceutically acceptable salt thereof.

(6) The tricyclic compound according to any of (1), (2), (3) or (4), wherein X is the formula (b3-1)

(b3-1)

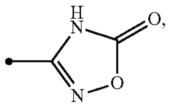

or a pharmaceutically acceptable salt thereof.

(7) The tricyclic compound according to any of (1), (2), (3), (4), (5) or (6), wherein A is the formula (a15), (a16), (a17), (a18), (a19), (a21), (a22), (a23), (a24), (a25), (a26), (a28) or (a29)

(a15)

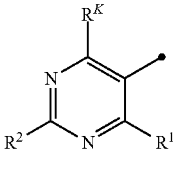

(a16)

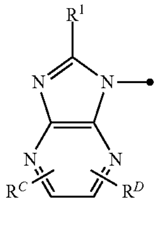

-continued (a17)

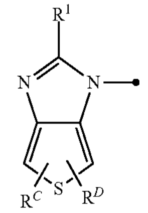

(a18)

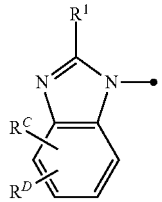

(a19)

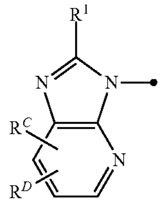

(a21)

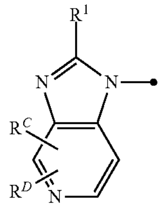

(a22)

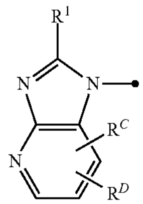

(a23)

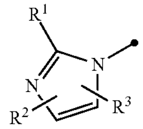

(a24)

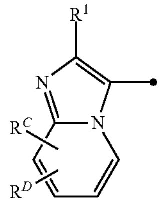

(a25)

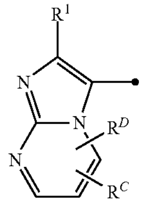

-continued (a26)

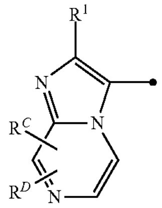

(a28)

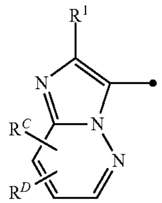

(a29)

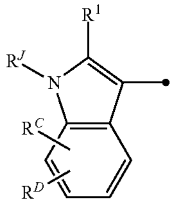

(wherein $R^1$, $R^2$, $R^3$, $R^C$, $R^D$, $R^K$, and $R^J$ are each as defined above), or a pharmaceutically acceptable salt thereof.

(8) The tricyclic compound according to any of (1), (2), (3), (4), (5) or (6), wherein A is the formula (a18)

(a18)

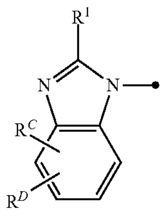

(wherein $R^1$, $R^C$, and $R^D$ are each as defined above), or a pharmaceutically acceptable salt thereof.

(9) The tricyclic compound according to any of (1), (2), (3), (4), (5) or (6), wherein A is the formula (a24)

(a24)

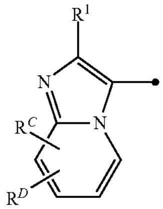

(wherein $R^1$, $R^C$, and $R^D$ are each as defined above), or a pharmaceutically acceptable salt thereof.

(10) The tricyclic compound according to any of (1), (2), (3), (4), (5) or (6), wherein A is the formula (a26)

(a26)

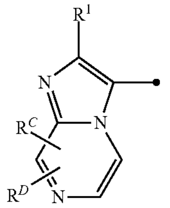

(wherein $R^1$, $R^C$, and $R^D$ are each as defined above), or a pharmaceutically acceptable salt thereof.

(11) The tricyclic compound according to any of (1), (2), (3), (4), (5), (6), (7), (8), (9) or (10), wherein $R^1$ is cyano; halogen; lower alkoxy; lower alkyl optionally substituted by 1 to 3 substituents of halogen, lower alkylamino, di-lower alkylamino, cycloalkyl or lower alkoxy; cycloalkyl optionally substituted by 1 to 3 substituents of halogen or lower alkyl; an aromatic heterocyclic group; an aliphatic heterocyclic group; or di-lower alkylamino, or a pharmaceutically acceptable salt thereof.

(12) The tricyclic compound according to any of (1), (2), (3), (4), (5), (6), (7), (8), (9) or (10), wherein $R^1$ is lower alkyl optionally substituted by 1 to 3 substituents of halogen or lower alkoxy, or a pharmaceutically acceptable salt thereof.

(13) The tricyclic compound according to any of (1), (2), (3), (4), (5), (6), (7), (8), (9) or (10), wherein $R^1$ is cycloalkyl, or a pharmaceutically acceptable salt thereof.

(14) The tricyclic compound according to any of (1), (2), (3), (4), (5), (6), (7), (8), (9), (10), (11), (12) or (13), wherein $R^C$ and $R^D$ are the same or different and each is a hydrogen atom; cyano; lower alkyl optionally substituted by 1 to 3 substituents of halogen, hydroxy or lower alkoxy; lower alkoxy optionally substituted by 1 to 3 halogens; lower alkylsulfanyl; lower alkylsulfonyl; cycloalkyl; lower alkynyl; —CONR$^{H-1}$R$^{I-1}$ (wherein R$^{H-1}$ and R$^{I-1}$ are the same or different and each is a hydrogen atom or lower alkyl, or R$^{H-1}$ and R$^{I-1}$ form, together with the adjacent nitrogen atom, a nitrogen-containing heterocyclic group); —NR$^{Fa-1}$R$^{Ga-1}$ (wherein R$^{Fa-1}$ and R$^{Ga-1}$ are the same or different and each is a hydrogen atom or lower alkyl); or halogen, or a pharmaceutically acceptable salt thereof.

(15) The tricyclic compound according to any of (1), (2), (3), (4), (5), (6), (7), (8), (9), (10), (11), (12) or (13), wherein $R^C$ and $R^D$ are the same or different and each is lower alkyl optionally substituted by 1 to 3 substituents of halogen, hydroxy or lower alkoxy; lower alkoxy optionally substituted by 1 to 3 halogens; or halogen, or a pharmaceutically acceptable salt thereof.

(16) The tricyclic compound according to (14) or (15), wherein $R^C$ is a hydrogen atom, or a pharmaceutically acceptable salt thereof.

(17) The tricyclic compound according to any of (1), (2), (3), (4), (5), (6), (7), (8), (9), (10), (11), (12), (13), (14), (15) or (16), wherein $R^A$ is a hydrogen atom or halogen, or a pharmaceutically acceptable salt thereof.

(18) A pharmaceutical composition comprising the tricyclic compound or the pharmaceutically acceptable salt thereof according to any of (1) to (17), as an active ingredient.

(19) A PPAR γ agonist comprising the tricyclic compound or the pharmaceutically acceptable salt thereof according to any of (1) to (17) as an active ingredient.

(20) A therapeutic and/or prophylactic agent for a disease associated with PPAR γ, which comprises the tricyclic compound or the pharmaceutically acceptable salt thereof according to any of (1) to (17), as an active ingredient.

(21) The agent according to (20), wherein the disease associated with PPAR γ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(22) A method of activating PPAR γ, comprising administering the tricyclic compound or the pharmaceutically acceptable salt thereof according to any of (1) to (17).

(23) A therapeutic and/or prophylactic method of a disease associated with PPAR γ, comprising administering the tricyclic compound or the pharmaceutically acceptable salt thereof according to any of (1) to (17).

(24) The method of (23), wherein the disease associated with PPAR γ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(25) Use of the tricyclic compound or the pharmaceutically acceptable salt thereof according to any of (1) to (17), for the manufacture of a PPAR γ agonist.

(26) Use of the tricyclic compound or the pharmaceutically acceptable salt thereof according to any of (1) to (17), for the manufacture of a therapeutic and/or prophylactic agent for a disease associated with PPAR γ.

(27) The use according to (26), wherein the disease associated with PPAR γ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(28) The tricyclic compound according to any of (1) to (17) or a pharmaceutically acceptable salt thereof, for use in activating PPARγ.

(29) The tricyclic compound according to any of (1) to (17) or a pharmaceutically acceptable salt thereof, for use in the treatment and/or prophylaxis of a disease associated with PPARγ.

(30) The tricyclic compound according to (29) or a pharmaceutically acceptable salt thereof, wherein the disease associated with PPARγ is a disease selected from the group consisting of type 2 diabetes, impaired glucose tolerance, insulin resistance syndrome, hypertension, hyperlipidemia, metabolic syndrome, visceral obesity, obesity, and hypertriglyceridemia.

Effect of the Invention

According to the present invention, a dibenzoxepin derivative having a PPAR γ function regulatory activity, which is useful as a therapeutic and/or prophylactic agent for, for example, type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), inflammatory neuropsychiatric diseases (e.g., multiple sclerosis etc.), neurodegenerative neuropsychiatric diseases (e.g., Alzheimer's disease, Parkinson's disease etc.), cardiovascular diseases such as arteriosclerosis, cardiac disease, cerebral apoplexy, renal diseases, or the like, or a pharmaceutically acceptable salt thereof and the like are provided.

The dibenzoxepin derivative or a pharmaceutically acceptable salt thereof disclosed in the present invention is superior in the metabolic stability in human, and has preferable properties as an active ingredient of the pharmaceutical product used for the above-mentioned diseases.

In addition, the present invention provides a PPARγ function modulator containing a dibenzoxepin derivative as an active ingredient.

DESCRIPTION OF EMBODIMENTS

Hereinafter a compound represented by the general formula (I) is referred to as compound (I). The same applies to the compounds of other formula numbers.

In the definition of each group of the general formula (I), examples of lower alkyl, and the lower alkyl moiety of lower alkoxy, lower alkylsulfanyl, lower alkylsulfonyl, lower alkanoyloxy, lower alkanoyl, lower alkoxycarbonyl, lower alkylcarbamoyl, di-lower alkylcarbamoyl, lower alkylamino, and di-lower alkylamino include straight chain or branched alkyl having 1-10 carbon atoms. More specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like. Preferable examples thereof include straight chain or branched alkyl having 1-6 carbon atoms, which is more specifically methyl, ethyl, propyl, isopropyl, butyl, isobutyl, sec-butyl, tert-butyl, pentyl, isopentyl, neopentyl, hexyl and the like. Two lower alkyl moieties of di-lower alkylcarbamoyl and di-lower alkylamino may be the same or different.

Examples of the lower alkenyl include straight chain or branched alkenyl having 2-10 carbon atoms, and more specific examples thereof include vinyl, allyl, 1-propenyl, butenyl, pentenyl, hexenyl, heptenyl, octenyl, nonenyl, decenyl and the like. Preferable examples thereof include straight chain or branched alkenyl having 2-6 carbon atoms, and more specific examples thereof include vinyl, allyl, 1-propenyl, butenyl, pentenyl, hexenyl and the like.

Examples of the lower alkynyl include straight chain or branched alkynyl having 2-10 carbon atoms, and more specific examples thereof include ethynyl, propynyl, butynyl, pentynyl, hexynyl, heptynyl, octynyl, nonynyl, decynyl and the like. Preferable examples thereof include straight chain or branched alkynyl having 2-6 carbon atoms, and more specific examples thereof include ethynyl, propynyl, butynyl, pentynyl, hexynyl and the like.

Examples of cycloalkyl include cycloalkyl having 3 to 8 carbon atoms, and more specific examples thereof include cyclopropyl, cyclobutyl, cyclopentyl, cyclohexyl, cycloheptyl, cyclooctyl and the like. Preferable examples thereof include cycloalkyl having 3-6 carbon atoms, and more specific examples thereof include cyclopropyl, cyclobutyl, cyclopentyl, cyclohexyl and the like.

Examples of aralkyl and the aralkyl moiety of aralkyloxy include aralkyl having 7 to 16 carbon atoms, and more specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of aryl and the aryl moiety of aryloxy include aryl having 6-14 carbon atoms, and more specific examples thereof include phenyl, naphthyl, azulenyl, anthryl and the like.

Examples of the aliphatic heterocyclic group and the aliphatic heterocyclic group moiety of aliphatic heterocyclylcarbonyl include a 5-membered or 6-membered monocyclic aliphatic heterocyclic group comprising at least one atom selected from a nitrogen atom, an oxygen atom and a sulfur atom, a bicyclic or tricyclic condensed aliphatic heterocyclic group with 3- to 8-membered rings fused together containing at least one atom selected from a nitrogen atom, an oxygen atom and a sulfur atom, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like. Preferable examples thereof include a 5-membered or 6-membered monocyclic aliphatic heterocyclic group containing at least one atom selected from a nitrogen atom, an oxygen atom and a sulfur atom, and the like, and more specific examples thereof include pyrrolidinyl, piperidino, piperidinyl, 1,2,5,6-tetrahydropyridyl, imidazolidinyl, pyrazolidinyl, piperazinyl, pyrazolinyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic condensed aromatic heterocyclic group with 3- to 8-membered rings fused together, containing at least one atom selected from a nitrogen atom, an oxygen atom and a sulfur atom, and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl and the like. Preferable examples thereof include a 5-membered or 6-membered monocyclic aromatic heterocyclic group having at least one atom selected from a nitrogen atom, an oxygen atom and a sulfur atom and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl and the like.

Examples of the nitrogen-containing heterocyclic group formed together with the adjacent nitrogen atom thereto include a 5-membered or 6-membered monocyclic heterocyclic group with 3- to 8-membered rings fused together, containing at least one nitrogen atom (said monocyclic heterocyclic group may contain other nitrogen atom(s), oxygen atom(s) or sulfur atom(s)), a bicyclic or tricyclic fused heterocyclic group containing at least one nitrogen atom (said fused heterocyclic group may contain other nitrogen atom(s), oxygen atom(s) or sulfur atom(s)), and the like, and more specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl and the like. Preferable examples thereof include a 5-membered or 6-membered monocyclic heterocyclic group containing at least one nitrogen atom (said monocyclic heterocyclic group may contain other nitrogen atom(s), oxygen atom(s) or sulfur atom(s)) and the like, and more specific examples thereof include pyrrolidinyl, piperidino, pyrrolyl, imidazolidinyl, imidazolyl, pyrazolidinyl, pyrazolinyl, pyrazolyl, piperazinyl, oxazolidinyl, 2H-oxazolyl, thioxazolidinyl, 2H-thioxazolyl, morpholino, thiomorpholinyl and the like.

Halogen means each atom of fluorine, chlorine, bromine or iodine.

The substituents of the lower alkyl optionally having substituent(s), the lower alkylsulfonyl optionally having substituent(s), the lower alkenyl optionally having substituent(s), the lower alkynyl optionally having substituent(s), the lower alkoxy optionally having substituent(s), the lower alkylsulfanyl optionally having substituent(s), the lower alkanoyloxy optionally having substituent(s), the lower alkanoyl optionally having substituent(s), the lower alkoxycarbonyl optionally having substituent(s), the lower alkylcarbamoyl optionally having substituent(s), and the di-lower alkylcarbamoyl optionally having substituent(s) are the same or different and examples thereof include 1 to 3 substituents selected from the group consisting of halogen, hydroxy, sulfanyl, nitro, cyano, carboxy, carbamoyl, $C_{3-8}$ cycloalkyl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

The substituents of the aryl optionally having substituent(s), the aryloxy optionally having substituent(s), the aralkyl optionally having substituent(s), the aralkyloxy optionally having substituent(s) and the aromatic heterocyclic group optionally having substituent(s) are the same or different and examples thereof include 1 to 3 substituents selected from the group consisting of halogen, hydroxy, sulfanyl, nitro, cyano, carbamoyl, $C_{1-10}$ alkyl, trifluoromethyl, $C_{3-8}$ cycloalkyl, $C_{6-14}$ aryl, aliphatic heterocyclic group, aromatic heterocyclic group, $C_{1-10}$-alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ are the same or different and each as defined above), $C_{2-11}$ alkanoyl, $C_{7-15}$ aroyl, $C_{1-10}$ alkoxycarbonyl, $C_{6-14}$ aryloxycarbonyl, $C_{1-10}$-alkylcarbamoyl, di-$C_{1-10}$ alkylcarbamoyl and the like.

The substituents of the cycloalkyl optionally having substituent(s), the aliphatic heterocyclic group optionally having substituent(s), the aliphatic heterocyclylcarbonyl optionally having substituent(s) and the nitrogen-containing heterocyclic group formed together with the adjacent nitrogen atom optionally having substituent(s) are the same or different and examples thereof include 1 to 3 substituents selected from the group consisting of oxo, halogen, hydroxy, sulfanyl, nitro, cyano, carbamoyl, $C_{1-10}$ alkyl, trifluoromethyl, $C_{3-8}$ cycloalkyl, $C_{6-14}$ aryl, aliphatic heterocyclic group, aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ are the same or different and each is as defined above), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

Examples of the $C_{1-10}$ alkyl and the $C_{1-10}$ alkyl moiety of the $C_{1-10}$ alkoxy, the $C_{2-11}$ alkanoyloxy, the $C_{1-10}$-alkylsulfanyl, the $C_{2-11}$ alkanoyl, the $C_{1-10}$ alkoxycarbonyl, the $C_{1-10}$-alkylcarbamoyl and the di-$C_{1-10}$ alkylcarbamoyl include the groups recited as examples of the aforementioned lower alkyl. Two $C_{1-10}$ alkyl of the di-$C_{1-10}$ alkylcarbamoyl may be the same or different.

Examples of the $C_{3-8}$ cycloalkyl and the cycloalkyl moiety of the $C_{3-8}$ cycloalkoxy include the groups recited as examples of the aforementioned cycloalkyl.

Examples of the $C_{6-14}$ aryl and the aryl moiety of the $C_{6-14}$ aryloxy, the $C_{7-15}$ aroyl, the $C_{7-15}$ aroyloxy and the $C_{6-14}$ aryloxycarbonyl include the groups recited as examples of the aforementioned aryl.

Examples of $C_{7-16}$ aralkyl and the $C_{7-16}$ aralkyl moiety of the $C_{7-16}$ aralkyloxy and the $C_{7-16}$ aralkyloxycarbonyl include the groups recited as examples of the aforementioned aralkyl.

Examples of the aliphatic heterocyclic group, the aromatic heterocyclic group and the halogen include the groups recited as examples of the aforementioned aliphatic heterocyclic group, the aforementioned aromatic heterocyclic group and the aforementioned halogen, respectively.

The pharmaceutically acceptable salt of compound (I) comprises, for example, pharmaceutically acceptable acid addition salts, metal salts, ammonium salts, organic amine addition salts, amino acid addition salts and the like. Examples of the pharmaceutically acceptable acid addition salt of compound (I) include inorganic acid salts such as hydrochloride, hydrobromide, nitrate, sulfate, phosphate and the like, organic acid salts such as acetate, oxalate, maleate, fumarate, citrate, benzoate, methanesulfonate etc., and the like. Examples of the pharmaceutically acceptable metal salts include alkali metal salts such as sodium salt, potassium salt and the like, alkaline earth metal salts such as magnesium salt, calcium salt and the like, aluminum salt, zinc salt and the like. Examples of the pharmaceutically acceptable ammonium salt include salts of ammonium, tetramethylammonium and the like. Examples of the pharmaceutically acceptable organic amine addition salt include addition salts of morpholine, piperidine and the like. Examples of the pharmaceutically acceptable amino acid addition salt include addition salts of lysine, glycine, phenylalanine, aspartic acid, glutamic acid and the like.

The production methods of compound (I) are explained in the following.

In the production methods shown below, when the defined groups change under the conditions of the production methods or are inappropriate for performing the production methods, the desired compound can be produced by performing the methods for the introduction and removal of the protecting groups conventionally performed in the synthetic organic chemistry (e.g., methods described in Protective Groups in Organic Synthesis, third edition, T. W. Greene, John Wiley & Sons Inc., 1999 etc.) or the like. If necessary, the order of the reaction steps such as substituent introduction or the like can also be changed.

Production Method 1

A compound represented by the following formula (VII), which is a synthetic intermediate for compound (I), can be produced by the following steps.

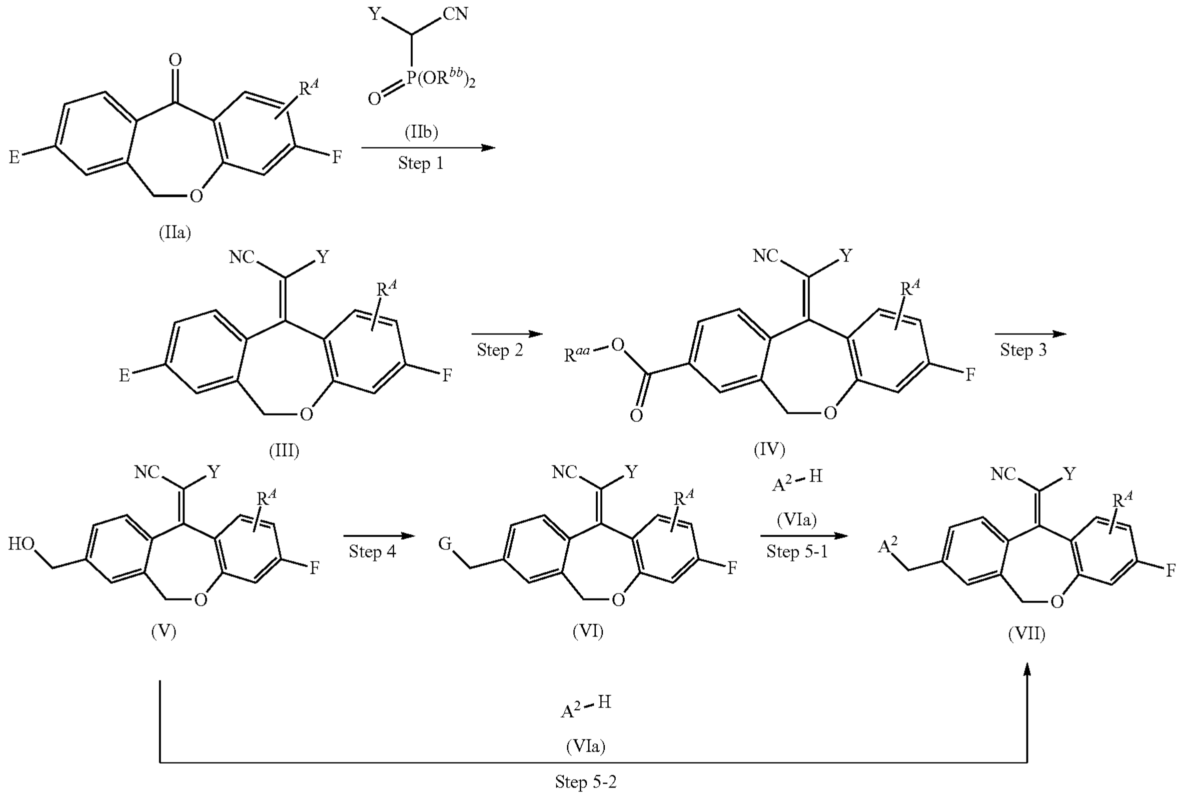

[wherein $R^A$ and Y are each as defined above, E is a chlorine atom, a bromine atom, an iodine atom, trifluoromethanesulfonyloxy, methanesulfonyloxy, benzenesulfonyloxy, p-toluenesulfonyloxy or the like, G is a leaving group such as a chlorine atom, a bromine atom, an iodine atom, trifluoromethanesulfonyloxy, methanesulfonyloxy, benzenesulfonyloxy, p-toluenesulfonyloxy and the like, $R^{aa}$ and $R^{bb}$ are each lower alkyl such as methyl, ethyl, propyl and the like, and $A^2$ is (a1)-(a14), and (a16)-(a23)

(a1)

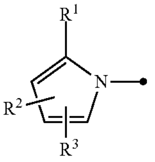

(a2)

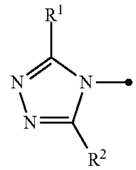

-continued (a3)

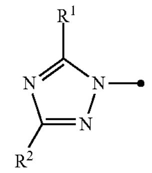

(a4)

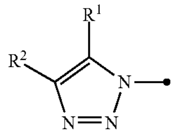

(a5)

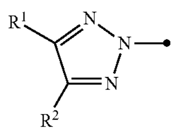

(a6)

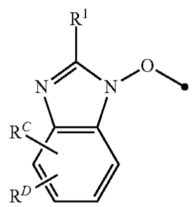

-continued
(a7)
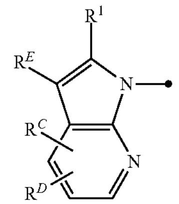
(a8)
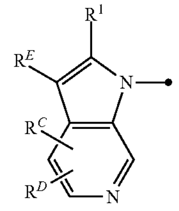
(a9)
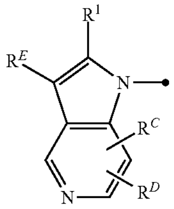
(a10)
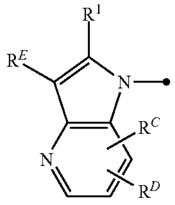
(a11)
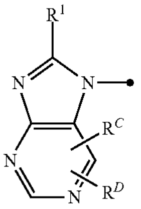
(a12)
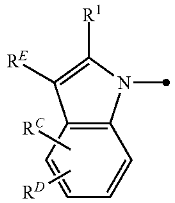
(a13)
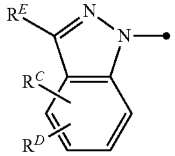
-continued
(a14)
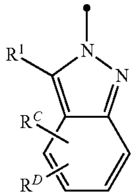
(a16)
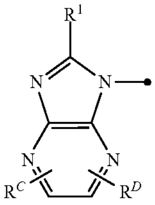
(a17)
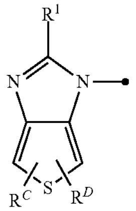
(a18)
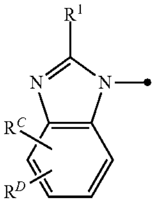
(a19)
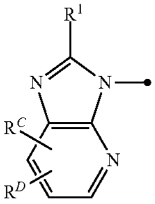
(a20)
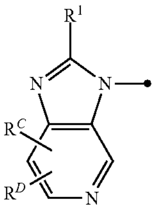
(a21)
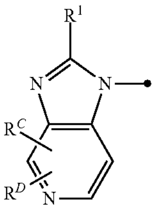

-continued (a22)

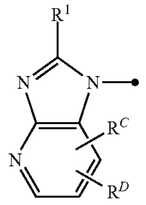

(a23)

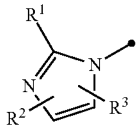

(wherein $R^1$, $R^2$, $R^3$, $R^C$, $R^D$ and RE are each as defined above)].

Step 1

Compound (III) can be obtained by reacting compound (IIa) with 1 equivalent—5 equivalents of compound (IIb) in the presence of 1 equivalent—large excess of a base in a solvent at a temperature between −20° C. and the boiling point of the solvent to be used for 5 min-120 hr.

Examples of the base include sodium hydride, potassium hydride, butyllithium, lithium diisopropylamide (LDA), lithium bistrimethylsilylamide, sodium bistrimethylsilylamide, sodium methoxide, potassium ethoxide, potassium tert-butoxide, potassium carbonate, sodium hydroxide, 1,8-diazabicyclo[5.4.0]-7-undecene (DBU), triethylamine, diisopropylethylamine and the like. Examples of the solvent include dimethylformamide (DMF), dimethylacetamide (DMA), N-methylpyrrolidone (NMP), dimethyl sulfoxide (DMSO), tetrahydrofuran (THF), acetonitrile and the like, and these can be used alone or in a mixture.

Here, compound (IIa) can be obtained by the method described in Journal of Medicinal Chemistry, 1996, vol. 39, p. 246, EP2072507 or the like, and compound (IIb) is commercially available or can be obtained by a known method (e.g., J. Chem. Soc. Perkin Trans. 1, 1992, p. 313, Synthesis, 1987, p. 411) or a method analogous thereto.

Step 2

Compound (IV) can be produced by reacting compound (III) in a solvent, in the presence of carbon monoxide, 0.1-10 equivalents of a base and 0.001-0.5 equivalents of a palladium catalyst at a temperature between −20° C. and the boiling point of the solvent to be used for 5 min-72 hr.

Examples of the base include potassium carbonate, cesium carbonate, potassium phosphate, potassium hydroxide, sodium hydroxide, potassium tert-butoxide, triethylamine, diisopropylethylamine, N-methylmorpholine, pyridine, DBU and the like.

Examples of the palladium catalyst include palladium acetate, tris(dibenzylideneacetone)dipalladium ($Pd_2(dba)_3$), tetrakis(triphenylphosphine)palladium, 1,1'-bis(diphenylphosphino)ferrocene dichloropalladium.dichloromethane 1:1 adduct and the like. Examples of the solvent include methanol, ethanol, propanol, butanol and the like. Furthermore, in addition to the above-mentioned solvent, chloroform, 1,2-dichloroethane, ethyl acetate, acetonitrile, THF, 1,2-dimethoxyethane (DME), 1,4-dioxane, DMF, DMA, NMP and the like can be used alone or in a mixture.

Step 3

Compound (V) can be obtained by reacting compound (IV) in the presence of 1 equivalent—large excess of a reducing agent in a solvent at a temperature between −20° C. and the boiling point of the solvent to be used for 5 min-120 hr.

Examples of the reducing agent include sodium borohydride, lithium borohydride, lithium aluminum hydride, diisobutylaluminum hydride and the like. Examples of the solvent include THF, diethyl ether, dioxane, dichloromethane, hexane, toluene and the like, and these can be used alone or in a mixture.

Step 4

Compound (VI) can be obtained by reacting compound (V) in the presence of 1 equivalent—large excess of a halogenating agent or sulfonylating agent in a solvent or without solvent at a temperature between −20° C. and the boiling point of the solvent to be used for 5 min-72 hr. Examples of the halogenating agent include thionyl chloride; phosphorus tribromide; boron tribromide; a combination of triphenylphosphine, 2,6-lutidine and carbon tetrachloride; a combination of triphenylphosphine, 2,6-lutidine and carbon tetrabromide; a combination of methanesulfonyl chloride and lithium chloride; a combination of methanesulfonic anhydride and lithium chloride; a combination of methanesulfonyl chloride and lithium bromide; a combination of methanesulfonic anhydride and lithium bromide, and the like. Examples of the sulfonylating agent include trifluoromethanesulfonyl chloride, methanesulfonyl chloride, methanesulfonic anhydride, benzenesulfonyl chloride, p-toluenesulfonyl chloride and the like. Examples of the solvent include THF, DMF, DMA, dichloromethane, dichloroethane, acetonitrile and the like, and these can be used alone or in a mixture.

Step 5-1

Compound (VII) can be obtained by reacting compound (VI) with 1 equivalent—5 equivalents of compound (VIa) in the presence of, if necessary, 1 equivalent—large excess of a base in a solvent at a temperature between −20° C. and the boiling point of the solvent to be used for 5 min-120 hr.

Examples of the base include sodium carbonate, potassium carbonate, lithium carbonate, cesium carbonate, sodium hydrogen carbonate, potassium hydrogen carbonate, lithium hydrogen carbonate, sodium hydroxide, potassium hydroxide, lithium hydroxide, sodium methoxide, potassium ethoxide, potassium tert-butoxide, sodium hydride, potassium hydride, LDA, lithium bistrimethylsilylamide, sodium bistrimethylsilylamide, triethylamine, diisopropylethylamine, tributylamine, dicyclohexylmethylamine and the like. Examples of the solvent include DMF, DMA, NMP, DMSO, THF, acetonitrile, isopropyl alcohol and the like, and these can be used alone or in a mixture.

Compound (VIa) is commercially available or can be obtained by a known method (e.g., U.S. Pat. No. 5,332,744, EP-B-400835, JP-A-5-783228 or the like) or a method analogous thereto.

Step 5-2

Compound (VII) can be produced by reacting compound (V) with preferably 1-10 equivalents of compound (VIa) in a solvent in the presence of preferably 1-10 equivalents of a phosphine compound and preferably 1-10 equivalents of an azo compound at a temperature between −78° C. and the boiling point of the solvent to be used for 5 min-72 hr.

Examples of the phosphine compound include triphenylphosphine, tributylphosphine and the like. Examples of the azo compound include diethyl azodicarboxylate (DEAD), di-tert-butyl azadicarboxylate (DBAD), diisopropyl azadicarboxylate, N,N,N',N'-tetramethylazadicarboxamide, 1,1'-(azadicarbonyl)dipiperazine, N,N,N',N'-tetraisopropylazadicarboxamide and the like. Preferable examples of the combination of the phosphine compound and the azo compound to be used include a combination of triphenylphosphine and DEAD or DBAD. Examples of the solvent include dichloromethane, chloroform, 1,2-dichloroethane, toluene, ethyl acetate, acetonitrile, diethyl ether, THF, DME, 1,4-dioxane, DMF, DMA, NMP and the like, and these can be used alone or in a mixture.

Production Method 2

A compound represented by the following formula (X), which is a synthetic intermediate for compound (I), can be produced by the following steps.

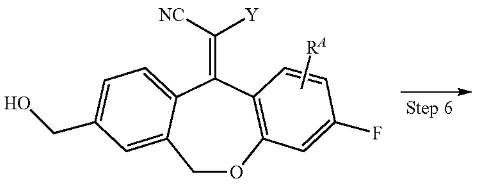

(V)

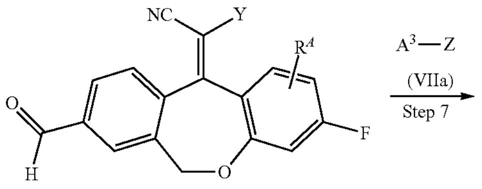

(VIII)

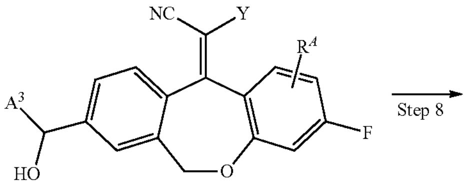

(IX)

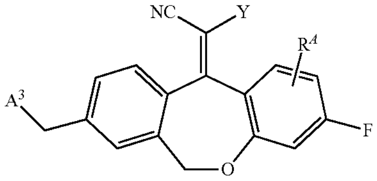

(X)

[wherein $R^A$ and Y are each as defined above, Z is a chlorine atom, a bromine atom, or an iodine atom, and $A^3$ is (a24)-(a29)

(a24)

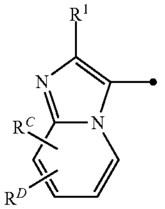

-continued (a25)

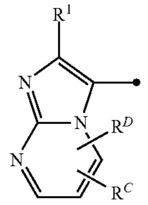

(a26)

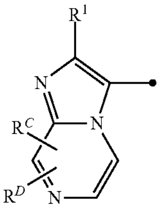

(a27)

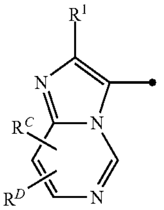

(a28)

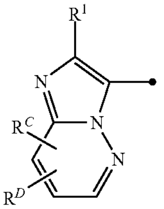

(a29)

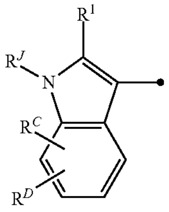

(wherein $R^1$, $R^C$, $R^D$ and $R^J$ are as defined above)].

Step 6

Compound (VIII) can be produced by treating compound (V) in a solvent, with preferably 1-10 equivalents of an oxidant at a temperature between −20° C. and the boiling point of the solvent to be used for 5 min-72 hr.

Examples of the oxidant include manganese dioxide, chromic acid, pyridinium chlorochromate (PCC), pyridinium dichlorochromate (PDC), potassium permanganate, sulfur trioxide-pyridine, oxone (registered trade mark), DMSO/oxalyl chloride, Dess-Martin periodinane (DMPI) and the like. Examples of the solvent include dichloromethane, chloroform, 1,2-dichloroethane, toluene, ethyl acetate, acetonitrile, diethyl ether, THF, DME, dioxane, DMF, DMA, NMP, DMSO, pyridine, hydrochloric acid, acetic acid, propionic acid, acetic anhydride, sulfuric acid, water and the like, and these can be used alone or in a mixture.

Step 7

Compound (IX) can be produced by reacting compounds (VIII) and (VIIa) in the presence of preferably 1-10 equivalents of an organic metal reagent in a solvent at a temperature between −78° C. and the boiling point of the solvent to be used for 5 min-72 hr.

Examples of the organic metal reagent include methyllithium, butyllithium, sec-butyllithium, phenyllithium, methylmagnesium chloride, ethylmagnesium chloride, isopropylmagnesium chloride, phenylmagnesium chloride, isopropylmagnesium chloride lithium chloride complex and the like. Examples of the solvent include toluene, diethyl ether, THF, DME, 1,4-dioxane, hexane and the like, and these can be used alone or in a mixture.

Step 8

Compound (X) can be produced by reacting compound (IX) with 1 equivalent—a large excess of alkylchlorosilane and 1 equivalent—a large excess of sodium iodide in a solvent at a temperature between −20° C. and the boiling point of the solvent to be used for 5 min-72 hr, or by reacting compound (IX) in 1 equivalent—a large excess of alkylsilane and 1 equivalent—a large excess of trifluoroacetic acid at a temperature between −20° C. and the boiling point of the solvent to be used for 5 min-72 hr.

Examples of the alkylchlorosilane include trimethylchlorosilane, triethylchlorosilane, dimethyldichlorosilane and the like. Examples of the solvent include dichloromethane, hexane, acetonitrile and the like, and these can be used alone or in a mixture. Examples of the alkylsilane include trimethylsilane, triethylsilane, tripropylsilane, and triisopropylsilane.

As another method besides the above-mentioned steps 7 and 8, compound (X) can be produced by reacting compound (VIII) with preferably 1-10 equivalents of $A^3$-H (wherein $A^3$ is as defined above), in a solvent, in the presence of preferably 1-10 equivalents of a reducing agent and preferably 1-10 equivalents of Brønsted acid, at a temperature between −78° C. and the boiling point of the solvent to be used for 5 min-72 hr. Examples of the reducing agent include sodium borohydride, lithium borohydride, triethylsilane and the like. Examples of the Brønsted acid include hydrochloric acid, sulfuric acid, trifluoroacetic acid, acetic acid, methanesulfonic acid and the like. Examples of the solvent include toluene, THF, DME, 1,4-dioxane, DMF and the like, and these can be used alone or in a mixture.

Here, compound (VIIa) is commercially available or can be obtained by a known method (e.g., Bioorganic and Chemistry Letter, 2008, vol. 18, p 688) or a method analogous thereto.

Production Method 3

A compound represented by the following formula (XII), which is a synthetic intermediate for compound (I), can be produced by the following steps.

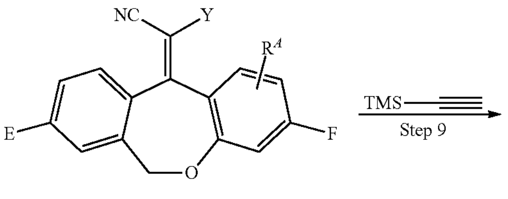

(III)

-continued

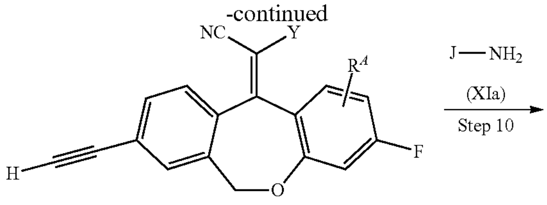

(XI)

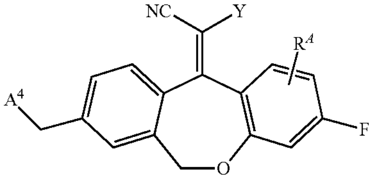

(XII)

[wherein E, $R^A$ and Y are each as defined above, J is (d1)-(d5)

(d1)

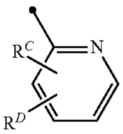

(d2)

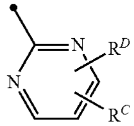

(d3)

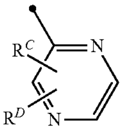

(d4)

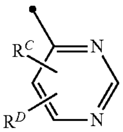

(d5)

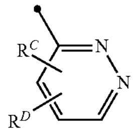

(wherein $R^C$, $R^D$ are each as defined above), and $A^4$ is (a24-1)-(a28-1)

(a24-1)

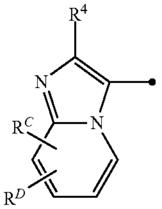

-continued (a25-1)

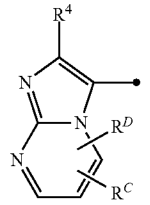

(a26-1)

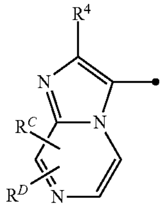

(a27-1)

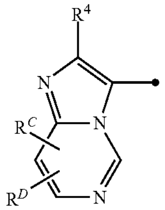

(a28-1)

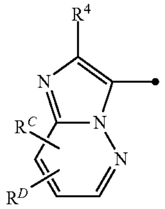

(wherein $R^4$ is a hydrogen atom, lower alkyl or cycloalkyl, and $R^C$ and $R^D$ are each as defined above)].

Step 9

Compound (XI) can be produced by reacting compound (III), for example, in a solvent such as toluene, dioxane, THF, DMF, DMA and the like, in the presence of 0.001-0.5 equivalents of copper (I) iodide, 1-10 equivalents of trimethylsilylacetylene, preferably 0.1-10 equivalents of a base and preferably 0.001-0.5 equivalent of a palladium catalyst at a temperature between −20° C. and the boiling point of the solvent to be used for 5 min-72 hr, and successively reacting, for example, in a solvent such as methanol, ethanol, isopropyl alcohol, THF, DMF, DMA and the like, for example, in the presence of 1—a large excess of a base or tetrabutylammonium fluoride at a temperature between −20° C. and the boiling point of the solvent to be used for 5 min-72 hr. The above-mentioned steps can also be performed sequentially by adding a base to the reaction mixture continuously without isolating the resultant product.

Examples of the base include potassium carbonate, potassium phosphate, potassium hydroxide, sodium hydroxide, potassium tert-butoxide, triethylamine, diisopropylethylamine, pyridine, DBU and the like. Examples of the palladium catalyst include palladium acetate, tris(dibenzylideneacetone)dipalladium, tetrakis(triphenylphosphine) palladium, 1,1'-bis(diphenylphosphino)ferrocene dichloropalladium.dichloromethane 1:1 adduct, bis(triphenylphosphine)dichloropalladium and the like.

Step 10

Compound (XII) can be produced by reacting compound (XI) in the presence of compound (XIa), and $R^4$—CHO (wherein $R^4$ is as defined above), preferably in the presence of 0.001-0.5 equivalents of copper trifluoromethanesulfonate and preferably 0.001-0.5 equivalents of copper chloride in a solvent at a temperature between −20° C. and the boiling point of the solvent to be used for 5 min-72 hr.

Examples of $R^4$—CHO (wherein $R^4$ is as defined above) include formaldehyde, propanecarboxyaldehyde, cyclopropanecarboxyaldehyde, isopropylcarboxyaldehyde, cyclobutanecarboxyaldehyde, cyclopentanecarboxyaldehyde and the like. Examples of the solvent include THF, 1,4-dioxane, dichloroethane, chloroform, toluene, DMF, DMA and the like, and these can be used alone or in a mixture.

Production Method 4

Compounds represented by the following formulas (XIV), (XVII), which are synthetic intermediates for compound (I), can be produced by the following steps.

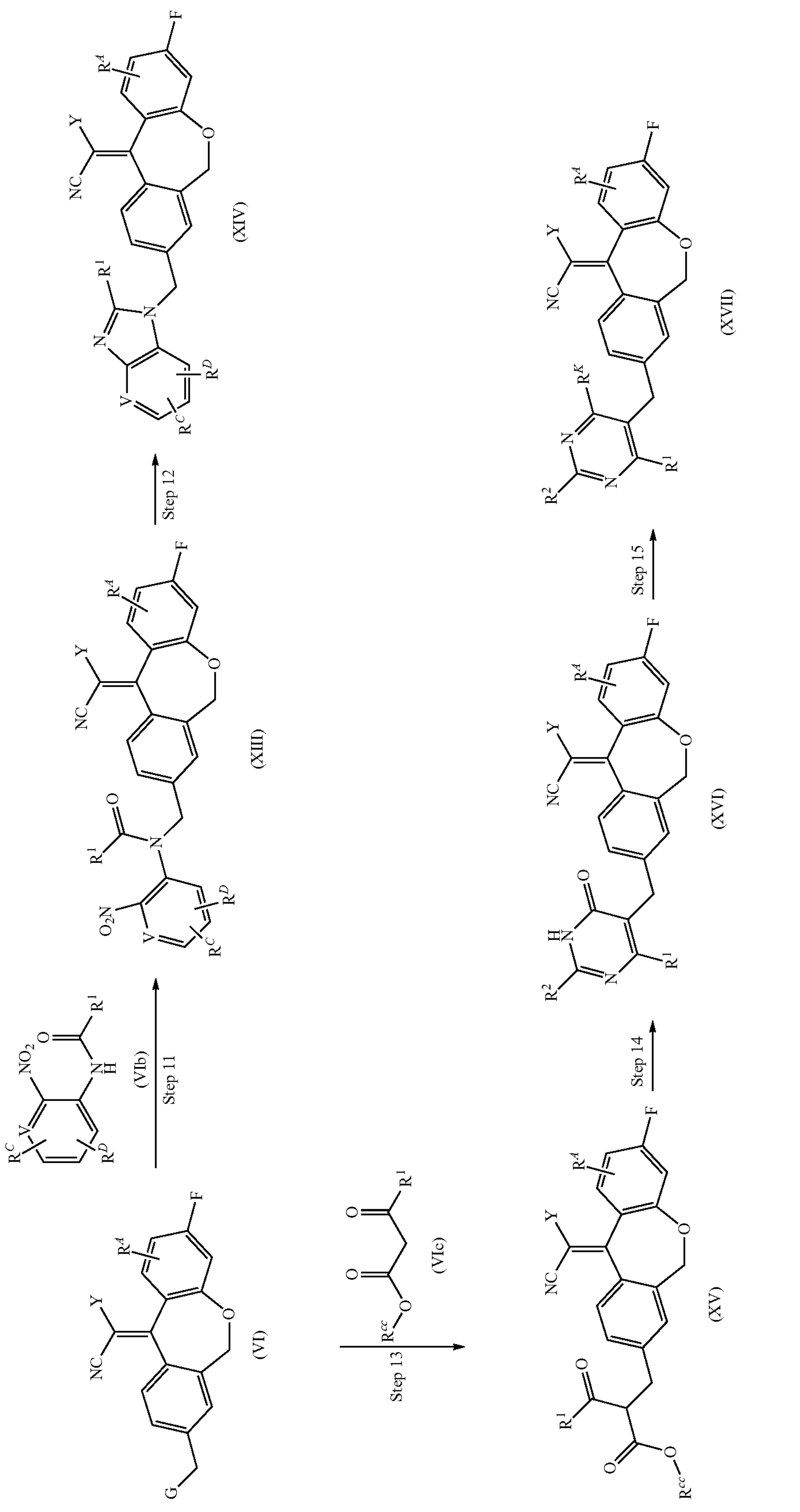
Step 11
Step 12
Step 13
Step 14
Step 15
(VI)
(VIb)
(VIc)
(XIII)
(XIV)
(XV)
(XVI)
(XVII)

(wherein G, $R^1$, $R^2$, $R^A$, $R^C$, $R^D$, $R^K$ and Y are each as defined above, $R^{cc}$ is lower alkyl such as methyl, ethyl and the like, and V is a carbon atom or a nitrogen atom).

Step 11

Compound (XIII) can be produced by reacting compound (VI) with compound (VIb) in a solvent in the presence of preferably 1—a large excess of a base, at a temperature between −20° C. and the boiling point of the solvent to be used for 5 min-72 hr.

Examples of the base include sodium hydride, potassium hydride, sodium methoxide, potassium tert-butoxide, potassium carbonate, sodium carbonate, sodium hydroxide, LDA and the like. Examples of the solvent include DMF, DMA, THF, DME, 1,4-dioxane, NMP and the like, and these can be used alone or in a mixture. Here, compound (VIb) is commercially available or can be obtained by a known method (e.g., Synthesis, 2008, vol. 19, p 3065 and the like) or a method analogous thereto.

Step 12

Compound (XIV) can be produced by reacting compound (XIII) in a solvent in the presence of preferably 1—a large excess of a reducing agent at a temperature between −20° C. and the boiling point of the solvent to be used for 5 min-72 hr. Examples of the reducing agent include iron, stannic chloride, zinc and the like. Examples of the solvent include acetic acid, ethanol, DME, 1,4-dioxane, DMF, NMP and the like, and these can be used alone or in a mixture.

Step 13

Compound (XV) can be produced by reacting compound (VI) with compound (VIc) in a solvent in the presence of preferably 1—a large excess of a base, at a temperature between −20° C. and the boiling point of the solvent to be used for 5 min-72 hr. Examples of the base include sodium hydride, potassium hydride, sodium methoxide, potassium tert-butoxide, potassium carbonate, sodium carbonate, sodium hydroxide, LDA and the like. Examples of the solvent include DMF, DMA, THF, DME, 1,4-dioxane, NMP and the like, and these can be used alone or in a mixture.

Step 14

Compound (XVI) can be produced by reacting compound (XV) in a solvent in the presence of an inorganic acid salt of $R^2$—C(=NH)$NH_2$ (wherein $R^2$ is as defined above) and 1—a large excess of a base, at a temperature between −20° C. and the boiling point of the solvent to be used for 5 min-72 hr.

Examples of the base include sodium hydride, sodium methoxide, sodium ethoxide, potassium carbonate, sodium carbonate, sodium hydroxide, LDA and the like. Examples of the solvent include DMF, ethanol, methanol, THF, DME, 1,4-dioxane and the like, and these can be used alone or in a mixture Step 15

Compound (XVII) can be produced by reacting compound (XVI) in the presence of phosphorus oxychloride, by adding a solvent such as acetonitrile, chloroform, 1,2-dichloroethane and the like if necessary, at a temperature between room temperature and the boiling point of the solvent to be used for 5 min-72 hr, and successively reacting, for example, in a solvent such as methanol, ethanol, isopropyl alcohol, THF, DMF, DMA and the like in the presence of, for example, 1 equivalent—a large excess of $R^kH$ (wherein $R^k$ is as defined above) or an anionic nucleophilic species thereof, at a temperature between room temperature and the boiling point of the solvent to be used for 5 min-72 hr. Examples of $R^kH$ (wherein $R^k$ is as defined above) or an anionic nucleophilic species thereof include sodium methoxide, sodium ethoxide, dimethylamine, azetidine, morpholine, piperidine, piperazine and the like.

Production Method 5

Of compounds (1), a compound represented by (Ic), (Ia), (Ib), (Ie), (Id) wherein X is the following formula (b15), (b1-1), (b3-1), (b4-1), (b5-1)

(b15)

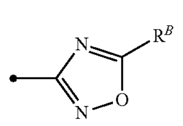

(b1-1)

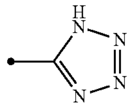

(b3-1)

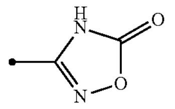

(b4-1)

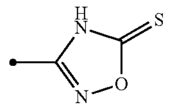

(b5-1)

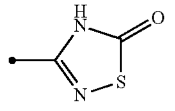

(wherein $R^B$ is as defined above) can be produced by the following steps.

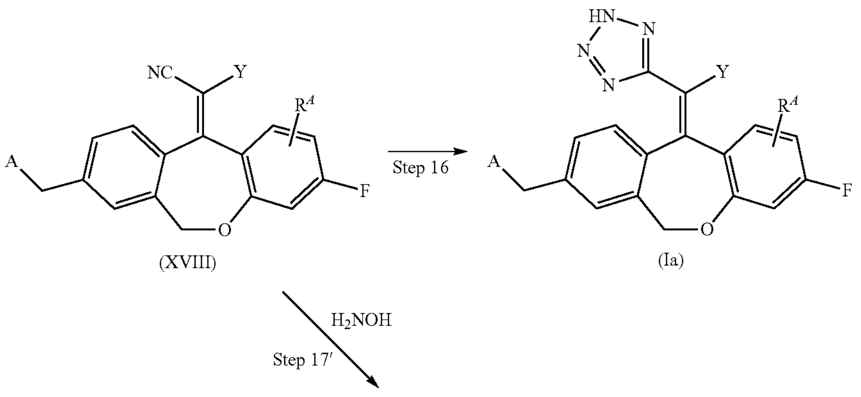

(XVIII)

(Ia)

-continued

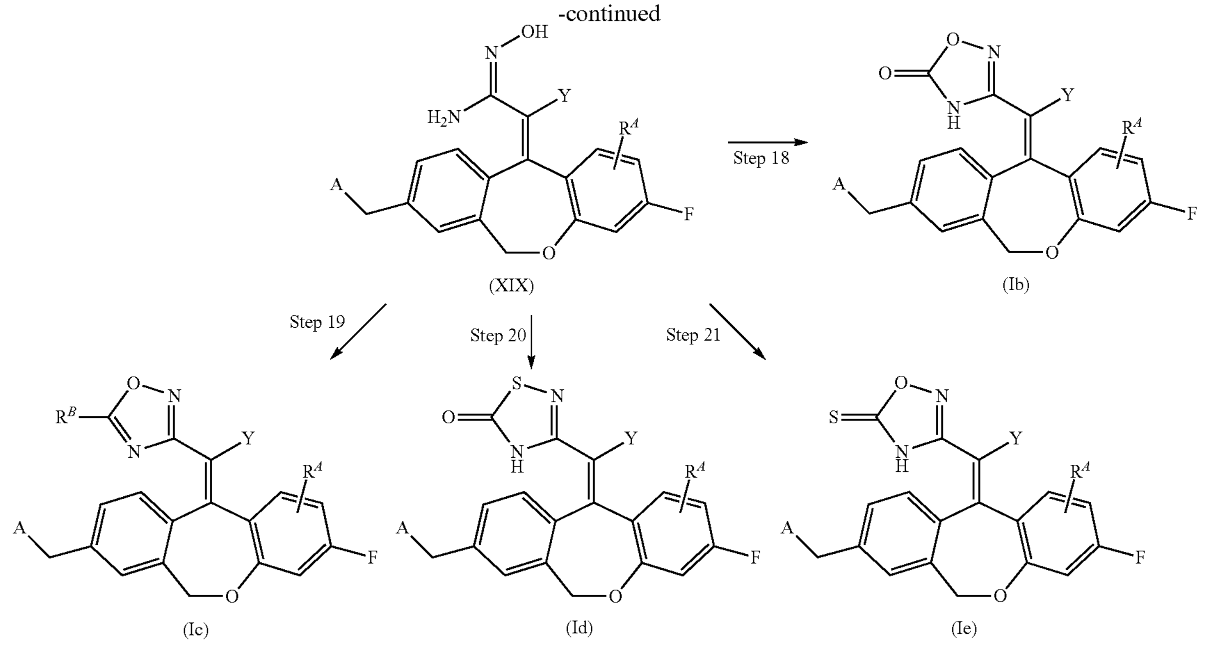

(wherein A, $R^A$, $R^B$ and Y are each as defined above).

Step 16

Compound (Ia) can be obtained by reacting compound (XVIII) with 1 equivalent—10 equivalents of sodium azide in a solvent in the presence of 1 equivalent—large excess of a weak acid for 5 min-120 hr at a temperature between −20° C. and the boiling point of the solvent to be used.

Examples of the weak acid include ammonium chloride, triethylamine hydrochloride and the like. Examples of the solvent include DMF, DMA, NMP, DMSO and the like, and these can be used alone or in a mixture.

Compound (XVIII) can be synthesized by a known method (e.g., WO2010/016549 and the like) or a method analogous thereto.

In addition, as another method, compound (Ia) can also be obtained by reacting compound (XVIII) with 1 equivalent—10 equivalents of sodium azide in a solvent in the presence of 0.01-10 equivalents of an additive at a temperature between −10° C. and the boiling point of the solvent to be used for 1 hr-120 hr.

Examples of the additive include tributyltin chloride, trimethyltin chloride, dibutyltin oxide and the like. Examples of the solvent include toluene, xylene and the like, and these can be used alone or in a mixture.

Step 17

Compound (XIX) can be obtained by reacting compound (XVIII) with 1 equivalent—large excess of hydroxylamine in a solvent at a temperature between −20° C. and the boiling point of the solvent to be used for 5 min-120 hr.

As hydroxylamine, for example, an inorganic acid salt such as hydroxylamine hydrochloride or the like can be used. In this case, approximately an equivalent of a base such as sodium methoxide, sodium hydrogen carbonate or the like is preferably copresent. Examples of the solvent include methanol, ethanol, DMF, DMA, DMSO and the like, and these can be used alone or in a mixture.

Step 18

Compound (Ib) can be obtained by reacting compound (XIX) with 1 equivalent—a large excess of chlorocarbonate ester in the presence of 1 equivalent—a large excess of a base, for example, in a solvent such as THF, DMF, DMA, toluene, xylene, dichloromethane and the like, at a temperature between −20° C. and the boiling point of the solvent to be used for 5 min-72 hr, and successively reacting, for example, in a solvent such as THF, DMF, DMA, toluene, xylene and the like or a mixed solvent such as toluene-THF and the like, in the presence of, if necessary, a catalytic amount—10 equivalents of a base, at a temperature between −20° C. and the boiling point of the solvent to be used for 5 min-72 hr. The above-mentioned steps can also be performed sequentially by adding chlorocarbonate ester and a base to the reaction mixture continuously without isolating the resultant product.

Examples of the base used for the reaction with chlorocarbonate ester include potassium tert-butoxide, potassium carbonate, DBU, triethylamine and the like. Examples of the chlorocarbonate ester include methyl chlorocarbonate, ethyl chlorocarbonate, propyl chlorocarbonate, phenyl chlorocarbonate and the like. Examples of the base used for intermediate carbonate ester include triethylamine, pyridine, 4-dimethylaminopyridine, diazabicycloundecene and the like.

Compound (Ib) can be obtained by reacting compound (XIX) with 1 equivalent—a large excess of N,N'-carbonyldiimidazole (CDI) in the presence of 1 equivalent—a large excess of a base, at a temperature between −20° C. and the boiling point of the solvent to be used for 5 min-72 hr.

Examples of the base include potassium tert-butoxide, potassium carbonate, DBU, triethylamine and the like. Examples of the solvent include THF, DMF, DMA, 1,4-dioxane and the like, and these can be used alone or in a mixture.

Step 19

Compound (Ic) can be obtained by reacting compound (XIX) with 1 equivalent—a large excess of $(R^{B-4}CO)_2O$ (wherein $R^{B-4}$ is lower alkyl optionally having substituent(s) or cycloalkyl optionally having substituent(s)), in the presence of 1 equivalent—a large excess of a base if necessary, in a solvent at a temperature between −20° C. and the boiling point of the solvent to be used for 5 min-72 hr. Examples of $(R^{B-4}CO)_2O$ (wherein $R^{B-4}$ is as defined above) include acetic anhydride, propionic anhydride, trifluoroacetic anhydride and the like. Examples of the base include triethylamine, pyridine, 4-dimethylaminopyridine, diazabicycloundecene and the like. Examples of the solvent include THF, 1,4-dioxane, dichloromethane, chloroform, acetonitrile, acetone, DMF, DMA, DMSO and the like, and these can be used alone or in a mixture. As another method, it can be obtained by reacting compound (XIX) with 1 equivalent—a large excess of $R^BC(OR^L)_3$ (wherein $R^B$ is as defined above, and $R^L$ is lower alkyl), in a solvent or without solvent, at a temperature between −20° C. and the boiling point of the solvent to be used for 5 min-72 hr. Examples of the above-mentioned $R^BC(OR^L)_3$ (wherein $R^B$ and $R^L$ are each as defined above) include trimethyl orthoformate, triethyl orthoformate, trimethyl orthoacetate, triethyl orthoacetate and the like. Examples of the solvent include THF, 1,4-dioxane, dichloromethane, chloroform, acetonitrile, acetone, DMF, DMA, DMSO and the like, and these can be used alone or in a mixture.

Step 20

Compound (Id) can be obtained by reacting compound (XIX) with 1 equivalent—a large excess of N,N'-thiocarbonyldiimidazole in the presence of 1 equivalent—a large excess of a Lewis acid in a solvent at a temperature between −20° C. and the boiling point of the solvent to be used for 5 min-72 hr. Examples of the Lewis acid include boron trifluoride diethyl ether complex, stannous chloride, zinc chloride, silica gel and the like. Examples of the solvent include THF, 1,4-dioxane, dichloromethane, chloroform, methanol, ethanol and the like, and these can be used alone or in a mixture.

Step 21

Compound (Ie) can be obtained by reacting compound (XIX) with 1 equivalent—a large excess of N,N'-thiocarbonyldiimidazole, in the presence of 1 equivalent—a large excess of a base in a solvent at a temperature between −20° C. and the boiling point of the solvent to be used for 5 min-72 hr.

Examples of the base include triethylamine, pyridine, 4-dimethylaminopyridine, diazabicycloundecene and the like. Examples of the solvent include THF, 1,4-dioxane, dichloromethane, chloroform, acetonitrile, acetone and the like, and these can be used alone or in a mixture.

Using a method similar to that in steps 16-21, the nitrile group of compound (VII), (X), (XII), (XIV), (XVII) can also be converted in the same manner as in the cyano of group of compound (XVIII).

Production Method 6

Of compounds (1), a compound represented by (If), (Ig), (Ih) wherein X is the following formula (b14), (b16) or (b6-1)

(b14)

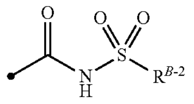

(b16)

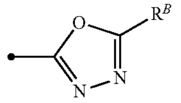

(b6-1)

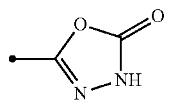

(wherein $R^B$, $R^{B-2}$ are as defined above) can be produced by the following steps.

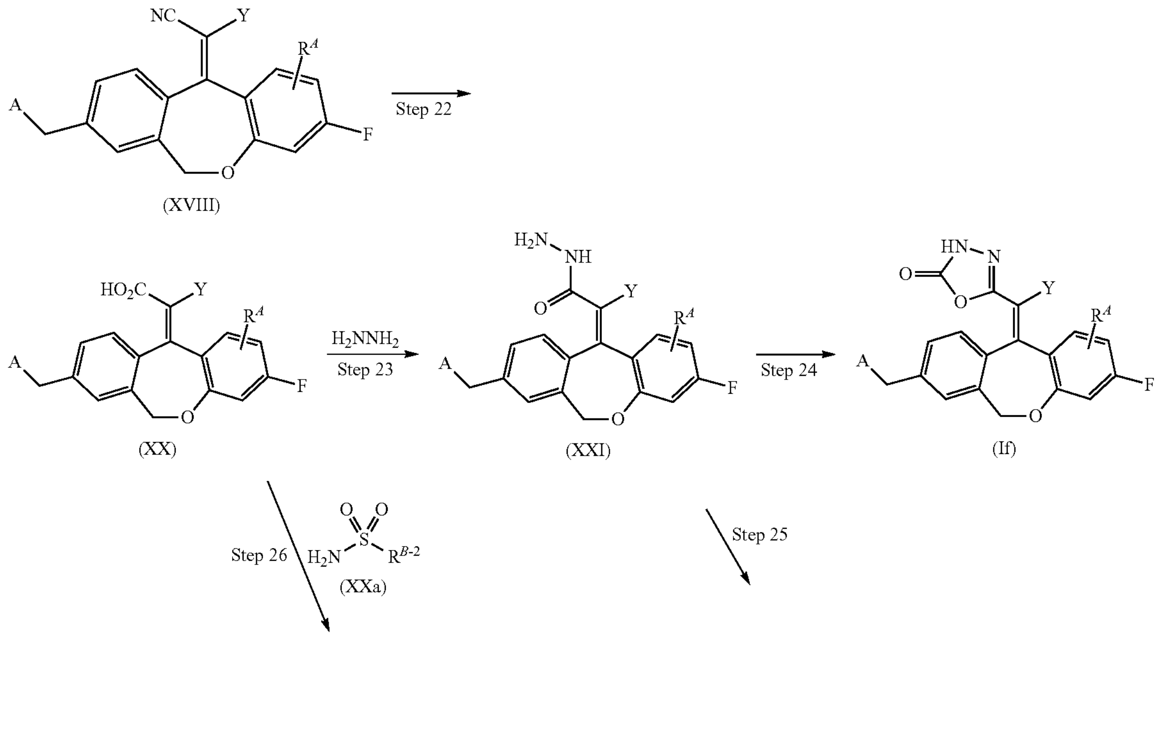

(XVIII) (XX) (XXI) (If) (XXa)

-continued

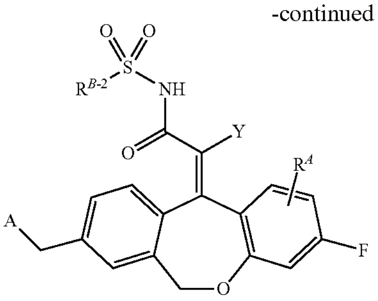

(Ig)

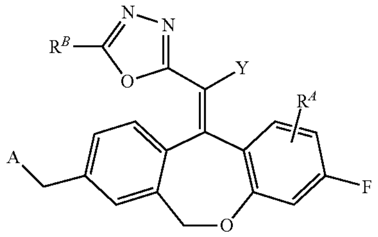

(Ih)

(wherein A, $R^A$, $R^B$, $R^{B-2}$ and Y are each as defined above).

Step 22

Compound (XX) can be obtained, for example, by hydrolyzing the cyano group by reacting compound (XVIII) in the presence of a base such as lithium hydroxide, sodium hydroxide, potassium hydroxide, barium hydroxide and the like, in a suitable water-containing solvent such as a water-containing solvent of methanol, ethanol, ethylene glycol, dioxane, glyme and the like, at a temperature between room temperature and the boiling point of the solvent to be used for 1 hr-120 hr, or in an aqueous solution of sulfuric acid, hydrochloric acid, acetic acid or the like or a mixture of acids thereof at a temperature between room temperature and the boiling point of the solvent to be used for 1 hr-120 hr. Alternatively, it can also be obtained by once obtaining the corresponding amide compound as an intermediate and then performing the above-mentioned reaction.

Step 23

Compound (XXI) can be obtained by reacting compound (XX) in the presence of 1 equivalent—50 equivalents of a condensing agent, 1 equivalent—large excess of hydrazine and, if necessary, a base in a solvent at a temperature between −20° C. and the boiling point of the solvent to be used for 5 min-72 hr. Examples of the condensing agent include N,N'-carbonyldiimidazole, dicyclohexylcarbodiimide, 1-ethyl-3-(3-dimethylaminopropyl)carbodiimide hydrochloride and the like. Examples of the base include triethylamine, pyridine, 4-dimethylaminopyridine, diazabicycloundecene and the like. Examples of the solvent include THF, 1,4-dioxane, dichloromethane, chloroform, acetonitrile, acetone and the like, and these can be used alone or in a mixture.

Step 24

Compound (If) can be obtained by reacting compound (XXI) with 1 equivalent—50 equivalents of N,N'-carbonyldiimidazole in the presence of, if necessary, a base in a solvent at a temperature between −20° C. and the boiling point of the solvent to be used for 5 min-72 hr. Examples of the base include triethylamine, pyridine, 4-dimethylaminopyridine, diazabicycloundecene and the like. Examples of the solvent include THF, 1,4-dioxane, dichloromethane, chloroform, acetonitrile, acetone and the like, and these can be used alone or in a mixture.

Step 25

Compound (Ih) can be obtained by reacting compound (XXI) with 1 equivalent—a large excess of $(R^{B-4}CO)_2O$ (wherein $R^{B-4}$ is as defined above) in the presence of 1 equivalent—a large excess of a base if necessary in a solvent at a temperature between −20° C. and the boiling point of the solvent to be used for 5 min-72 hr. Examples of the above-mentioned $(R^{B-4}CO)_2O$ (wherein $R^{B-4}$ is as defined above) include acetic anhydride, propionic anhydride, trifluoroacetic anhydride and the like. Examples of the base include triethylamine, pyridine, 4-dimethylaminopyridine, DBU and the like. Examples of the solvent include THF, 1,4-dioxane, dichloromethane, chloroform, acetonitrile, acetone, DMF, DMA, DMSO and the like, and these can be used alone or in a mixture. As another method, it can be obtained by reacting compound (XXI) with 1 equivalent—a large excess of $R^BC(OR^L)_3$ (wherein $R^B$ and $R^L$ are each as defined above), in a solvent or without solvent, at a temperature between −20° C. and the boiling point of the solvent to be used for 5 min-72 hr. Examples of the aforementioned $R^BC(OR^L)_3$ (wherein $R^B$ and $R^L$ are each as defined above) include trimethyl orthoformate, triethyl orthoformate, trimethyl orthoacetate, triethyl orthoacetate and the like. Examples of the solvent include THF, 1,4-dioxane, dichloromethane, chloroform, acetonitrile, acetone, DMF, DMA, DMSO and the like, and these can be used alone or in a mixture.

Step 26

Compound (Ig) can be obtained by treating compound (XX) with 1-50 equivalents of a condensing agent, and reacting the compound with 1-50 equivalents of compound (XXa) in the presence of 1-30 equivalents of a base, in a solvent at a temperature between −20° C. and the boiling point of the solvent to be used for 5 min-72 hr.

Examples of the condensing agent include CDI, 1-(3-dimethylaminopropyl)-3-ethylcarbodiimide (EDCI) or hydrochloride thereof, dicyclohexylcarbodiimide (DCC) and the like. Examples of the solvent include dichloromethane, acetonitrile, toluene, ethyl acetate, THF, 1,4-dioxane, DMF, NMP and the like, and these can be used alone or in a mixture. Examples of the base include diazabicycloundecene, triethylamine, 4-dimethylaminopyridine, N,N-dimethylaniline, pyridine, N-methylmorpholine and the like. Compound (XXa) can be obtained as a commercially available product.

Using a method similar to that in steps 22-26, the nitrile group of compound (VII), (X), (XII), (XIV), (XVII) can also be converted in the same manner as in the cyano of group of compound (XVIII).

Production Method 7

Of compounds (1), a compound wherein X is the following formula (b1)-(b6)

(b1)

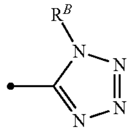

-continued (b2)

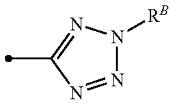

(b3)

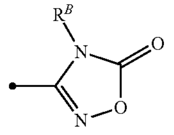

(b4)

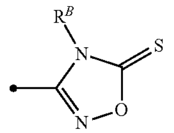

(b5)

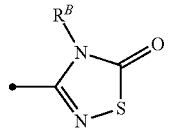

(b6)

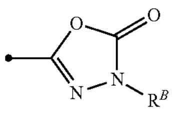

(wherein $R^B$ is as defined above), and $R^B$ is a hydrogen atom is the compound (Ia), (Ib), (Ie), (Id) or (If) synthesized in Production method 5 or 6, and a compound wherein $R^B$ is lower alkyl optionally having substituent(s) or cycloalkyl optionally having substituent(s) can be obtained by treating the compound (1a), (Ib), (Ie), (Id) or (If) synthesized in Production method 5 or 6 with $R^{B-1}U$ (wherein U is a leaving group such as a chlorine atom, a bromine atom, an iodine atom, trifluoromethanesulfonyloxy, methanesulfonyloxy, benzenesulfonyloxy, p-toluenesulfonyloxy and the like, and $R^{B-1}$ is lower alkyl optionally having substituent(s), or cycloalkyl optionally having substituent(s)) and a base in a solvent. Examples of the base include sodium hydride, sodium methoxide, potassium tert-butoxide, potassium carbonate, sodium hydroxide, diazabicycloundecene (DBU), triethylamine, diisopropylethylamine and the like. Examples of the solvent include DMF, DMA, THF, DME, 1,4-dioxane, NMP and the like, and these can be used alone or in a mixture.

As another method, it can be obtained by reacting (Ia), (Ib), (Ie), (Id) or (If) with 1 equivalent—5 equivalents of $R^{B-1}OH$ (wherein $R^{B-1}$ is as defined above) in the presence of 1 equivalent—large excess of a condensing agent and, if necessary, 1 equivalent—large excess of a phosphine compound in a solvent at a temperature between −20° C. and the boiling point of the solvent to be used for 5 min-72 hr.

Examples of the condensing agent include diethyl azodicarboxylate, diisopropyl azodicarboxylate, di(tert-butyl) azodicarboxylate, (cyanomethylene)trimethylphosphorane, (cyanomethylene)tributylphosphorane and the like. Examples of the phosphine compound include triphenylphosphine, tributylphosphine, polymer supported triphenylphosphine and the like. Examples of the solvent include THF, DMF, dichloromethane, acetonitrile and the like, and these can be used alone or in a mixture.

The functional groups contained in X, Y, A, $R^A$ and the like in compound (I) can also be converted by a known method (e.g., the method described in Comprehensive Organic Transformations 2nd edition, R. C. Larock, Vch Verlagsgesellschaft Mbh, 1999 and the like) or a method analogous thereto.

The intermediates and the desired compounds in the above-mentioned production methods can be isolated and purified by applying separation and purification methods usually used in the synthetic organic chemistry such as filtration, extraction, washing, drying, concentration, recrystallization, various chromatographies and the like. In addition, intermediates can also be subjected to a next reaction without particular purification.

Some of compounds (I) contain a stereoisomer such as a geometric isomer, an optical isomer or the like, a tautomer and the like. The present invention comprises all possible isomers and mixtures thereof including these.

In compound (I), each atom may be partly or entirely substituted by the corresponding isotope atom, and the present invention also encompasses a compound substituted by such isotope atom(s). For example, a hydrogen atom of compound (I) may be partly or entirely a hydrogen atom with atomic weight 2 (deuterium atom).

Compound (I) wherein each atom is partly or entirely substituted by the corresponding isotope atom can be produced using a commercially available building block and by a method similar to each of the above-mentioned production methods. Compound (I) wherein each atom is partly or entirely substituted by a deuterium atom can also be synthesized by, for example, 1) a method including deuterating carboxylic acid and the like by using deuterium peroxide under basic conditions (see U.S. Pat. No. 3,849,458), 2) a method including deuterating alcohol, carboxylic acid and the like by using an iridium complex as a catalyst and deuterated water as a deuterium source [see Journal of American Chemical Society (J. Am. Chem. Soc.), Vol. 124, No. 10, 2092 (2002)], 3) a method including deuterating fatty acid by using palladium carbon as a catalyst and deuterium gas alone as a deuterium source [see LIPIDS, Vol. 9, No. 11, 913 (1974)], 4) a method including deuterating acrylic acid, methyl acrylate, methacrylic acid, methyl methacrylate and the like by using a metal such as platinum, palladium, rhodium, ruthenium, iridium and the like as a catalyst and deuterated water or deuterated water and deuterium gas as a deuterium source (see JP-B-5-19536, JP-A-61-277648 and JP-A-61-275241), 5) a method including deuterating acrylic acid, methyl methacrylate and the like by using a catalyst such as palladium, nickel, copper or copper chromite and the like and deuterated water as a deuterium source (see JP-A-63-198638) and the like.

When a salt of compound (I) is to be obtained, compound (I) obtained in the form of a salt can be directly purified. When it is obtained in a free form, compound (I) may be dissolved or suspended in a suitable solvent, and an acid or a base is added thereto to form a salt, which may be isolated and purified.

While compound (I) and pharmaceutically acceptable salts thereof may exist in the form of adducts with water or various solvents, these adducts are also comprised in the present invention.

Specific examples of compound (I) obtained by the present invention are shown in Table 1 to Table 14. However, the compound of the present invention is not limited to them. In the Tables, Me is methyl.

TABLE 1
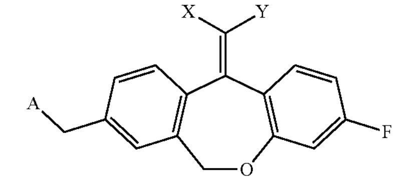
| Compound No. | A | X | Y |
|---|---|---|---|
| 1a | 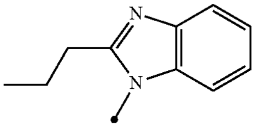 | 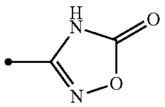 | Me |
| 1b | 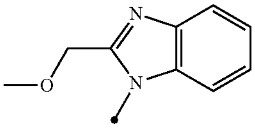 | 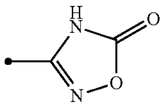 | Me |
| 1c | 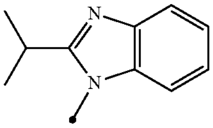 | 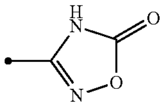 | Me |
| 1d | 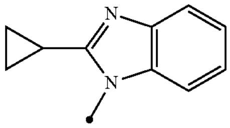 | 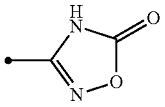 | Me |
| 1e | 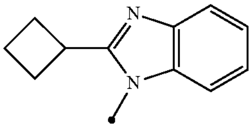 | 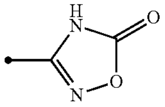 | Me |
| 1f | 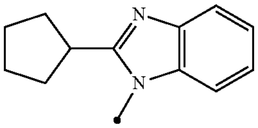 | 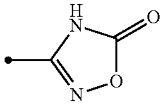 | Me |
| 1g | 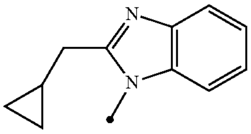 | 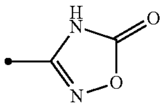 | Me |
| 1h | 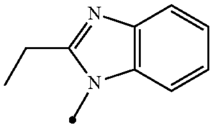 | 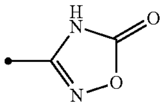 | Me |
| 1i | 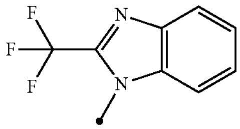 | 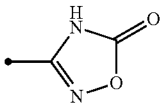 | Me |
TABLE 1-continued
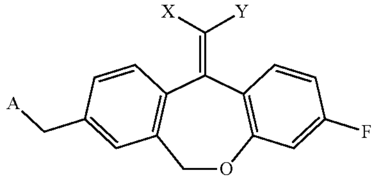
| Compound No. | A | X | Y |
|---|---|---|---|
| 1j | 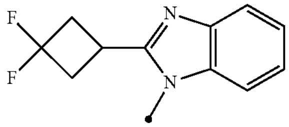 | 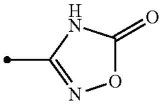 | Me |
| 1l | 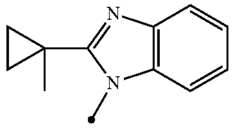 | 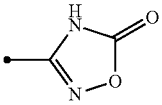 | Me |
| 1m | 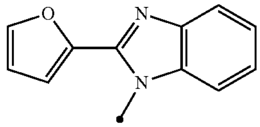 | 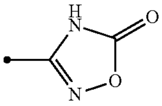 | Me |
| 1n | 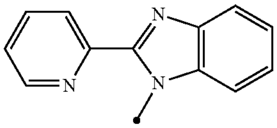 | 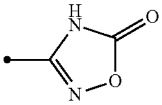 | Me |
TABLE 2
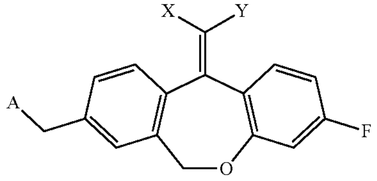
| Compound No. | A | X | Y |
|---|---|---|---|
| 2a | 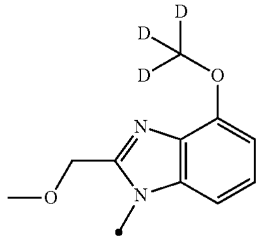 | 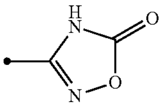 | Me |
| 2b | 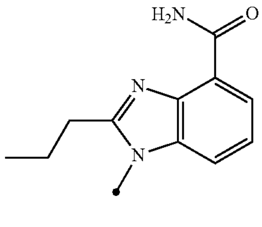 | 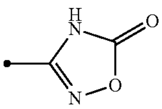 | Me |

TABLE 2-continued
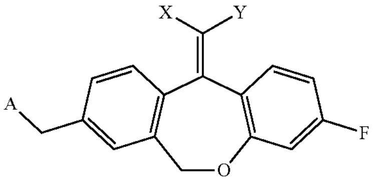
| Compound No. | A | X | Y |
|---|---|---|---|
| 2c | 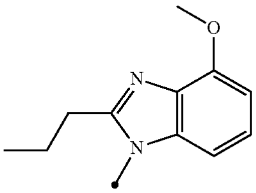 | 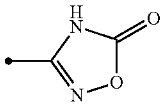 | Me |
| 2d | 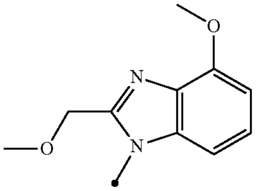 | 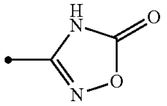 | Me |
| 2e | 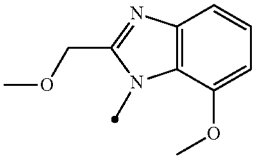 | 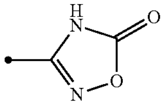 | Me |
| 2f | 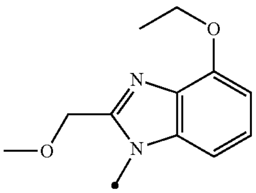 | 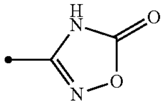 | Me |
| 2g | 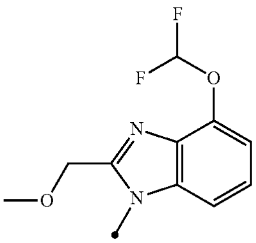 | 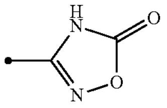 | Me |
| 2h | 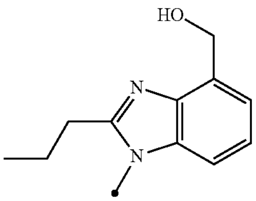 | 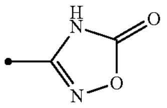 | Me |
TABLE 2-continued
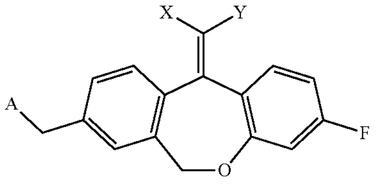
| Compound No. | A | X | Y |
|---|---|---|---|
| 2i | 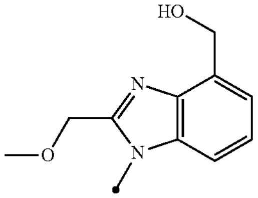 | 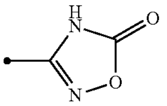 | Me |
| 2j | 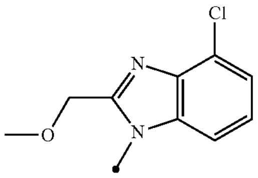 | 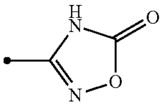 | Me |
| 2k | 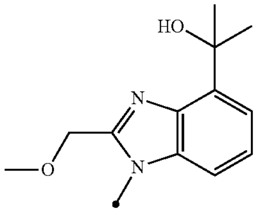 | 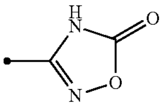 | Me |
| 2l | 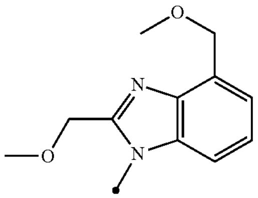 | 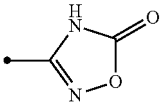 | Me |
| 2m | 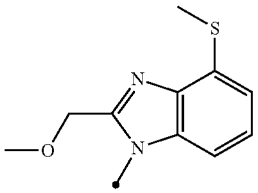 | 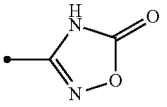 | Me |
| 2n | 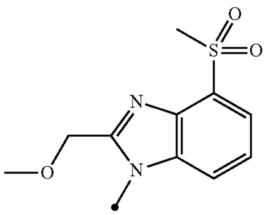 | 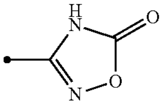 | Me |

TABLE 2-continued
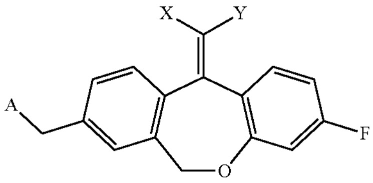
| Compound No. | A | X | Y |
|---|---|---|---|
| 2o | 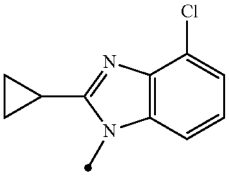 | 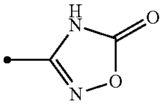 | Me |
TABLE 3
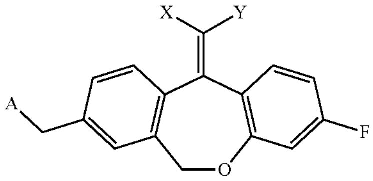
| Compound No. | A | X | Y |
|---|---|---|---|
| 3a | 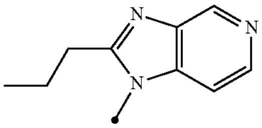 | 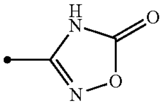 | Me |
| 3b | 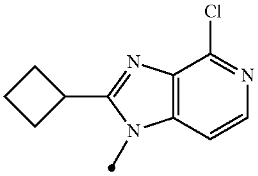 | 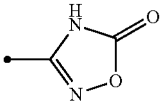 | Me |
| 3c | 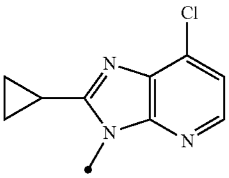 | 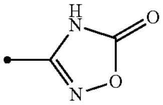 | Me |
| 3d | 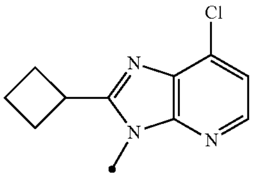 | 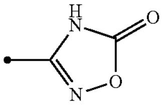 | Me |
TABLE 3-continued
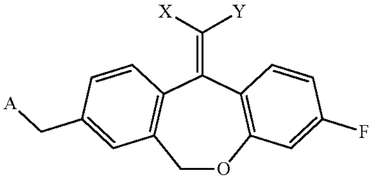
| Compound No. | A | X | Y |
|---|---|---|---|
| 3e | 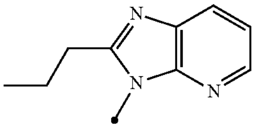 | 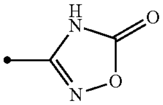 | Me |
| 3g | 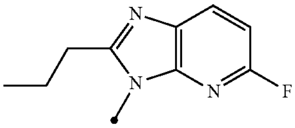 | 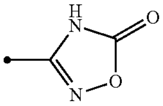 | Me |
| 3h | 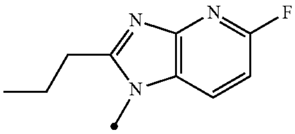 | 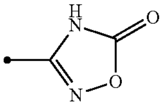 | Me |
| 3i | 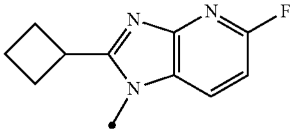 | 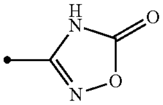 | Me |
| 3j | 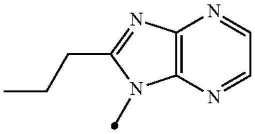 | 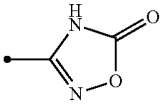 | Me |
TABLE 4
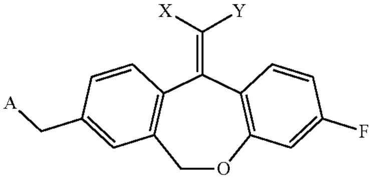
| Compound No. | A | X | Y |
|---|---|---|---|
| 4a | 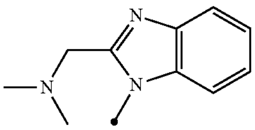 | 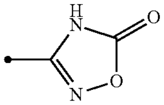 | Me |
| 4b | 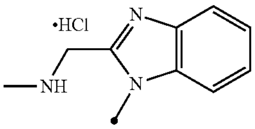 | 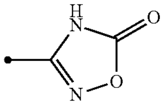 | Me |

TABLE 4-continued
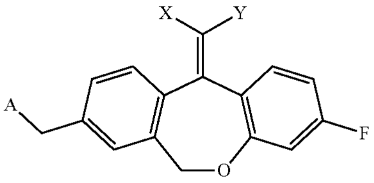
| Compound No. | A | X | Y |
|---|---|---|---|
| 4c | 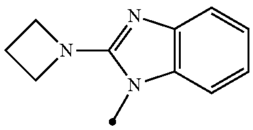 | 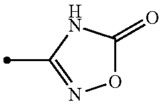 | Me |
| 4d | 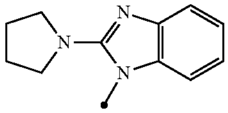 | 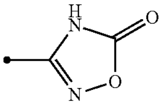 | Me |
| 4e | 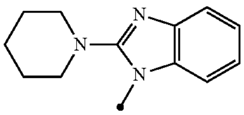 | 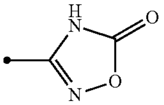 | Me |
| 4f | 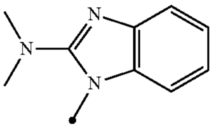 | 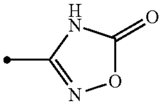 | Me |
| 4g | 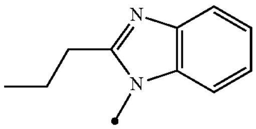 | 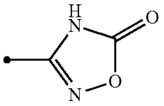 | 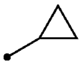 |
| 4h | 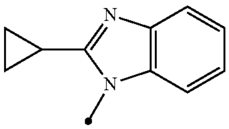 | 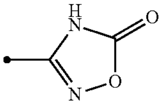 | 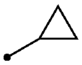 |
| 4i | 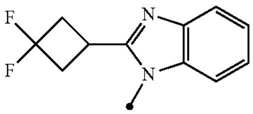 | 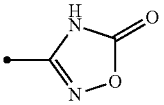 | 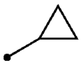 |
| 4j | 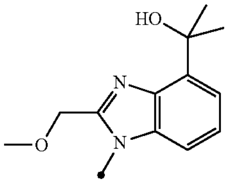 | 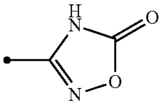 | 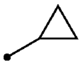 |
TABLE 4-continued
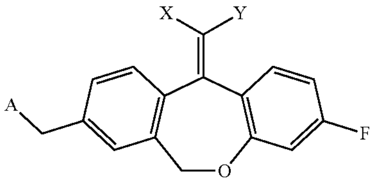
| Compound No. | A | X | Y |
|---|---|---|---|
| 4k | 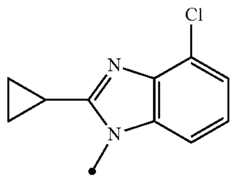 | 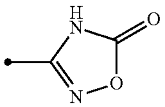 | 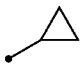 |
| 4l | 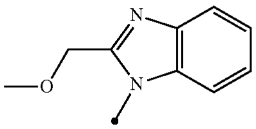 | 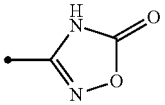 | Et |
TABLE 5
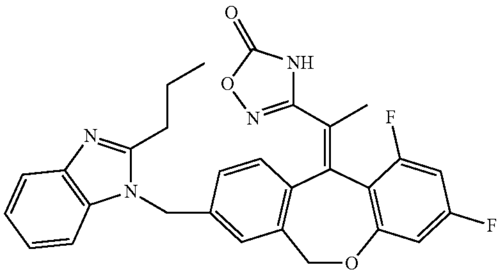 [SMILES: CCCc1nc2ccccc2n1Cc1ccc2c(c1)COc1cc(F)cc(F)c1/C2=C(\C)c1noc(=O)[nH]1]
Compound No. 5a
TABLE 6
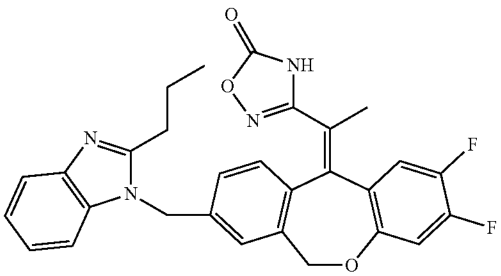 [SMILES: CCCc1nc2ccccc2n1Cc1ccc2c(c1)COc1cc(F)c(F)cc1/C2=C(\C)c1noc(=O)[nH]1]
Compound No. 6a TABLE 7
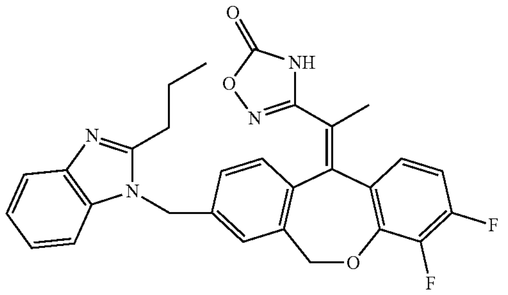 [SMILES: CCCc1nc2ccccc2n1Cc1ccc2c(c1)COc1c(ccc(F)c1F)/C2=C(\C)c1noc(=O)[nH]1]
Compound
No. 7a
TABLE 8
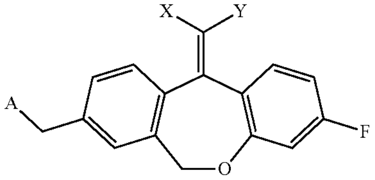
| Compound No. | A | X | Y |
|---|---|---|---|
| 8a | 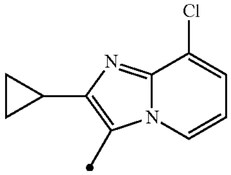 | 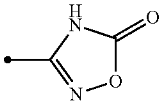 | Me |
| 8b | 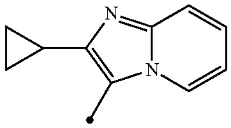 | 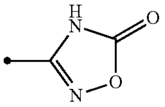 | Me |
| 8c | 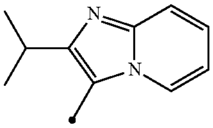 | 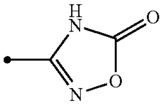 | Me |
| 8d | 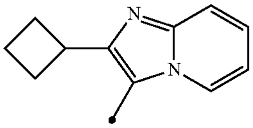 | 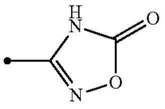 | Me |
| 8e | 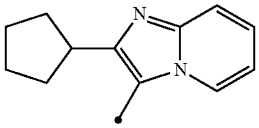 | 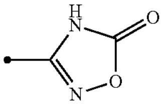 | Me |
| 8f | 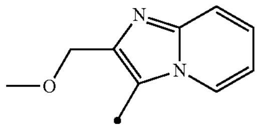 | 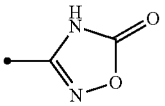 | Me |
TABLE 8-continued
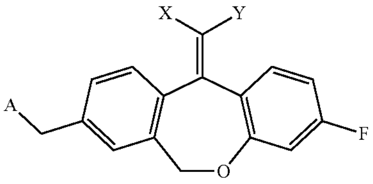
| Compound No. | A | X | Y |
|---|---|---|---|
| 8g | 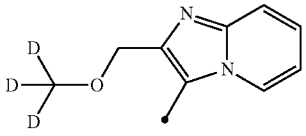 | 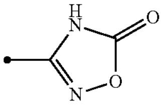 | Me |
| 8h | 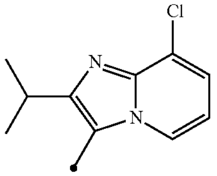 | 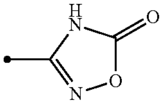 | Me |
| 8i | 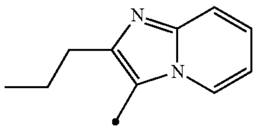 | 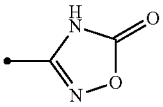 | Me |
| 8j | 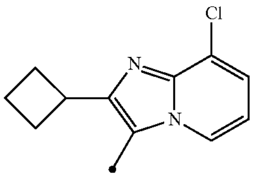 | 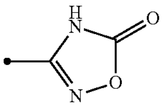 | Me |
| 8k | 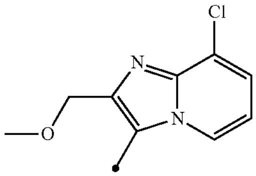 | 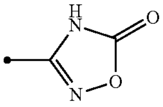 | Me |
| 8l | 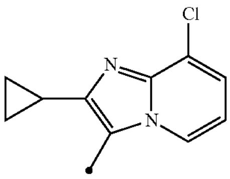 | 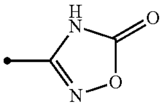 | H |
| 8m | 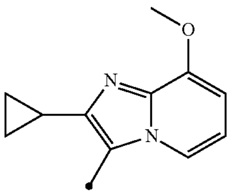 | 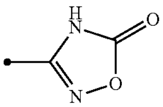 | H |

TABLE 8-continued
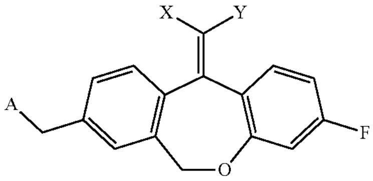
| Compound No. | A | X | Y |
|---|---|---|---|
| 8n | 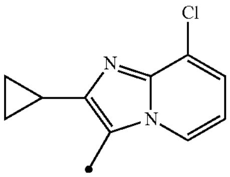 | 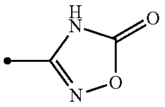 | F |
TABLE 9
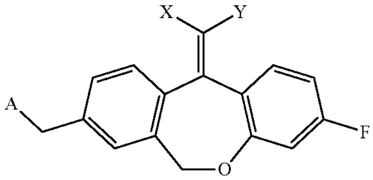
| Compound No. | A | X | Y |
|---|---|---|---|
| 9a | 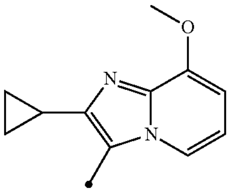 | 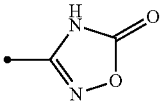 | Me |
| 9b | 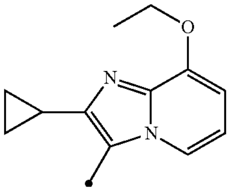 | 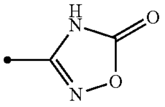 | Me |
| 9c | 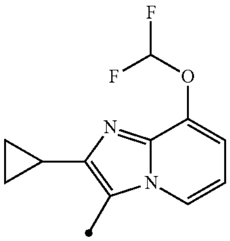 | 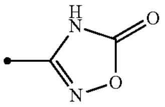 | Me |
TABLE 9-continued
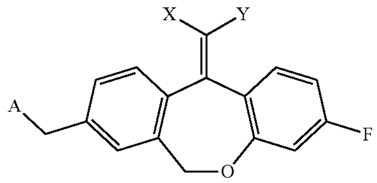
| Compound No. | A | X | Y |
|---|---|---|---|
| 9d | 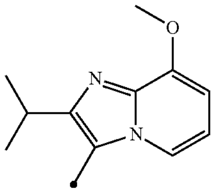 | 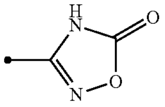 | Me |
| 9e | 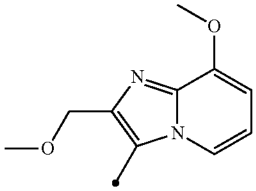 | 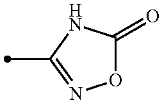 | Me |
| 9f | 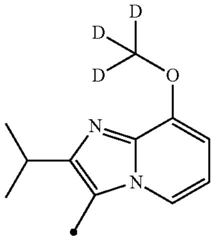 | 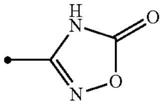 | Me |
| 9g | 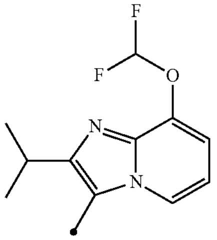 | 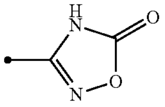 | Me |
| 9h | 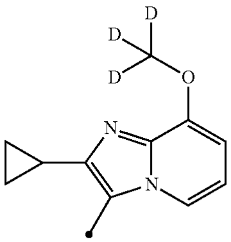 | 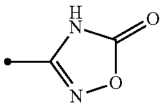 | Me |
| 9i | 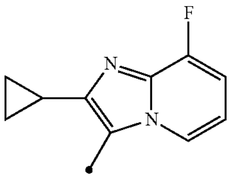 | 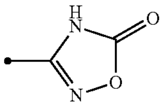 | Me |

TABLE 9-continued
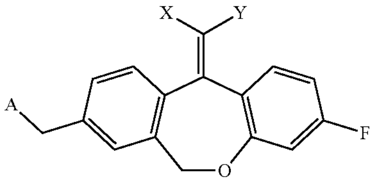
| Compound No. | A | X | Y |
|---|---|---|---|
| 9j | 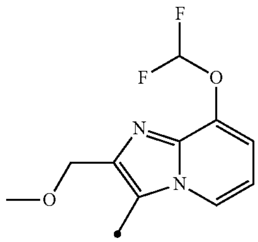 | 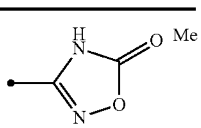 | Me |
| 9k | 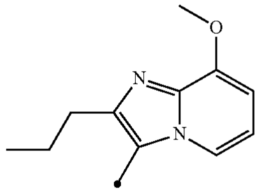 | 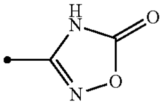 | Me |
| 9l | 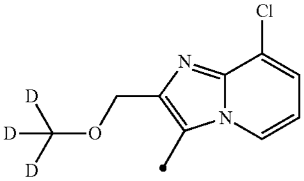 | 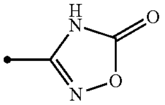 | Me |
TABLE 10
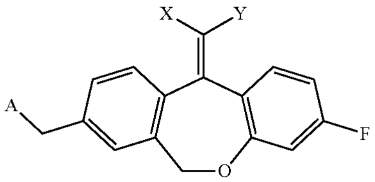
| Compound No. | A | X | Y |
|---|---|---|---|
| 10a | 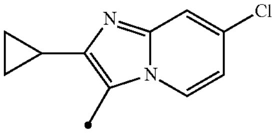 | 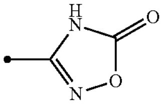 | Me |
| 10b | 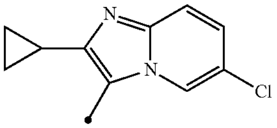 | 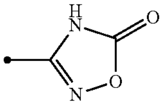 | Me |
TABLE 10-continued
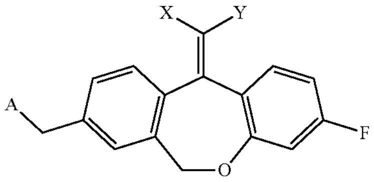
| Compound No. | A | X | Y |
|---|---|---|---|
| 10c | 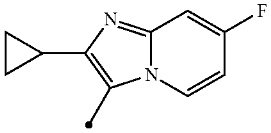 | 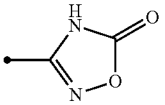 | Me |
| 10d | 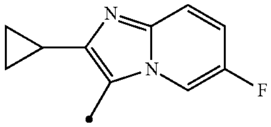 | 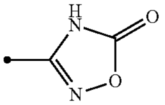 | Me |
| 10e | 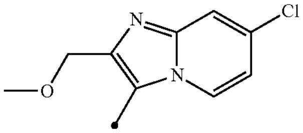 | 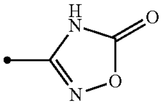 | Me |
| 10g | 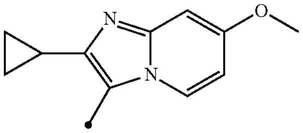 | 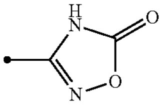 | Me |
| 10h | 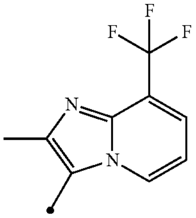 | 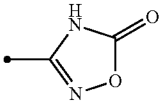 | Me |
| 10i | 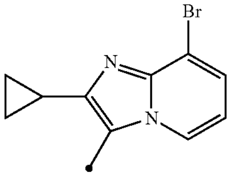 | 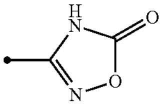 | Me |
| 10j | 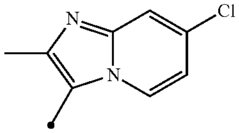 | 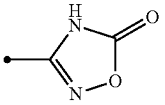 | Me |
| 10k | 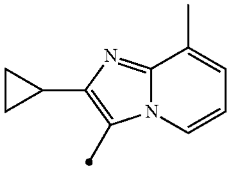 | 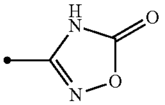 | Me |

TABLE 10-continued
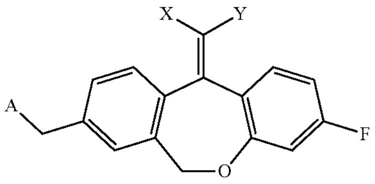
| Compound No. | A | X | Y |
|---|---|---|---|
| 10l | 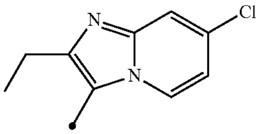 | 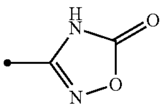 | Me |
TABLE 11
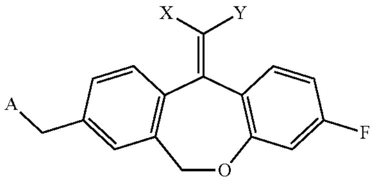
| Compound No. | A | X | Y |
|---|---|---|---|
| 11a | 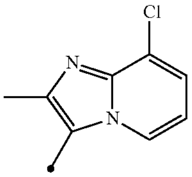 | 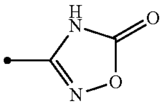 | Me |
| 11b | 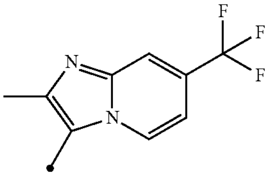 | 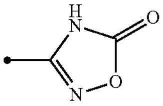 | Me |
| 11c | 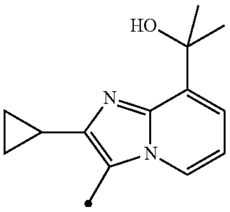 | 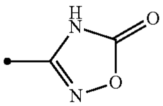 | Me |
TABLE 11-continued
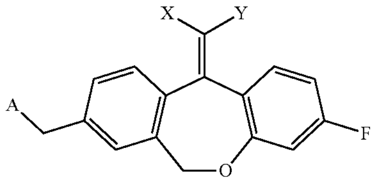
| Compound No. | A | X | Y |
|---|---|---|---|
| 11d | 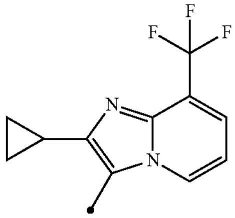 | 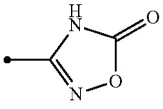 | Me |
| 11e | 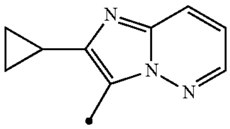 | 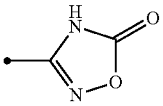 | Me |
| 11f | 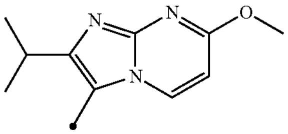 | 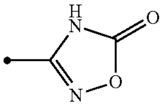 | Me |
| 11g | 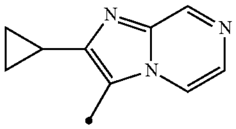 | 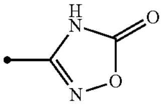 | Me |
| 11h | 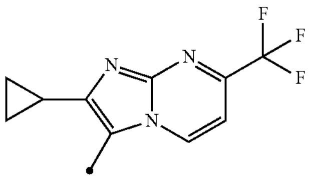 | 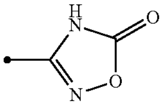 | Me |
| 11i | 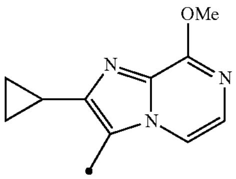 | 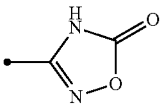 | Me |
| 11j | 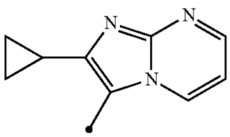 | 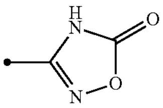 | Me |

TABLE 12
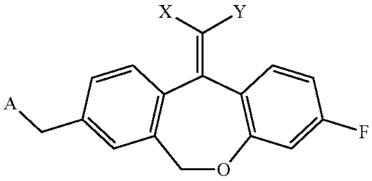
| Compound No. | A | X | Y |
| --- | --- | --- | --- |
| 12a | 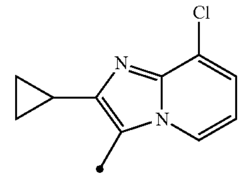 | 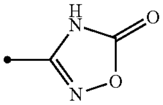 | 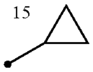 |
| 12b | 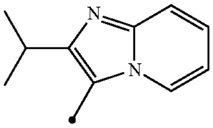 | 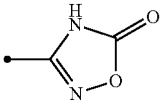 | 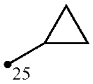 |
| 12c | 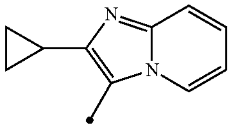 | 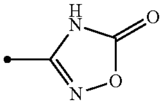 | 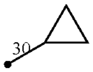 |
| 12d | 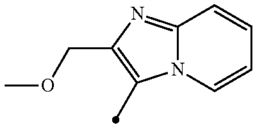 | 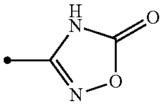 | 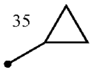 |
| 12e | 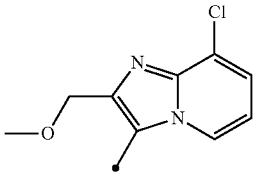 | 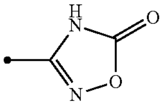 | 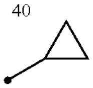 |
| 12f | 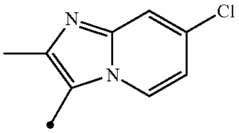 | 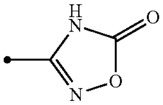 | 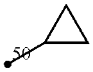 |
| 12g | 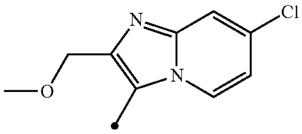 | 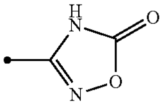 | 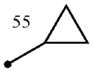 |
| 12h | 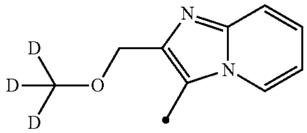 | 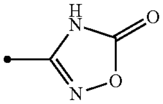 | 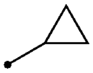 |

TABLE 13
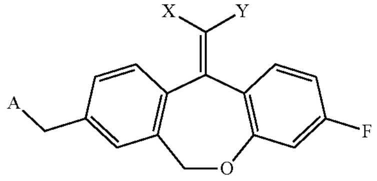
| Compound No. | A | X | Y |
|---|---|---|---|
| 13a | 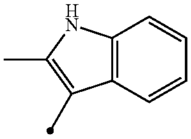 | 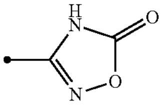 | Me |
| 13b | 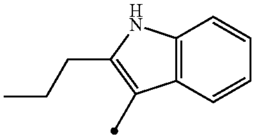 | 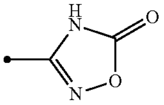 | Me |
| 13c | 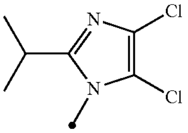 | 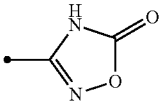 | Me |
| 13d | 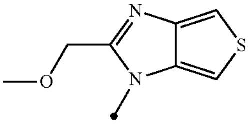 | 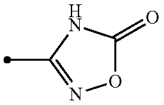 | Me |
| 13e | 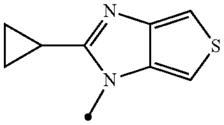 | 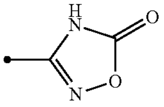 | Me |
| 13f | 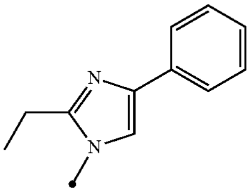 | 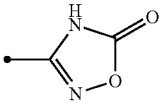 | Me |
| 13g | 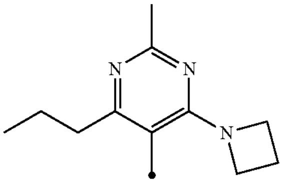 | 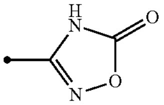 | Me |
| 13h | 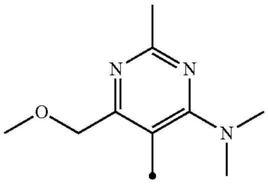 | 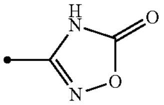 | Me |
TABLE 14
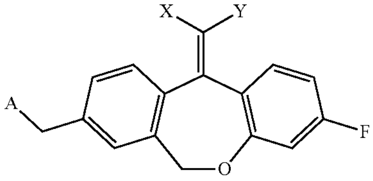
| Compound No. | A | X | Y |
|---|---|---|---|
| 14a | 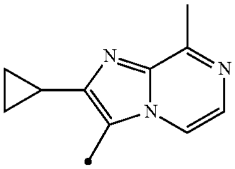 | 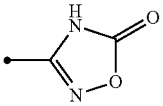 | Me |
| 14b | 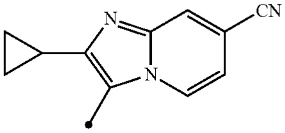 | 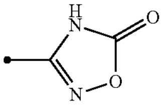 | Me |
| 14c | 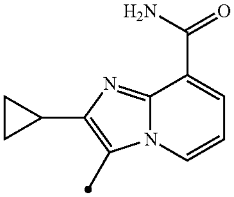 | 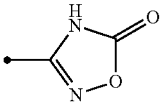 | Me |
| 14d | 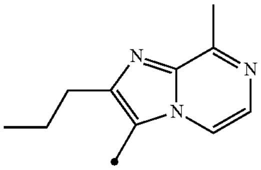 | 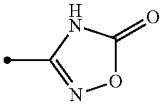 | Me |
| 14e | 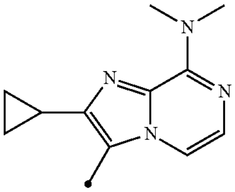 | 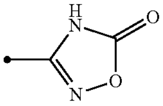 | Me |
| 14f | 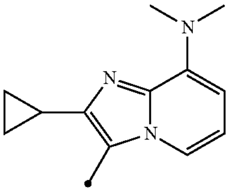 | 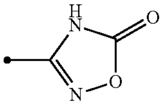 | Me |
| 14g | 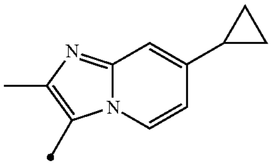 | 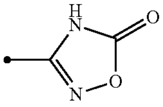 | Me |

TABLE 14-continued

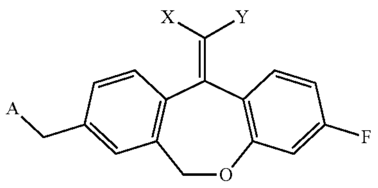

| Compound No. | A | X | Y |
|---|---|---|---|
| 14h | 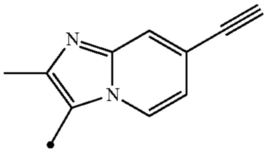 | 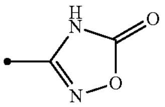 | Me |
| 14i | 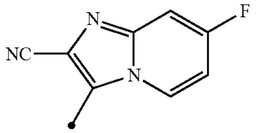 | 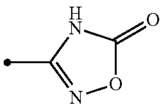 | Me |
| 14j | 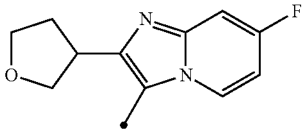 | 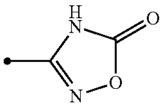 | Me |
| 14k | 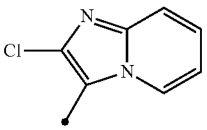 | 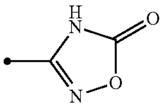 | Me |
| 14l | 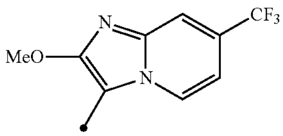 | 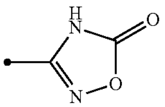 | Me |

Next, the pharmacological action of the representative compound (I) is specifically explained by Test Examples.

Test Example 1

PPAR γ Activation Action Based on Transactivation Assay of PPAR γ by Transient Gene Transfer The agonist activity of the test compound to PPAR γ was determined by a transactivation assay method using a chimeric nuclear receptor of a DNA binding region of a yeast transcription factor GAL4 and a PPAR γ ligand binding region. Specifically, the PPAR γ agonist activity of the test compound was evaluated by the following method based on the method of Lehmann et al. (J Biol. Chem., 1995, vol. 270, page 12953).

HEK293EBNA cells cultured in Dulbecco's Modified Eagle medium (Invitrogen) containing 10 v/v % fetal bovine serum (Invitrogen) were used. 30 mL of the above-mentioned cells (density: $1\times10^5$ cells/mL) were inoculated in a 10 $cm^2$ culture dish (Iwaki Glass), and cultured overnight. Using SuperFect Transfection Reagent (QIAGEN), a plasmid expressing a GAL4-PPAR γ chimeric nuclear receptor fusing 174-475 amino acids, which are human PPAR γ ligand binding domain, and 1-147 amino acids, which are GAL4 DNA binding domain, and a reporter plasmid expressing a GAL4 responsive luciferase were transiently introduced into the cells at a proportion of 4:1. After 5 hr from transfection, the cells were detached from the culture dish, and the detached cells (density: $2\times10^4$ cells/mL) were inoculated by 100 μL in each well of a 96 well white plate (SUMITOMO BAKELITE), and cultured overnight. The medium was removed, the test compound diluted in various concentrations with serum-free Dulbecco's Modified Eagle medium was added by 100 μL, and the mixture was reacted under a 5% carbon dioxide gas stream (5% $CO_2$) at 37° C. for 24 hr. On the other hand, as a positive control, 10 μmol/L of pioglitazone (100 μL) was added, and the mixture was reacted under a 5% carbon dioxide gas stream (5% $CO_2$) at 37° C. for 24 hr. As a substrate of luciferase, 100 μL of Steady-Glo (Promega) was added to each well and the mixture was thoroughly stirred. Immediately thereafter, the chemical luminescence due to luciferase was measured using TopCount NTX (Packard).

The agonist activity (activity rate (%)) of the test compound to PPAR γ was calculated according to the following formula, as a relative activity when the agonist activity on addition of pioglitazone (10 mol/L) was 100%.

$$\text{activity rate (\%)} = \frac{\begin{pmatrix}\text{luminescence intensity}\\\text{with addition of}\\\text{test compound}\end{pmatrix} - \begin{pmatrix}\text{luminescence intensity}\\\text{without addition of}\\\text{test compound}\end{pmatrix}}{\begin{pmatrix}\text{luminescence intensity}\\\text{with addition of}\\\text{pioglitazone 10 }\mu\text{mol/L}\end{pmatrix} - \begin{pmatrix}\text{luminescence intensity}\\\text{without addition of}\\\text{test compound}\end{pmatrix}} \times 100$$

The activity rate at which the test compound shows the maximum activity is referred as efficacy and the concentration showing 50% activity rate of the efficacy was calculated as $EC_{50}$ value. The results are shown in Table 15.

TABLE 15

| compound No. | $EC_{50}$ value (nmol/L) | compound No. | $EC_{50}$ value (nmol/L) |
|---|---|---|---|
| 1a | 7.4 | 8c | 33.3 |
| 1b | 11.7 | 8f | 31.7 |
| 1d | 9.0 | 8n | 54.5 |
| 1j | 7.2 | 9h | 11.9 |
| 2a | 45.6 | 9i | 13.9 |
| 2b | 59.5 | 10a | 6.4 |
| 3b | 22.8 | 10c | 12.7 |
| 3i | 8.5 | 10e | 5.3 |
| 4a | 33.5 | 11b | 13.9 |
| 4g | 54.9 | 11h | 19.0 |
| 4l | 38.0 | 12a | 18.8 |
| 6a | 11.5 | 12c | 78.2 |
| 7a | 27.7 | 13c | 39.9 |
| 8a | 4.2 | 13d | 36.7 |
| 8b | 27.7 | 13g | 209 |
| 14a | 15.9 | 14d | 7.4 |
| 14g | 130 | 14h | 304 |
| 14i | 239 | 14j | 83 |

From the above-mentioned results, compound (I) or a pharmaceutically acceptable salt thereof provided in the present invention are shown to be useful as agents for treating and/or preventing diseases related to PPAR γ, such as type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), inflammatory neuropsychiatric diseases (e.g., multiple sclerosis etc.), neurodegenerative neuropsychiatric diseases (e.g., Alzheimer's disease, Parkinson's disease etc.), cardiovascular diseases such as arteriosclerosis, cardiac disease, cerebral apoplexy, renal diseases, or the like.

Experimental Example 2

Metabolic Stability Evaluation in Human Liver Microsome

Human liver microsome (pool of 50 donors) was purchased from XenoTech. A reaction mixture containing phosphate buffer (100 mmol/L, pH 7.4), ethylenediamine tetraacetic acid (0.1 mmol/L), magnesium chloride (6 mmol/L), human liver microsome (0.2 mg/mL protein) and test compound (1 μmol/L) was prepared. The reaction mixture was preincubated at 37° C. for 5 min, β-NADPH (1 mmol/L) was added and the mixture was incubated at 37° C. for 30 min. The protein was removed with acetonitrile from the sample after the reaction and the sample was measured by LC-MS/MS. The ratio of the organic solvent in the reaction mixture was set to about 0.5%, and the reaction was performed in 2 samples.

The elimination rate constant ($k_e$) was calculated from the linear regression of the logarithm plot of the residual ratio of the test compound and at 30 min after the reaction, and the liver inherent clearance ($C_{int}$) was calculated by the following formula.

$$hCL_{int}(\text{L/h/kg}) = \frac{k_e}{a} \times b \times c \times \frac{1}{1000}$$

$k_e$: elimination rate constant (1/h)
a: concentration (mg/mL) of liver microsome in the reaction mixture
b: liver microsome amount per liver unit weight (32.3 mg/g liver)
c: liver weight per unit body weight (25.7 g liver/kg body weight)
Each test compound was tested in two samples, and the average thereof was calculated. The results are shown in Table 16.

TABLE 16

| compound No. | hCLint (L/h/kg) | compound No. | hCLint (L/h/kg) |
|---|---|---|---|
| 1a | 3.2 | 8c | 3.0 |
| 1b | 1.9 | 8f | 1.0 |
| 1d | 1.4 | 8n | 1.1 |
| 1j | 1.7 | 9h | 1.5 |
| 2a | 0.44 | 9i | 4.3 |
| 2b | 1.6 | 10a | 6.1 |
| 3b | 0.57 | 10c | 3.9 |
| 3i | 1.3 | 10e | 2.4 |
| 4a | 1.9 | 11b | 2.1 |
| 4g | 4.7 | 11h | 5.4 |
| 4l | 2.2 | 12a | 4.7 |
| 6a | 2.0 | 12c | 3.9 |
| 7a | 2.9 | 13c | 5.3 |
| 8a | 2.2 | 13d | 1.6 |
| 8b | 2.4 | 13g | 3.9 |
| 14a | 1.8 | 14d | 3.7 |
| 14g | 1.7 | 14h | 2.2 |
| 14i | 7.6 | 14j | 0.68 |

From the above-mentioned results, it was revealed that compound (I) and a pharmaceutically acceptable salt thereof provided in the present invention have high metabolic stability in human. That is, it was revealed that compound (I) or a pharmaceutically acceptable salt thereof have preferable properties as a pharmaceutical product to be used for the treatment and/or prophylaxis of diseases related to PPAR γ, such as type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), inflammatory neuropsychiatric diseases (e.g., multiple sclerosis etc.), neurodegenerative neuropsychiatric diseases (e.g., Alzheimer's disease, Parkinson's disease etc.), cardiovascular diseases such as arteriosclerosis, cardiac disease, cerebral apoplexy, renal diseases, or the like.

While compound (I) or pharmaceutically acceptable salts thereof can be administered alone as they are, generally, they are desirably provided as various pharmaceutical preparations. In addition, such pharmaceutical preparations are used for animals and humans.

The pharmaceutical preparation relating to the present invention can contain, as an active ingredient, compound (I) or a pharmaceutically acceptable salt thereof alone or as a mixture with an active ingredient for any other treatment. Moreover, the pharmaceutical preparation can be produced by mixing the active ingredient with one or more kinds of pharmaceutically acceptable carriers (e.g., diluent, solvent, excipient and the like) according to any method well known in the technical field of pharmaceutics.

As the administration route, a route most effective for the treatment is desirably employed, which may be an oral or parenteral route such as intravenous route and the like.

The dosage form may be, for example, tablet, injection and the like.

A form suitable for oral administration, such as tablet and the like, can be produced by using an excipient such as lactose and the like, a disintegrant such as starch and the like, a lubricant such as magnesium stearate and the like, a binder such as hydroxypropylcellulose and the like.

A form suitable for parenteral administration, such as injection and the like, can be produced by using a diluent such as a salt solution, a glucose solution, a mixture of salt solution and a glucose solution, or the like, or a solvent, or the like.

While the dose and administration frequency of compound (I) or a pharmaceutically acceptable salt thereof varies depending on the mode of administration, age and body weight of patients, nature and severity of the symptom to be treated or the like, it is generally within the range of 0.01 to 1000 mg, preferably 0.05 to 100 mg, for oral administration to an adult, which is administered at once or in several portions a day. In the case of parenteral administration such as intravenous administration or the like, 0.001 to 1000 mg, preferably 0.01 to 100 mg, is administered to an adult at once or in several portions a day. However, these doses and administration frequencies vary depending on the aforementioned various conditions.

The present invention is explained in more detail in the following by Examples and Reference Examples, which are not to be construed as limitative.

The proton nuclear magnetic resonance spectrum ($^1$H NMR) used in the Examples and Reference Examples were measured at 270 MHz, 300 MHz or 400 MHz, and exchanging protons may not be clearly observed depending on the compound and measurement conditions. The indication of the multiplicity of the signals is conventional, where br means an apparently broad signal.

Example 1

(E)-3-(1-{3-fluoro-8-[(2-propyl-1H-benzo[d]imidazol-1-yl)methyl]dibenzo[b,e]oxepin-11(6H)-ylidene}ethyl)-1,2,4-oxadiazol-5(4H)-one (Compound 1a)

(E)-2-{3-fluoro-8-[(2-propyl-1H-benzo[d]imidazol-1-yl)methyl]dibenzo[b,e]oxepin-11(6H)-ylidene}propanenitrile (640 mg, 1.47 mmol) obtained in Reference Example 1A was dissolved in ethanol (7 mL), hydroxylamine (50% aqueous solution, 4.83 mL, 73.3 mmol) was added, and the mixture was heated under reflux for 16 hr. Water was added to the mixture, and the mixture was extracted 3 times with chloroform. The combined organic layers were dried over anhydrous magnesium sulfate, and concentrated under reduced pressure. The obtained residue was dissolved in dichloromethane (7 mL), triethylamine (0.41 mL, 2.93 mmol) and ethyl chlorocarbonate (0.28 mL, 2.93 mmol) were added at 0° C., and the mixture was stirred at room temperature for 1 hr. Saturated aqueous sodium hydrogen carbonate solution was added to the mixture, and the mixture was extracted 3 times with chloroform. The combined organic layers were dried over anhydrous magnesium sulfate, and concentrated under reduced pressure. The obtained residue was dissolved in toluene (3 mL)-THF (3 mL) mixed solvent, potassium tert-butoxide (328 mg, 2.93 mmol) was added, and the mixture was stirred at room temperature for 20 min. To the mixture was added 5% aqueous citric acid solution, and the mixture was extracted 3 times with chloroform. The combined organic layers were dried over anhydrous magnesium sulfate, and concentrated under reduced pressure. The residue was purified by silica gel column chromatography (chloroform/methanol=95/5 v/v) to give the title compound (compound 1a) (700 mg, 95%).

ESIMS m/z: 497 $(M+H)^+$; $^1H$ NMR (270 MHz, $CDCl_3$, δ): 0.98 (t, J=7.4 Hz, 3H), 1.74-1.94 (m, 2H), 2.28 (s, 3H), 2.79 (t, J=7.4 Hz, 2H), 4.65 (d, J=12.0 Hz, 1H), 5.34 (s, 2H), 5.45 (d, J=12.0 Hz, 1H), 6.48-6.56 (m, 1H), 6.60-6.70 (m, 1H), 6.95-7.30 (m, 7H), 7.67-7.74 (m, 1H).

Example 2

(E)-3-[1-(3-fluoro-8-{[2-(methoxymethyl)-1H-benzo[d]imidazol-1-yl]methyl}dibenzo[b,e]oxepin-11(6H)-ylidene)ethyl]-1,2,4-oxadiazol-5(4H)-one (Compound 1b)

Using (E)-2-(3-fluoro-8-{[2-(methoxymethyl)-1H-benzo[d]imidazol-1-yl]methyl}dibenzo[b,e]oxepin-11(6H)-ylidene)propanenitrile (540 mg, 1.23 mmol) obtained in Reference Example 1B, and in the same manner as in Example 1, the title compound (compound 1b) (267 mg, 44%) was obtained.

ESIMS m/z: 499 $(M+H)^+$; $^1H$ NMR (300 MHz, $CDCl_3$, δ): 2.28 (s, 3H), 3.35 (s, 3H), 4.70 (s, 2H), 4.74 (d, J=12.5 Hz, 1H), 5.45-5.59 (m, 3H), 6.53 (dd, J=10.3, 2.6 Hz, 1H), 6.61-6.72 (m, 1H), 7.07 (dd, J=8.8, 6.6 Hz, 1H), 7.13-7.20 (m, 3H), 7.20-7.34 (m, 3H), 7.77-7.83 (m, 1H).

Example 3

(E)-3-(1-{3-fluoro-8-[(2-isopropyl-1H-benzo[d]imidazol-1-yl)methyl]dibenzo[b,e]oxepin-11(6H)-ylidene}ethyl)-1,2,4-oxadiazol-5(4H)-one (Compound 1c)

Using (E)-2-{3-fluoro-8-[(2-isopropyl-1H-benzo[d]imidazol-1-yl)methyl]dibenzo[b,e]oxepin-11(6H)-ylidene}propanenitrile (240 mg, 0.55 mmol) obtained in Reference Example 1C, and in the same manner as in Example 1, the title compound (compound 1c) (156 mg, 57%) was obtained.

ESIMS m/z: 497 $(M+H)^+$; $^1H$ NMR (300 MHz, $CDCl_3$, δ): 1.34-1.46 (m, 6H), 2.28 (s, 3H), 3.05-3.19 (m, 1H), 4.75 (d, J=12.9 Hz, 1H), 5.36-5.45 (m, 2H), 5.51 (d, J=12.9 Hz, 1H), 6.54 (dd, J=10.2, 2.6 Hz, 1H), 6.61-6.71 (m, 1H), 7.02-7.30 (m, 7H), 7.77-7.83 (m, 1H).

Example 4

(E)-3-(1-{8-[(2-cyclopropyl-1H-benzo[d]imidazol-1-yl)methyl]-3-fluorodibenzo[b,e]oxepin-11(6H)-ylidene}ethyl)-1,2,4-oxadiazol-5(4H)-one (Compound 1d)

Using (E)-2-{8-[(2-cyclopropyl-1H-benzo[d]imidazol-1-yl)methyl]-3-fluorodibenzo[b,e]oxepin-11(6H)-ylidene}propanenitrile (180 mg, 0.413 mmol) obtained in Reference Example 1D, and in the same manner as in Example 1, the title compound (compound 1d) (114 mg, 56%) was obtained.

ESIMS m/z: 495 $(M+H)^+$; $^1H$ NMR (270 MHz, $CDCl_3$, δ): 1.00-1.12 (m, 2H), 1.17-1.35 (m, 2H), 1.78-1.93 (m, 1H), 2.29 (s, 3H), 4.73 (d, J=12.8 Hz, 1H), 5.40-5.60 (m, 3H), 6.46-6.59 (m, 1H), 6.59-6.75 (m, 1H), 6.99-7.34 (m, 7H), 7.57-7.78 (m, 1H).

Example 5

(E)-3-(1-{8-[(2-cyclobutyl-1H-benzo[d]imidazol-1-yl)methyl]-3-fluorodibenzo[b,e]oxepin-11(6H)-ylidene}ethyl)-1,2,4-oxadiazol-5(4H)-one (Compound 1e)

Using (E)-2-{8-[(2-cyclobutyl-1H-benzo[d]imidazol-1-yl)methyl]-3-fluorodibenzo[b,e]oxepin-11(6H)-ylidene}propanenitrile (170 mg, 0.379 mmol) obtained in Reference Example 1E, and in the same manner as in Example 1, the title compound (compound 1e) (108 mg, 56%) was obtained.

ESIMS m/z: 509 $(M+H)^+$; $^1H$ NMR (270 MHz, $CDCl_3$, δ): 1.92-2.17 (m, 2H), 2.23-2.41 (m, 5H), 2.46-2.66 (m, 2H), 3.55-3.73 (m, 1H), 4.69 (d, J=12.8 Hz, 1H), 5.28 (s, 2H), 5.48 (d, J=12.8 Hz, 1H), 6.48-6.59 (m, 1H), 6.59-6.74 (m, 1H), 6.93-7.32 (m, 7H), 7.72-7.83 (m, 1H).

Example 6

(E)-3-(1-{8-[(2-cyclopentyl-1H-benzo[d]imidazol-1-yl)methyl]-3-fluorodibenzo[b,e]oxepin-11(6H)-ylidene}ethyl)-1,2,4-oxadiazol-5(4H)-one (Compound 1f)

Using (E)-2-{8-[(2-cyclopentyl-1H-benzo[d]imidazol-1-yl)methyl]-3-fluorodibenzo[b,e]oxepin-11(6H)- ylidene}propanenitrile (148 mg, 0.32 mmol) obtained in Reference Example 1F, and in the same manner as in Example 1, the title compound (compound 1f) (53 mg, 32%) was obtained.

ESIMS m/z: 523 $(M+H)^+$; $^1H$ NMR (270 MHz, $CDCl_3$, δ): 1.58-1.78 (m, 2H), 1.78-2.14 (m, 6H), 2.27 (s, 3H), 3.09-3.27 (m, 1H), 4.74 (d, J=12.8 Hz, 1H), 5.36-5.46 (m, 2H), 5.51 (d, J=12.8 Hz, 1H), 6.48-6.59 (m, 1H), 6.59-6.74 (m, 1H), 6.95-7.32 (m, 7H), 7.68-7.85 (m, 1H).

Example 7

(E)-3-[1-(8-{[2-(cyclopropylmethyl)-1H-benzo[d]imidazol-1-yl]methyl}-3-fluorodibenzo[b,e]oxepin-11(6H)-ylidene)ethyl]-1,2,4-oxadiazol-5(4H)-one (Compound 1g)

Using (E)-2-(8-{[2-(cyclopropylmethyl)-1H-benzo[d]imidazol-1-yl]methyl}-3-fluorodibenzo[b,e]oxepin-11(6H)-ylidene)propanenitrile (172 mg, 0.383 mmol) obtained in Reference Example 1G, and in the same manner as in Example 1, the title compound (compound 1g) (99 mg, 49%) was obtained.

ESIMS m/z: 509 $(M+H)^+$; $^1H$ NMR (270 MHz, $CDCl_3$, δ): 0.20-0.30 (m, 2H), 0.49-0.50 (m, 2H), 1.11-1.21 (m, 1H), 2.28 (s, 3H), 2.78 (d, J=6.8 Hz, 2H), 4.68 (d, J=12.7 Hz, 1H), 5.39 (s, 2H), 5.47 (d, J=12.7 Hz, 1H), 6.52 (dd, J=2.4, 10.2 Hz, 1H), 6.60-6.70 (m, 1H), 7.00 (s, 1H), 7.02-7.30 (m, 6H), 7.75 (d, J=7.8 Hz, 1H).

Example 8

(E)-3-(1-{8-[(2-ethyl-1H-benzo[d]imidazol-1-yl)methyl]-3-fluorodibenzo[b,e]oxepin-11(6H)-ylidene}ethyl)-1,2,4-oxadiazol-5(4H)-one (Compound 1h)

Using (E)-2-{8-[(2-ethyl-1H-benzo[d]imidazol-1-yl)methyl]-3-fluorodibenzo[b,e]oxepin-11(6H)-ylidene}propanenitrile (168 mg, 0.397 mmol) obtained in Reference Example 1H, and in the same manner as in Example 1, the title compound (compound 1h) (85 mg, 42%) was obtained.

ESIMS m/z: 483 $(M+H)^+$; $^1H$ NMR (270 MHz, $CDCl_3$, δ): 1.25 (t, J=7.4 Hz, 3H), 2.15 (s, 3H), 2.81 (q, J=7.4 Hz, 2H), 4.93 (d, J=12.7 Hz, 1H), 5.47 (s, 2H), 5.48 (d, J=12.7 Hz, 1H), 6.65 (dd, J=2.9, 10.7 Hz, 1H), 6.79 (dt, J=2.6, 8.5 Hz, 1H), 7.70-7.29 (m, 6H), 7.40-7.49 (m, 1H), 7.53-7.61 (m, 1H).

Example 9

(E)-3-[1-(3-fluoro-8-{[2-(trifluoromethyl)-1H-benzo[d]imidazol-1-yl]methyl}dibenzo[b,e]oxepin-11(6H)-ylidene)ethyl]-1,2,4-oxadiazol-5(4H)-one (Compound 1i)

Using (E)-2-(3-fluoro-8-{[2-(trifluoromethyl)-1H-benzo[d]imidazol-1-yl]methyl}dibenzo[b,e]oxepin-11(6H)-ylidene)propanenitrile (138 mg, 0.298 mmol) obtained in Reference Example 1I, and in the same manner as in Example 1, the title compound (compound 1I) (100 mg, 64%) was obtained.

ESIMS m/z: 523 $(M+H)^+$; $^1H$ NMR (270 MHz, DMSO-$d_6$, δ): 2.17 (s, 3H), 4.92 (d, J=12.6 Hz, 1H), 5.48 (d, J=12.6 Hz, 1H), 5.73 (s, 2H), 6.57-6.72 (m, 1H), 6.73-6.87 (m, 1H), 7.05-7.10 (m, 2H), 7.18-7.31 (m, 2H), 7.33-7.51 (m, 2H), 7.59-7.69 (m, 1H), 7.79-7.93 (m, 1H), 12.11 (br s, 1H).

Example 10

(E)-3-[1-(8-{[2-(3,3-difluorocyclobutyl)-1H-benzo[d]imidazol-1-yl]methyl}-3-fluorodibenzo[b,e]oxepin-11(6H)-ylidene)ethyl]-1,2,4-oxadiazol-5(4H)-one (Compound 1j)

Using (E)-2-(8-{[2-(3,3-difluorocyclobutyl)-1H-benzo[d]imidazol-1-yl]methyl}-3-fluorodibenzo[b,e]oxepin-11(6H)-ylidene)propanenitrile (125 mg, 0.26 mmol) obtained in Reference Example 1J, and in the same manner as in Example 1, the title compound (compound 1j) (70 mg, 50%) was obtained.

ESIMS m/z: 545 $(M+H)^+$; $^1H$ NMR (300 MHz, DMSO-$d_6$, δ): 2.16 (s, 3H), 2.79-3.10 (m, 4H), 3.65-3.82 (m, 1H), 4.93 (d, J=12.5 Hz, 1H), 5.44-5.54 (m, 3H), 6.65 (dd, J=10.6, 2.6 Hz, 1H), 6.75-6.84 (m, 1H), 7.03-7.12 (m, 2H), 7.17-7.28 (m, 4H), 7.44-7.52 (m, 1H), 7.64-7.70 (m, 1H), 12.15 (br s, 1H).

Example 11

(E)-3-[1-(3-fluoro-8-{[2-(1-methylcyclopropyl)-1H-benzo[d]imidazol-1-yl]methyl}dibenzo[b,e]oxepin-11(6H)-ylidene)ethyl]-1,2,4-oxadiazol-5(4H)-one (Compound 1l)

Using (E)-2-(3-fluoro-8-{[2-(1-methylcyclopropyl)-1H-benzo[d]imidazol-1-yl]methyl}dibenzo[b,e]oxepin-11(6H)-ylidene)propanenitrile (58 mg, 0.129 mmol) obtained in Reference Example 1L, and in the same manner as in Example 1, the title compound (compound 1l) (37 mg, 56%) was obtained.

ESIMS m/z: 509 $(M+H)^+$; $^1H$ NMR (270 MHz, $CDCl_3$, δ): 0.74-0.92 (m, 2H), 1.01-1.16 (m, 2H), 1.37 (s, 3H), 2.28 (s, 3H), 4.66 (d, J=12.8 Hz, 1H), 5.36-5.64 (m, 3H), 6.47-6.58 (m, 1H), 6.58-6.69 (m, 1H), 6.94-7.23 (m, 7H), 7.55-7.68 (m, 1H).

Example 12

(E)-3-[1-(3-fluoro-8-{[2-(furan-2-yl)-1H-benzo[d]imidazol-1-yl]methyl}dibenzo[b,e]oxepin-11(6H)-ylidene)ethyl]-1,2,4-oxadiazol-5(4H)-one (Compound 1m)

Using (E)-2-(3-fluoro-8-{[2-(furan-2-yl)-1H-benzo[d]imidazol-1-yl]methyl}dibenzo[b,e]oxepin-11(6H)-ylidene)propanenitrile (145 mg, 0.31 mmol) obtained in Reference Example 1M, and in the same manner as in Example 1, the title compound (compound 1m) (59 mg, 36%) was obtained.

ESIMS m/z: 521 $(M+H)^+$; $^1H$ NMR (270 MHz, DMSO-$d_6$, δ): 2.14 (s, 3H), 4.88 (d, J=12.8 Hz, 1H), 5.46 (d, J=12.8 Hz, 1H), 5.78 (s, 2H), 6.69-6.70 (m, 1H), 6.75-6.81 (m, 1H), 7.03-7.11 (m, 3H), 7.20-7.28 (m, 5H), 7.51-7.54 (m, 1H), 7.67-7.70 (m, 1H), 7.90-7.91 (m, 1H).

Example 13

(E)-3-[1-(3-fluoro-8-{[2-(pyridin-2yl)-1H-benzo[d]imidazol-1-yl]methyl}dibenzo[b,e]oxepin-11(6H)-ylidene)ethyl]-1,2,4-oxadiazol-5(4H)-one (Compound 1n)

Using (E)-2-(3-fluoro-8-{[2-(pyridin-2-yl)-1H-benzo[d]imidazol-1-yl]methyl}dibenzo[b,e]oxepin-11(6H)-ylidene)

propanenitrile (120 mg, 0.28 mmol) obtained in Reference Example 1N, and in the same manner as in Example 1, the title compound (compound 1n) (26 mg, 19%) was obtained.

ESIMS m/z: 532 $(M+H)^+$; $^1$H NMR (270 MHz, $CDCl_3$, δ): 2.26 (s, 3H), 4.71 (d, J=12.8 Hz, 1H), 5.48 (d, J=12.8 Hz, 1H), 6.11-6.25 (m, 2H), 6.48-6.67 (m, 2H), 7.02-7.36 (m, 8H), 7.82-7.90 (m, 2H), 8.45-8.48 (m, 1H), 8.60-8.62 (m, 1H).

Example 14

(E)-3-[1-(3-fluoro-8-{[4-(methoxy-$d_3$)-2-(methoxymethyl)-1H-benzo[d]imidazol-1-yl]methyl}dibenzo[b,e]oxepin-11(6H)-ylidene)ethyl]-1,2,4-oxadiazol-5(4H)-one (Compound 2a)

(E)-2-(3-fluoro-8-{[4-(methoxy-$d_3$)-2-(methoxymethyl)-1H-benzo[d]imidazol-1-yl]methyl}dibenzo[b,e]oxepin-11(6H)-ylidene)propanenitrile (25 mg, 0.053 mmol) obtained in Reference Example 2A was dissolved in ethanol (1 mL), hydroxylamine (50% aqueous solution, 0.16 mL, 2.65 mmol) was added, and the mixture was stirred with heating under reflux for 16 hr. Water was added to the mixture, and the mixture was extracted 3 times with chloroform. The combined organic layers were dried over anhydrous magnesium sulfate, and concentrated under reduced pressure. The obtained residue (24 mg) was dissolved in 1,4-dioxane (1 mL), 1,8-diazabicyclo[5,4,0]undec-7-ene (11 μL, 0.071 mmol) and 1,1'-carbonyldiimidazole (15 mg, 0.095 mmol) were added, and the mixture was stirred with heating under reflux for 2 hr. To the mixture was added 1 mol/L hydrochloric acid, and the mixture was extracted 3 times with chloroform-methanol (10/1) mixed solvent. The combined organic layers were dried over anhydrous magnesium sulfate, and concentrated under reduced pressure. The residue was purified by reversed-phase liquid chromatography (water/acetonitrile=70/30-10/90) to give the title compound (compound 2a) (14 mg, 50%).

ESIMS m/z: 532 $(M+H)^+$; $^1$H NMR (300 MHz, $CDCl_3$, δ): 2.28 (s, 3H), 3.32 (s, 3H), 4.66-4.75 (m, 3H), 5.42-5.58 (m, 3H), 6.53 (dd, J=10.3, 2.6 Hz, 1H), 6.60-6.74 (m, 2H), 6.83 (d, J=7.7 Hz, 1H), 7.02-7.13 (m, 2H), 7.13-7.24 (m, 3H).

Example 15

(E)-1-({3-fluoro-11-[1-(5-oxo-4,5-dihydro-1,2,4-oxadiazol-3-yl)ethylidene]-6,11-dihydrodibenzo[b,e]oxepin-8-yl}methyl)-2-propyl-1H-benzo[d]imidazole-4-carboxamide (Compound 2b)

Using (E)-1-{[11-(1-cyanoethylidene)-3-fluoro-6,11-dihydrodibenzo[b,e]oxepin-8-yl]methyl}-2-propyl-1H-benzo[d]imidazole-4-carboxamide (97 mg, 0.20 mmol) obtained in Reference Example 2B, and in the same manner as in Example 1, the title compound (compound 2b) (7.8 mg, 7%) was obtained.

ESIMS m/z: 540 $(M+H)^+$; $^1$H NMR (300 MHz, DMSO-$d_6$, δ): 0.93 (t, J==7.5 Hz, 3H), 1.65-1.82 (m, 2H), 2.16 (s, 3H), 2.86 (t, J=7.5 Hz, 2H), 4.94 (d, J=12.5 Hz, 1H), 5.48 (d, J=12.5 Hz, 1H), 5.57 (s, 2H), 6.65 (dd, J=10.8, 2.7 Hz, 1H), 6.79 (td, J=8.3, 2.7 Hz, 1H), 7.04-7.13 (m, 2H), 7.20-7.32 (m, 3H), 7.68 (d, J=7.3 Hz, 1H), 7.71 (br s, 1H), 7.83 (d, J=7.3 Hz, 1H), 9.27 (br d, J=3.3 Hz, 1H).

Example 16

(E)-3-(1-{3-fluoro-8-[(4-methoxy-2-propyl-1H-benzo[d]imidazol-1-yl)methyl]dibenzo[b,e]oxepin-11(6H)-ylidene}ethyl)-1,2,4-oxadiazol-5(4H)-one (Compound 2c)

Using (E)-2-{3-fluoro-8-[(4-methoxy-2-propyl-1H-benzo[d]imidazol-1-yl)methyl]dibenzo[b,e]oxepin-11(6H)-ylidene}propanenitrile (445 mg, 0.95 mmol) obtained in Reference Example 2C, and in the same manner as in Example 1, the title compound (compound 2c) (281 mg, 56%) was obtained.

ESIMS m/z: 527 $(M+H)^+$; $^1$H NMR (300 MHz, $CDCl_3$, δ): 0.97 (t, J=7.3 Hz, 3H), 1.77-1.93 (m, 2H), 2.28 (s, 3H), 2.77 (t, J=7.3 Hz, 2H), 4.00 (s, 3H), 4.69 (d, J=12.5 Hz, 1H), 5.35 (s, 2H), 5.49 (d, J=12.5 Hz, 1H), 6.53 (dd, J=10.3, 2.6 Hz, 1H), 6.61-6.72 (m, 2H), 6.76 (d, J=8.1 Hz, 1H), 6.98 (br s, 1H), 7.03-7.20 (m, 4H).

Example 17

(E)-3-[1-(3-fluoro-8-{[4-methoxy-2-(methoxymethyl)-1H-benzo[d]imidazol-1-yl]methyl}dibenzo[b,e]oxepin-11(6H)-ylidene)ethyl]-1,2,4-oxadiazol-5(4H)-one (Compound 2d)

Using (E)-2-(3-fluoro-8-{[4-methoxy-2-(methoxymethyl)-1H-benzo[d]imidazol-1-yl]methyl}dibenzo[b,e]oxepin-11(6H)-ylidene)propanenitrile (70 mg, 0.15 mmol) obtained in Reference Example 2D, and in the same manner as in Example 1, the title compound (compound 2d) (45 mg, 55%) was obtained.

ESIMS m/z: 529 $(M+H)^+$; $^1$H NMR (270 MHz, $CDCl_3$, δ): 2.25 (s, 3H), 3.34 (s, 3H), 4.02 (s, 3H), 4.62-4.71 (m, 3H), 5.43-5.55 (m, 3H), 6.50-6.56 (m, 1H), 6.62-6.66 (m, 1H), 6.70-6.72 (m, 1H), 7.05-7.10 (m, 2H), 7.15-7.24 (m, 4H).

Example 18

(E)-3-[1-(3-fluoro-8-{[7-methoxy-2-(methoxymethyl)-1H-benzo[d]imidazol-1-yl]methyl}dibenzo[b,e]oxepin-11(6H)-ylidene)ethyl]-1,2,4-oxadiazol-5(4H)-one (Compound 2e)

Using (E)-2-(3-fluoro-8-{[7-methoxy-2-(methoxymethyl)-1H-benzo[d]imidazol-1-yl]methyl}dibenzo[b,e]oxepin-11(6H)-ylidene)propanenitrile (67 mg, 0.14 mmol) obtained in Reference Example 2E, and in the same manner as in Example 1, the title compound (compound 2e) (28 mg, 36%) was obtained.

ESIMS m/z: 529 $(M+H)^+$; $^1$H NMR (270 MHz, $CDCl_3$, δ): 2.28 (s, 3H), 3.32 (s, 3H), 3.81 (s, 3H), 4.63 (s, 2H), 4.74 (d, J=12.8 Hz, 1H), 5.51 (d, J=12.8 Hz, 1H), 5.77 (s, 2H), 6.51-6.55 (m, 1H), 6.62-6.74 (m, 2H), 7.04-7.23 (m, 5H), 7.37-7.40 (m, 1H).

Example 19

(E)-3-[1-(8-{[4-ethoxy-2-(methoxymethyl)-1H-benzo[d]imidazol-1-yl]methyl}-3-fluorodibenzo[b,e]oxepin-11(6H)-ylidene)ethyl]-1,2,4-oxadiazol-5(4H)-one (Compound 2f)

Using (E)-2-(8-{[4-ethoxy-2-(methoxymethyl)-1H-benzo[d]imidazol-1-yl]methyl}-3-fluorodibenzo[b,e]oxepin-11(6H)-ylidene)propanenitrile (81 mg, 0.17 mmol) obtained in Reference Example 2F, and in the same manner as in Example 1, the title compound (compound 2f) (39 mg, 43%) was obtained.

ESIMS m/z: 543 $(M+H)^+$; $^1$H NMR (300 MHz, $CDCl_3$, δ): 1.54 (t, J=7.0 Hz, 3H), 2.27 (s, 3H), 3.32 (s, 3H), 4.28 (q, J=7.0 Hz, 2H), 4.65-4.75 (m, 3H), 5.41-5.56 (m, 3H), 6.52 (dd, J=10.3, 2.6 Hz, 1H), 6.60-6.68 (m, 1H), 6.70 (d, J=8.1 Hz, 1H), 6.81 (d, J=8.1 Hz, 1H), 7.01-7.11 (m, 2H), 7.11-7.22 (m, 3H).

Example 20

(E)-3-[1-(8-{[4-(difluoromethoxy)-2-(methoxymethyl)-1H-benzo[d]imidazol-1-yl]methyl}-3-fluorodibenzo[b,e]oxepin-11(6H)-ylidene)ethyl]-1,2,4-oxadiazol-5(4H)-one (Compound 2g)

Using (E)-2-(8-{[4-(difluoromethoxy)-2-(methoxymethyl)-1H-benzo[d]imidazol-1-yl]methyl}-3-fluorodibenzo[b,e]oxepin-11(6H)-ylidene)propanenitrile (35 mg, 0.065 mmol) obtained in Reference Example 2G, and in the same manner as in Example 1, the title compound (compound 2g) (25 mg, 68%) was obtained.

ESIMS m/z: 565 $(M+H)^+$; $^1H$ NMR (300 MHz, $CDCl_3$, δ): 2.28 (s, 3H), 3.35 (s, 3H), 4.69 (s, 2H), 4.76 (d, J=12.5 Hz, 1H), 5.46-5.58 (m, 3H), 6.54 (dd, J=10.3, 2.6 Hz, 1H), 6.60-6.75 (m, 1H), 7.02-7.30 (m, 7H), 7.29 (t, J=76.6 Hz, 1H).

Example 21

(E)-3-[1-(3-fluoro-8-{[4-(hydroxymethyl)-2-propyl-1H-benzo[d]imidazol-1-yl]methyl}dibenzo[b,e]oxepin-11(6H)-ylidene)ethyl]-1,2,4-oxadiazol-5(4H)-one (Compound 2h)

Using (E)-2-(3-fluoro-8-{[4-(hydroxymethyl)-2-propyl-1H-benzo[d]imidazol-1-yl]methyl}dibenzo[b,e]oxepin-11(6H)-ylidene)propanenitrile (105 mg, 0.23 mmol) obtained in Reference Example 2H, and in the same manner as in Example 1, the title compound (compound 2h) (16 mg, 14%) was obtained.

ESIMS m/z: 527 $(M+H)^+$; $^1H$ NMR (300 MHz, $CDCl_3$, δ): 1.00 (t, J=7.3 Hz, 3H), 1.58-2.01 (m, 3H), 2.28 (s, 3H), 2.79 (t, J=7.3 Hz, 2H), 4.75 (d, J=12.8 Hz, 1H), 5.13 (s, 2H), 5.37 (s, 2H), 5.51 (d, J=12.8 Hz, 1H), 6.53 (dd, J=10.1, 2.4 Hz, 1H), 6.61-6.72 (m, 1H), 7.00-7.22 (m, 7H).

Example 22

(E)-3-[1-(3-fluoro-8-{[4-(hydroxymethyl)-1H-benzo[d]imidazol-1-yl]methyl}dibenzo[b,e]oxepin-11(6H)-ylidene)ethyl]-1,2,4-oxadiazol-5(4H)-one (Compound 2i)

Using (E)-2-(3-fluoro-8-{[4-(hydroxymethyl)-2-(methoxymethyl)-1H-benzo[d]imidazol-1-yl]methyl}dibenzo[b,e]oxepin-11(6H)-ylidene)propanenitrile (215 mg, 0.46 mmol) obtained in Reference Example 2I, and in the same manner as in Example 1, the title compound (compound 2i) (38 mg, 16%) was obtained.

ESIMS m/z: 529 $(M+H)^+$; $^1H$ NMR (400 MHz, $CDCl_3$, δ): 2.28 (s, 3H), 3.35 (s, 3H), 4.68 (s, 2H), 4.75 (d, J=12.7 Hz, 1H), 5.13 (s, 2H), 5.44-5.58 (m, 3H), 6.53 (dd, J=9.8, 2.9 Hz, 1H), 6.62-6.70 (m, 1H), 7.03-7.11 (m, 1H), 7.11-7.29 (m, 6H).

Example 23

(E)-3-[1-(8-{[4-chloro-2-(methoxymethyl)-1H-benzo[d]imidazol-1-yl]methyl}-3-fluorodibenzo[b,e]oxepin-11(6H)-ylidene)ethyl]-1,2,4-oxadiazol-5(4H)-one (Compound 2j)

Using (E)-2-(8-{[4-chloro-2-(methoxymethyl)-1H-benzo[d]imidazol-1-yl]methyl}-3-fluorodibenzo[b,e]oxepin-11(6H)-ylidene)propanenitrile (100 mg, 0.21 mmol) obtained in Reference Example 2J, and in the same manner as in Example 1, the title compound (compound 2j) (47 mg, 42%) was obtained.

ESIMS m/z: 533 $(M+H)^+$; $^1H$ NMR (300 MHz, $CDCl_3$, δ): 2.16 (s, 3H), 3.25 (s, 3H), 4.70 (s, 2H), 4.92 (d, J=12.5 Hz, 1H), 5.48 (d, J=12.5 Hz, 1H), 5.55 (s, 2H), 6.65 (dd, J=10.6, 2.6 Hz, 1H), 6.79 (dt, J=8.2, 2.7 Hz, 1H), 7.05 (d, J=7.7 Hz, 1H), 7.11-7.17 (m, 1H), 7.20 (d, J=8.1 Hz, 1H), 7.23-7.33 (m, 3H), 7.41 (d, J=8.1 Hz, 1H).

Example 24

(E)-3-[1-(3-fluoro-8-{[4-(2-hydroxypropan-2-yl)-2-(methoxymethyl)-1H-benzo[d]imidazol-1-yl]methyl}dibenzo[b,e]oxepin-11(6H)-ylidene)ethyl]-1,2,4-oxadiazol-5(4H)-one (Compound 2k)

Using (E)-2-(3-fluoro-8-{[4-(2-hydroxypropan-2-yl)-2-(methoxymethyl)-1H-benzo[d]imidazol-1-yl]methyl}dibenzo[b,e]oxepin-11(6H)-ylidene)propanenitrile (170 mg, 0.35 mmol) obtained in Reference Example 2K, and in the same manner as in Example 1, the title compound (compound 2k) (100 mg, 50%) was obtained.

ESIMS m/z: 557 $(M+H)^+$; $^1H$ NMR (270 MHz, $CDCl_3$, δ): 1.70 (s, 6H), 2.27 (s, 3H), 3.37 (s, 3H), 4.73-4.98 (m, 3H), 5.59-5.68 (m, 3H), 6.50-6.69 (m, 2H), 7.04-7.18 (m, 4H), 7.35-7.52 (m, 3H).

Example 25

(E)-3-[1-(8-{[2,4-bis(methoxymethyl)-1H-benzo[d]imidazol-1-yl]methyl}-3-fluorodibenzo[b,e]oxepin-11(6H)-ylidene)ethyl]-1,2,4-oxadiazol-5(4H)-one (Compound 2l)

Using (E)-2-(8-{[2,4-bis(methoxymethyl)-1H-benzo[d]imidazol-1-yl]methyl}-3-fluorodibenzo[b,e]oxepin-11(6H)-ylidene)propanenitrile (153 mg, 0.32 mmol) obtained in Reference Example 2L, and in the same manner as in Example 1, the title compound (compound 2l) (122 mg, 70%) was obtained.

ESIMS m/z: 543 $(M+H)^+$; $^1H$ NMR (270 MHz, $CDCl_3$, δ): 2.27 (s, 3H), 3.35 (s, 3H), 3.51 (s, 3H), 4.70 (s, 2H), 4.73 (d, J=12.8 Hz, 1H), 4.96 (s, 2H), 5.50 (s, 2H), 5.51 (d, J=12.8 Hz, 1H), 6.50-6.71 (m, 2H), 7.10-7.38 (m, 7H).

Example 26

(E)-3-[1-(3-fluoro-8-{[2-(methoxymethyl)-4-(methylthio)-1H-benzo[d]imidazol-1-yl]methyl}dibenzo[b,e]oxepin-11(6H)-ylidene)ethyl]-1,2,4-oxadiazol-5(4H)-one (Compound 2m)

Using (E)-2-(3-fluoro-8-{[2-(methoxymethyl)-4-(methylthio)-1H-benzo[d]imidazol-1-yl]methyl}dibenzo[b,e]oxepin-11(6H)-ylidene)propionitrile (100 mg, 0.21 mmol) obtained in Reference Example 2M, and in the same manner as in Example 1, the title compound (compound 2m) (14 mg, 12%) was obtained.

ESIMS m/z: 545 $(M+H)^+$; $^1H$ NMR (270 MHz, $CDCl_3$, δ): 2.24 (s, 3H), 2.61 (s, 3H), 3.34 (s, 3H), 4.69 (s, 3H), 4.72 (d, J=12.8 Hz, 1H), 5.47 (d, J=4.8 Hz, 1H), 5.52 (d, J=12.8 Hz, 1H), 6.49-6.70 (m, 3H), 6.97-7.15 (m, 5H), 7.24 (t, J=7.9 Hz, 1H).

Example 27

(E)-3-[1-(3-fluoro-8-{[2-(methoxymethyl)-4-(methylsulfonyl)-1H-benzo[d]imidazol-1-yl]methyl}dibenzo[b,e]oxepin-11(6H)-ylidene)ethyl]-1,2,4-oxadiazol-5(4H)-one (Compound 2n)

Using (E)-2-(3-fluoro-8-{[2-(methoxymethyl)-4-(methylsulfonyl)-1H-benzo[d]imidazol-1-yl]methyl}dibenzo[b,e]oxepin-11(6H)-ylidene)propionitrile (79 mg, 0.15 mmol) obtained in Reference Example 2N, and in the same manner as in Example 1, the title compound (compound 2n) (9.5 mg, 11%) was obtained.

ESIMS m/z: 577 $(M+H)^+$; $^1H$ NMR (270 MHz, $CDCl_3$, δ): 2.29 (s, 3H), 3.37 (s, 3H), 3.43 (s, 3H), 4.65-4.75 (m, 3H), 5.46-5.59 (m, 3H), 6.49-6.53 (m, 1H), 6.62-6.69 (m, 1H), 7.08-7.16 (m, 4H), 7.33-7.39 (m, 1H) 7.51-7.54 (m, 1H), 7.86-7.89 (m, 1H).

Example 28

(E)-3-(1-{8-[(4-chloro-2-cyclopropyl-1H-benzo[d]imidazol-1-yl)methyl]-3-fluorodibenzo[b,e]oxepin-11(6H)-ylidene}ethyl)-1,2,4-oxadiazol-5(4H)-one (Compound 2o)

Using (E)-2-{8-[(4-chloro-2-cyclopropyl-1H-benzo[d]imidazol-1-yl)methyl]-3-fluorodibenzo[b,e]oxepin-11(6H)-ylidene}propanenitrile (105 mg, 0.22 mmol) obtained in Reference Example 2P, and in the same manner as in Example 1, the title compound (compound 2o) (43 mg, 36%) was obtained.

ESIMS m/z: 529 $(M+H)^+$; $^1H$ NMR (300 MHz, $CDCl_3$, δ): 1.01-1.10 (m, 2H), 1.23-1.32 (m, 2H), 1.80-1.91 (m, 1H), 2.28 (s, 3H), 4.75 (d, J=12.8 Hz, 1H), 5.42 (s, 2H), 5.51 (d, J=12.8 Hz, 1H), 6.54 (dd, J=10.3, 2.6 Hz, 1H), 6.61-6.70 (m, 1H), 7.04-7.12 (m, 4H), 7.13-7.19 (m, 2H), 7.22-7.26 (m, 1H).

Example 29

(E)-3-(1-{3-fluoro-8-[(2-propyl-1H-imidazo[4,5-c]pyridin-1-yl)methyl]dibenzo[b,e]oxepin-11(6H)-ylidene}ethyl)-1,2,4-oxadiazol-5(4H)-one (Compound 3a)

Using (E)-2-{3-fluoro-8-[(2-propyl-1H-imidazo[4,5-c]pyridin-1-yl)methyl]dibenzo[b,e]oxepin-11(6H)-ylidene}propanenitrile (50 mg, 0.114 mmol) obtained in Reference Example 3A, and in the same manner as in Example 1, the title compound (compound 3a) (15 mg, 26%) was obtained.

ESIMS m/z: 498 $(M+H)^+$; $^1H$ NMR (270 MHz, $CDCl_3$, δ): 1.01 (t, J=7.4 Hz, 3H), 1.76-2.03 (m, 2H), 2.30 (s, 3H), 2.81 (t, J=7.4 Hz, 2H), 4.47 (d, J=12.6 Hz, 1H), 5.28-5.48 (m, 3H), 6.48-6.55 (m, 1H), 6.62-6.71 (m, 1H), 6.73-6.76 (m, 1H), 7.00-7.29 (m, 4H), 8.13 (d, J=5.8 Hz, 1H), 8.86 (s, 1H).

Example 30

(E)-3-(1-{8-[(4-chloro-2-cyclobutyl-1H-imidazo[4,5-c]pyridin-1-yl)methyl]-3-fluorodibenzo[b,e]oxepin-11(6H)-ylidene}ethyl)-1,2,4-oxadiazol-5(4H)-one (Compound 3b)

Using (E)-2-{8-[(4-chloro-2-cyclobutyl-1H-imidazo[4,5-c]pyridin-1-yl)methyl]-3-fluorodibenzo[b,e]oxepin-11(6H)-ylidene}propanenitrile (87 mg, 0.179 mmol) obtained in Reference Example 3B, and in the same manner as in Example 1, the title compound (compound 3b) (54 mg, 55%) was obtained.

ESIMS m/z: 544 $(M+H)^+$; $^1H$ NMR (270 MHz, DMSO-$d_6$, δ): 1.74-2.21 (m, 7H), 2.22-2.44 (m, 2H), 3.67-3.89 (m, 1H), 4.93 (d, J=12.8 Hz, 1H), 5.39-5.55 (m, 3H), 6.58-6.73 (m, 1H), 6.73-6.88 (m, 1H), 7.02-7.12 (m, 1H), 7.11-7.30 (m, 2H), 7.58 (d, J=5.6 Hz, 1H), 8.07 (d, J=5.6 Hz, 1H), 8.31 (s, 1H)

Example 31

(E)-3-(1-{8-[(7-chloro-2-cyclopropyl-3H-imidazo[4,5-b]pyridin-3-yl)methyl]-3-fluorodibenzo[b,e]oxepin-11(6H)-ylidene}ethyl)-1,2,4-oxadiazol-5(4H)-one (Compound 3c)

Using (E)-2-{8-[(7-chloro-2-cyclopropyl-3H-imidazo[4,5-b]pyridin-3-yl)methyl]-3-fluorodibenzo[b,e]oxepin-11(6H)-ylidene}propanenitrile (107 mg, 0.228 mmol) obtained in Reference Example 3C, and in the same manner as in Example 1, the title compound (compound 3c) (65 mg, 54%) was obtained.

ESIMS m/z: 530 $(M+H)^+$; $^1H$ NMR (270 MHz, $CDCl_3$, δ): 1.05-1.17 (m, 2H), 1.24-1.33 (m, 2H), 1.85-1.97 (m, 1H), 2.28 (s, 3H), 4.78 (d, J=12.8 Hz, 1H), 5.45-5.68 (m, 3H), 6.47-6.58 (m, 1H), 6.58-6.71 (m, 1H), 6.98-7.29 (m, 5H), 8.14 (d, J=5.4 Hz, 1H).

Example 32

(E)-3-(1-{8-[(7-chloro-2-cyclobutyl-3H-imidazo[4,5-b]pyridin-3-yl)methyl]-3-fluorodibenzo[b,e]oxepin-11(6H)-ylidene}ethyl)-1,2,4-oxadiazol-5(4H)-one (Compound 3d)

Using (E)-2-{8-[(7-chloro-2-cyclobutyl-3H-imidazo[4,5-b]pyridin-3-yl)methyl]-3-fluorodibenzo[b,e]oxepin-11(6H)-ylidene}propanenitrile (100 mg, 0.206 mmol) obtained in Reference Example 3D, and in the same manner as in Example 1, the title compound (compound 3d) (28 mg, 25%) was obtained.

ESIMS m/z: 544 $(M+H)^+$; $^1H$ NMR (270 MHz, $CDCl_3$, δ): 1.19-1.42 (m, 2H), 1.91-2.19 (m, 2H), 2.30 (s, 3H), 2.47-2.73 (m, 2H), 3.55-3.77 (m, 1H), 4.77 (d, J=12.8 Hz, 1H), 5.27-5.60 (m, 3H), 6.46-6.59 (m, 1H), 6.59-6.75 (m, 1H), 6.97-7.22 (m, 4H), 7.23-7.30 (m, 1H), 8.11-8.26 (m, 1H).

Example 33

(E)-3-(1-{3-fluoro-8-[(2-propyl-3H-imidazo[4,5-b]pyridin-3-yl)methyl]dibenzo[b,e]oxepin-11(6H)-ylidene}ethyl)-1,2,4-oxadiazol-5(4H)-one (Compound 3e)

Using (E)-2-{3-fluoro-8-[(2-propyl-3H-imidazo[4,5-b]pyridin-1-yl)methyl]dibenzo[b,e]oxepin-11(6H)-ylidene}propanenitrile (44 mg, 0.10 mmol) obtained in Reference Example 3E, and in the same manner as in Example 1, the title compound (compound 3e) (26 mg, 52%) was obtained.

ESIMS m/z: 498 $(M+H)^+$; $^1H$ NMR (270 MHz, $CDCl_3$, δ): 0.98 (t, J=7.2 Hz, 3H), 1.75-1.95 (m, 2H), 2.26 (s, 3H), 2.77 (t, J=7.2 Hz, 2H), 4.72 (d, J=12.8 Hz, 1H), 5.39-5.55 (m, 3H), 6.45-6.57 (m, 1H), 6.58-6.70 (m, 1H), 7.00-7.25 (m, 5H), 7.96-8.04 (m, 1H), 8.23-8.32 (m, 1H).

Example 34

(E)-3-(1-{3-fluoro-8-[(5-fluoro-2-propyl-3H-imidazo[4,5-b]pyridin-3-yl)methyl]dibenzo[b,e]oxepin-11(6H)-ylidene}ethyl)-1,2,4-oxadiazol-5(4H)-one (Compound 3g)

Using (E)-2-{3-fluoro-8-[(5-fluoro-2-propyl-3H-imidazo[4,5-b]pyridin-3-yl)methyl]dibenzo[b,e]oxepin-11(6H)-ylidene}propanenitrile (46 mg, 0.101 mmol) obtained in Reference Example 3G, and in the same manner as in Example 1, the title compound (compound 3g) (14 mg, 27%) was obtained.

ESIMS m/z: 516 $(M+H)^+$; $^1H$ NMR (270 MHz, $CDCl_3$, δ): 0.93-1.09 (m, 3H), 1.69-1.91 (m, 2H), 2.30 (s, 3H), 2.69-2.78 (m, 2H), 4.80 (d, J=12.8 Hz, 1H), 5.40 (s, 2H), 5.54 (d, J=12.8 Hz, 1H), 6.42-6.58 (m, 1H), 6.58-6.72 (m, 1H), 6.75-6.93 (m, 1H), 7.01-7.23 (m, 4H), 7.97-8.10 (m, 1H).

Example 35

(E)-3-(1-{3-fluoro-8-[(5-fluoro-2-propyl-1H-imidazo[4,5-b]pyridin-1-yl)methyl]dibenzo[b,e]oxepin-11(6H)-ylidene}ethyl)-1,2,4-oxadiazol-5(4H)-one (Compound 3h)

Using (E)-2-{3-fluoro-8-[(5-fluoro-2-propyl-1H-imidazo[4,5-b]pyridin-1-yl)methyl]dibenzo[b,e]oxepin-11(6H)-ylidene}propanenitrile (56 mg, 0.123 mmol) obtained in Reference Example 3H, and in the same manner as in Example 1, the title compound (compound 3h) (4 mg, 6%) was obtained.

ESIMS m/z: 516 $(M+H)^+$; $^1H$ NMR (270 MHz, $CDCl_3$, δ): 0.84-1.12 (m, 3H), 1.67-1.95 (m, 2H), 2.37 (s, 3H), 2.79-3.01 (m, 2H), 4.63-4.81 (m, 1H), 5.37 (s, 2H), 5.53-5.72 (m, 1H), 6.43-6.84 (m, 3H), 6.84-6.99 (m, 1H), 6.98-7.12 (m, 1H), 7.12-7.37 (m, 2H), 7.40-7.62 (m, 1H).

Example 36

(E)-3-(1-{8-[(2-cyclobutyl-5-fluoro-1H-imidazo[4,5-b]pyridin-1-yl)methyl]-3-fluorodibenzo[b,e]oxepin-11(6H)-ylidene}ethyl)-1,2,4-oxadiazol-5(4H)-one (Compound 3i)

Using (E)-2-{8-[(2-cyclobutyl-5-fluoro-1H-imidazo[4,5-b]pyridin-1-yl)methyl]-3-fluorodibenzo[b,e]oxepin-11(6H)-ylidene}propanenitrile (100 mg, 0.213 mmol) obtained in Reference Example 3I, and in the same manner as in Example 1, the title compound (compound 3i) (66 mg, 31%) was obtained.

ESIMS m/z: 528 $(M+H)^+$; $^1H$ NMR (270 MHz, $CDCl_3$, δ): 1.95-2.12 (m, 2H), 2.21-2.41 (m, 5H), 2.52-2.71 (m, 2H), 3.56-3.69 (m, 1H), 4.74 (d, J=12.8 Hz, 1H), 5.28 (s, 2H), 5.52 (d, J=12.8 Hz, 1H), 6.50-6.61 (m, 1H), 6.60-6.71 (m, 1H), 6.71-6.79 (m, 1H), 6.98 (s, 1H), 7.03-7.14 (m, 2H), 7.16-7.30 (m, 1H), 7.39-7.52 (m, 1H).

Example 37

(E)-3-(1-{3-fluoro-8-[(2-propyl-1H-imidazo[4,5-b]pyrazin-1-yl)methyl]dibenzo[b,e]oxepin-11(6H)-ylidene}ethyl)-1,2,4-oxadiazol-5(4H)-one (Compound 3j)

Using (E)-2-{3-fluoro-8-[(2-propyl-1H-imidazo[4,5-b]pyrazin-1-yl)methyl]dibenzo[b,e]oxepin-11(6H)-ylidene}propanenitrile (219 mg, 0.50 mmol) obtained in Reference Example 3J, and in the same manner as in Example 1, the title compound (compound 3j) (93 mg, 37%) was obtained.

ESIMS m/z: 499 $(M+H)^+$; $^1H$ NMR (300 MHz, $CDCl_3$, δ): 0.99 (t, J=7.3 Hz, 3H), 1.80-1.95 (m, 2H), 2.29 (s, 3H), 2.85 (t, J=7.5 Hz, 2H), 4.77 (d, J=12.8 Hz, 1H), 5.41-5.54 (m, 2H), 5.56 (d, J=12.8 Hz, 1H), 6.53 (dd, J=9.9, 2.6 Hz, 1H), 6.60-6.69 (m, 1H), 7.10 (dd, J=8.6, 6.4 Hz, 1H), 7.14-7.21 (m, 3H), 8.26 (d, J=2.9 Hz, 1H), 8.47 (d, J=2.9 Hz, 1H).

Example 38

(E)-3-{1-[8-({2-[(dimethylamino)methyl]-1H-benzo[d]imidazol-1-yl}methyl)-3-fluorodibenzo[b,e]oxepin-11(6H)-ylidene]ethyl}-1,2,4-oxadiazol-5(4H)-one (Compound 4a)

Using (E)-2-[8-({2-[(dimethylamino)methyl]-1H-benzo[d]imidazol-1-yl}methyl)-3-fluorodibenzo[b,e]oxepin-11(6H)-ylidene]propanenitrile (57 mg, 0.13 mmol) obtained in Reference Example 4A, and in the same manner as in Example 1, the title compound (compound 4a) (10 mg, 15%) was obtained.

ESIMS m/z: 512 $(M+H)^+$; $^1H$ NMR (300 MHz, $CDCl_3$, δ): 2.32 (s, 3H), 2.93 (s, 6H), 4.22 (d, J=14.7 Hz, 1H), 4.67 (d, J=14.7 Hz, 1H), 4.81 (d, J=12.8 Hz, 1H), 5.54 (s, 2H), 5.61 (d, J=12.8 Hz, 1H), 6.49-6.60 (m, 2H), 6.60-6.68 (m, 1H), 7.01 (d, J=7.7 Hz, 1H), 7.11 (dd, J=8.8, 6.6 Hz, 1H), 7.26-7.28 (m, 1H), 7.35-7.41 (m, 3H), 7.80-7.87 (m, 1H).

Example 39

(E)-3-{1-[3-fluoro-8-({2-[(methylamino)methyl]-1H-benzo[d]imidazol-1-yl}methyl)dibenzo[b,e]oxepin-11(6H)-ylidene]ethyl}-1,2,4-oxadiazol-5(4H)-one monohydrochloride (Compound 4b)

(E)-tert-butyl [1-({3-fluoro-11-[1-(5-oxo-4,5-dihydro-1,2,4-oxadiazol-3-yl)ethylidene]-6,11-dihydrodibenzo[b,e]oxepin-8-yl}methyl)-1H-benzo[d]imidazol-2-yl]methyl(methyl)carbamate (45 mg, 0.075 mmol) obtained in Reference Example 4B was dissolved in dichloromethane (1 mL), trifluoroacetic acid (0.17 mL, 2.26 mmol) was added, and the mixture was stirred at room temperature for 3 hr. To the mixture was added saturated aqueous sodium hydrogen carbonate, and the mixture was extracted 3 times with chloroform-methanol (10/1) mixed solvent. The combined organic layers were dried over anhydrous magnesium sulfate, and concentrated under reduced pressure. The residue was purified by silica gel column chromatography (chloroform/methanol=10/1 v/v). To the obtained compound was added hydrogen chloride (4 mol/L 1,4-dioxane solution, 0.38 mL), and the mixture was stirred at room temperature for 30 min and concentrated under reduced pressure. To the residue was added ethyl acetate (1 mL), and the mixture was stirred at room temperature for 30 min. The precipitated crystals were collected by suction filtration to give the title compound (compound 4b) (17 mg, 43%).

ESIMS m/z: 498 $(M+H)^+$; $^1H$ NMR (300 MHz, DMSO-$d_6$, δ): 2.17 (s, 3H), 2.73 (s, 3H), 4.58 (br s, 2H), 4.94 (d, J=12.5 Hz, 1H), 5.46-5.58 (m, 3H), 6.65 (dd, J=10.8, 2.4 Hz, 1H), 6.75-6.85 (m, 1H), 7.09 (d, J=7.7 Hz, 1H), 7.14-7.38 (m, 5H), 7.47-7.54 (m, 1H), 7.66-7.74 (m, 1H), 9.44 (br s, 1H), 12.32 (br s, 1H).

Example 40

(E)-3-[1-(8-{[2-(azetidin-1-yl)-1H-benzo[d]imidazol-1-yl]methyl}-3-fluorodibenzo[b,e]oxepin-11(6H)-ylidene)ethyl]-1,2,4-oxadiazol-5(4H)-one (Compound 4c)

Using (E)-2-(8-{[2-(azetidin-1-yl)-1H-benzo[d]imidazol-1-yl]methyl}-3-fluorodibenzo[b,e]oxepin-11(6H)-ylidene)propanenitrile (56 mg, 0.12 mmol) obtained in Reference Example 4C, and in the same manner as in Example 1, the title compound (compound 4c) (16 mg, 25%) was obtained.

ESIMS m/z: 510 $(M+H)^+$; $^1H$ NMR (300 MHz, $CDCl_3$, δ): 2.27 (s, 3H), 2.31-2.44 (m, 2H), 4.28-4.44 (m, 4H), 4.76 (d, J=12.8 Hz, 1H), 5.09-5.25 (m, 2H), 5.67 (d, J=12.8 Hz, 1H), 6.50 (dd, J=10.3, 2.6 Hz, 1H), 6.61-6.70 (m, 1H), 6.85-6.92 (m, 1H), 7.02-7.31 (m, 6H), 7.51 (d, J=7.3 Hz, 1H).

Example 41

(E)-3-[1-(3-fluoro-8-{[2-(pyrrolidin-1-yl)-1H-benzo[d]imidazol-1-yl]methyl}dibenzo[b,e]oxepin-11(6H)-ylidene)ethyl]-1,2,4-oxadiazol-5(4H)-one (Compound 4d)

Using (E)-2-(3-fluoro-8-{[2-(pyrrolidin-1-yl)-1H-benzo[d]imidazol-1-yl]methyl}dibenzo[b,e]oxepin-11(6H)-ylidene)propanenitrile (140 mg, 0.30 mmol) obtained in Reference Example 4D, and in the same manner as in Example 1, the title compound (compound 4d) (37 mg, 23%) was obtained.

ESIMS m/z: 524 $(M+H)^+$; $^1H$ NMR (300 MHz, $CDCl_3$, δ): 1.85-1.98 (m, 4H), 2.27 (s, 3H), 3.47-3.58 (m, 4H), 4.71 (d, J=12.5 Hz, 1H), 5.29 (s, 2H), 5.51 (d, J=12.5 Hz, 1H), 6.53 (dd, J=10.3, 2.6 Hz, 1H), 6.60-6.70 (m, 1H), 6.90-7.21 (m, 7H), 7.48 (d, J=7.7 Hz, 1H).

Example 42

(E)-3-[1-(3-fluoro-8-{[2-(piperidin-1-yl)-1H-benzo[d]imidazol-1-yl]methyl}dibenzo[b,e]oxepin-11(6H)-ylidene)ethyl]-1,2,4-oxadiazol-5(4H)-one (Compound 4e)

Using (E)-2-(3-fluoro-8-{[2-(piperidin-1-yl)-1H-benzo[d]imidazol-1-yl]methyl}dibenzo[b,e]oxepin-11(6H)-ylidene)propanenitrile (123 mg, 0.26 mmol) obtained in Reference Example 4E, and in the same manner as in Example 1, the title compound (compound 4e) (48 mg, 35%) was obtained.

ESIMS m/z: 538 $(M+H)^+$; $^1H$ NMR (300 MHz, $CDCl_3$, δ): 1.54-1.74 (m, 6H), 2.28 (s, 3H), 3.14-3.22 (m, 4H), 4.78 (d, J=12.5 Hz, 1H), 5.22 (s, 2H), 5.53 (d, J=12.5 Hz, 1H), 6.55 (dd, J=10.3, 2.6 Hz, 1H), 6.62-6.71 (m, 1H), 6.95 (d, J=8.1 Hz, 1H), 7.04-7.13 (m, 2H), 7.14-7.26 (m, 4H), 7.62 (d, J=7.3 Hz, 1H).

Example 43

(E)-3-[1-(8-{[2-(dimethylamino)-1H-benzo[d]imidazol-1-yl]methyl}-3-fluorodibenzo[b,e]oxepin-11(6H)-ylidene)ethyl]-1,2,4-oxadiazol-5(4H)-one (Compound 4f)

Using (E)-2-(8-{[2-(dimethylamino)-1H-benzo[d]imidazol-1-yl]methyl}-3-fluorodibenzo[b,e]oxepin-11(6H)-ylidene)propanenitrile (100 mg, 0.23 mmol) obtained in Reference Example 4F, and in the same manner as in Example 1, the title compound (compound 4f) (56 mg, 50%) was obtained.

ESIMS m/z: 498 $(M+H)^+$; $^1H$ NMR (270 MHz, $CDCl_3$, δ): 2.28 (s, 3H), 3.04 (s, 6H), 4.77 (d, J=12.6 Hz, 1H), 5.18-5.36 (m, 2H), 5.66 (d, J=12.6 Hz, 1H), 6.54 (dd, J=10.4, 2.5 Hz, 1H), 6.62-6.71 (m, 1H), 6.88-6.95 (m, 1H), 7.04-7.31 (m, 6H), 7.58 (d, J=7.9 Hz, 1H).

Example 44

(E)-3-(cyclopropyl{3-fluoro-8-[(2-propyl-1H-benzo[d]imidazol-1-yl)methyl]dibenzo[b,e]oxepin-11(6H)-ylidene}methyl)-1,2,4-oxadiazol-5(4H)-one (Compound 4g)

Using (E)-2-cyclopropyl-2-{3-fluoro-8-[(2-propyl-1H-benzo[d]imidazol-1-yl)methyl]dibenzo[b,e]oxepin-11(6H)-ylidene)acetonitrile (132 mg, 0.29 mmol) obtained in Reference Example 4G, and in the same manner as in Example 1, the title compound (compound 4g) (88 mg, 59%) was obtained.

ESIMS m/z: 523 $(M+H)^+$; $^1H$ NMR (270 MHz, $CDCl_3$, δ): 0.53-1.00 (m, 7H), 1.59-1.69 (m, 2H), 2.05-2.14 (m, 1H), 2.91-3.02 (m, 2H), 4.64 (d, J=12.5 Hz, 1H), 5.39 (s, 2H), 5.69 (d, J=12.5 Hz, 1H), 6.48-6.52 (m, 1H), 6.62-6.68 (m, 1H), 6.89-6.93 (m, 1H), 7.07-7.08 (m, 1H), 7.23-7.40 (m, 4H), 7.48-7.53 (m, 1H), 7.83-7.86 (m, 1H).

Example 45

(E)-3-(cyclopropyl{8-[(2-cyclopropyl-1H-benzo[d]imidazol-1-yl)methyl]-3-fluorodibenzo[b,e]oxepin-11(6H)-ylidene}methyl)-1,2,4-oxadiazol-5(4H)-one (Compound 4h)

Using (E)-2-cyclopropyl-2-{8-[(2-cyclopropyl-1H-benzo[d]imidazol-1-yl)methyl]-3-fluorodibenzo[b,e]oxepin-11(6H)-ylidene)acetonitrile (133 mg, 0.29 mmol) obtained in Reference Example 4H, and in the same manner as in Example 1, the title compound (compound 4h) (98 mg, 65%) was obtained.

ESIMS m/z: 521 $(M+H)^+$; $^1H$ NMR (270 MHz, $CDCl_3$, δ): 0.47-1.04 (m, 8H), 1.74-1.81 (m, 1H), 2.00-2.07 (m, 1H), 4.39 (d, J=12.8 Hz, 1H), 5.32-5.47 (m, 3H), 6.45-6.49 (m, 1H), 6.60-6.66 (m, 1H), 6.87 (br s, 1H), 7.08-7.21 (m, 5H), 7.38-7.43 (m, 1H), 7.59-7.62 (m, 1H).

Example 46

(E)-3-[cyclopropyl(8-{[2-(3,3-difluorocyclobutyl)-1H-benzo[d]imidazol-1-yl]methyl}-3-fluorodibenzo[b,e]oxepin-11(6H)-ylidene)methyl]-1,2,4-oxadiazol-5(4H)-one (Compound 4i)

Using (E)-2-cyclopropyl-2-(8-{[2-(3,3-difluorocyclobutyl)-1H-benzo[d]imidazol-1-yl]methyl}-3-fluorodibenzo[b,e]oxepin-11(6H)-ylidene)acetonitrile (152 mg, 0.297 mmol) obtained in Reference Example 4I, and in the same manner as in Example 1, the title compound (compound 4i) (66 mg, 39%) was obtained.

ESIMS m/z: 571 $(M+H)^+$; $^1H$ NMR (270 MHz, $CDCl_3$, δ): 0.42-1.02 (m, 4H), 1.96-2.05 (m, 1H), 2.75-2.83 (m, 2H), 2.97-3.11 (m, 2H), 3.35-3.40 (m, 1H), 4.67 (d, J=12.8 Hz, 1H), 5.27 (s, 2H), 5.48 (d, J=12.8 Hz, 1H), 6.52-6.56 (m, 1H), 6.63-6.70 (m, 1H), 6.91-6.97 (m, 2H), 7.12-7.14 (m, 1H), 7.20-7.32 (m, 3H), 7.40-7.45 (m, 1H), 7.76-7.79 (m, 1H).

Example 47

(E)-3-[cyclopropyl (3-fluoro8-{[4-(2-hydroxypropan-2-yl)-2-(methoxymethyl)-1H-benzo[d]imidazol-1-yl]methyl}dibenzo[b,e]oxepin-11(6H)-ylidene) methyl]-1,2,4-oxadiazol-5(4H)-one (Compound 4j)

Using (E)-2-cyclopropyl-2-(3-fluoro-8-{[4-(2-hydroxypropan-2-yl)-2-(methoxymethyl)-1H-benzo[d]imidazol-1-yl]methyl}dibenzo[b,e]oxepin-11(6H)-ylidene)acetonitrile (139 mg, 0.265 mmol) obtained in Reference Example 4J, and in the same manner as in Example 1, the title compound (compound 4j) (62 mg, 40%) was obtained.

ESIMS m/z: 583 $(M+H)^+$; $^1$H NMR (270 MHz, $CDCl_3$, δ): 0.41-0.97 (m, 4H), 1.69 (s, 6H), 2.00-2.06 (m, 1H), 3.34 (s, 3H), 4.62-4.70 (m, 2H), 4.84 (d, J=13.8 Hz, 1H), 5.48-5.65 (m, 3H), 6.49-6.54 (m, 1H), 6.62-6.64 (m, 1H), 7.03-7.08 (m, 2H), 7.16-7.19 (m, 1H), 7.32-7.50 (m, 4H).

Example 48

(E)-3-({8-[(4-chloro-2-cyclopropyl-1H-benzo[d]imidazol-1-yl)methyl]-3-fluorodibenzo[b,e]oxepin-11(6H)-ylidene}(cyclopropyl)methyl)-1,2,4-oxadiazol-5(4H)-one (Compound 4k)

Using (E)-2-{8-[(4-chloro-2-cyclopropyl-1H-benzo[d]imidazol-1-yl)methyl]-3-fluorodibenzo[b,e]oxepin-11(6H)-ylidene}-2-cyclopropylacetonitrile (115 mg, 0.232 mmol) obtained in Reference Example 4K, and in the same manner as in Example 1, the title compound (compound 4k) (52 mg, 40%) was obtained.

ESIMS m/z: 555 $(M+H)^+$; $^1$H NMR (270 MHz, $CDCl_3$, δ): 0.40-1.05 (m, 8H), 1.76-1.87 (m, 1H), 1.94-2.04 (m, 1H), 4.65 (d, J=12.2 Hz, 1H), 5.42-5.48 (m, 3H), 6.51-6.56 (m, 1H), 6.62-6.68 (m, 1H), 6.91-6.92 (m, 1H), 7.07-7.21 (m, 5H), 7.40-7.46 (m, 1H).

Example 49

(E)-3-[1-(3-fluoro-8-{[2-(methoxymethyl)-1H-benzo[d]imidazol-1-yl]methyl}dibenzo[b,e]oxepin-11(6H)-ylidene)propyl]-1,2,4-oxadiazol-5(4H)-one (Compound 4l)

Using (E)-2-(3-fluoro-8-{[2-(methoxymethyl)-1H-benzo[d]imidazol-1-yl]methyl}dibenzo[b,e]oxepin-11(6H)-ylidene)butanenitrile (171 mg, 0.377 mmol) obtained in Reference Example 4L, and in the same manner as in Example 1, the title compound (compound 4l) (100 mg, 51%) was obtained.

ESIMS m/z: 513 $(M+H)^+$; $^1$H NMR (270 MHz, $CDCl_3$, δ): 1.07-1.21 (m, 3H), 2.57-2.86 (m, 2H), 3.34 (s, 3H), 4.55-4.74 (m, 3H), 5.35-5.58 (m, 3H), 6.47-6.56 (m, 1H), 6.58-6.75 (m, 1H), 6.95-7.15 (m, 4H), 7.17-7.32 (m, 3H), 7.67-7.85 (m, 1H).

Example 50

(E)-3-(1-{1,3-difluoro-8-[(2-propyl-1H-benzo[d]imidazol-1-yl)methyl]dibenzo[b,e]oxepin-11(6H)-ylidene}ethyl)-1,2,4-oxadiazol-5(4H)-one (Compound 5a)

Using (E)-2-{1,3-difluoro-8-[(2-propyl-1H-benzo[d]imidazol-1-yl)methyl]dibenzo[b,e]oxepin-11(6H)-ylidene}propanenitrile (183 mg, 0.40 mmol) obtained in Reference Example 5A, and in the same manner as in Example 1, the title compound (compound 5a) (93 mg, 45%) was obtained.

ESIMS m/z: 515 $(M+H)^+$; $^1$H NMR (300 MHz, $CDCl_3$, δ): 1.00 (t, J=7.5 Hz, 3H), 1.79-1.94 (m, 2H), 2.17 (d, J=3.3 Hz, 3H), 2.80 (t, J=7.5 Hz, 2H), 4.72 (d, J=12.8 Hz, 1H), 5.37 (s, 2H), 5.55 (d, J=12.8 Hz, 1H), 6.33-6.39 (m, 1H), 6.41-6.50 (m, 1H), 7.01 (br s, 1H), 7.09-7.29 (m, 5H), 7.72-7.77 (m, 1H).

Example 51

(E)-3-(1-{2,3-difluoro-8-[(2-propyl-1H-benzo[d]imidazol-1-yl)methyl]dibenzo[b,e]oxepin-11(6H)-ylidene}ethyl)-1,2,4-oxadiazol-5(4H)-one (Compound 6a)

Using (E)-2-{2,3-difluoro-8-[(2-propyl-1H-benzo[d]imidazol-1-yl)methyl]dibenzo[b,e]oxepin-11(6H)-ylidene}propanenitrile (132 mg, 0.29 mmol) obtained in Reference Example 6A, and in the same manner as in Example 1, the title compound (compound 6a) (36 mg, 24%) was obtained.

ESIMS m/z: 515 $(M+H)^+$; $^1$H NMR (270 MHz, $CD_3OD$, δ): 0.89 (t, J=7.2 Hz, 3H), 1.59-1.76 (m, 2H), 2.13 (s, 3H), 2.90-3.01 (m, 2H), 4.64-4.79 (m, 1H), 5.45 (d, J=12.8 Hz, 1H), 5.52-5.62 (m, 2H), 6.57-6.67 (m, 1H), 7.01-7.11 (m, 3H), 7.12-7.18 (m, 1H), 7.29-7.41 (m, 2H), 7.43-7.51 (m, 1H), 7.58-7.67 (m, 1H).

Example 52

(E)-3-(1-{3,4-difluoro-8-[(2-propyl-1H-benzo[d]imidazol-1-yl)methyl]dibenzo[b,e]oxepin-11(6H)-ylidene}ethyl)-1,2,4-oxadiazol-5(4H)-one (Compound 7a)

Using (E)-2-{3,4-difluoro-8-[(2-propyl-1H-benzo[d]imidazol-1-yl)methyl]dibenzo[b,e]oxepin-11(6H)-ylidene}propanenitrile (40 mg, 0.088 mmol) obtained in Reference Example 7A, and in the same manner as in Example 1, the title compound (compound 7a) (24 mg, 53%) was obtained.

ESIMS m/z: 515 $(M+H)^+$; $^1$H NMR (300 MHz, $CDCl_3$, δ): 0.90 (t, J=7.3 Hz, 3H), 1.68-1.85 (m, 2H), 2.28 (s, 3H), 2.94 (t, J=7.3 Hz, 2H), 4.86 (d, J=12.8 Hz, 1H), 5.43 (s, 2H), 5.63 (d, J=12.8 Hz, 1H), 6.69-6.80 (m, 1H), 6.84-6.93 (m, 1H), 6.94-7.02 (m, 1H), 7.10-7.18 (m, 2H), 7.26-7.42 (m, 3H), 7.80 (d, J=8.1 Hz, 1H).

Example 53

(E)-3-(1-{8-[(8-chloro-2-cyclopropylimidazo[1,2-a]pyridin-3-yl)methyl]-3-fluorodibenzo[b,e]oxepin-11(6H)-ylidene}ethyl)-1,2,4-oxadiazol-5(4H)-one (Compound 8a)

Using (E)-2-{8-[(8-chloro-2-cyclopropylimidazo[1,2-a]pyridin-3-yl)methyl]-3-fluorodibenzo[b,e]oxepin-11(6H)-ylidene}propanenitrile (170 mg, 0.362 mmol) obtained in Reference Example 8A, and in the same manner as in Example 1, the title compound (compound 8a) (70 mg, 37%) was obtained.

ESIMS m/z: 529 $(M+H)^+$; $^1$H NMR (270 MHz, $CDCl_3$, δ): 0.86-1.16 (m, 4H), 1.92-2.10 (m, 1H), 2.27 (s, 3H), 4.27-4.42

(m, 2H), 4.68 (d, J=12.6 Hz, 1H), 5.48 (d, J=12.6 Hz, 1H), 6.43-6.57 (m, 1H), 6.57-6.68 (m, 2H), 7.02-7.20 (m, 5H), 7.50-7.58 (m, 1H).

Example 54

(E)-3-(1-{8-[(2-cyclopropylimidazo[1,2-a]pyridin-3-yl)methyl]-3-fluorodibenzo[b,e]oxepin-11(6H)-ylidene}ethyl)-1,2,4-oxadiazol-5(4H)-one (Compound 8b)

Using (E)-2-{8-[(2-cyclopropylimidazo[1,2-a]pyridin-3-yl)methyl]-3-fluorodibenzo[b,e]oxepin-11(6H)-ylidene}propanenitrile (201 mg, 0.462 mmol) obtained in Reference Example 8B, and in the same manner as in Example 1, the title compound (compound 8b) (62 mg, 27%) was obtained.

ESIMS m/z: 495 $(M+H)^+$; $^1$H NMR (270 MHz, $CDCl_3$, δ): 0.93-1.07 (m, 2H), 1.07-1.21 (m, 2H), 1.95-2.09 (m, 1H), 2.29 (s, 3H), 4.29-4.47 (m, 2H), 4.74 (d, J=12.8 Hz, 1H), 5.50 (d, J=12.8 Hz, 1H), 6.47-6.58 (m, 1H), 6.59-6.75 (m, 2H), 7.01-7.25 (m, 5H), 7.44-7.54 (m, 1H), 7.54-7.63 (m, 1H).

Example 55

(E)-3-(1-{3-fluoro-8-[(2-isopropylimidazo[1,2-a]pyridin-3-yl)methyl]dibenzo[b,e]oxepin-11(6H)-ylidene}ethyl)-1,2,4-oxadiazol-5(4H)-one (Compound 8c)

Using (E)-2-{3-fluoro-8-[(2-isopropylimidazo[1,2-a]pyridin-3-yl)methyl]dibenzo[b,e]oxepin-11(6H)-ylidene}propanenitrile (52 mg, 0.119 mmol) obtained in Reference Example 8C, and in the same manner as in Example 1, the title compound (compound 8c) (25 mg, 42%) was obtained.

ESIMS m/z: 497 $(M+H)^+$; $^1$H NMR (270 MHz, $CDCl_3$, δ): 1.31-1.45 (m, 6H), 2.27 (s, 3H), 3.10-3.30 (m, 1H), 4.19-4.33 (m, 2H), 4.66 (d, J=12.8 Hz, 1H), 5.50 (d, J=12.8 Hz, 1H), 6.46-6.58 (m, 1H), 6.58-6.66 (m, 1H), 6.66-6.77 (m, 1H), 7.01-7.16 (m, 5H), 7.47-7.55 (m, 1H), 7.56-7.64 (m, 1H).

Example 56

(E)-3-(1-{8-[(2-cyclobutylimidazo[1,2-a]pyridin-3-yl)methyl]-3-fluorodibenzo[b,e]oxepin-11(6H)-ylidene}ethyl)-1,2,4-oxadiazol-5(4H)-one (Compound 8d)

Using (E)-2-{8-[(2-cyclobutylimidazo[1,2-a]pyridin-3-yl)methyl]-3-fluorodibenzo[b,e]oxepin-11(6H)-ylidene}propanenitrile (125 mg, 0.278 mmol) obtained in Reference Example 8D, and in the same manner as in Example 1, the title compound (compound 8d) (30 mg, 21%) was obtained.

ESIMS m/z: 509 $(M+H)^+$; $^1$H NMR (270 MHz, $CDCl_3$, δ): 1.89-2.15 (m, 2H), 2.19-2.42 (m, 5H), 2.43-2.70 (m, 2H), 3.65-3.83 (m, 1H), 4.15-4.32 (m, 2H), 4.63 (d, J=12.8 Hz, 1H), 5.46 (d, J=12.8 Hz, 1H), 6.45-6.57 (m, 1H), 6.56-6.75 (m, 2H), 6.93-7.21 (m, 5H), 7.46-7.57 (m, 1H), 7.57-7.66 (m, 1H).

Example 57

(E)-3-(1-{8-[(2-cyclopentylimidazo[1,2-a]pyridin-3-yl)methyl]-3-fluorodibenzo[b,e]oxepin-11(6H)-ylidene}ethyl)-1,2,4-oxadiazol-5(4H)-one (Compound 8e)

Using (E)-2-{8-[(2-cyclopentylimidazo[1,2-a]pyridin-3-yl)methyl]-3-fluorodibenzo[b,e]oxepin-11(6H)-ylidene}propanenitrile (92 mg, 0.198 mmol) obtained in Reference Example 8E, and in the same manner as in Example 1, the title compound (compound 8e) (30 mg, 29%) was obtained.

ESIMS m/z: 523 $(M+H)^+$; $^1$H NMR (270 MHz, $CDCl_3$, δ): 1.18-2.12 (m, 8H), 2.29 (s, 3H), 3.13-3.39 (m, 1H), 4.26-4.40 (m, 2H), 4.75 (d, J=12.8 Hz, 1H), 5.51 (d, J=12.8 Hz, 1H), 6.49-6.58 (m, 1H), 6.60-6.78 (m, 2H), 6.98-7.29 (m, 5H), 7.53-7.68 (m, 2H).

Example 58

(E)-3-[1-(3-fluoro8-{[2-(methoxymethyl)imidazo[1,2-a]pyridin-3-yl]methyl}dibenzo[b,e]oxepin-11(6H)-ylidene)ethyl]-1,2,4-oxadiazol-5(4H)-one (Compound 8f)

Using (E)-2-(3-fluoro8-{[2-(methoxymethyl)imidazo[1,2-a]pyridin-3-yl]methyl}dibenzo[b,e]oxepin-11(6H)-ylidene)propanenitrile (84 mg, 0.19 mmol) obtained in Reference Example 8F, and in the same manner as in Example 1, the title compound (compound 8f) (40 mg, 42%) was obtained.

ESIMS m/z: 499 $(M+H)^+$; $^1$H NMR (270 MHz, $CDCl_3$, δ): 2.29 (s, 3H), 3.48 (s, 3H), 4.41 (s, 2H), 4.76-4.80 (m, 3H), 5.63 (d, J=12.1 Hz, 1H), 6.42-6.46 (m, 1H), 6.62-6.68 (m, 1H), 7.04-7.22 (m, 5H), 7.61-7.66 (m, 1H), 7.85-7.87 (m, 1H), 8.11-8.14 (m, 1H).

Example 59

(E)-3-{1-[3-fluoro-8-({2-[(methoxy-$d_3$)-methyl]imidazo[1,2-a]pyridin-3-yl}methyl)dibenzo[b,e]oxepin-11(6H)-ylidene]ethyl}-1,2,4-oxadiazol-5(4H)-one (Compound 8g)

Using (E)-2-[3-fluoro-8-({2-[(methoxy-$d_3$)-methyl]imidazo[1,2-a]pyridin-3-yl}methyl)dibenzo[b,e]oxepin-11(6H)-ylidene]propanenitrile (110 mg, 0.25 mmol) obtained in Reference Example 8G, and in the same manner as in Example 1, the title compound (compound 8g) (38 mg, 30%) was obtained.

ESIMS m/z: 502 $(M+H)^+$; $^1$H NMR (270 MHz, DMSO-$d_6$, δ): 2.15 (s, 3H), 4.32-4.44 (m, 2H), 4.58 (s, 2H), 4.87 (d, J=12.7 Hz, 1H), 5.48 (d, J=12.7 Hz, 1H), 6.65 (d, J=10.7 Hz, 1H), 6.70-6.90 (m, 2H), 7.00 (d, J=7.8 Hz, 1H), 7.14-7.30 (m, 3H), 7.30 (s, 1H), 7.51 (d, J=8.8 Hz, 1H), 8.10 (d, J=6.8 Hz, 1H), 12.11 (br s, 1H).

Example 60

(E)-3-(1-{8-[(8-chloro-2-isopropylimidazo[1,2-a]pyridin-3-yl)methyl]-3-fluorodibenzo[b,e]oxepin-11(6H)-ylidene}ethyl)-1,2,4-oxadiazol-5(4H)-one (Compound 8h)

Using (E)-2-{8-[(8-chloro-2-isopropylimidazo[1,2-a]pyridin-3-yl)methyl]-3-fluorodibenzo[b,e]oxepin-11(6H)-ylidene}propanenitrile (263 mg, 0.56 mmol) obtained in Reference Example 8H, and in the same manner as in Example 1, the title compound (compound 8h) (159 mg, 54%) was obtained.

ESIMS m/z: 531 $(M+H)^+$; $^1$H NMR (300 MHz, DMSO-$d_6$, δ): 1.19-1.29 (m, 6H), 2.15 (s, 3H), 3.12-3.26 (m, 1H), 4.35 (s, 2H), 4.90 (d, J=12.5 Hz, 1H), 5.47 (d, J=12.5 Hz, 1H), 6.65 (dd, J=10.6, 2.6 Hz, 1H), 6.72-6.83 (m, 2H), 7.01 (d, J=7.7

Hz, 1H), 7.05-7.12 (m, 1H), 7.18-7.27 (m, 2H), 7.34 (dd, J=7.3, 0.7 Hz, 1H), 8.08 (d, J=5.9 Hz, 1H), 12.09 (br s, 1H).

Example 61

(E)-3-(1-{3-fluoro-8-[(2-propylimidazo[1,2-a]pyridin-3-yl)methyl]dibenzo[b,e]oxepin-11(6H)-ylidene}ethyl)-1,2,4-oxadiazol-5(4H)-one (Compound 8i)

Using (E)-2-{3-fluoro-8-[(2-propylimidazo[1,2-a]pyridin-3-yl)methyl]dibenzo[b,e]oxepin-11(6H)-ylidene}propanenitrile (148 mg, 0.338 mmol) obtained in Reference Example 8I, and in the same manner as in Example 1, the title compound (compound 8i) (29 mg, 17%) was obtained.

ESIMS m/z: 497 $(M+H)^+$; $^1H$ NMR (270 MHz, $CDCl_3$, $CD_3OD$, δ): 0.98 (t, J=7.2 Hz, 3H), 1.77-1.89 (m, 2H), 2.25 (s, 3H), 2.78 (t, J=7.2 Hz, 2H), 4.24 (d, J=17.6 Hz, 1H), 4.31 (d, J=17.6 Hz, 1H), 4.72 (d, J=12.7 Hz, 1H), 5.51 (d, J=12.7 Hz, 1H), 6.53 (d, J=9.8 Hz, 1H), 6.60-6.79 (m, 2H), 7.00-7.19 (m, 5H), 7.75-7.64 (m, 2H).

Example 62

(E)-3-(1-{8-[(8-chloro-2-cyclobutylimidazo[1,2-a]pyridin-3-yl)methyl]-3-fluorodibenzo[b,e]oxepin-11(6H)-ylidene}ethyl)-1,2,4-oxadiazol-5(4H)-one (Compound 8j)

Using (E)-2-{8-[(8-chloro-2-cyclobutylimidazo[1,2-a]pyridin-3-yl)methyl]-3-fluorodibenzo[b,e]oxepin-11(6H)-ylidene}propanenitrile (84 mg, 0.174 mmol) obtained in Reference Example 8J, and in the same manner as in Example 1, the title compound (compound 8j) (18 mg, 19%) was obtained.

ESIMS m/z: 543 $(M+H)^+$; $^1H$ NMR (270 MHz, $CDCl_3$, δ): 1.84-2.14 (m, 2H), 2.21-2.42 (m, 5H), 2.56-2.74 (m, 2H), 3.70-3.92 (m, 1H), 4.23-4.42 (m, 2H), 4.73 (d, J=12.8 Hz, 1H), 5.50 (d, J=12.8 Hz, 1H), 6.44-6.57 (m, 1H), 6.58-6.77 (m, 2H), 7.01-7.18 (m, 4H), 7.18-7.31 (m, 1H), 7.52-7.60 (m, 1H).

Example 63

(E)-3-[1-(8-{[8-chloro-2-(methoxymethyl)imidazo[1,2-a]pyridin-3-yl]methyl}-3-fluorodibenzo[b,e]oxepin-11(6H)-ylidene)ethyl]-1,2,4-oxadiazol-5(4H)-one (Compound 8k)

Using (E)-2-(3-fluoro-8-{[8-chloro-2-(methoxymethyl)imidazo[1,2-a]pyridin-3-yl]methyl}dibenzo[b,e]oxepin-11(6H)-ylidene)propanenitrile (100 mg, 0.211 mmol) obtained in Reference Example 8K, and in the same manner as in Example 14, the title compound (compound 8k) (48 mg, 42%) was obtained.

ESIMS m/z: 531 $(M-H)^-$; $^1H$ NMR (270 MHz, DMSO-$d_6$, δ): 2.15 (s, 3H), 3.29 (s, 3H), 4.38 (d, J=17.0 Hz, 1H), 4.44 (d, J=17.0 Hz, 1H), 4.61 (s, 2H), 4.48 (d, J=12.8 Hz, 1H), 4.88 (d, J=12.8 Hz, 1H), 6.65 (dd, J=2.9, 10.7 Hz, 1H), 6.71-6.89 (m, 2H), 7.00 (d, J=7.8 Hz, 1H), 7.12-7.32 (m, 2H), 7.29 (s, 1H), 7.41 (d, J=7.8 Hz, 1H), 8.13 (d, J=6.8 Hz, 1H), 12.10 (s, 1H).

Example 64

(E)-3-({8-[(8-chloro-2-cyclopropylimidazo[1,2-a]pyridin-3-yl)methyl]-3-fluorodibenzo[b,e]oxepin-11(6H)-ylidene}methyl)-1,2,4-oxadiazol-5(4H)-one (Compound 8l)

Using (E)-2-{8-[(8-chloro-2-cyclopropylimidazo[1,2-a]pyridin-3-yl)methyl]-3-fluorodibenzo[b,e]oxepin-11(6H)-ylidene}acetonitrile (225 mg, 0.494 mmol) obtained in Reference Example 8L, and in the same manner as in Example 1, the title compound (compound 8l) (52 mg, 32%) was obtained.

ESIMS m/z: 515 $(M+H)^+$; $^1H$ NMR (300 MHz, $CDCl_3$, δ): 1.02-1.08 (m, 2H), 1.19-1.24 (m, 2H), 2.02-2.10 (m, 1H), 4.44 (s, 2H), 4.82 (br s, 1H), 5.44 (br s, 1H), 6.52-6.57 (m, 2H), 6.63-6.75 (m, 2H), 7.18-7.38 (m, 5H), 7.57 (d, J=5.9 Hz, 1H).

Example 65

(E)-3-({8-[(2-cyclopropyl-8-methoxyimidazo[1,2-a]pyridin-3-yl)methyl]-3-fluorodibenzo[b,e]oxepin-11(6H)-ylidene}methyl)-1,2,4-oxadiazol-5(4H)-one (Compound 8m)

Using (E)-2-{8-[(2-cyclopropyl-8-methoxyimidazo[1,2-a]pyridin-3-yl)methyl]-3-fluorodibenzo[b,e]oxepin-11(6H)-ylidene}acetonitrile (93 mg, 0.206 mmol) obtained in Reference Example 8M, and in the same manner as in Example 1, the title compound (compound 8m) (17 mg, 16%) was obtained.

ESIMS m/z: 511 $(M+H)^+$; $^1H$ NMR (300 MHz, $CDCl_3$, δ): 0.97-1.04 (m, 2H), 1.20-1.27 (m, 2H), 1.98-2.08 (m, 1H), 3.99 (s, 3H), 4.41 (s, 2H), 4.79 (br s, 1H), 5.42 (br s, 1H), 6.44 (d, J=7.3 Hz, 1H), 6.51-6.57 (m, 2H), 6.61-6.74 (m, 2H), 7.16-7.37 (m, 5H).

Example 66

(Z)-3-({8-[(8-chloro-2-cyclopropylimidazo[1,2-a]pyridin-3-yl)methyl]-3-fluorodibenzo[b,e]oxepin-11(6H)-ylidene}fluoromethyl)-1,2,4-oxadiazol-5(4H)-one (Compound 8n)

Using (Z)-2-{8-[(8-chloro-2-cyclopropylimidazo[1,2-a]pyridin-3-yl)methyl]-3-fluorodibenzo[b,e]oxepin-11(6H)-ylidene}-2-fluoroacetonitrile (46 mg, 0.097 mmol) obtained in Reference Example 8N, and in the same manner as in Example 1, the title compound (compound 8n) (11 mg, 21%) was obtained.

ESIMS m/z: 533 $(M+H)^+$; $^1H$ NMR (270 MHz, $CDCl_3$, δ): 1.01-1.16 (m, 2H), 1.18-1.29 (m, 2H), 2.00-2.12 (m, 1H), 4.39 (s, 2H), 4.77 (d, J=12.8 Hz, 1H), 5.56 (d, J=12.8 Hz, 1H), 6.44-6.57 (m, 1H), 6.58-6.71 (m, 1H), 6.90-7.01 (m, 1H), 7.01-7.14 (m, 1H), 7.20-7.30 (m, 2H), 7.36-7.49 (m, 2H), 7.62-7.77 (m, 1H).

Example 67

(E)-3-(1-{8-[(2-cyclopropyl-8-methoxyimidazo[1,2-a]pyridin-3-yl)methyl]-3-fluorodibenzo[b,e]oxepin-11(6H)-ylidene}ethyl)-1,2,4-oxadiazol-5(4H)-one (Compound 9a)

Using (E)-2-{8-[(2-cyclopropyl-8-methoxyimidazo[1,2-a]pyridin-3-yl)methyl]-3-fluorodibenzo[b,e]oxepin-11(6H)- ylidene}propanenitrile (100 mg, 0.215 mmol) obtained in Reference Example 9A, and in the same manner as in Example 1, the title compound (compound 9a) (65 mg, 55%) was obtained.

ESIMS m/z: 525 $(M+H)^+$; $^1$H NMR (270 MHz, $CDCl_3$, δ): 0.09-1.03 (m, 2H), 1.09-1.25 (m, 2H), 1.93-2.07 (m, 1H), 2.27 (s, 3H), 3.95 (s, 3H), 4.32 (d, J=17.4 Hz, 1H), 4.40 (d, J=17.4 Hz, 1H), 4.73 (d, J=12.6 Hz, 1H), 5.49 (d, J=12.6 Hz, 1H), 6.40 (d, J=7.2 Hz, 1H), 6.45-6.73 (m, 3H), 7.01-7.30 (m, 5H).

Example 68

(E)-3-(1-{8-[(2-cyclopropyl-8-ethoxyimidazo[1,2-a]pyridin-3-yl)methyl]-3-fluorodibenzo[b,e]oxepin-11(6H)-ylidene}ethyl)-1,2,4-oxadiazol-5(4H)-one (Compound 9b)

Using (E)-2-{8-[(2-cyclopropyl-8-ethoxyimidazo[1,2-a]pyridin-3-yl)methyl]-3-fluorodibenzo[b,e]oxepin-11(6H)-ylidene}propanenitrile (160 mg, 0.334 mmol) obtained in Reference Example 9B, and in the same manner as in Example 1, the title compound (compound 9b) (60 mg, 33%) was obtained.

ESIMS m/z: 539 $(M+H)^+$; $^1$H NMR (270 MHz, $CDCl_3$, δ): 0.90-1.00 (m, 2H), 1.09-1.19 (m, 2H), 1.48 (t, J=6.8 Hz, 3H), 1.94-2.06 (m, 1H), 2.26 (s, 3H), 4.19 (q, J=6.8 Hz, 2H), 4.32 (d, J=17.0 Hz, 1H), 4.38 (d, J=17.0 Hz, 1H), 4.69 (d, J=12.7 Hz, 1H), 5.47 (d, J=12.7 Hz, 1H), 6.39 (d, J=7.8 Hz, 1H), 6.51 (d, J=7.8 Hz, 1H), 6.57-6.70 (m, 2H), 7.01-7.28 (m, 5H).

Example 69

(E)-3-[1-(8-{[2-cyclopropyl-8-(difluoromethoxy)imidazo[1,2-a]pyridin-3-yl]methyl}-3-fluorodibenzo[b,e]oxepin-11(6H)-ylidene)ethyl]-1,2,4-oxadiazol-5(4H)-one (Compound 9c)

Using (E)-2-(8-{[2-cyclopropyl-8-(difluoromethoxy)imidazo[1,2-a]pyridin-3-yl]methyl}-3-fluorodibenzo[b,e]oxepin-11(6H)-ylidene)propanenitrile (205 mg, 0.409 mmol) obtained in Reference Example 9C, and in the same manner as in Example 1, the title compound (compound 9c) (52 mg, 23%) was obtained.

ESIMS m/z: 561 $(M+H)^+$; $^1$H NMR (270 MHz, $CDCl_3$, δ): 0.95-1.08 (m, 2H), 1.08-1.19 (m, 2H), 1.94-2.08 (m, 1H), 2.31 (s, 3H), 4.27-4.49 (m, 2H), 4.79 (d, J=12.8 Hz, 1H), 5.52 (d, J=12.8 Hz, 1H), 6.50-6.59 (m, 1H), 6.63-6.74 (m, 2H), 6.84-6.99 (m, 1H), 7.05-7.23 (m, 4H), 7.35-7.61 (m, 2H).

Example 70

(E)-3-(1-{3-fluoro-8-[(2-isopropyl-8-methoxyimidazo[1,2-a]pyridin-3-yl)methyl]dibenzo[b,e]oxepin-11(6H)-ylidene}ethyl)-1,2,4-oxadiazol-5(4H)-one (Compound 9d)

Using (E)-2-{3-fluoro-8-[(2-isopropyl-8-methoxyimidazo[1,2-a]pyridin-3-yl)methyl]dibenzo[b,e]oxepin-11(6H)-ylidene}propanenitrile (148 mg, 0.32 mmol) obtained in Reference Example 9D, and in the same manner as in Example 1, the title compound (compound 9d) (68 mg, 41%) was obtained.

ESIMS m/z: 527 $(M+H)^+$; $^1$H NMR (270 MHz, $CDCl_3$, δ): 1.36-1.50 (m, 6H), 2.27 (s, 3H), 3.12-3.28 (m, 1H), 3.97 (s, 3H), 4.23-4.37 (m, 2H), 4.72 (d, J=12.7 Hz, 1H), 5.50 (d, J=12.7 Hz, 1H), 6.41 (d, J=7.8 Hz, 1H), 6.48-6.57 (m, 1H), 6.59-6.71 (m, 2H), 7.02-7.19 (m, 4H), 7.22 (d, J=6.8 Hz, 1H).

Example 71

(E)-3-[1-(3-fluoro-8-{[8-methoxy-2-(methoxymethyl)imidazo[1,2-a]pyridin-3-yl]methyl}dibenzo[b,e]oxepin-11(6H)-ylidene)ethyl]-1,2,4-oxadiazol-5(4H)-one (Compound 9e)

Using (E)-2-(3-fluoro-8-{[8-methoxy-2-(methoxymethyl)imidazo[1,2-a]pyridin-3-yl]methyl}dibenzo[b,e]oxepin-11(6H)-ylidene)propanenitrile (75 mg, 0.16 mmol) obtained in Reference Example 9E, and in the same manner as in Example 14, the title compound (compound 9e) (35 mg, 42%) was obtained.

ESIMS m/z: 529 $(M+H)^+$; $^1$H NMR (270 MHz, $CDCl_3$, δ): 2.28 (s, 3H), 3.39 (s, 3H), 3.96 (s, 3H), 4.37 (s, 2H), 4.66 (d, J=12.7 Hz, 1H), 4.67 (s, 2H), 5.51 (d, J=12.7 Hz, 1H), 6.45-6.68 (m, 2H), 6.64 (t, J=7.3 Hz, 1H), 6.77 (t, J=6.8 Hz, 1H), 7.04-7.21 (m, 4H), 7.35 (d, J=6.8 Hz, 1H).

Example 72

(E)-3-[1-(3-fluoro-8-{[2-isopropyl-8-(methoxy-$d_3$)-imidazo[1,2-a]pyridin-3-yl]methyl}dibenzo[b,e]oxepin-11(6H)-ylidene)ethyl]-1,2,4-oxadiazol-5(4H)-one (Compound 9f)

Using (E)-2-(3-fluoro-8-{[2-isopropyl-8-(methoxy-$d_3$)-imidazo[1,2-a]pyridin-3-yl]methyl}dibenzo[b,e]oxepin-11(6H)-ylidene)propanenitrile (123 mg, 0.26 mmol) obtained in Reference Example 9F, and in the same manner as in Example 1, the title compound (compound 9f) (57 mg, 41%) was obtained.

ESIMS m/z: 530 $(M+H)^+$; $^1$H NMR (300 MHz, $CDCl_3$, δ): 1.37-1.48 (m, 6H), 2.28 (s, 3H), 3.15-3.29 (m, 1H), 4.21-4.39 (m, 2H), 4.73 (d, J=12.5 Hz, 1H), 5.53 (d, J=12.5 Hz, 1H), 6.43-6.57 (m, 2H), 6.60-6.75 (m, 2H), 7.03-7.18 (m, 4H), 7.21-7.27 (m, 1H).

Example 73

(E)-3-[1-(8-{[8-(difluoromethoxy)-2-isopropylimidazo[1,2-a]pyridin-3-yl]methyl}-3-fluorodibenzo[b,e]oxepin-11(6H)-ylidene)ethyl]-1,2,4-oxadiazol-5(4H)-one (Compound 9g)

Using (E)-2-(8-{[8-(difluoromethoxy)-2-isopropylimidazo[1,2-a]pyridin-3-yl]methyl}-3-fluorodibenzo[b,e]oxepin-11(6H)-ylidene)propanenitrile (149 mg, 0.30 mmol) obtained in Reference Example 9G, and in the same manner as in Example 1, the title compound (compound 9g) (65 mg, 39%) was obtained.

ESIMS m/z: 563 $(M+H)^+$; $^1$H NMR (300 MHz, $CDCl_3$, δ): 1.34-1.44 (m, 6H), 2.28 (s, 3H), 3.14-3.27 (m, 1H), 4.25-4.39 (m, 2H), 4.77 (d, J=12.5 Hz, 1H), 5.52 (d, J=12.5 Hz, 1H), 6.54 (dd, J=10.3, 2.6 Hz, 1H), 6.61-6.70 (m, 2H), 6.85-6.93 (m, 1H), 7.07 (dd, J=8.6, 6.4 Hz, 1H), 7.10-7.18 (m, 3H), 7.44 (dd, J=7.0, 0.7 Hz, 1H), 7.51 (t, J=74.4 Hz, 1H).

Example 74

(E)-3-[1-(8-{[2-cyclopropyl-8-(methoxy-$d_3$)-imidazo[1,2-a]pyridin-3-yl]methyl}-3-fluorodibenzo[b,e]oxepin-11(6H)-ylidene)ethyl]-1,2,4-oxadiazol-5(4H)-one (Compound 9h)

Using (E)-2-(8-{[2-cyclopropyl-8-(methoxy-$d_3$-)imidazo[1,2-a]pyridin-3-yl]methyl}-3-fluorodibenzo[b,e]oxepin-11

(6H)-ylidene)propanenitrile (147 mg, 0.31 mmol) obtained in Reference Example 9H, and in the same manner as in Example 1, the title compound (compound 9h) (51 mg, 31%) was obtained.

ESIMS m/z: 528 $(M+H)^+$; $^1H$ NMR (300 MHz, $CDCl_3$, δ): 0.91-1.01 (m, 2H), 1.12-1.22 (m, 2H), 1.93-2.07 (m, 1H), 2.28 (s, 3H), 4.28-4.44 (m, 2H), 4.73 (d, J=12.5 Hz, 1H), 5.49 (d, J=12.5 Hz, 1H), 6.39 (d, J=7.7 Hz, 1H), 6.53 (dd, J=10.3, 2.6 Hz, 1H), 6.57-6.69 (m, 2H), 7.06 (dd, J=8.8, 6.6 Hz, 1H), 7.11-7.17 (m, 2H), 7.19-7.26 (m, 2H).

Example 75

(E)-3-(1-{8-[(2-cyclopropyl-8-fluoroimidazo[1,2-a]pyridin-3-yl)methyl]-3-fluorodibenzo[b,e]oxepin-11(6H)-ylidene}ethyl)-1,2,4-oxadiazol-5(4H)-one (Compound 9i)

Using (E)-2-{8-[(2-cyclopropyl-8-fluoroimidazo[1,2-a]pyridin-3-yl)methyl]-3-fluorodibenzo[b,e]oxepin-11(6H)-ylidene}propanenitrile (155 mg, 0.342 mmol) obtained in Reference Example 9I, and in the same manner as in Example 1, the title compound (compound 9i) (32 mg, 17%) was obtained.

ESIMS m/z: 513 $(M+H)^+$; $^1H$ NMR (270 MHz, $CDCl_3$, δ): 0.95-1.09 (m, 2H), 1.09-1.22 (m, 2H), 1.99-2.10 (m, 1H), 2.28 (s, 3H), 4.35 (d, J=17.6 Hz, 1H), 4.42 (d, J=17.6 Hz, 1H), 4.75 (d, J=12.7 Hz, 1H), 5.51 (d, J=12.7 Hz, 1H), 6.53 (dd, J=2.9, 9.8 Hz, 1H), 6.54-6.70 (m, 2H), 6.77-6.84 (m, 1H), 7.05-7.27 (m, 4H), 7.41 (d, J=6.8 Hz, 1H).

Example 76

(E)-3-[1-(8-{[8-(difluoromethoxy)-2-(methoxymethyl)imidazo[1,2-a]pyridin-3-yl]methyl}-3-fluorodibenzo[b,e]oxepin-11(6H)-ylidene)ethyl]-1,2,4-oxadiazol-5(4H)-one (Compound 9j)

Using (E)-2-(8-{[8-(difluoromethoxy)-2-(methoxymethyl)imidazo[1,2-a]pyridin-3-yl]methyl}-3-fluorodibenzo[b,e]oxepin-11(6H)-ylidene)propanenitrile (48 mg, 0.089 mmol) obtained in Reference Example 9J, and in the same manner as in Example 14, the title compound (compound 9j) (19 mg, 36%) was obtained.

ESIMS m/z: 565 $(M+H)^+$; $^1H$ NMR (270 MHz, $CDCl_3$, δ): 2.28 (s, 3H), 3.44 (s, 3H), 4.36 (d, J=12.9 Hz, 1H), 4.45 (d, J=12.9 Hz, 1H), 4.71 (s, 2H), 4.75 (d, J=12.6 Hz, 1H), 5.52 (d, J=12.6 Hz, 1H), 6.53 (dd, J=2.6, 10.2 Hz, 1H), 6.66 (d t, J=2.6, 8.3 Hz, 1H), 6.78 (t, J=7.1 Hz, 1H), 6.95-7.28 (m, 5H), 7.21 (t, J=72.4 Hz, 1H), 7.56 (d, J=5.9 Hz, 1H).

Example 77

(E)-3-(1-{3-fluoro-8-[(8-methoxy-2-propylimidazo[1,2-a]pyridin-3-yl)methyl]dibenzo[b,e]oxepin-11(6H)-ylidene}ethyl)-1,2,4-oxadiazol-5(4H)-one (Compound 9k)

Using (E)-2-{3-fluoro-8-[(8-methoxy-2-cyclopropylimidazo[1,2-a]pyridin-3-yl)methyl]dibenzo[b,e]oxepin-11(6H)-ylidene}propanenitrile (74 mg, 0.158 mmol) obtained in Reference Example 9K, and in the same manner as in Example 1, the title compound (compound 9k) (2.5 mg, 3%) was obtained.

ESIMS m/z: 527 $(M+H)^+$; $^1H$ NMR (270 MHz, $CDCl_3$, δ): 0.90 (t, J=7.3 Hz, 3H), 1.70-1.90 (m, 2H), 2.23 (s, 3H), 2.77-2.95 (m, 2H), 3.96 (s, 3H), 4.26 (s, 2H), 4.74 (d, J=12.8 Hz, 1H), 5.65 (d, J=12.8 Hz, 1H), 6.48 (dd, J=10.3, 2.6 Hz, 1H), 6.60-6.73 (m, 1H), 6.78-6.93 (m, 2H), 6.94-7.21 (m, 4H), 7.41 (d, J=6.6 Hz, 1H).

Example 78

(E)-3-[1-(8-{[8-chloro-2-(methoxy-$d_3$-methyl)imidazo[1,2-a]pyridin-3-yl]methyl}-3-fluorodibenzo[b,e]oxepin-11(6H)-ylidene)ethyl]-1,2,4-oxadiazol-5(4H)-one (Compound 9l)

Using (E)-2-(8-{[8-chloro-2-(methoxy-$d_3$-methyl)imidazo[1,2-a]pyridin-3-yl]methyl}-3-fluorodibenzo[b,e]oxepin-11(6H)-ylidene)propanenitrile (135 mg, 0.28 mmol) obtained in Reference Example 9L, and in the same manner as in Example 1, the title compound (compound 9l) (78 mg, 51%) was obtained.

ESIMS m/z: 536 $(M+H)^+$; $^1H$ NMR (270 MHz, $CDCl_3$, δ): 2.29 (s, 3H), 4.42 (s, 2H), 4.65 (d, J=12.7 Hz, 1H), 4.70 (s, 2H), 5.48 (d, J=12.7 Hz, 1H), 6.50-6.55 (m, 1H), 6.64-6.76 (m, 2H), 7.05-7.15 (m, 2H), 7.16 (d, J=7.8 Hz, 1H), 7.23-7.29 (m, 2H), 7.60 (d, J=6.8 Hz, 1H).

Example 79

(E)-3-(1-{8-[(7-chloro-2-cyclopropylimidazo[1,2-a]pyridin-3-yl)methyl]-3-fluorodibenzo[b,e]oxepin-11(6H)-ylidene}ethyl)-1,2,4-oxadiazol-5(4H)-one (Compound 10a)

Using (E)-2-{8-[(7-chloro-2-cyclopropylimidazo[1,2-a]pyridin-3-yl)methyl]-3-fluorodibenzo[b,e]oxepin-11(6H)-ylidene}propanenitrile (83 mg, 0.177 mmol) obtained in Reference Example 10A, and in the same manner as in Example 1, the title compound (compound 10a) (42 mg, 44%) was obtained.

ESIMS m/z: 529 $(M+H)^+$; $^1H$ NMR (270 MHz, DMSO-$d_6$, δ): 0.82-0.99 (m, 4H), 2.09-2.20 (m, 1H), 2.15 (s, 3H), 4.38 (d, J=17.1 Hz, 1H), 4.44 (d, J=17.1 Hz, 1H), 4.90 (d, J=12.7 Hz, 1H), 5.49 (d, J=12.7 Hz, 1H), 6.65 (dd, J=10.8, 2.0 Hz, 1H), 6.74-6.84 (m, 1H), 6.84 (dd, J=7.8, 2.0 Hz, 1H), 7.02 (d, J=7.8, 1H), 7.16 (d, J=7.8, 1H), 7.19-7.20 (m, 1H), 7.26 (s, 1H), 7.57 (d, J=2.0, 1H), 8.09 (d, J=7.8, 1H).

Example 80

(E)-3-(1-{8-[(6-chloro-2-cyclopropylimidazo[1,2-a]pyridin-3-yl)methyl]-3-fluorodibenzo[b,e]oxepin-11(6H)-ylidene}ethyl)-1,2,4-oxadiazol-5(4H)-one (Compound 10b)

Using (E)-2-{8-[(6-chloro-2-cyclopropylimidazo[1,2-a]pyridin-3-yl)methyl]-3-fluorodibenzo[b,e]oxepin-11(6H)-ylidene}propanenitrile (88 mg, 0.187 mmol) obtained in Reference Example 10B, and in the same manner as in Example 1, the title compound (compound 10b) (37 mg, 36%) was obtained.

ESIMS m/z: 529 $(M+H)^+$; $^1H$ NMR (270 MHz, $CDCl_3$, δ): 0.95-1.20 (m, 4H), 1.94-2.07 (m, 1H), 2.28 (s, 3H), 4.34 (s, 2H), 4.80 (d, J=12.7 Hz, 1H), 5.54 (d, J=12.7 Hz, 1H), 6.50-6.73 (m, 2H), 7.00-7.30 (m, 5H), 7.45 (d, J=9.8 Hz, 1H), 7.67 (s, 1H).

Example 81

(E)-3-(1-{8-[(2-cyclopropyl-7-fluoroimidazo[1,2-a]pyridin-3-yl)methyl]-3-fluorodibenzo[b,e]oxepin-11(6H)-ylidene}ethyl)-1,2,4-oxadiazol-5(4H)-one (Compound 10c)

Using (E)-2-{8-[(2-cyclopropyl-7-fluoroimidazo[1,2-a]pyridin-3-yl)methyl]-3-fluorodibenzo[b,e]oxepin-11(6H)-ylidene}propanenitrile (21 mg, 0.046 mmol) obtained in Reference Example 10C, and in the same manner as in Example 1, the title compound (compound 10c) (1.6 mg, 7%) was obtained.

ESIMS m/z: 513 $(M+H)^+$; $^1$H NMR (270 MHz, $CDCl_3$, δ): 0.91-1.18 (m, 4H), 1.89-2.08 (m, 1H), 2.29 (s, 3H), 4.26-4.50 (m, 2H), 4.78 (d, J=12.8 Hz, 1H), 5.53 (d, J=12.8 Hz, 1H), 6.39-6.77 (m, 3H), 7.00-7.30 (m, 5H), 7.44-7.59 (m, 1H).

Example 82

(E)-3-(1-{8-[(2-cyclopropyl-6-fluoroimidazo[1,2-a]pyridin-3-yl)methyl]-3-fluorodibenzo[b,e]oxepin-11(6H)-ylidene}ethyl)-1,2,4-oxadiazol-5(4H)-one (Compound 10d)

Using (E)-2-{8-[(2-cyclopropyl-6-fluoroimidazo[1,2-a]pyridin-3-yl)methyl]-3-fluorodibenzo[b,e]oxepin-11(6H)-ylidene}propanenitrile (110 mg, 0.24 mmol) obtained in Reference Example 10D, and in the same manner as in Example 14, the title compound (compound 10d) (48 mg, 39%) was obtained.

ESIMS m/z: 513 $(M+H)^+$; $^1$H NMR (300 MHz, $CDCl_3$, δ): 0.96-1.16 (m, 4H), 1.94-2.07 (m, 1H), 2.28 (s, 3H), 4.35 (s, 2H), 4.80 (d, J=12.5 Hz, 1H), 5.54 (d, J=12.5 Hz, 1H), 6.54 (dd, J=10.3, 2.6 Hz, 1H), 6.61-6.70 (m, 1H), 6.97-7.11 (m, 2H), 7.11-7.26 (m, 3H), 7.48 (dd, J=10.1, 4.9 Hz, 1H), 7.52-7.58 (m, 1H).

Example 83

(E)-3-{1-(8-{[7-chloro-2-(methoxymethyl)imidazo[1,2-a]pyridin-3-yl]methyl}-3-fluorodibenzo[b,e]oxepin-11(6H)-ylidene)ethyl}-1,2,4-oxadiazol-5(4H)-one (Compound 10e)

Using (E)-2-(8-{[7-chloro-2-(methoxymethyl)imidazo[1,2-a]pyridin-3-yl]methyl}-3-fluorodibenzo[b,e]oxepin-11(6H)-ylidene)propanenitrile (72 mg, 0.15 mmol) obtained in Reference Example 10E, and in the same manner as in Example 14, the title compound (compound 10e) (16 mg, 19%) was obtained.

ESIMS m/z: 533 $(M+H)^+$; $^1$H NMR (270 MHz, DMSO-$d_6$, δ): 2.15 (s, 3H), 3.27 (s, 3H), 4.39 (s, 2H), 4.56 (s, 2H), 4.87 (d, J=12.5 Hz, 1H), 5.48 (d, J=12.5 Hz, 1H), 6.65 (dd, J=2.6, 10.8 Hz, 1H), 6.79 (d t, J=2.7, 8.3 Hz, 1H), 6.81-6.96 (m, 1H), 7.18 (d, J=7.9 Hz, 1H), 7.22 (d, J=6.9 Hz, 1H), 7.25 (d, J=6.9 Hz, 1H), 7.27 (s, 1H), 7.70 (s, 1H), 8.16 (d, J=7.6 Hz, 1H), 12.08 (br s, 1H).

Example 84

(E)-3-(1-{8-[(2-cyclopropyl-7-methoxyimidazo[1,2-a]pyridin-3-yl)methyl]-3-fluorodibenzo[b,e]oxepin-11(6H)-ylidene}ethyl)-1,2,4-oxadiazol-5(4H)-one (Compound 10g)

Using (E)-2-{8-[(2-cyclopropyl-7-methoxyimidazo[1,2-a]pyridin-3-yl)methyl]-3-fluorodibenzo[b,e]oxepin-11(6H)-ylidene}propanenitrile (127 mg, 0.27 mmol) obtained in Reference Example 10G, and in the same manner as in Example 1, the title compound (compound 10g) (7.2 mg, 5%) was obtained.

ESIMS m/z: 525 $(M+H)^+$; $^1$H NMR (300 MHz, $CDCl_3$, δ): 0.92-1.02 (m, 2H), 1.04-1.12 (m, 2H), 1.89-2.01 (m, 1H), 2.28 (s, 3H), 3.78 (s, 3H), 4.23-4.39 (m, 2H), 4.74 (d, J=12.5 Hz, 1H), 5.52 (d, J=12.5 Hz, 1H), 6.43 (dd, J=7.3, 2.6 Hz, 1H), 6.53 (dd, J=10.3, 2.6 Hz, 1H), 6.60-6.68 (m, 2H), 6.85 (d, J=2.2 Hz, 1H), 7.02-7.22 (m, 4H), 7.40 (d, J=7.3 Hz, 1H).

Example 85

(E)-3-[1-(3-fluoro-8-{[2-methyl-8-(trifluoromethyl)imidazo[1,2-a]pyridin-3-yl]methyl}dibenzo[b,e]oxepin-11(6H)-ylidene)ethyl]-1,2,4-oxadiazol-5(4H)-one (Compound 10h)

Using (E)-2-(3-fluoro-8-{[2-methyl-8-(trifluoromethyl)imidazo[1,2-a]pyridin-3-yl]methyl}dibenzo[b,e]oxepin-11(6H)-ylidene)propanenitrile (74 mg, 0.16 mmol) obtained in Reference Example 10H, and in the same manner as in Example 14, the title compound (compound 10h) (9.5 mg, 11%) was obtained.

ESIMS m/z: 537 $(M+H)^+$; $^1$H NMR (270 MHz, $CDCl_3$, δ): 2.21 (s, 3H), 2.34 (s, 3H), 4.19-4.40 (m, 3H), 5.42 (d, J=12.5 Hz, 1H), 6.48 (dd, J=2.6, 10.3 Hz, 1H), 6.63-6.74 (m, 2H), 6.85 (t, J=7.0 Hz, 1H), 7.11-7.21 (m, 1H), 7.23-7.32 (m, 2H), 7.56 (d, J=7.3 Hz, 1H), 7.55 (d, J=7.0 Hz, 1H).

Example 86

(E)-3-(1-{8-[(8-bromo-2-cyclopropylimidazo[1,2-a]pyridin-3-yl)methyl]-3-fluorodibenzo[b,e]oxepin-11(6H)-ylidene}ethyl)-1,2,4-oxadiazol-5(4H)-one (Compound 10i)

Using (E)-2-{8-[(8-bromo-2-cyclopropylimidazo[1,2-a]pyridin-3-yl)methyl]-3-fluorodibenzo[b,e]oxepin-11(6H)-ylidene}propanenitrile (72 mg, 0.14 mmol) obtained in Reference Example 10I, and in the same manner as in Example 1, the title compound (compound 10i) (30 mg, 38%) was obtained.

ESIMS m/z: 573 $(M+H)^+$; $^1$H NMR (270 MHz, $CDCl_3$, δ): 0.90-1.29 (m, 4H), 1.89-2.08 (m, 1H), 2.22 (s, 3H), 4.21-4.36 (m, 2H), 4.68 (d, J=12.7 Hz, 1H), 5.54 (d, J=12.7 Hz, 1H), 6.45 (dd, J=10.2, 2.4 Hz, 1H), 6.49-6.60 (m, 1H), 6.66-6.75 (m, 1H), 6.95-7.20 (m, 4H), 7.42 (d, J=7.8 Hz, 1H), 7.60 (d, J=6.8 Hz, 1H).

Example 87

(E)-3-[1-(8-{[7-chloro-2-methylimidazo[1,2-a]pyridin-3-yl]methyl}dibenzo[b,e]oxepin-11(6H)-ylidene)ethyl]-1,2,4-oxadiazolo-5(4H)-one (Compound 10j)

Using (E)-2-(8-{[7-chloro-2-methylimidazo[1,2-a]pyridin-3-yl]methyl}-3-fluorodibenzo[b,e]oxepin-11(6H)-ylidene)propanenitrile (360 mg, 0.811 mmol) obtained in Reference Example 10J, and in the same manner as in Example 14, the title compound (compound 10j) (84 mg, 20%) was obtained.

ESIMS m/z: 503 $(M+H)^+$; $^1$H NMR (270 MHz, DMSO-$d_6$, δ): 2.15 (s, 3H), 2.37 (s, 3H), 4.28 (d, J=17.1 Hz, 1H), 4.34 (d, J=17.1 Hz, 1H), 4.92 (d, J=11.7 Hz, 1H), 5.47 (d, J=11.7 Hz,

1H), 6.65 (d, J=10.7 Hz, 1H), 6.81-6.90 (m, 2H), 7.00 (d, J=7.8 Hz, 1H), 7.01-7.29 (m, 3H), 7.59 (s, 1H), 8.11 (d, J=6.8 Hz, 1H), 12.10 (br s, 1H).

Example 88

(E)-3-(1-{8-[(2-cyclopropyl-8-methylimidazo[1,2-a]pyridin-3-yl)methyl]-3-fluorodibenzo[b,e]oxepin-11(6H)-ylidene}ethyl)-1,2,4-oxadiazol-5(4H)-one (Compound 10k)

Using (E)-2-{8-[(2-cyclopropyl-8-methylimidazo[1,2-a]pyridin-3-yl)methyl]-3-fluorodibenzo[b,e]oxepin-11(6H)-ylidene}propanenitrile (180 mg, 0.40 mmol) obtained in Reference Example 10K, and in the same manner as in Example 1, the title compound (compound 10k) (85 mg, 42%) was obtained.

ESIMS m/z: 509 $(M+H)^+$; $^1H$ NMR (270 MHz, $CDCl_3$, δ): 0.94-1.24 (m, 4H), 1.95-2.10 (m, 1H), 2.27 (s, 3H), 2.53 (s, 3H), 4.29-4.44 (m, 2H), 4.72 (d, J=12.7 Hz, 1H), 5.47 (d, J=12.7 Hz, 1H), 6.53 (dd, J=10.2, 2.4 Hz, 1H), 6.55-6.69 (m, 2H), 6.88 (d, J=6.8 Hz, 1H), 7.00-7.18 (m, 3H), 7.21 (d, J=7.8 Hz, 1H), 7.46 (d, J=6.8 Hz, 1H).

Example 89

(E)-3-(1-{8-[(7-chloro-2-ethylimidazo[1,2-a]pyridin-3-yl)methyl]-3-fluorodibenzo[b,e]oxepin-11(6H)-ylidene}ethyl)-1,2,4-oxadiazol-5(4H)-one (Compound 10l)

Using (E)-2-{8-[(7-chloro-2-ethylimidazo[1,2-a]pyridin-3-yl)methyl]-3-fluorodibenzo[b,e]oxepin-11(6H)-ylidene}propanenitrile (200 mg, 0.437 mmol) obtained in Reference Example 10L, and in the same manner as in Example 1, the title compound (compound 10l) (112 mg, 50%) was obtained.

ESIMS m/z: 517 $(M+H)^+$; $^1H$ NMR (270 MHz, DMSO-$d_6$, δ): 1.21 (t, J=7.5 Hz, 3H), 2.15 (s, 3H), 2.72 (q, J=7.5 Hz, 2H), 4.32 (s, 2H), 4.91 (d, J=12.5 Hz, 1H), 5.48 (d, J=12.5 Hz, 1H), 6.65 (dd, J=2.7, 10.7 Hz, 1H), 6.79 (dt, J=2.6, 8.4 Hz, 1H), 6.85 (dd, J=2.2, 7.3 Hz, 1H), 7.01 (d, J=7.7 Hz, 1H), 7.12 (d, J=7.7 Hz, 1H), 7.17-7.29 (m, 2H), 7.63 (d, J=1.8 Hz, 1H), 8.11 (d, J=7.3 Hz, 1H), 12.11 (br s, 1H).

Example 90

(E)-3-(1-{8-[(8-chloro-2-methylimidazo[1,2-a]pyridin-3-yl)methyl]-3-fluorodibenzo[b,e]oxepin-11(6H)-ylidene}ethyl)-1,2,4-oxadiazol-5(4H)-one (Compound 11a)

Using (E)-2-{8-[(8-chloro-2-methylimidazo[1,2-a]pyridin-3-yl)methyl]-3-fluorodibenzo[b,e]oxepin-11(6H)-ylidene}propanenitrile (329 mg, 0.741 mmol) obtained in Reference Example 11A, and in the same manner as in Example 1, the title compound (compound 11a) (18 mg, 5%) was obtained.

ESIMS m/z: 503 $(M+H)^+$; $^1H$ NMR (270 MHz, $CDCl_3$, δ): 2.16 (s, 3H), 2.34 (s, 3H), 3.96-4.43 (m, 3H), 5.37 (d, J=12.8 Hz, 1H), 6.39-6.56 (m, 2H), 6.58-6.82 (m, 2H), 7.12-7.40 (m, 4H), 7.47-7.60 (m, 1H).

Example 91

(E)-3-[1-(3-fluoro-8-{[2-methyl-7-(trifluoromethyl)imidazo[1,2-a]pyridin-3-yl]methyl}dibenzo[b,e]oxepin-11(6H)-ylidene)ethyl]-1,2,4-oxadiazol-5(4H)-one (Compound 11b)

Using (E)-2-(3-fluoro-8-{[2-methyl-7-(trifluoromethyl)imidazo[1,2-a]pyridin-3-yl]methyl}dibenzo[b,e]oxepin-11(6H)-ylidene)propanenitrile (450 mg, 0.943 mmol) obtained in Reference Example 11B, and in the same manner as in Example 14, the title compound (compound 11b) (350 mg, 70%) was obtained.

ESIMS m/z: 537 $(M+H)^+$; $^1H$ NMR (270 MHz, $CDCl_3$, δ): 2.27 (s, 3H), 2.62 (s, 3H), 4.27-4.40 (m, 2H), 4.74-4.78 (m, 1H), 5.48-5.55 (m, 1H), 6.62-6.68 (m, 1H), 7.03-7.16 (m, 5H), 7.27-7.35 (m, 2H), 7.73-7.74 (m, 1H).

Example 92

(E)-3-[1-(8-{[2-cyclopropyl-8-(2-hydroxypropan-2-yl)imidazo[1,2-a]pyridin-3-yl]methyl}-3-fluorodibenzo[b,e]oxepin-11(6H)-ylidene)ethyl]-1,2,4-oxadiazol-5(4H)-one (Compound 11c)

Using (E)-2-(8-{[2-cyclopropyl-8-(2-hydroxypropan-2-yl)imidazo[1,2-a]pyridin-3-yl]methyl}-3-fluorodibenzo[b,e]oxepin-11(6H)-ylidene)propanenitrile (240 mg, 0.49 mmol) obtained in Reference Example 11C, and in the same manner as in Example 1, the title compound (compound 11c) (68 mg, 25%) was obtained.

ESIMS m/z: 553 $(M+H)^+$; $^1H$ NMR (300 MHz, $CDCl_3$, δ): 0.92-1.03 (m, 2H), 1.06-1.15 (m, 2H), 1.67 (s, 3H), 1.67 (s, 3H), 1.93-2.04 (m, 1H), 2.28 (s, 3H), 4.29-4.45 (m, 2H), 4.79 (d, J=12.8 Hz, 1H), 5.52 (d, J=12.8 Hz, 1H), 6.54 (dd, J=9.9, 2.6 Hz, 1H), 6.61-6.71 (m, 2H), 6.92-6.98 (m, 1H), 7.02-7.10 (m, 1H), 7.12-7.26 (m, 3H), 7.48 (d, J=6.6 Hz, 1H).

Example 93

(E)-3-[1-(8-{[2-cyclopropyl-8-(trifluoromethyl)imidazo[1,2-a]pyridin-3-yl]methyl}-3-fluorodibenzo[b,e]oxepin-11(6H)-ylidene)ethyl]-1,2,4-oxadiazol-5(4H)-one (Compound 11d)

Using (E)-2-(8-{[2-cyclopropyl-8-(trifluoromethyl)imidazo[1,2-a]pyridin-3-yl]methyl}-3-fluorodibenzo[b,e]oxepin-11(6H)-ylidene)propanenitrile (290 mg, 0.58 mmol) obtained in Reference Example 11D, and in the same manner as in Example 1, the title compound (compound 11d) (149 mg, 46%) was obtained.

ESIMS m/z: 563 $(M+H)^+$; $^1H$ NMR (270 MHz, DMSO-$d_6$, δ): 0.90-0.95 (m, 4H), 2.15 (s, 3H), 2.11-2.24 (m, 1H), 4.35-4.54 (m, 2H), 4.92 (d, J=12.7 Hz, 1H), 5.49 (d, J=12.7 Hz, 1H), 6.65 (dd, J=10.7, 2.0 Hz, 1H), 6.74-6.82 (m, 1H), 6.91 (t, J=6.8 Hz, 1H), 7.03 (d, J=7.8 Hz, 1H), 7.14-7.30 (m, 2H), 7.30 (s, 1H), 7.58 (d, J=7.8 Hz, 1H), 8.53 (d, J=6.8 Hz, 1H), 12.10 (br s, 1H).

Example 94

(E)-3-(1-{8-[(2-cyclopropylimidazo[1,2-b]pyridazin-3-yl)methyl]-3-fluorodibenzo[b,e]oxepin-11(6H)-ylidene}ethyl)-1,2,4-oxadiazol-5(4H)-one (Compound 11e)

Using (E)-2-{8-[(2-cyclopropylimidazo[1,2-b]pyridazin-3-yl)methyl]-3-fluorodibenzo[b,e]oxepin-11(6H)- ylidene}propanenitrile (40 mg, 0.092 mmol) obtained in Reference Example 11E, and in the same manner as in Example 14, the title compound (compound 11e) (2.2 mg, 4.4%) was obtained.

ESIMS m/z: 496 $(M+H)^+$; $^1$H NMR (300 MHz, $CDCl_3$, δ): 1.01-1.17 (m, 4H), 2.05-2.11 (m, 1H), 2.27 (s, 3H), 4.48 (s, 2H), 4.79 (d, J=12.5 Hz, 1H), 5.53 (d, J=12.5 Hz, 1H), 6.52 (dd, J=10.3, 2.6 Hz, 1H). 6.60-6.67 (m, 1H), 6.91-7.14 (m, 3H), 7.30-7.35 (m, 2H), 7.80 (dd, J=9.0, 1.6 Hz, 1H), 8.21-8.24 (m, 1H).

Example 95

(E)-3-(1-{3-fluoro-8-[(2-isopropyl-7-methoxyimidazo[1,2-a]pyrimidin-3-yl)methyl]dibenzo[b,e]oxepin-11(6H)-ylidene}ethyl)-1,2,4-oxadiazol-5(4H)-one (Compound 11f)

Using (E)-2-{3-fluoro-8-[(2-isopropyl-7-methoxyimidazo[1,2-a]pyrimidin-3-yl)methyl]dibenzo[b,e]oxepin-11(6H)-ylidene}propanenitrile (110 mg, 0.235 mmol) obtained in Reference Example 11F, and in the same manner as in Example 1, the title compound (compound 11f) (6.8 mg, 5%) was obtained.

ESIMS m/z: 528 $(M+H)^+$; $^1$H NMR (270 MHz, $CDCl_3$, δ): 1.30-1.46 (m, 6H), 2.17 (s, 3H), 3.02-3.20 (m, 1H), 4.01 (s, 3H), 4.09-4.27 (m, 2H), 4.72 (d, J=12.8 Hz, 1H), 5.54 (d, J=12.8 Hz, 1H), 6.14-6.29 (m, 1H), 6.46-6.57 (m, 1H), 6.57-6.67 (m, 1H), 6.94-7.20 (m, 3H), 7.21-7.30 (m, 1H), 7.58-7.70 (m, 1H).

Example 96

(E)-3-(1-{8-[(2-cyclopropylimidazo[1,2-a]pyrazin-3-yl)methyl]-3-fluorodibenzo[b,e]oxepin-11(6H)-ylidene}ethyl)-1,2,4-oxadiazol-5(4H)-one (Compound 11g)

Using (E)-2-{8-[(2-cyclopropylimidazo[1,2-a]pyrazin-3-yl)methyl]-3-fluorodibenzo[b,e]oxepin-11(6H)-ylidene}propanenitrile (28 mg, 0.177 mmol) obtained in Reference Example 11G, and in the same manner as in Example 14, the title compound (compound 11g) (8.9 mg, 28%) was obtained.

ESIMS m/z: 496 $(M+H)^+$; $^1$H NMR (270 MHz, DMSO-$d_6$, δ): 0.82-1.09 (m, 4H), 2.00-2.30 (m, 1H), 2.16 (s, 3H), 4.47 (s, 2H), 4.91 (d, J=12.5 Hz, 1H), 5.49 (d, J=12.5 Hz, 1H), 6.65 (dd, J=10.4, 2.4 Hz, 1H), 6.73-6.85 (m, 1H), 6.77 (d, J=8.2 Hz, 1H), 7.14-7.36 (m, 3H), 7.77 (d, J=4.6 Hz, 1H), 8.22 (d, J=4.6 Hz, 1H), 8.86 (s, 1H), 12.11 (br s, 1H).

Example 97

(E)-3-[1-(8-{[2-cyclopropyl-7-(trifluoromethyl)imidazo[1,2-a]pyrimidin-3-yl]methyl}-3-fluorodibenzo[b,e]oxepin-11(6H)-ylidene)ethyl]-1,2,4-oxadiazol-5(4H)-one (Compound 11h)

Using (E)-2-(8-{[2-cyclopropyl-7-(trifluoromethyl)imidazo[1,2-a]pyrimidin-3-yl]methyl}-3-fluorodibenzo[b,e]oxepin-11(6H)-ylidene)propanenitrile (91 mg, 0.180 mmol) obtained in Reference Example 11H, and in the same manner as in Example 1, the title compound (compound 11h) (1.0 mg, 1%) was obtained.

ESIMS m/z: 564 $(M+H)^+$; $^1$H NMR (270 MHz, $CDCl_3$, δ): 0.80-0.95 (m, 2H), 1.02-1.19 (m, 2H), 1.90-2.10 (m, 1H), 2.29 (s, 3H), 4.28-4.60 (m, 2H), 4.71-4.85 (m, 1H), 5.46-5.62 (m, 1H), 6.47-6.59 (m, 1H), 6.59-6.73 (m, 1H), 6.99-7.35 (m, 5H), 7.97-8.07 (m, 1H).

Example 98

(E)-3-(1-{8-[(2-cyclopropyl-8-methoxyimidazo[1,2-a]pyrazin-3-yl)methyl]-3-fluorodibenzo[b,e]oxepin-11(6H)-ylidene}ethyl)-1,2,4-oxadiazol-5(4H)-one (Compound 11i)

Using (E)-2-{8-[(2-cyclopropyl-8-methoxyimidazo[1,2-a]pyrazin-3-yl)methyl]-3-fluorodibenzo[b,e]oxepin-11(6H)-ylidene}propanenitrile (31 mg, 0.67 mmol) obtained in Reference Example 11I, and in the same manner as in Example 1, the title compound (compound 11i) (9.0 mg, 26%) was obtained.

ESIMS m/z: 526 $(M+H)^+$; $^1$H NMR (270 MHz, $CDCl_3$, δ): 1.10-1.48 (m, 4H), 1.95-2.12 (m, 1H), 2.32 (s, 3H), 4.12 (s, 3H), 4.25-4.48 (m, 2H), 4.76 (d, J=12.8 Hz, 1H), 5.51 (d, J=12.8 Hz, 1H), 6.46-6.77 (m, 2H), 6.98-7.41 (m, 6H).

Example 99

(E)-3-(1-{8-[(2-cyclopropylimidazo[1,2-a]pyrimidin-3-yl)methyl]-3-fluorodibenzo[b,e]oxepin-11(6H)-ylidene}ethyl)-1,2,4-oxadiazol-5(4H)-one (Compound 11j)

Using (E)-2-{8-[(2-cyclopropylimidazo[1,2-a]pyrimidin-3-yl)methyl]-3-fluorodibenzo[b,e]oxepin-11(6H)-ylidene}propanenitrile (118 mg, 0.362 mmol) obtained in Reference Example 11J, and in the same manner as in Example 1, the title compound (compound 11j) (2.2 mg, 1.5%) was obtained.

ESIMS m/z: 496 $(M+H)^+$; $^1$H NMR (270 MHz, $CDCl_3$, δ): 0.74-0.93 (m, 2H), 1.00-1.19 (m, 2H), 1.99-2.15 (m, 1H), 2.29 (s, 3H), 4.39 (s, 2H), 4.73 (d, J=12.7 Hz, 1H), 5.55 (d, J=12.7 Hz, 1H), 6.51 (d, J=10.7 Hz, 1H), 6.59-6.72 (m, 1H), 6.89-7.30 (m, 1H), 7.06-7.28 (m, 4H), 7.96 (dd, J=6.8, Hz, 1H), 8.37-8.48 (m, 1H).

Example 100

(E)-3-({8-[(8-chloro-2-cyclopropylimidazo[1,2-a]pyridin-3-yl)methyl]-3-fluorodibenzo[b,e]oxepin-11(6H)-ylidene}(cyclopropyl)methyl)-1,2,4-oxadiazol-5(4H)-one (Compound 12a)

Using (E)-2-({8-[(8-chloro-2-cyclopropylimidazo[1,2-a]pyridin-3-yl)methyl]-3-fluorodibenzo[b,e]oxepin-11(6H)-ylidene}-2-cyclopropylacetonitrile (260 mg, 0.524 mmol) obtained in Reference Example 12A, and in the same manner as in Example 14, the title compound (compound 12a) (34 mg, 12%) was obtained.

ESIMS m/z: 555 $(M+H)^+$; $^1$H NMR (270 MHz, $CD_3O$ H, δ): 0.27-0.95 (m, 8H), 1.92-2.07 (m, 2H), 4.32-4.43 (m, 2H), 4.69-4.72 (m, 1H), 5.44-5.47 (m, 1H), 6.42-6.46 (m, 1H), 6.58-6.63 (m, 1H), 6.99-7.01 (m, 2H), 7.06-7.10 (m, 2H), 7.38-7.42 (m, 2H), 7.80-7.86 (m, 1H).

Example 101

(E)-3-(cyclopropyl{3-fluoro-8-[(2-isopropylimidazo[1,2-a]pyridin-3-yl)methyl]dibenzo[b,e]oxepin-11(6H)-ylidene}methyl)-1,2,4-oxadiazol-5(4H)-one (Compound 12b)

Using (E)-2-cyclopropyl-2-(3-fluoro-{8-[(2-isopropylimidazo[1,2-a]pyridin-3-yl)methyl]dibenzo[b,e]oxepin-11

(6H)-ylidene}acetonitrile (260 mg, 0.524 mmol) obtained in Reference Example 12B, and in the same manner as in Example 1, the title compound (compound 12b) (20 mg, 10%) was obtained.

ESIMS m/z: 523 $(M+H)^+$; $^1$H NMR (270 MHz, $CDCl_3$, δ): 0.46-0.99 (m, 4H), 1.24-1.30 (m, 6H), 1.98-2.09 (m, 1H), 3.20-3.32 (m, 1H), 4.18-4.31 (m, 2H), 4.57-4.61 (m, 1H), 5.57-5.61 (m, 1H), 6.61-6.67 (m, 1H), 6.79-6.91 (m, 1H), 7.03-7.08 (m, 2H), 7.17-7.22 (m, 2H), 7.39-7.50 (m, 2H), 7.61-7.68 (m, 1H), 7.80-7.83 (m, 1H).

Example 102

(E)-3-(cyclopropyl{8-[(2-isopropylimidazo[1,2-a]pyridin-3-yl)methyl]-3-fluorodibenzo[b,e]oxepin-11(6H)-ylidene}methyl)-1,2,4-oxadiazol-5(4H)-one (Compound 12c)

Using (E)-2-cyclopropyl-2-{8-[(2-cyclopropylimidazo[1,2-a]pyridin-3-yl)methyl]dibenzo[b,e]oxepin-11(6H)-ylidene}acetonitrile (152 mg, 0.329 mmol) obtained in Reference Example 12C, and in the same manner as in Example 1, the title compound (compound 12c) (25 mg, 15%) was obtained.

ESIMS m/z: 521 $(M+H)^+$; $^1$H NMR (270 MHz, $CDCl_3$, δ): 0.45-1.14 (m, 8H), 1.94-2.08 (m, 1H), 3.61-3.67 (m, 1H), 4.20-4.30 (m, 2H), 4.52-4.56 (m, 1H), 5.48-5.52 (m, 1H), 6.39-6.43 (m, 1H), 6.61-6.66 (m, 3H), 6.92-7.03 (m, 3H), 7.17-7.19 (m, 1H), 7.43-7.48 (m, 1H), 7.61-7.66 (m, 1H).

Example 103

(E)-3-(cyclopropyl{3-fluoro-8-[(2-(methoxymethyl)imidazo[1,2-a]pyridin-3-yl)methyl]dibenzo[b,e]oxepin-11(6H)-ylidene}methyl)-1,2,4-oxadiazol-5(4H)-one (Compound 12d)

Using (E)-2-cyclopropyl-2-{3-fluoro-8-[(2-(methoxymethyl)imidazo[1,2-a]pyridin-3-yl)methyl]dibenzo[b,e]oxepin-11(6H)-ylidene}acetonitrile (150 mg, 0.322 mmol) obtained in Reference Example 12D, and in the same manner as in Example 14, the title compound (compound 12d) (61 mg, 36%) was obtained.

ESIMS m/z: 525 $(M+H)^+$; $^1$H NMR (270 MHz, $CDCl_3$, δ): 0.52-1.18 (m, 4H), 2.03-2.15 (m, 1H), 3.34 (s, 3H), 4.28 (d, J=12.7 Hz, 1H), 4.31 (s, 2H), 4.58 (s, 2H), 5.23 (d, J=12.7 Hz, 1H), 6.44 (d, J=10.7 Hz, 1H), 6.62 (t, J=8.3 Hz, 1H), 6.76 (t, J=6.8 Hz, 1H), 6.86 (s, 1H), 7.06-7.20 (m, 3H), 7.42 (t, J=7.8 Hz, 1H), 7.49 (d, J=9.8 Hz, 1H), 7.65 (d, J=6.8 Hz, 1H).

Example 104

(E)-3-({8-[(8-chloro-2-(methoxymethyl)imidazo[1,2-a]pyridin-3-yl)methyl]-3-fluorodibenzo[b,e]oxepin-11(6H)-ylidene}(cyclopropyl)methyl)-1,2,4-oxadiazol-5(4H)-one (Compound 12e)

Using (E)-2-{8-[(8-chloro-2-(methoxymethyl)imidazo[1,2-a]pyridin-3-yl)methyl]-3-fluorodibenzo[b,e]oxepin-11(6H)-ylidene}-2-cyclopropylacetonitrile (82 mg, 0.17 mmol) obtained in Reference Example 12E, and in the same manner as in Example 14, the title compound (compound 12e) (17 mg, 19%) was obtained.

ESIMS m/z: 559 $(M+H)^+$; $^1$H NMR (270 MHz, $CDCl_3$, δ): 0.45-1.02 (m, 4H), 1.96-2.05 (m, 1H), 3.43 (s, 3H), 4.37 (s, 2H), 4.46-4.51 (m, 1H), 4.67 (s, 2H), 5.49-5.53 (m, 1H), 6.30-6.35 (m, 1H), 6.58-6.67 (m, 1H), 7.01-7.06 (m, 2H), 7.12-7.22 (m, 2H), 7.42-7.52 (m, 2H), 7.75-7.77 (m, 1H).

Example 105

(E)-3-({8-[(7-chloro-2-methylimidazo[1,2-a]pyridin-3-yl)methyl]-3-fluorodibenzo[b,e]oxepin-11(6H)-ylidene}(cyclopropyl)methyl)-1,2,4-oxadiazol-5(4H)-one (Compound 12f)

Using (E)-2-{8-[(7-chloro-2-methylimidazo[1,2-a]pyridin-3-yl)methyl]-3-fluorodibenzo[b,e]oxepin-11(6H)-ylidene}-2-cyclopropylacetonitrile (120 mg, 0.26 mmol) obtained in Reference Example 12F, and in the same manner as in Example 14, the title compound (compound 12f) (19 mg, 14%) was obtained.

ESIMS m/z: 529 $(M+H)^+$; $^1$H NMR (270 MHz, $CDCl_3$, δ): 0.46-1.05 (m, 4H), 2.00-2.10 (m, 1H), 2.40 (s, 3H), 4.20 (s, 2H), 4.44 (d, J=12.2 Hz, 1H), 5.45 (d, J=12.2 Hz, 1H), 6.39 (dd, J=2.4, 7.8 Hz, 1H), 6.59-6.68 (m, 1H), 6.93 (s, 1H), 6.59-6.68 (m, 1H), 6.95-7.08 (m, 2H), 7.19 (d, J=7.8 Hz, 1H), 7.40-7.50 (m, 1H), 7.63-7.78 (m, 1H).

Example 106

(E)-3-({8-[(7-chloro-2-(methoxymethyl)imidazo[1,2-a]pyridin-3-yl)methyl]-3-fluorodibenzo[b,e]oxepin-11(6H)-ylidene}(cyclopropyl)methyl)-1,2,4-oxadiazol-5(4H)-one (Compound 12g)

Using (E)-2-(8-{[7-chloro-2-(methoxymethyl)imidazo[1,2-a]pyridin-3-yl]methyl}-3-fluorodibenzo[b,e]oxepin-11(6H)-ylidene)-2-cyclopropylacetonitrile (80 mg, 0.16 mmol) obtained in Reference Example 12G, and in the same manner as in Example 14, the title compound (compound 12g) (19 mg, 21%) was obtained.

ESIMS m/z: 559 $(M+H)^+$; $^1$H NMR (270 MHz, DMSO-$d_6$, δ): 0.34-0.87 (m, 4H), 1.96-2.03 (m, 1H), 3.36 (s, 3H), 4.37-4.43 (m, 2H), 4.55 (s, 2H), 4.85-4.88 (m, 1H), 5.48-5.51 (m, 1H), 6.65-6.67 (m, 1H), 6.79-6.90 (m, 1H), 6.98-7.08 (m, 1H), 7.18-7.25 (m, 3H), 7.43-7.47 (m, 1H), 7.60-7.68 (m, 1H), 8.10-8.26 (m, 1H).

Example 107

(E)-3-({3-fluoro-8-[2-(methoxy-$d_3$methyl)imidazo[1,2-a]pyridin-3-yl)methyl]dibenzo[b,e]oxepin-11(6H)-ylidene}(cyclopropyl)methyl)-1,2,4-oxadiazol-5(4H)-one (Compound 12h)

Using (E)-2-cyclopropyl-2-(3-fluoro-8-{[2-(methoxy-$d_3$methyl)imidazo[1,2-a]pyridin-3-yl]methyl}dibenzo[b,e]oxepin-11(6H)-ylidene)acetonitrile (92 mg, 0.20 mmol) obtained in Reference Example 12H, and in the same manner as in Example 14, the title compound (compound 12h) (17 mg, 16%) was obtained.

ESIMS m/z: 528 $(M+H)^+$; $^1$H NMR (270 MHz, $CDCl_3$, δ): 0.44-1.00 (m, 4H), 1.99-2.07 (m, 1H), 4.36 (s, 2H), 4.65-4.86 (m, 3H), 5.69 (d, J=12.5 Hz, 1H), 6.26-6.31 (m, 1H), 6.57-6.64 (m, 1H), 7.00-7.02 (m, 1H), 7.18-7.21 (m, 3H), 7.42-7.47 (m, 1H), 7.54-7.61 (m, 1H), 7.84-8.00 (m, 2H).

Example 108

(E)-3-(1-{3-fluoro-8-[(2-methyl-1H-indol-3-yl)methyl]dibenzo[b,e]oxepin-11(6H)-ylidene}ethyl)-1,2,4-oxadiazol-5(4H)-one (Compound 13a)

Using (E)-2-{3-fluoro-8-[(2-methyl-1H-indol-3-yl)methyl]dibenzo[b,e]oxepin-11(6H)-ylidene}propanenitrile (100 mg, 0.245 mmol) obtained in Reference Example 13A, and in the same manner as in Example 14, the title compound (compound 13a) (65 mg, 57%) was obtained.

ESIMS m/z: 468 $(M+H)^+$; $^1H$ NMR (270 MHz, $CDCl_3$, δ): 2.27 (s, 3H), 2.39 (s, 3H), 4.10 (s, 2H), 4.77 (d, J=12.7 Hz, 1H), 5.51 (d, J=12.7 Hz, 1H), 6.52 (dd, J=10.2, 2.4 Hz, 1H), 6.64 (td, J=8.1, 2.4 Hz, 1H), 7.00-7.14 (m, 4H), 7.26-7.36 (m, 4H), 7.86 (br s, 1H).

Example 109

(E)-3-(1-{3-fluoro-8-[(2-propyl-1H-indol-3-yl)methyl]dibenzo[b,e]oxepin-11(6H)-ylidene}ethyl)-1,2,4-oxadiazol-5(4H)-one (Compound 13b)

Using (E)-2-{3-fluoro-8-[(2-propyl-1H-indol-3-yl)methyl]dibenzo[b,e]oxepin-11(6H)-ylidene}propanenitrile (120 mg, 0.275 mmol) obtained in Reference Example 13B, and in the same manner as in Example 14, the title compound (compound 13b) (48 mg, 35%) was obtained.

ESIMS m/z: 496 $(M+H)^+$; $^1H$ NMR (270 MHz, $CDCl_3$, δ): 0.93 (t, J=7.5 Hz, 3H), 1.61-1.70 (m, 2H), 2.26 (s, 3H), 2.69-2.73 (m, 2H), 4.10 (s, 2H), 4.77 (d, J=12.7 Hz, 1H), 5.51 (d, J=12.7 Hz, 1H), 6.50-6.53 (m, 1H), 6.61-6.65 (m, 1H), 7.02-7.07 (m, 3H), 7.10-7.13 (m, 1H), 7.23-7.32 (m, 4H), 7.89 (br s, 1H).

Example 110

(E)-3-(1-{8-[(4,5-dichloro-2-isopropyl-1H-imidazol-1-yl)methyl]-3-fluorodibenzo[b,e]oxepin-11(6H)-ylidene}ethyl)-1,2,4-oxadiazol-5(4H)-one (Compound 13c)

Using (E)-2-{8-[(4,5-dichloro-2-isopropyl-1H-imidazol-1-yl)methyl]-3-fluorodibenzo[b,e]oxepin-11(6H)-ylidene}propanenitrile (150 mg, 0.329 mmol) obtained in Reference Example 13C, and in the same manner as in Example 1, the title compound (compound 13c) (100 mg, 59%) was obtained.

ESIMS m/z: 515 $(M+H)^+$; $^1H$ NMR (270 MHz, $CDCl_3$, δ): 1.03-1.35 (m, 6H), 2.30 (s, 3H), 2.73-2.98 (m, 1H), 4.77-4.94 (m, 1H), 5.05-5.26 (m, 2H), 5.50-5.67 (m, 1H), 6.48-6.77 (m, 2H), 7.02-7.38 (m, 4H).

Example 111

(E)-3-[1-(3-fluoro-8-{[2-(methoxymethyl)-1H-thieno[3,4-d]imidazol-1-yl]methyl}dibenzo[b,e]oxepin-11(6H)-ylidene)ethyl]-1,2,4-oxadiazol-5(4H)-one (Compound 13d)

Using (E)-2-(3-fluoro-8-{[2-(methoxymethyl)-1H-thieno[3,4-d]imidazol-1-yl]methyl}dibenzo[b,e]oxepin-11(6H)-ylidene)propanenitrile (165 mg, 0.37 mmol) obtained in Reference Example 13D, and in the same manner as in Example 1, the title compound (compound 13d) (47 mg, 25%) was obtained.

ESIMS m/z: 505 $(M+H)^+$; $^1H$ NMR (270 MHz, DMSO-$d_6$, δ): 2.17 (s, 3H), 3.27 (s, 3H), 4.57 (s, 2H), 4.96 (d, J=12.8 Hz, 1H), 5.17 (s, 2H), 5.52 (d, J=12.8 Hz, 1H), 6.60 (s, 1H), 6.61-6.72 (m, 1H), 6.72-6.90 (m, 1H), 7.08 (d, J=7.9 Hz, 1H), 7.15-7.35 (m, 3H), 7.42 (s, 1H), 12.14 (br s, 1H).

Example 112

(E)-3-(1-{8-[(2-cyclopropyl-1H-thieno[3,4-d]imidazol-1-yl)methyl]-3-fluorodibenzo[b,e]oxepin-11(6H)-ylidene}ethyl)-1,2,4-oxadiazol-5(4H)-one (Compound 13e)

Using (E)-2-{8-[(2-cyclopropyl-1H-thieno[3,4-d]imidazol-1-yl)methyl]-3-fluorodibenzo[b,e]oxepin-11(6H)-ylidene}propanenitrile (160 mg, 0.36 mmol) obtained in Reference Example 13E, and in the same manner as in Example 1, the title compound (compound 13e) (65 mg, 36%) was obtained.

ESIMS m/z: 501 $(M+H)^+$; $^1H$ NMR (270 MHz, DMSO-$d_6$, δ): 0.90-1.19 (m, 4H), 2.04-2.20 (m, 1H), 2.17 (s, 3H), 4.96 (d, J=12.5 Hz, 1H), 5.34 (s, 2H), 5.52 (d, J=12.5 Hz, 1H), 6.58-6.72 (m, 2H), 6.74-6.86 (m, 1H), 6.95 (d, J=2.6 Hz, 1H), 7.09 (d, J=7.9 Hz, 1H), 7.19-7.29 (m, 2H), 7.39-7.44 (m, 1H), 12.16 (br s, 1H).

Example 113

(E)-3-(1-{8-[(2-ethyl-4-phenyl-1H-imidazol-1-yl)methyl]-3-fluorodibenzo[b,e]oxepin-11(6H)-ylidene}ethyl)-1,2,4-oxadiazol-5(4H)-one (Compound 13f)

Using (E)-2-{8-[(2-ethyl-4-phenyl-1H-imidazol-1-yl)methyl]-3-fluorodibenzo[b,e]oxepin-11(6H)-ylidene}propanenitrile (114 mg, 0.254 mmol) obtained in Reference Example 13F, and in the same manner as in Example 1, the title compound (compound 13f) (54 mg, 42%) was obtained.

ESIMS m/z: 509 $(M+H)^+$; $^1H$ NMR (270 MHz, $CDCl_3$, δ): 1.28 (t, J=7.4 Hz, 3H), 2.24 (s, 3H), 2.66 (q, J=7.4 Hz, 2H), 4.75 (d, J=12.8 Hz, 1H), 5.11 (s, 2H), 5.49 (d, J=12.8 Hz, 1H), 6.49-6.59 (m, 1H), 6.59-6.70 (m, 1H), 6.93-7.28 (m, 6H), 7.29-7.41 (m, 2H), 7.67-7.83 (m, 2H).

Example 114

(E)-3-[1-(8-{[4-(azetidin-1-yl)-2-methyl-6-propylpyrimidin-5-yl]methyl}-3-fluorodibenzo[b,e]oxepin-11(6H)-ylidene)ethyl]-1,2,4-oxadiazol-5(4H)-one (Compound 13g)

Using (E)-2-(8-{[4-(azetidin-1-yl)-2-methyl-6-propylpyrimidin-5-yl]methyl}-3-fluorodibenzo[b,e]oxepin-11(6H)-ylidene)propanenitrile (143 mg, 0.305 mmol) obtained in Reference Example 13G, and in the same manner as in Example 1, the title compound (compound 13g) (36 mg, 12%) was obtained.

ESIMS m/z: 528 $(M+H)^+$; $^1H$ NMR (270 MHz, $CDCl_3$, δ): 0.85 (t, J=7.6 Hz, 3H), 1.56 (q, J=7.6 Hz, 2H), 2.19-2.55 (m, 4H), 2.28 (s, 3H), 2.50 (s, 3H), 3.92 (s, 2H), 4.04-4.20 (m, 4H), 4.77 (d, J=12.7 Hz, 1H), 5.57 (d, J=12.7 Hz, 1H), 6.50-6.58 (m, 1H), 6.60-6.70 (m, 1H), 7.03 (d, J=7.8 Hz, 1H), 7.04 (s, 1H), 7.10-7.21 (m, 2H).

Example 115

(E)-3-[1-(8-{[4-(dimethylamino)-6-(methoxymethyl)-2-methylpyrimidin-5-yl]methyl}-3-fluorodibenzo[b,e]oxepin-11(6H)-ylidene)ethyl]-1,2,4-oxadiazol-5(4H)-one (Compound 13h)

Using (E)-2-(8-{[4-(dimethylamino)-6-(methoxymethyl)-2-methylpyrimidin-5-yl]methyl}-3-fluorodibenzo[b,e]oxepin-11(6H)-ylidene)propanenitrile (93 mg, 0.202 mmol) obtained in Reference Example 13H, and in the same manner as in Example 1, the title compound (compound 13h) (23 mg, 22%) was obtained.

ESIMS m/z: 518 $(M+H)^+$; $^1H$ NMR (270 MHz, $CDCl_3$, δ): 2.28 (s, 3H), 2.57 (s, 3H), 2.93 (s, 6H), 3.30 (s, 3H), 4.14 (s, 2H), 4.21 (d, J=11.7 Hz, 1H), 4.25 (d, J=11.7 Hz, 1H), 4.78 (d, J=12.7 Hz, 1H), 5.55 (d, J=12.7 Hz, 1H), 6.50-6.70 (m, 2H), 7.05-7.15 (m, 4H).

Example 116

(E)-3-(1-{8-[(2-cyclopropyl-8-methylimidazo[1,2-a]pyrazin-3-yl)methyl]-3-fluorodibenzo[b,e]oxepin-11(6H)-ylidene}ethyl)-1,2,4-oxadiazol-5(4H)-one (Compound 140a)

Using (E)-2-{8-[(2-cyclopropyl-8-methylimidazo[1,2-a]pyrazin-3-yl)methyl]-3-fluorodibenzo[b,e]oxepin-11(6H)-ylidene}propanenitrile (90 mg, 0.20 mmol) obtained in Reference Example 14A, and in the same manner as in Example 1, the title compound (compound 14a) (23 mg, 22%) was obtained.

ESIMS m/z: 510 $(M+H)^+$; $^1H$ NMR (300 MHz, $CDCl_3$, δ): 0.99-1.08 (m, 2H), 1.09-1.18 (m, 2H), 1.97-2.08 (m, 1H), 2.28 (s, 3H), 2.82 (s, 3H), 4.30-4.46 (m, 2H), 4.76 (d, J=12.5 Hz, 1H), 5.51 (d, J=12.5 Hz, 1H), 6.53 (dd, J=10.3, 2.6 Hz, 1H), 6.61-6.69 (m, 1H), 7.07 (dd, J=8.8, 6.6 Hz, 1H), 7.12-7.23 (m, 3H), 7.44 (d, J=4.4 Hz, 1H), 7.62 (d, J=4.4 Hz, 1H).

Example 117

(E)-2-cyclopropyl-3-({3-fluoro-11(6H)-[1-(5-oxo-4,5-dihydro-1,2,4-oxadiazol-3-yl)ethylidene]dibenzo[b,e]oxepin-8-yl}methyl)imidazo[1,2-a]pyridine-7-carbonitrile (compound 14b)

[step 1] Using (E)-3-{[11(6H)-(1-cyanoethylidene)-3-fluorodihydrodibenzo[b,e]oxepin-8-yl]methyl}-2-cyclopropylimidazo[1,2-a]pyridine-7-carboxamide (1.6 g, 3.3 mmol) obtained in Reference Example 14B, and in the same manner as in Example 14, (E)-2-cyclopropyl-3-({3-fluoro-11(6H)-[1-(5-oxo-4,5-dihydro-1,2,4-oxadiazol-3-yl)ethylidene]dibenzo[b,e]oxepin-8-yl}methyl)imidazo[1,2-a]pyridine-7-carboxamide (0.21 g, 12%) was obtained.

ESIMS m/z: 538 $(M+H)^+$; $^1H$ NMR (400 MHz, DMSO-$d_6$, δ): 0.89-0.98 (m, 4H), 2.12-2.20 (m, 1H), 2.15 (s, 3H), 4.37-4.50 (m, 2H), 4.89 (d, J=12.7 Hz, 1H), 5.48 (d, J=12.7 Hz, 1H), 6.65 (dd, J=10.7, 2.0 Hz, 1H), 6.75-6.82 (m, 1H), 7.02 (d, J=7.8 Hz, 1H), 7.14-7.30 (m, 4H), 7.46 (br s, 1H), 7.93-8.04 (m, 2H), 8.15 (d, J=6.8 Hz, 1H).

[step 2] (E)-2-cyclopropyl-3-({3-fluoro-11(6H)-[1-(5-oxo-4,5-dihydro-1,2,4-oxadiazol-3-yl)ethylidene]dibenzo[b,e]oxepin-8-yl}methyl)imidazo[1,2-a]pyridine-7-carboxamide (83 mg, 0.15 mmol) obtained in step 1 was suspended in THF (0.77 mL), and triethylamine (0.11 mL, 0.77 mmol) was added. Under ice-cooling, trifluoroacetic anhydride (0.11 mL, 0.77 mmol) was added, and the mixture was stirred at room temperature for 4 hr. Saturated aqueous sodium hydrogen carbonate solution was added to the mixture, and the mixture was extracted 3 times with chloroform-methanol mixed solvent. The combined organic layers were dried over anhydrous magnesium sulfate, and concentrated under reduced pressure. The residue was purified by silica gel column chromatography (chloroform/methanol=100/0 v/v-90/10 v/v) to give the title compound (compound 14b) (41 mg, 51%).

ESIMS m/z: 520 $(M+H)^+$; $^1H$ NMR (300 MHz, DMSO-$d_6$, δ): 0.91-1.02 (m, 4H), 2.15 (s, 3H), 2.16-2.26 (m, 1H), 4.40-4.56 (m, 2H), 4.90 (d, J=12.8 Hz, 1H), 5.48 (d, J=12.8 Hz, 1H), 6.65 (dd, J=10.6, 2.6 Hz, 1H), 6.74-6.83 (m, 1H), 7.02 (d, J=7.7 Hz, 1H), 7.09 (dd, J=7.1, 1.6 Hz, 1H), 7.14-7.26 (m, 2H), 7.26-7.30 (m, 1H), 8.13-8.16 (m, 1H), 8.29 (d, J=6.6 Hz, 1H).

Example 118

(E)-2-cyclopropyl-3-({3-fluoro-11(6H)-[1-(5-oxo-4,5-dihydro-1,2,4-oxadiazol-3-yl)ethylidene]dibenzo[b,e]oxepin-8-yl}methyl)imidazo[1,2-a]pyridine-8-carboxamide (Compound 14c)

Using (E)-3-{[11(6H)-(1-cyanoethylidene)-3-fluorodibenzo[b,e]oxepin-8-yl]methyl}-2-cyclopropylimidazo[1,2-a]pyridine-8-carboxamide (0.62 g, 1.3 mmol) obtained in Reference Example 14C, and in the same manner as in Example 14, the title compound (compound 14c) (0.25 g, 36%) was obtained.

ESIMS m/z: 538 $(M+H)^+$; $^1H$ NMR (400 MHz, DMSO-$d_6$, δ): 0.92-1.03 (m, 4H), 2.15 (s, 3H), 2.16-2.26 (m, 1H), 4.40-4.52 (m, 2H), 4.90 (d, J=12.7 Hz, 1H), 5.48 (d, J=12.7 Hz, 1H), 6.64 (dd, J=10.7, 2.9 Hz, 1H), 6.74-6.81 (m, 1H), 6.93-6.99 (m, 1H), 7.02 (d, J=7.8 Hz, 1H), 7.16-7.25 (m, 2H), 7.29 (br s, 1H), 7.85-7.93 (m, 2H), 8.30 (d, J=7.8 Hz, 1H), 9.45 (d, J=2.9 Hz, 1H).

Example 119

(E)-3-(1-{3-fluoro-8-[(8-methyl-2-propylimidazo[1,2-a]pyrazin-3-yl)methyl]dibenzo[b,e]oxepin-11(6H)-ylidene}ethyl)-1,2,4-oxadiazol-5(4H)-one (Compound 14d)

Using (E)-2-{3-fluoro-8-[(8-methyl-2-propylimidazo[1,2-a]pyrazin-3-yl)methyl]dibenzo[b,e]oxepin-11(6H)-ylidene}propanenitrile (0.32 g, 0.71 mmol) obtained in Reference Example 14D, and in the same manner as in Example 1, the title compound (compound 14d) (0.14 g, 39%) was obtained.

ESIMS m/z: 512 $(M+H)^+$; $^1H$ NMR (300 MHz, DMSO-$d_6$, δ): 0.87 (d, J=7.3 Hz, 3H), 1.57-1.71 (m, 2H), 2.15 (s, 3H), 2.69 (s, 3H), 2.72 (t, J=7.3 Hz, 2H), 4.28-4.41 (m, 2H), 4.90 (d, J=12.5 Hz, 1H), 5.47 (d, J=12.5 Hz, 1H), 6.65 (dd, J=10.6, 2.6 Hz, 1H), 6.74-6.83 (m, 1H), 7.01 (d, J=7.7 Hz, 1H), 7.07-7.14 (m, 1H), 7.18-7.27 (m, 2H), 7.63 (d, J=4.8 Hz, 1H), 8.06 (d, J=4.8 Hz, 1H), 12.10 (br s, 1H).

Example 120

(E)-3-[1-(8-{[2-cyclopropyl-8-(dimethylamino)imidazo[1,2-a]pyrazin-3-yl]methyl}-3-fluorodibenzo[b,e]oxepin-11(6H)-ylidene)ethyl]-1,2,4-oxadiazol-5(4H)-one (Compound 14e)

Using (E)-2-(8-{[2-cyclopropyl-8-(dimethylamino)imidazo[1,2-a]pyrazin-3-yl]methyl}-3-fluorodibenzo[b,e]oxepin-11(6H)-ylidene)propanenitrile (177 mg, 0.369 mmol) obtained in Reference Example 14E, and in the same manner as in Example 14, the title compound (compound 14e) (25 mg, 13%) was obtained.

ESIMS m/z: 539 $(M+H)^+$; $^1H$ NMR (300 MHz, DMSO-$d_6$, δ): 0.83-0.94 (m, 4H), 2.06-2.15 (m, 1H), 2.15 (s, 3H), 3.40 (s, 6H), 4.30-4.35 (m, 2H), 4.90 (d, J=12.8 Hz, 1H), 5.49 (d,

J=12.8 Hz, 1H), 6.65 (dd, J=10.6, 2.6 Hz, 1H), 6.74-6.83 (m, 1H), 7.02 (d, J=7.7 Hz, 1H), 7.11-7.29 (m, 4H), 7.42 (d, J=4.4 Hz, 1H), 12.11 (br s, 1H).

Example 121

(E)-3-[1-(8-{[2-cyclopropyl-8-(dimethylamino)imidazo[1,2-a]pyridin-3-yl]methyl}-3-fluorodibenzo[b,e]oxepin-11(6H)-ylidene)ethyl]-1,2,4-oxadiazol-5(4H)-one (Compound 14f)

Using (E)-2-(8-{[2-cyclopropyl-8-(dimethylamino)imidazo[1,2-a]pyridin-3-yl]methyl}-3-fluorodibenzo[b,e]oxepin-11(6H)-ylidene)propanenitrile (94 mg, 0.20 mmol) obtained in Reference Example 14F, and in the same manner as in Example 14, the title compound (compound 14f) (29 mg, 28%) was obtained.

ESIMS m/z: 538 $(M+H)^+$; $^1$H NMR (300 MHz, $CDCl_3$, δ): 0.90-1.00 (m, 2H), 1.10-1.19 (m, 2H), 1.94-2.05 (m, 1H), 2.27 (s, 3H), 3.15 (s, 6H), 4.27-4.43 (m, 2H), 4.76 (d, J=12.6 Hz, 1H), 5.51 (d, J=12.6 Hz, 1H), 6.25 (d, J=7.5 Hz, 1H), 6.49-6.69 (m, 3H), 7.06 (dd, J=8.6, 6.6 Hz, 1H), 7.11-7.25 (m, 4H).

Example 122

(E)-3-(1-{8-[(7-cyclopropyl-2-methylimidazo[1,2-a]pyridin-3-yl)methyl]-3-fluorodibenzo[b,e]oxepin-11(6H)-ylidene}ethyl)-1,2,4-oxadiazol-5(4H)-one (Compound 14g)

Using (E)-2-{8-[(7-cyclopropyl-2-methylimidazo[1,2-a]pyridin-3-yl)methyl]-3-fluorodibenzo[b,e]oxepin-11(6H)-ylidene}propanenitrile (280 mg, 0.62 mmol) obtained in Reference Example 14G, and in the same manner as in Example 1, the title compound (compound 14g) (80 mg, 25%) was obtained.

ESIMS m/z: 509 $(M+H)^+$; $^1$H NMR (270 MHz, DMSO-$d_6$, δ): 0.67-0.78 (m, 2H), 0.86-1.04 (m, 2H), 1.87-2.00 (m, 1H), 2.16 (s, 3H), 2.34 (s, 3H), 4.15-4.34 (m, 2H), 4.89 (d, J=12.4 Hz, 1H), 5.47 (d, J=12.4 Hz, 1H), 6.39-6.53 (m, 1H), 6.58-6.70 (m, 1H), 6.71-6.85 (m, 1H), 6.89-7.06 (m, 1H), 7.06-7.28 (m, 4H), 7.80-7.95 (m, 1H).

Example 123

(E)-3-(1-{8-[(7-ethynyl-2-methylimidazo[1,2-a]pyridin-3-yl)methyl]-3-fluorodibenzo[b,e]oxepin-11(6H)-ylidene}ethyl)-1,2,4-oxadiazol-5(4H)-one (Compound 14h)

Using (E)-2-{8-[(7-ethynyl-2-methylimidazo[1,2-a]pyridin-3-yl)methyl]-3-fluorodibenzo[b,e]oxepin-11(6H)-ylidene}propanenitrile (152 mg, 0.35 mmol) obtained in Reference Example 14H, and in the same manner as in Example 1, the title compound (compound 14h) (8 mg, 5%) was obtained.

ESIMS m/z: 493 $(M+H)^+$; $^1$H NMR (270 MHz, DMSO-$d_6$, δ): 2.15 (s, 3H), 2.40 (s, 3H), 4.29-4.42 (m, 2H), 4.49 (s, 1H), 4.92 (d, J=12.4 Hz, 1H), 5.47 (d, J=12.4 Hz, 1H), 6.61-6.72 (m, 1H), 6.74-6.84 (m, 1H), 6.90-7.06 (m, 1H), 7.07-7.30 (m, 2H), 7.66-7.80 (m, 1H), 8.14-8.26 (m, 1H), 8.54-8.65 (m, 1H).

Example 124

(E)-3-(1-{8-[(2-cyano-7-fluoroimidazo[1,2-a]pyridin-3-yl)methyl]-3-fluorodibenzo[b,e]oxepin-11(6H)-ylidene}ethyl)-1,2,4-oxadiazol-5(4H)-one (Compound 14i)

[step 1] Using (E)-3-({11(6H)-[1-(cyanoethylidene)]-3-fluorodibenzo[b,e]oxepin}methyl)-7-fluoroimidazo[1,2-a]pyridine-2-carboxamide (330 mg, 0.73 mmol) obtained in Reference Example 14I, and in the same manner as in Example 1, (E)-7-fluoro-3-({3-fluoro-11-[1-(5-oxo-1,2,4-oxadiazol-3-yl)ethylidene]dibenzo[b,e]oxepin-8-yl}methyl)imidazo[1,2-a]pyridine-2-carboxamide (98 mg, 26%) was obtained.

ESIMS m/z: 516 $(M+H)^+$; $^1$H NMR (270 MHz, DMSO-$d_6$, δ): 2.16 (s, 3H), 4.67-4.84 (m, 2H), 4.89 (d, J=12.4 Hz, 1H), 5.46 (d, J=12.4 Hz, 1H), 6.58-6.68 (m, 1H), 6.75-6.83 (m, 1H), 6.94-7.03 (m, 2H), 7.18-7.26 (m, 2H), 7.31-7.37 (m, 1H), 7.39-7.54 (m, 2H), 7.71-7.79 (m, 1H), 8.28-8.36 (m, 1H).

[step 2] (E)-7-fluoro-3-({3-fluoro-11-[1-(5-oxo-1,2,4-oxadiazol-3-yl)ethylidene]dibenzo[b,e]oxepin-8-yl}methyl)imidazo[1,2-a]pyridine-2-carboxamide (113 mg, 0.22 mmol) obtained in step 1 was dissolved in THF (2 mL), triethylamine (67 mg, 0.66 mmol) and trifluoroacetic anhydride (138 mg, 0.66 mmol) were added and the mixture was stirred at room temperature for 2 hr. Furthermore, triethylamine (89 mg, 0.88 mmol) and trifluoroacetic anhydride (184 mg, 0.88 mmol) were added, and the mixture was stirred at room temperature for 8 hr. Water was added to the reaction mixture, and the mixture was extracted 3 times with chloroform. The combined organic layers were dried over anhydrous magnesium sulfate, and concentrated under reduced pressure. The obtained residue was purified by silica gel column chromatography (chloroform/methanol=9/1 v/v) to give the title compound (compound 14i) (15 mg, 14%).

ESIMS m/z: 498 $(M+H)^+$; $^1$H NMR (270 MHz, DMSO-$d_6$, δ): 2.16 (s, 3H), 4.40-4.60 (m, 2H), 4.93 (d, J=12.4 Hz, 1H), 5.49 (d, J=12.4 Hz, 1H), 6.58-6.71 (m, 1H), 6.71-6.89 (m, 1H), 6.99-7.37 (m, 5H), 7.49-7.66 (m, 1H), 8.30-8.47 (m, 1H), 12.11 (br s, 1H).

Example 125

(E)-3-(1-{8-[(7-fluoro-2-(tetrahydrofuran-3-yl)imidazo[1,2-a]pyridin-3-yl)methyl]-3-fluorodibenzo[b,e]oxepin-11(6H)-ylidene}ethyl)-1,2,4-oxadiazol-5(4H)-one (Compound 14j)

Using (E)-2-(8-{[7-fluoro-2-(tetrahydrofuran-3-yl)imidazo[1,2-a]pyridin-3-yl]methyl}-3-fluorodibenzo[b,e]oxepin-11(6H)-ylidene)propanenitrile (104 mg, 0.215 mmol) obtained in Reference Example 14J, and in the same manner as in Example 1, the title compound (compound 14j) (25 mg, 21%) was obtained.

ESIMS m/z: 543 $(M+H)^+$; $^1$H NMR (270 MHz, $CDCl_3$, δ): 2.24-2.49 (m, 5H), 3.52-3.71 (m, 1H), 3.87-4.05 (m, 2H), 4.05-4.23 (m, 2H), 4.23-4.42 (m, 2H), 4.76 (d, J=12.4 Hz, 1H), 5.55 (d, J=12.4 Hz, 1H), 6.50-6.72 (m, 3H), 7.04-7.20 (m, 4H), 7.20-7.35 (m, 1H), 7.50-7.64 (m, 1H).

Example 126

(E)-3-(1-{8-[(2-chloroimidazo[1,2-a]pyridin-3-yl)methyl]-3-fluorodibenzo[b,e]oxepin-11(6H)-ylidene}ethyl)-1,2,4-oxadiazol-5(4H)-one (Compound 14k)

Using (E)-2-{8-[(2-chloroimidazo[1,2-a]pyridin-3-yl)methyl]-3-fluorodibenzo[b,e]oxepin-11(6H)- ylidene}propanenitrile (106 mg, 0.247 mmol) obtained in Reference Example 14K, and in the same manner as in Example 1, the title compound (compound 14k) (5.5 mg, 4.3%) was obtained.

ESIMS m/z: 489 $(M+H)^+$; $^1H$ NMR (270 MHz, $CDCl_3$, δ): 1.99 (s, 3H), 4.35 (s, 2H), 4.92 (d, J=12.7 Hz, 1H), 5.47 (d, J=12.7 Hz, 1H), 6.63-6.82 (m, 2H), 6.92-7.03 (m, 3H), 7.17-7.25 (m, 2H), 7.28-7.33 (m, 2H), 7.54-7.56 (m, 1H).

Example 127

(E)-3-[1-(3-fluoro-8-{[2-methoxy-7-(trifluoromethyl)imidazo[1,2-a]pyridin-3-yl]methyl}dibenzo[b,e]oxepin-11(6H)-ylidene)ethyl]-1,2,4-oxadiazol-5(4H)-one (Compound 14l)

Using (E)-2-(3-fluoro-8-{[2-methoxy-7-(trifluoromethyl)imidazo[1,2-a]pyridin-3-yl]methyl}-dibenzo[b,e]oxepin-11(6H)-ylidene)propanenitrile (220 mg, 0.446 mmol) obtained in Reference Example 14L, and in the same manner as in Example 1, the title compound (compound 14l) (26 mg, 11%) was obtained.

ESIMS m/z: 553 $(M+H)^+$; $^1H$ NMR (270 MHz, $CDCl_3$, δ): 2.28 (s, 3H), 4.14 (s, 3H), 4.19-4.34 (m, 2H), 4.81 (d, J=12.7 Hz, 1H), 5.53 (d, J=12.7 Hz, 1H), 6.52-6.56 (m, 1H), 6.62-6.72 (m, 1H), 6.96-6.99 (m, 1H), 7.04-7.09 (m, 1H), 7.13-7.16 (m, 1H), 7.21-7.23 (m, 2H), 7.70-7.73 (m, 1H), 7.80-7.81 (m, 1H).

Example 128

Tablet (Compound 1a)

A tablet having the following formulation is prepared by a conventional method. Compound 1a (40g), lactose (286.8 g) and potato starch (60g) are mixed, and a 10% aqueous solution (120g) of hydroxypropylcellulose is added. The obtained mixture is kneaded, granulated, dried, and sieved by conventional methods to give granules for tableting. Thereto is added magnesium stearate (1.2 g), and the mixture is tableted by a tableting machine with a punch (diameter 8 mm) (manufactured by Kikusui, RT-15) to give tablets (containing active ingredient 20 mg per tablet).

| Formulation | |
|---|---|
| compound 1a | 20 mg |
| lactose | 143.4 mg |
| potato starch | 30 mg |
| hydroxypropylcellulose | 6 mg |
| magnesium stearate | 0.6 mg |
| | 200 mg |

Example 129

Injection (Compound 1a)

An injection having the following formulation is prepared by a conventional method. Compound 1a (1g) is added to distilled water for injection and the mixture is mixed. Further, hydrochloric acid and aqueous sodium hydroxide solution are added to adjust the pH to 7, and distilled water for injection is added to make the total amount 1000 mL. The obtained mixture is aseptically filled in a glass vial by 2 mL to give an injection (containing active ingredient 2 mg per vial).

| Formulation | |
|---|---|
| compound 1a | 2 mg |
| hydrochloric acid | q.s. |
| aqueous sodium hydroxide solution | q.s. |
| distilled water for injection | q.s. |
| | 2.00 mL |

Reference Example 1A

(E)-2-{3-fluoro-8-[(2-propyl-1H-benzo[d]imidazol-1-yl)methyl]dibenzo[b,e]oxepin-11(6H)-ylidene}propanenitrile 2-Propyl-1H-benzo[d]imidazole (Synthetic Communication, 2002, vol. 32, p 3703, 246 mg, 1.54 mmol) and (E)-2-[8-(bromomethyl)-3-fluorodibenzo[b,e]oxepin-11(6H)-ylidene]propanenitrile (550 mg, 1.54 mmol) obtained in Reference Example 1 were dissolved in DMF (7 mL), potassium carbonate (1.06 g, 7.68 mmol) was added and the mixture was stirred overnight. To the mixture was added water (20 mL), and the precipitated crystals were collected by suction filtration to give the title compound (640 mg, 94%).

ESIMS m/z: 438 $(M+H)^+$; $^1H$ NMR (300 MHz, $CDCl_3$, δ): 1.02 (t, J=7.4 Hz, 3H), 1.77-1.97 (m, 2H), 2.23 (s, 3H), 2.80 (t, J=7.4 Hz, 2H), 4.73 (d, J=12.6 Hz, 1H), 5.32-5.48 (m, 3H), 6.51-6.58 (m, 1H), 6.59-6.69 (m, 1H), 6.94-7.07 (m, 3H), 7.11-7.29 (m, 3H), 7.43 (d, J=7.8 Hz, 1H), 7.78 (d, J=7.5 Hz, 1H).

Reference Example 1B

(E)-2-(3-fluoro-8-{[2-(methoxymethyl)-1H-benzo[d]imidazol-1-yl]methyl}dibenzo[b,e]oxepin-11(6H)-ylidene)propanenitrile Using 2-methoxymethyl-1H-benzo[d]imidazole (Journal of Organometallic Chemistry, 2008, vol. 26, p 3889; 244 mg, 1.51 mmol) and (E)-2-[8-(bromomethyl)-3-fluorodibenzo[b,e]oxepin-11(6H)-ylidene]propanenitrile (550 mg, 1.54 mmol) obtained in Reference Example 1, and in the same manner as in Reference Example 1A, the title compound (576 mg, 87%) was obtained.

ESIMS m/z: 440 $(M+H)^+$; $^1H$ NMR (300 MHz, $CDCl_3$, δ): 2.23 (s, 3H), 3.36 (s, 3H), 4.66-4.77 (m, 3H), 5.40 (d, J=12.5 Hz, 1H), 5.44-5.58 (m, 2H), 6.55 (dd, J=10.3, 2.6 Hz, 1H), 6.60-6.68 (m, 1H), 6.98-7.08 (m, 2H), 7.15-7.22 (m, 1H), 7.23-7.33 (m, 3H), 7.42 (d, J=7.7 Hz, 1H), 7.77-7.84 (m, 1H).

Reference Example 1C

(E)-2-{3-fluoro-8-[(2-isopropyl-1H-benzo[d]imidazol-1-yl)methyl]dibenzo[b,e]oxepin-11(6H)-ylidene}propanenitrile Using 2-isopropyl-1H-benzo[d]imidazole (Angewandte Chemie, International Edition, 2010, vol. 9, p 1656; 89 mg, 0.56 mmol) and (E)-2-[8-(bromomethyl)-3-fluorodibenzo[b,e]oxepin-11(6H)-ylidene]propanenitrile (200 mg, 0.56 mmol) obtained in Reference Example 1, and in the same manner as in Reference Example 1A, the title compound (240 mg, 98%) was obtained.

ESIMS m/z: 438 $(M+H)^+$; $^1H$ NMR (270 MHz, $CDCl_3$, δ): 1.33-1.46 (m, 6H), 2.23 (s, 3H), 3.04-3.20 (m, 1H), 4.72 (d, J=12.8 Hz, 1H), 5.31-5.46 (m, 3H), 6.55 (dd, J=10.2, 2.3 Hz,

1H), 6.60-6.69 (m, 1H), 6.94-6.98 (m, 1H), 7.02 (dd, J=8.7, 6.4 Hz, 1H), 7.09-7.16 (m, 1H), 7.16-7.21 (m, 2H), 7.22-7.30 (m, 1H), 7.43 (d, J=7.9 Hz, 1H), 7.77-7.84 (m, 1H).

Reference Example 1D (E)-2-{8-[(2-cyclopropyl-1H-benzo[d]imidazol-1-yl)methyl]-3-fluorodibenzo[b,e]oxepin-11(6H)-ylidene}propanenitrile Using 2-cyclopropyl-1H-benzo[d]imidazole (Europeane Journal of Organic Chemistry, 2000, p 1229, 69 mg, 0.434 mmol) and (E)-2-[8-(bromomethyl)-3-fluorodibenzo[b,e]oxepin-11(6H)-ylidene]propanenitrile (160 mg, 0.447 mmol) obtained in Reference Example 1, and in the same manner as in Reference Example 1A, the title compound (182 mg, 95%) was obtained.

ESIMS m/z: 436 $(M+H)^+$; $^1$H NMR (270 MHz, $CDCl_3$, δ): 0.96-1.15 (m, 2H), 1.15-1.32 (m, 2H), 1.81-1.99 (m, 1H), 2.23 (s, 3H), 4.73 (d, J=12.8 Hz, 1H), 5.32-5.57 (m, 3H), 6.52-6.60 (m, 1H), 6.59-6.69 (m, 1H), 6.98-7.07 (m, 2H), 7.16-7.29 (m, 4H), 7.41-7.48 (m, 1H), 7.66-7.75 (m, 1H).

Reference Example 1E (E)-2-{8-[(2-cyclobutyl-1H-benzo[d]imidazol-1-yl)methyl]-3-fluorodibenzo[b,e]oxepin-11(6H)-ylidene}propanenitrile Using 2-cyclobutyl-1H-benzo[d]imidazole (72 mg, 0.419 mmol) and (E)-2-[8-(bromomethyl)-3-fluorodibenzo[b,e]oxepin-11(6H)-ylidene]propanenitrile (150 mg, 0.419 mmol) obtained in Reference Example 1, and in the same manner as in Reference Example 1A, the title compound (170 mg, 90%) was obtained.

ESIMS m/z: 450 $(M+H)^+$; $^1$H NMR (270 MHz, $CDCl_3$, δ): 1.88-2.12 (m, 2H), 2.23 (s, 3H), 2.25-2.41 (m, 2H), 2.48-2.72 (m, 2H), 3.54-3.73 (m, 1H), 4.72 (d, J=12.8 Hz, 1H), 5.28 (s, 2H), 5.39 (d, J=12.8 Hz, 1H), 6.49-6.73 (m, 2H), 6.89-7.31 (m, 6H), 7.36-7.49 (m, 1H), 7.77-7.88 (m, 1H).

Reference Example 1F (E)-2-{8-[(2-cyclopentyl-1H-benzo[d]imidazol-1-yl)methyl]-3-fluorodibenzo[b,e]oxepin-11(6H)-ylidene}propanenitrile Using 2-cyclopentyl-1H-benzo[d]imidazole (62 mg, 0.335 mmol) and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 1A, the title compound (148 mg, 95%) was obtained.

ESIMS m/z: 464 $(M+H)^+$; $^1$H NMR (270 MHz, $CDCl_3$, δ): 1.53-1.76 (m, 2H), 1.78-2.16 (m, 6H), 2.23 (s, 3H), 3.03-3.27 (m, 1H), 4.72 (d, J=12.8 Hz, 1H), 5.27-5.47 (m, 3H), 6.46-6.74 (m, 2H), 6.92-7.10 (m, 2H), 7.10-7.32 (m, 4H), 7.38-7.50 (m, 1H), 7.75-7.86 (m, 1H).

Reference Example 1G (E)-2-(8-{[2-(cyclopropylmethyl)-1H-benzo[d]imidazol-1-yl]methyl}-3-fluorodibenzo[b,e]oxepin-11(6H)-ylidene)propanenitrile Using 2-cyclopropylmethyl-1H-benzo[d]imidazole (72 mg, 0.419 mmol) and (E)-2-[8-(bromomethyl)-3-fluorodibenzo[b,e]oxepin-11(6H)-ylidene]propanenitrile (150 mg, 0.419 mmol) obtained in Reference Example 1, and in the same manner as in Reference Example 1A, the title compound (175 mg, 93%) was obtained.

ESIMS m/z: 450 $(M+H)^+$; $^1$H NMR (270 MHz, $CDCl_3$, δ): 0.18-0.34 (m, 2H), 0.42-0.67 (m, 2H), 1.05-1.24 (m, 1H), 2.24 (s, 3H), 2.79 (d, J=6.7 Hz, 2H), 4.72 (d, J=12.6 Hz, 1H), 5.32-5.50 (m, 3H), 6.51-6.59 (m, 1H), 6.60-6.69 (m, 1H), 6.95-7.06 (m, 2H), 7.08-7.34 (m, 4H), 7.40-7.45 (m, 1H), 7.77-7.83 (m, 1H).

Reference Example 1H (E)-2-{8-[(2-ethyl-1H-benzo[d]imidazol-1-yl)methyl]-3-fluorodibenzo[b,e]oxepin-11(6H)-ylidene}propanenitrile Using 2-ethyl-1H-benzo[d]imidazole (61 mg, 0.419 mmol) and (E)-2-[8-(bromomethyl)-3-fluorodibenzo[b,e]oxepin-11(6H)-ylidene]propanenitrile (150 mg, 0.419 mmol) obtained in Reference Example 1, and in the same manner as in Reference Example 1A, the title compound (170 mg, 96%) was obtained.

ESIMS m/z: 424 $(M+H)^+$; $^1$H NMR (270 MHz, $CDCl_3$, δ): 1.43 (t, J=7.6 Hz, 3H), 2.24 (s, 3H), 2.84 (q, J=7.6 Hz, 2H), 4.72 (d, J=12.6 Hz, 1H), 5.29-5.44 (m, 3H), 6.50-6.59 (m, 1H), 6.59-6.68 (m, 1H), 6.90-7.07 (m, 2H), 7.11-7.30 (m, 4H), 7.37-7.46 (m, 1H), 7.73-7.85 (m, 1H).

Reference Example 1I (E)-2-(3-fluoro-8-{[2-(trifluoromethyl)-1H-benzo[d]imidazol-1-yl]methyl}dibenzo[b,e]oxepin-11(6H)-ylidene)propanenitrile Using 2-(trifluoromethyl)-1H-benzo[d]imidazole (62 mg, 0.335 mmol) and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 1A, the title compound (138 mg, 88%) was obtained.

ESIMS m/z: 464 $(M+H)^+$; $^1$H NMR (270 MHz, $CDCl_3$, δ): 2.23 (s, 3H), 4.75 (d, J=12.6 Hz, 1H), 5.40 (d, J=12.6 Hz, 1H), 5.55 (s, 2H), 6.51-6.59 (m, 1H), 6.59-6.70 (m, 1H), 7.00-7.07 (m, 2H), 7.16-7.31 (m, 2H), 7.33-7.49 (m, 3H), 7.86-7.98 (m, 1H).

Reference Example 1J (E)-2-(8-{[2-(3,3-difluorocyclobutyl)-1H-benzo[d]imidazol-1-yl]methyl}-3-fluorodibenzo[b,e]oxepin-11(6H)-ylidene)propanenitrile

[step 1] 3,3-Difluorocyclobutanecarboxylic acid (500 mg, 3.67 mmol) was dissolved in DMF (18 mL), 1,1'-carbonyldiimidazole (1.19 g, 7.35 mmol) was added, and the mixture was stirred at room temperature for 1 hr. To the mixture were added 2-nitroaniline (1.02 g, 7.35 mmol) and triethylamine (1.02 mL, 7.35 mmol), and the mixture was stirred at 80° C. for 13 hr. To the mixture were added 5% aqueous citric acid solution and ethanol (5 mL), and the mixture was stirred for 1 hr. The precipitated crystals were collected by suction filtration to give 3,3-difluoro-N-(2-nitrophenyl)cyclobutanecarboxamide (527 mg, 56%).

ESIMS m/z: 257 $(M+H)^+$; $^1$H NMR (300 MHz, $CDCl_3$, δ): 2.78-3.16 (m, 5H), 7.17-7.26 (m, 1H), 7.62-7.74 (m, 1H), 8.20-8.30 (m, 1H), 8.75-8.84 (m, 1H), 10.46 (br s, 1H).

[step 2] 3,3-Difluoro-N-(2-nitrophenyl)cyclobutanecarboxamide (400 mg, 1.56 mmol) obtained in step 1 was dissolved in ethanol (10 mL), methanol (40 mL), and ethyl acetate (40 mL), and 10% Pd—C (120 mg) was added. The reaction system was purged with hydrogen gas, and the mixture was stirred at room temperature for 3 hr. After completion of the reaction, the reaction mixture was filtered through celite, and the solution was concentrated under reduced pressure. To the obtained residue was added acetic acid (2.2 mL, 38.4 mmol), and the mixture was stirred at 80° C. for 1 hr. Under ice-cooling, saturated aqueous sodium hydrogen carbonate was added to the mixture, and the mixture was extracted 3 times with ethyl acetate. The combined organic layers were washed with water, dried over anhydrous magnesium sulfate and concentrated under reduced pressure. The residue was purified by silica gel column chromatography (hexane/ethyl acetate=100/0 v/v-30/70 v/v) to give 2-(3,3-difluorocyclobutyl)-1H-benzo[d]imidazole (135 mg, 42%).

ESIMS m/z: 209 $(M+H)^+$; $^1H$ NMR (300 MHz, DMSO-$d_6$, δ): 2.91-3.16 (m, 4H), 3.52-3.68 (m, 1H), 7.08-7.21 (m, 2H), 7.38-7.48 (m, 1H), 7.52-7.62 (m, 1H), 12.37 (br s, 1H).

[step 3] Using 2-(3,3-difluorocyclobutyl)-1H-benzo[d]imidazole (57 mg, 0.27 mmol) obtained in step 2 and (E)-2-[8-(bromomethyl)-3-fluorodibenzo[b,e]oxepin-11(6H)-ylidene]propanenitrile (100 mg, 0.28 mmol) obtained in Reference Example 1, and in the same manner as in Reference Example 1A, the title compound (127 mg, 96%) was obtained.

ESIMS m/z: 486 $(M+H)^+$; $^1H$ NMR (300 MHz, $CDCl_3$, δ): 2.23 (s, 3H), 2.75-2.98 (m, 2H), 3.00-3.28 (m, 2H), 3.34-3.49 (m, 1H), 4.73 (d, J=12.8 Hz, 1H), 5.33 (s, 2H), 5.40 (d, J=12.8 Hz, 1H), 6.56 (dd, J=9.9, 2.6 Hz, 1H), 6.60-6.70 (m, 1H), 6.92-6.97 (m, 1H), 7.03 (dd, J=8.6, 6.4 Hz, 1H), 7.06-7.12 (m, 1H), 7.19-7.36 (m, 3H), 7.44 (d, J=7.7 Hz, 1H), 7.78-7.85 (m, 1H).

Reference Example 1L

(E)-2-(3-fluoro-8-{[2-(1-methylcyclopropyl)-1H-benzo[d]imidazol-1-yl]methyl}dibenzo[b,e]oxepin-11(6H)-ylidene)propanenitrile Using 2-(1-methylcyclopropyl)-1H-benzo[d]imidazole (58 mg, 0.335 mmol) and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 1A, the title compound (60 mg, 40%) was obtained.

ESIMS m/z: 450 $(M+H)^+$; $^1H$ NMR (270 MHz, $CDCl_3$, δ): 0.78-0.89 (m, 2H), 1.10-1.19 (m, 2H), 1.39 (s, 3H), 2.23 (s, 3H), 4.74 (d, J=12.8 Hz, 1H), 5.39 (d, J=12.8 Hz, 1H), 5.55-5.61 (m, 2H), 6.50-6.62 (m, 1H), 6.62-6.71 (m, 1H), 6.96-7.11 (m, 3H), 7.12-7.30 (m, 3H), 7.39-7.51 (m, 1H), 7.70-7.82 (m, 1H).

Reference Example 1M

(E)-2-(3-fluoro-8-{[2-(furan-2-yl)-1H-benzo[d]imidazol-1-yl]methyl}dibenzo[b,e]oxepin-11(6H)-ylidene)propanenitrile Using commercially available 2-(furan-2-yl)-1H-benzo[d]imidazole (62 mg, 0.34 mmol) and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 1A, the title compound (146 mg, 94%) was obtained.

ESIMS m/z: 462 $(M+H)^+$; $^1H$ NMR (270 MHz, $CDCl_3$, δ): 2.23 (s, 3H), 4.72 (d, J=12.8 Hz, 1H), 5.39 (d, J=12.8 Hz, 1H), 5.67-5.79 (m, 2H), 6.52-6.67 (m, 3H), 6.99-7.07 (m, 2H), 7.11-7.13 (m, 1H), 7.25-7.34 (m, 4H), 7.43-7.45 (m, 1H), 7.56-7.57 (m, 1H), 7.82-7.85 (m, 1H).

Reference Example 1N

(E)-2-(3-fluoro-8-{[2-(pyridin-2-yl)-1H-benzo[d]imidazol-1-yl]methyl}dibenzo[b,e]oxepin-11(6H)-ylidene)propanenitrile Using commercially available 2-(pyridin-2-yl)-1H-benzo[d]imidazole (50 mg, 0.34 mmol) and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 1A, the title compound (123 mg, 86%) was obtained.

ESIMS m/z: 473 $(M+H)^+$; $^1H$ NMR (270 MHz, $CDCl_3$, δ): 2.21 (s, 3H), 4.70 (d, J=11.6 Hz, 1H), 5.37 (d, J=12.8 Hz, 1H), 6.19-6.24 (m, 2H), 6.50-6.55 (m, 1H), 6.58-6.65 (m, 1H), 6.97-7.02 (m, 1H), 7.14-7.15 (m, 1H), 7.29-7.39 (m, 6H), 7.79-7.89 (m, 2H), 8.45-8.48 (m, 1H), 8.60-8.62 (m, 1H).

Reference Example 2A

(E)-2-(3-fluoro-8-{[4-(methoxy-$d_3$)-2-(methoxymethyl)-1H-benzo[d]imidazol-1-yl]methyl}dibenzo[b,e]oxepin-11(6H)-ylidene)propanenitrile

[step 1] 2-Methoxy-6-nitroaniline (4.0 g, 23.8 mmol) was dissolved in DMA (24 mL), pyridine (5.8 mL, 71.4 mmol) and 2-methoxyacetyl chloride (6.5 mL, 71.4 mmol) were added at 0° C., and the mixture was stirred at room temperature for 1 hr. Under ice-cooling, methanol and aqueous ammonia solution were added to the mixture, and the mixture was stirred at room temperature for 30 min. Water was added, and the mixture was extracted 3 times with ethyl acetate. The combined organic layers were washed with water and saturated brine, dried over anhydrous magnesium sulfate, and concentrated under reduced pressure. The residue was purified by silica gel column chromatography (hexane/ethyl acetate=100/0 v/v-30/70 v/v) to give 2-methoxy-N-(2-methoxy-6-nitrophenyl)acetamide (5.4 g, 95%).

ESIMS m/z: 241 $(M+H)^+$; $^1H$ NMR (400 MHz, $CDCl_3$, δ): 3.54 (s, 3H), 3.94 (s, 3H), 4.06 (s, 2H), 7.14-7.19 (m, 1H), 7.30 (d, J=7.8 Hz, 1H), 7.52 (d, J=7.8 Hz, 1H), 8.54 (br s, 1H).

[step 2] 2-Methoxy-N-(2-methoxy-6-nitrophenyl)acetamide (5.4 g, 22.5 mmol) obtained in step 1 was dissolved in ethanol (45 mL), tin (II) chloride.2 hydrate (24.4 g, 108 mmol) was added, and the mixture was stirred with heating under reflux for 1 hr. After cooling to room temperature, 4 mol/L aqueous sodium hydroxide solution was added to the mixture. The mixture was filtered through celite, and the solution was extracted 3 times with ethyl acetate. The combined organic layers were dried over anhydrous magnesium sulfate, and concentrated under reduced pressure. The obtained brown oil (3.7 g) was suspended in diisopropyl ether (30 mL) and isopropyl alcohol (3 mL), and stirred at room temperature for 1 hr. The suspension was suction filtered, and the obtained solid was dried under reduced pressure to give 4-methoxy-2-(methoxymethyl)-1H-benzo[d]imidazole (1.38 g, 32%).

ESIMS m/z: 193 $(M+H)^+$; $^1H$ NMR (300 MHz, $CDCl_3$, δ): 3.49 (d, J=5.9 Hz, 3H), 3.98 (d, J=14.7 Hz, 3H), 4.76 (s, 2H), 6.70 (t, J=8.6 Hz, 1H), 7.05 (d, J=8.1 Hz, 0.5H), 7.17 (t, J=8.1 Hz, 1H), 7.36 (d, J=8.1 Hz, 0.5H), 9.60 (br s, 1H).

[step 3] Using 4-methoxy-2-(methoxymethyl)-1H-benzo[d]imidazole (1.3 g, 6.8 mmol) obtained in step 2 and (E)-2-[8-(bromomethyl)-3-fluorodibenzo[b,e]oxepin-11(6H)-ylidene]propanenitrile (2.5 g, 7.0 mmol) obtained in Reference Example 1, and in the same manner as in Reference Example 1A, (E)-2-(3-fluoro-8-{[4-methoxy-2-(methoxymethyl)-1H-benzo[d]imidazol-1-yl]methyl}dibenzo[b,e]oxepin-11(6H)-ylidene)propanenitrile (1.7 g, 53%) was obtained.

ESIMS m/z: 470 $(M+H)^+$; $^1$H NMR (270 MHz, $CDCl_3$, δ): 2.23 (s, 3H), 3.33 (s, 3H), 4.04 (s, 3H), 4.65-4.78 (m, 3H), 5.39 (d, J=12.5 Hz, 1H), 5.41-5.56 (m, 2H), 6.55 (dd, J=10.2, 2.3 Hz, 1H), 6.59-6.68 (m, 1H), 6.71 (d, J=7.9 Hz, 1H), 6.86 (d, J=8.2 Hz, 1H), 6.97-7.06 (m, 2H), 7.13-7.23 (m, 2H), 7.41 (d, J=7.9 Hz, 1H).

[step 4] (E)-2-(3-fluoro-8-{[4-methoxy-2-(methoxymethyl)-1H-benzo[d]imidazol-1-yl]methyl}dibenzo[b,e]oxepin-11(6H)-ylidene)propanenitrile (1.0 g, 2.1 mmol) obtained in step 3 was dissolved in dichloromethane (11 mL), boron tribromide (21.0 mL, 21.0 mmol, 1.0 mol/L dichloromethane solution) was added at 0° C., and the mixture was stirred at room temperature for 2 hr. To the mixture was added 2 mol/L aqueous sodium hydroxide solution, and the mixture was extracted 3 times with chloroform. The combined organic layers were dried over anhydrous magnesium sulfate, and concentrated under reduced pressure. The residue was purified by silica gel column chromatography (chloroform/methanol=100/0 v/v-90/10 v/v) to give (E)-2-(3-fluoro-8-{[4-hydroxy-2-(hydroxymethyl)-1H-benzo[d]imidazol-1-yl]methyl}dibenzo[b,e]oxepin-11(6H)-ylidene)propanenitrile (0.7 g, 75%).

ESIMS m/z: 442 $(M+H)^+$; $^1$H NMR (300 MHz, $CDCl_3$, δ): 1.36-1.97 (m, 1H), 2.22 (s, 3H), 4.74 (d, J=12.5 Hz, 1H), 4.85 (s, 2H), 5.32-5.45 (m, 3H), 6.54 (dd, J=10.1, 2.4 Hz, 1H), 6.59-6.69 (m, 1H), 6.76-6.88 (m, 2H), 7.01 (dd, J=8.6, 6.6 Hz, 1H), 7.05-7.10 (m, 1H), 7.12-7.23 (m, 2H), 7.42 (d, J=8.1 Hz, 1H).

[step 5] (E)-2-(3-fluoro-8-{[4-hydroxy-2-(hydroxymethyl)-1H-benzo[d]imidazol-1-yl]methyl}dibenzo[b,e]oxepin-11(6H)-ylidene)propanenitrile (52 mg, 0.12 mmol) obtained in step 4 was dissolved in THF (1 mL), deuterated methanol (0.10 mL, 2.36 mmol), triphenylphosphine (118 mg, 0.35 mmol, polymer support), (E)-di-tert-butyl diazene-1,2-dicarboxylate (54 mg, 0.24 mmol) were added, and the mixture was stirred at room temperature for 1 hr. To the mixture were further added triphenylphosphine (118 mg, 0.35 mmol, polymer support), and (E)-di-tert-butyl diazene-1,2-dicarboxylate (54 mg, 0.24 mmol), and the mixture was stirred at room temperature for 16 hr. The mixture was filtered through celite, and the solution was concentrated under reduced pressure. The residue was purified by silica gel column chromatography (hexane/ethyl acetate=70/30 v/v-0/100 v/v) to give (E)-2-(3-fluoro-8-{[2-(hydroxymethyl)-4-(methoxy-$d_3$)-1H-benzo[d]imidazol-1-yl]methyl}dibenzo[b,e]oxepin-11(6H)-ylidene)propanenitrile (29 mg, 54%).

ESIMS m/z: 459 $(M+H)^+$; $^1$H NMR (400 MHz, $CDCl_3$, δ): 2.23 (s, 3H), 4.71 (d, J=12.7 Hz, 1H), 4.85 (s, 2H), 5.38 (d, J=12.7 Hz, 1H), 5.38-5.50 (m, 2H), 6.54 (dd, J=10.2, 2.4 Hz, 1H), 6.59-6.67 (m, 1H), 6.70 (d, J=7.8 Hz, 1H), 6.84 (d, J=7.8 Hz, 1H), 6.97-7.05 (m, 2H), 7.12-7.21 (m, 2H), 7.41 (d, J=7.8 Hz, 1H).

[step 6] (E)-2-(3-fluoro-8-{[2-(hydroxymethyl)-4-(methoxy-$d_3$)-1H-benzo[d]imidazol-1-yl]methyl}dibenzo[b,e]oxepin-11(6H)-ylidene)propanenitrile (29 mg, 0.063 mmol) obtained in step 5 was dissolved in THF (1 mL), sodium hydride (3.3 mg, 0.082 mmol) and iodomethane (5.1 μL, 0.082 mmol) were added, and the mixture was stirred at room temperature for 5 hr. Water was added to the mixture, and the mixture was extracted 3 times with a mixed solvent of chloroform and methanol. The combined organic layers were dried over anhydrous magnesium sulfate, and concentrated under reduced pressure. The residue was purified by silica gel column chromatography (chloroform/methanol=99/1 v/v-90/10 v/v) to give the title compound (25 mg, 84%).

ESIMS m/z: 473 $(M+H)^+$; $^1$H NMR (300 MHz, $CDCl_3$, δ): 2.23 (s, 3H), 3.32 (s, 3H), 4.67-4.76 (m, 3H), 5.39 (d, J=12.5 Hz, 1H), 5.41-5.57 (m, 2H), 6.55 (dd, J=9.9, 2.6 Hz, 1H), 6.60-6.68 (m, 1H), 6.68-6.73 (m, 1H), 6.83-6.87 (m, 1H), 6.98-7.05 (m, 2H), 7.13-7.22 (m, 2H), 7.41 (d, J=7.7 Hz, 1H).

Reference Example 2B

(E)-1-{[11-(1-cyanoethylidene)-3-fluoro-6,11-dihydrodibenzo[b,e]oxepin-8-yl]methyl}-2-propyl-1H-benzo[d]imidazole-4-carboxamide

[step 1] To methyl 2-aminobenzoate (3.0 g, 19.8 mmol) was added butyric anhydride (9.7 mL, 59.4 mmol), and the mixture was stirred at room temperature for 3 hr. Under ice-cooling, to the mixture was added dropwise fuming nitric acid (3.2 mL) and the mixture was stirred at 0° C. for 15 min. Water was added to the mixture, and the mixture was neutralized by dropwise addition of 4 mol/L aqueous sodium hydroxide solution, and extracted 3 times with ethyl acetate. The combined organic layers were dried over anhydrous magnesium sulfate and purified by silica gel column chromatography (hexane/ethyl acetate=100/0 v/v-60/40 v/v) to give methyl 2-butylamido-3-nitrobenzoate (3.0 g, 57%).

ESIMS m/z: 267 $(M+H)^+$; $^1$H NMR (270 MHz, $CDCl_3$, δ): 1.01 (t, J=7.3 Hz, 3H), 1.67-1.86 (m, 2H), 2.43 (t, J=7.3 Hz, 2H), 3.97 (s, 3H), 7.24-7.36 (m, 1H), 8.09 (dd, J=8.1, 1.5 Hz, 1H), 8.21 (dd, J=8.1, 1.5 Hz, 1H), 10.39 (br s, 1H).

[step 2] Methyl 2-butylamido-3-nitrobenzoate (3.0 g, 11.3 mmol) obtained in step 1 was dissolved in methanol (42 mL), and 10% Pd—C (750 mg) was added. The reaction system was purged with hydrogen gas, and the mixture was stirred at room temperature for 5 hr. After completion of the reaction, and the mixture was filtered through celite, and the solution was concentrated under reduced pressure. To the obtained residue was added acetic acid (16 mL), and the mixture was stirred at 80° C. for 1 hr. Under ice-cooling, saturated aqueous sodium hydrogen carbonate was added to the mixture, and the mixture was extracted 3 times with ethyl acetate. The combined organic layers were washed with water, dried over anhydrous magnesium sulfate, and concentrated under reduced pressure. The residue was purified by silica gel column chromatography (hexane/ethyl acetate=90/10 v/v-40/60 v/v) to give methyl 2-propyl-1H-benzo[d]imidazole-4-carboxylate (1.8 g, 73%).

ESIMS m/z: 219 $(M+H)^+$; $^1$H NMR (300 MHz, $CDCl_3$, δ): 1.06 (t, J=7.3 Hz, 3H), 1.85-2.00 (m, 2H), 2.93 (t, J=7.3 Hz, 2H), 3.99 (s, 3H), 7.23-7.31 (m, 1H), 7.85 (dd, J=7.9, 0.9 Hz, 1H), 7.88-7.94 (m, 1H), 10.17 (br s, 1H).

[step 3] Using methyl 2-propyl-1H-benzo[d]imidazole-4-carboxylate (64 mg, 0.29 mmol) obtained in step 2 and (E)-2-[8-(bromomethyl)-3-fluorodibenzo[b,e]oxepin-11(6H)-ylidene]propanenitrile (110 mg, 0.31 mmol) obtained in Reference Example 1, and in the same manner as in Reference Example 1A, (E)-methyl 1-{[11-(cyanoethylidene)-3-fluoro-6,11-dihydrodibenzo[b,e]oxepin-8-yl]methyl}-2-propyl-1H-benzo[d]imidazole-4-carboxylate (120 mg, 83%) was obtained.

ESIMS m/z: 496 $(M+H)^+$; $^1$H NMR (300 MHz, $CDCl_3$, δ): 1.03 (t, J=7.3 Hz, 3H), 1.81-1.97 (m, 2H), 2.23 (s, 3H), 2.80-2.95 (m, 2H), 4.05 (s, 3H), 4.69 (d, J=12.5 Hz, 1H), 5.31-5.48 (m, 3H), 6.55 (dd, J=10.3, 2.6 Hz, 1H), 6.60-6.69 (m, 1H), 6.83-6.91 (m, 1H), 7.02 (dd, J=8.8, 6.2 Hz, 1H), 7.09-7.16 (m, 1H), 7.19-7.26 (m, 1H), 7.34 (dd, J=8.1, 1.5 Hz, 1H), 7.43 (d, J=8.1 Hz, 1H), 7.94 (dd, J=7.5, 1.5 Hz, 1H).

[step 4] (E)-methyl1-{[11-(cyanoethylidene)-3-fluoro-6,11-dihydrodibenzo[b,e]oxepin-8-yl]methyl}-2-propyl-1H-benzo[d]imidazole-4-carboxylate (115 mg, 0.23 mmol) obtained in step 3 was dissolved in THF (0.3 mL) and ethanol (1.7 mL), 4 mol/L aqueous sodium hydroxide solution (1.2 mL) was added, and the mixture was stirred at 50° C. for 30 min. After cooling to room temperature, the mixture was concentrated under reduced pressure. To the obtained residue were added 1 mol/L hydrochloric acid and water, and the precipitated crystals were collected by suction filtration to give (E)-1-{[11-(1-cyanoethylidene)-3-fluoro-6,11-dihydrodibenzo[b,e]oxepin-8-yl]methyl}-2-propyl-1H-benzo[d]imidazole-4-carboxylic acid (99 mg, 88%).

ESIMS m/z: 482 $(M+H)^+$; $^1H$ NMR (300 MHz, DMSO-$d_6$, δ): 0.94 (t, J=7.3 Hz, 3H), 1.60-1.78 (m, 2H), 2.16 (s, 3H), 3.00-3.17 (m, 2H), 4.96 (d, J=12.8 Hz, 1H), 5.46 (d, J=12.8 Hz, 1H), 5.71-5.85 (m, 2H), 6.70 (dd, J=10.6, 2.6 Hz, 1H), 6.78-6.87 (m, 1H), 7.22-7.35 (m, 2H), 7.35-7.56 (m, 3H), 7.84-8.03 (m, 2H).

[step 5] (E)-1-{[11-(1-cyanoethylidene)-3-fluoro-6,11-dihydrodibenzo[b,e]oxepin-8-yl]methyl}-2-propyl-1H-benzo[d]imidazole-4-carboxylic acid (97 mg, 0.20 mmol) obtained in step 4 was dissolved in THF (1.0 mL), 1,1'-carbonyldiimidazole (130 mg, 0.80 mmol) was added, and the mixture was stirred at 50° C. for 4 hr. After cooling to room temperature, 25% aqueous ammonia solution (55 μL, 0.80 mmol) was added, and the mixture was stirred at room temperature for 17 hr. To the mixture were added 1 mol/L hydrochloric acid and water, and the mixture was extracted 3 times with chloroform. The combined organic layers were washed with saturated aqueous sodium hydrogen carbonate, dried over anhydrous magnesium sulfate and concentrated under reduced pressure. The residue was purified by silica gel column chromatography (chloroform/methanol=100/0 v/v-93/7 v/v) to give the title compound (97 mg, 100%).

ESIMS m/z: 481 $(M+H)^+$; $^1H$ NMR (270 MHz, DMSO-$d_6$, δ): 0.95 (t, J 10=7.4 Hz, 3H), 1.71-1.87 (m, 2H), 2.15 (s, 3H), 2.91 (t, J=7.4 Hz, 2H), 4.97 (d, J=12.5 Hz, 1H), 5.45 (d, J=12.5 Hz, 1H), 5.59-5.68 (m, 2H), 6.69 (dd, J=10.5, 2.6 Hz, 1H), 6.76-6.87 (m, 1H), 7.14-7.36 (m, 4H), 7.42 (d, J=7.6 Hz, 1H), 7.65-7.76 (m, 2H), 7.84 (d, J=7.2 Hz, 1H), 9.23-9.33 (m, 1H).

Reference Example 2C

(E)-2-{3-fluoro-8-[(4-methoxy-2-propyl-1H-benzo[d]imidazol-1-yl)methyl]dibenzo[b,e]oxepin-11(6H)-ylidene}propanenitrile Using 4-methoxy-2-propyl-1H-benzo[d]imidazole (Journal of Pharmacy and Pharmacology; 1956, vol. 8, p 661, 338 mg, 1.78 mmol) and (E)-2-[8-(bromomethyl)-3-fluorodibenzo[b,e]oxepin-11(6H)-ylidene]propanenitrile (700 mg, 1.95 mmol) obtained in Reference Example 1, and in the same manner as in Reference Example 1A, the title compound (448 mg, 54%) was obtained.

ESIMS m/z: 468 $(M+H)^+$; $^1H$ NMR (270 MHz, $CDCl_3$, δ): 0.98 (t, J=7.4 Hz, 3H), 1.79-1.94 (m, 2H), 2.23 (s, 3H), 2.74-2.83 (m, 2H), 4.03 (s, 3H), 4.70 (d, J=12.6 Hz, 1H), 5.29-5.44 (m, 3H), 6.55 (dd, J=10.2, 2.6 Hz, 1H), 6.60-6.71 (m, 2H), 6.76-6.81 (m, 1H), 6.90-6.94 (m, 1H), 7.02 (dd, J=8.8, 6.4 Hz, 1H), 7.07-7.16 (m, 2H), 7.42 (d, J=7.6 Hz, 1H).

Reference Example 2D

(E)-2-(3-fluoro-8-{[4-methoxy-2-(methoxymethyl)-1H-benzo[d]imidazol-1-yl]methyl}dibenzo[b,e]oxepin-11(6H)-ylidene)propanenitrile Using 4-methoxy-2-(methoxymethyl)-1H-benzo[d]imidazole (64 mg, 0.34 mmol) obtained in Reference Example 2A, step 2 and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 1A, the title compound (70 mg, 45%) and (E)-2-(3-fluoro-8-{[4-methoxy-7-(methoxymethyl)-1H-benzo[d]imidazol-1-yl]methyl}dibenzo[b,e]oxepin-11(6H)-ylidene)propanenitrile were obtained.

ESIMS m/z: 470 $(M+H)^+$; $^1H$ NMR (270 MHz, $CDCl_3$, δ): 2.23 (s, 3H), 3.32 (s, 3H), 4.04 (s, 3H), 4.70-4.74 (m, 3H), 5.36-5.49 (m, 3H), 6.52-6.72 (m, 2H), 6.84-6.87 (m, 1H), 6.99-7.02 (m, 2H), 7.15-7.21 (m, 3H), 7.39-7.42 (m, 1H).

Reference Example 2E

(E)-2-(3-fluoro-8-{[7-methoxy-2-(methoxymethyl)-1H-benzo[d]imidazol-1-yl]methyl}dibenzo[b,e]oxepin-11(6H)-ylidene)propanenitrile Using 4-methoxy-2-(methoxymethyl)-1H-benzo[d]imidazole (64 mg, 0.34 mmol) obtained in Reference Example 2A, step 2 and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 2D, the title compound (67 mg, 43%) was obtained.

ESIMS m/z: 470 $(M+H)^+$; $^1H$ NMR (270 MHz, $CDCl_3$, δ): 2.24 (s, 3H), 3.32 (s, 3H), 3.80 (s, 3H), 4.61 (s, 2H), 4.73 (d, J=12.8 Hz, 1H), 5.39 (d, J=12.8 Hz, 1H), 5.78 (s, 2H), 6.52-6.57 (m, 1H), 6.60-6.67 (m, 1H), 6.70-6.73 (m, 1H), 6.99-7.05 (m, 2H), 7.15-7.21 (m, 2H), 7.38-7.41 (m, 2H).

Reference Example 2F

(E)-2-(8-{[4-ethoxy-2-(methoxymethyl)-1H-benzo[d]imidazol-1-yl]methyl}-3-fluorodibenzo[b,e]oxepin-11(6H)-ylidene)propanenitrile

[step 1] Using (E)-2-(3-fluoro-8-{[4-hydroxy-2-(hydroxymethyl)-1H-benzo[d]imidazol-1-yl]methyl}dibenzo[b,e]oxepin-11(6H)-ylidene)propanenitrile (201 mg, 0.46 mmol) obtained in Reference Example 2A, step 4, and ethanol (0.27 mL, 4.55 mmol) instead of deuterated methanol, and in the same manner as in Reference Example 2A, step 5, (E)-2-(8-{[4-ethoxy-2-(hydroxymethyl)-1H-benzo[d]imidazol-1-yl]methyl}-3-fluorodibenzo[b,e]oxepin-11(6H)-ylidene)propanenitrile (107 mg, 50%) was obtained.

ESIMS m/z: 470 $(M+H)^+$; $^1H$ NMR (270 MHz, $CDCl_3$, δ): 1.50-1.60 (m, 3H), 2.23 (s, 3H), 4.29 (q, J=7.0 Hz, 2H), 4.71 (d, J=12.8 Hz, 1H), 4.86 (s, 2H), 5.38 (d, J=12.8 Hz, 1H), 5.41-5.49 (m, 2H), 6.55 (dd, J=10.2, 2.6 Hz, 1H), 6.60-6.68 (m, 1H), 6.71 (d, J=7.6 Hz, 1H), 6.80-6.86 (m, 1H), 6.96-7.06 (m, 2H), 7.16-7.21 (m, 2H), 7.41 (d, J=7.6 Hz, 1H).

[step 2] Using (E)-2-(8-{[4-ethoxy-2-(hydroxymethyl)-1H-benzo[d]imidazol-1-yl]methyl}-3-fluorodibenzo[b,e]oxepin-11(6H)-ylidene)propanenitrile (105 mg, 0.22 mmol)

obtained in step 1, and in the same manner as in Reference Example 2A, step 6, the title compound (86 mg, 80%) was obtained.

ESIMS m/z: 484 $(M+H)^+$; $^1H$ NMR (400 MHz, $CDCl_3$, δ): 1.52-1.59 (m, 3H), 2.23 (s, 3H), 3.33 (s, 3H), 4.30 (q, J=6.8 Hz, 2H), 4.66-4.75 (m, 3H), 5.38 (d, J=12.7 Hz, 1H), 5.43-5.56 (m, 2H), 6.55 (dd, J=10.7, 2.9 Hz, 1H), 6.60-6.67 (m, 1H), 6.70 (d, J=8.8 Hz, 1H), 6.83 (d, J=8.8 Hz, 1H), 6.99-7.04 (m, 2H), 7.13-7.19 (m, 2H), 7.41 (d, J=8.8 Hz, 1H).

Reference Example 2G

(E)-2-(8-{[4-(difluoromethoxy)-2-(methoxymethyl)-1H-benzo[d]imidazol-1-yl]methyl}-3-fluorodibenzo[b,e]oxepin-11(6H)-ylidene)propanenitrile

[step 1] (E)-2-(3-fluoro-8-{[4-hydroxy-2-(hydroxymethyl)-1H-benzo[d]imidazol-1-yl]methyl}dibenzo[b,e]oxepin-11(6H)-ylidene)propanenitrile (245 mg, 0.56 mmol) obtained in Reference Example 2A, step 4 was dissolved in dichloromethane (2.8 mL), 2,6-lutidine (0.22 mL, 1.89 mmol) and tert-butyldimethylsilyl trifluoromethanesulfonate (0.38 mL, 1.67 mmol) were added under ice-cooling, and the mixture was stirred at room temperature for 1 hr. To the mixture was added saturated aqueous sodium hydrogen carbonate, and the mixture was extracted 3 times with chloroform. The combined organic layers were washed with 1 mol/L hydrochloric acid and saturated brine, dried over anhydrous magnesium sulfate and concentrated under reduced pressure. The obtained residue was dissolved in methanol (2.8 mL), potassium carbonate (384 mg, 2.77 mmol) was added, and the mixture was stirred at room temperature for 13 hr. Water was added to the mixture, and the mixture was extracted 3 times with chloroform. The combined organic layers were dried over anhydrous magnesium sulfate, and concentrated under reduced pressure. The residue was purified by silica gel column chromatography (chloroform/methanol=100/0 v/v-85/15 v/v) to give (E)-2-[8-({2-[(tert-butyldimethylsiloxy)methyl]-4-hydroxy-1H-benzo[d]imidazol-1-yl}methyl)-3-fluorodibenzo[b,e]oxepin-11(6H)-ylidene]propanenitrile (203 mg, 66%).

ESIMS m/z: 556 $(M+H)^+$; $^1H$ NMR (300 MHz, $CDCl_3$, δ): 0.01 (br s, 6H), 0.76-0.81 (m, 9H), 2.23 (s, 3H), 4.72 (d, J=12.5 Hz, 1H), 4.97 (s, 2H), 5.38 (d, J=12.5 Hz, 1H), 5.45-5.61 (m, 2H), 6.54 (dd, J=10.3, 2.6 Hz, 1H), 6.59-6.68 (m, 1H), 6.71-6.78 (m, 1H), 6.78-6.85 (m, 1H), 6.96-7.06 (m, 2H), 7.14 (t, J=7.9 Hz, 1H), 7.18-7.25 (m, 1H), 7.42 (d, J=7.7 Hz, 1H).

[step 2] (E)-2-[8-({2-[(tert-butyldimethylsiloxy)methyl]-4-hydroxy-1H-benzo[d]imidazol-1-yl}methyl)-3-fluorodibenzo[b,e]oxepin-11(6H)-ylidene]propanenitrile (200 mg, 0.36 mmol) obtained in step 1 was dissolved in DMF (5.5 mL), cesium carbonate (352 mg, 1.08 mmol) and sodium 2-chloro-2,2-difluoroacetate (165 mg, 1.08 mmol) were added, and the mixture was stirred at 60° C. for 1 hr. To the mixture was added saturated aqueous ammonium chloride solution, and the mixture was extracted 3 times with ethyl acetate. The combined organic layers were washed with water, dried over anhydrous magnesium sulfate and concentrated under reduced pressure. The residue was purified by silica gel column chromatography (hexane/ethyl acetate=100/0 v/v-20/80 v/v) to give (E)-2-(8-{[4-(difluoromethoxy)-2-(hydroxymethyl)-1H-benzo[d]imidazol-1-yl]methyl}-3-fluorodibenzo[b,e]oxepin-11(6H)-ylidene)propanenitrile (55 mg, 31%).

ESIMS m/z: 492 $(M+H)^+$; $^1H$ NMR (400 MHz, $CDCl_3$, δ): 2.23 (s, 3H), 4.74 (d, J=12.7 Hz, 1H), 4.88 (s, 2H), 5.39 (d, J=12.7 Hz, 1H), 5.43-5.54 (m, 2H), 6.55 (dd, J=10.2, 2.4 Hz, 1H), 6.61-6.67 (m, 1H), 6.97-7.09 (m, 4H), 7.15-7.21 (m, 2H), 7.29-7.62 (m, 2H).

[step 3] Using (E)-2-(8-{[4-(difluoromethoxy)-2-(hydroxymethyl)-1H-benzo[d]imidazol-1-yl]methyl}-3-fluorodibenzo[b,e]oxepin-11(6H)-ylidene)propanenitrile (55 mg, 0.11 mmol) obtained in step 2, and in the same manner as in Reference Example 2A, step 6, the title compound (35 mg, 62%) was obtained.

ESIMS m/z: 506 $(M+H)^+$; $^1H$ NMR (300 MHz, $CDCl_3$, δ): 2.23 (s, 3H), 3.37 (s, 3H), 4.70 (s, 2H), 4.75 (d, J=12.8 Hz, 1H), 5.40 (d, J=12.8 Hz, 1H), 5.43-5.58 (m, 2H), 6.55 (dd, J=10.3, 2.6 Hz, 1H), 6.61-6.69 (m, 1H), 6.98-7.12 (m, 4H), 7.16-7.22 (m, 2H), 7.33-7.61 (m, 2H).

Reference Example 2H

(E)-2-(3-fluoro-8-{[4-(hydroxymethyl)-2-propyl-1H-benzo[d]imidazol-1-yl]methyl}dibenzo[b,e]oxepin-11(6H)-ylidene)propanenitrile

[step 1] Methyl 2-propyl-1H-benzo[d]imidazole-4-carboxylate (350 mg, 1.6 mmol) obtained in Reference Example 2B, step 2 was dissolved in THF (16 mL), lithium aluminum hydride (303 mg, 8.0 mmol) was added, and the mixture was stirred at 80° C. for 3 hr. After completion of the reaction, saturated sodium sulfate aqueous solution (10 mL) was added to the mixture under ice-cooling. The mixture was stirred at room temperature for 1 hr, filtered through celite, and the solution was concentrated under reduced pressure to quantitatively give (2-propyl-1H-benzo[d]imidazol-4-yl)methanol (304 mg).

ESIMS m/z: 191 $(M+H)^+$; $^1H$ NMR (300 MHz, $CDCl_3$, δ): 1.03 (t, J=7.3 Hz, 3H), 1.81-1.95 (m, 2H), 2.87 (t, J=7.3 Hz, 2H), 5.07 (s, 2H), 6.99-7.09 (m, 1H), 7.16 (t, J=7.7 Hz, 1H), 7.49 (d, J=7.7 Hz, 1H).

[step 2] Using (2-propyl-1H-benzo[d]imidazol-4-yl)methanol (47 mg, 0.25 mmol) obtained in step 1 and (E)-2-[8-(bromomethyl)-3-fluorodibenzo[b,e]oxepin-11(6H)-ylidene]propanenitrile (92 mg, 0.26 mmol) obtained in Reference Example 1, and in the same manner as in Reference Example 1A, the title compound (106 mg, 92%) was obtained.

ESIMS m/z: 468 $(M+H)^+$; $^1H$ NMR (270 MHz, $CDCl_3$, δ): 1.01 (t, J=7.4 Hz, 3H), 1.77-1.93 (m, 2H), 2.23 (s, 3H), 2.74-2.84 (m, 2H), 4.18-4.35 (m, 1H), 4.73 (d, J=12.5 Hz, 1H), 5.15 (s, 2H), 5.32-5.46 (m, 3H), 6.55 (dd, J=10.2, 2.6 Hz, 1H), 6.60-6.69 (m, 1H), 6.94-6.98 (m, 1H), 7.02 (dd, J=8.7, 6.4 Hz, 1H), 7.07-7.18 (m, 4H), 7.43 (d, J=7.9 Hz, 1H).

Reference Example 2I

(E)-2-(3-fluoro-8-{[4-(hydroxymethyl)-2-(methoxymethyl)-1H-benzo[d]imidazol-1-yl]methyl}dibenzo[b,e]oxepin-11(6H)-ylidene)propanenitrile

[step 1] Methyl 2-(2-methoxyacetamido)benzoate (U.S. Pat. No. 5,091,403; 3.0 g, 13.4 mmol) was suspended in butyric anhydride (12.7 mL, 134.0 mmol), fuming nitric acid (2.3 mL, 51.1 mmol) was added dropwise under ice-cooling, and the mixture was stirred at 0° C. for 40 min. Water was added to the mixture, 4 mol/L aqueous sodium hydroxide solution was added dropwise to neutralize the mixture, and the mixture was extracted 3 times with ethyl acetate. The combined organic layers were dried over anhydrous magnesium sulfate, and concentrated under reduced pressure. The residue was purified by silica gel column chromatography (hexane/ethyl acetate=100/0 v/v-60/40 v/v) to give methyl 2-(2-methoxyacetamido)-3-nitrobenzoate (1.9 g, 51%).

ESIMS m/z: 269 $(M+H)^+$; $^1H$ NMR (300 MHz, $CDCl_3$, δ): 3.58 (s, 3H), 3.97 (s, 3H), 4.06 (s, 2H), 7.35 (t, J=8.1 Hz, 1H), 8.12 (dd, J=8.1, 1.5 Hz, 1H), 8.22 (dd, J=8.1, 1.5 Hz, 1H), 10.98 (br s, 1H).

[step 2] methyl 2-(2-methoxyacetamido)-3-nitrobenzoate (1.9 g, 6.9 mmol) obtained in step 1 was dissolved in a mixed solvent of ethanol (14 mL) and acetic acid (14 mL), reduced iron (2.3 g, 41.4 mmol) was added, and the mixture was stirred at 120° C. for 3 hr. After completion of the reaction, the mixture was filtered through celite. Saturated aqueous sodium hydrogen carbonate was added to the solution, and the mixture was extracted 3 times with ethyl acetate. The combined organic layers were dried over anhydrous magnesium sulfate, and concentrated under reduced pressure. The residue was purified by silica gel column chromatography (hexane/ethyl acetate=100/0 v/v-20/80 v/v) to give methyl 2-(methoxymethyl)-1H-benzo[d]imidazole-4-carboxylate (1.1 g, 71%).

ESIMS m/z: 221 $(M+H)^+$; $^1H$ NMR (300 MHz, $CDCl_3$, δ): 3.52 (s, 3H), 4.01 (s, 3H), 4.79 (s, 2H), 7.31 (t, J=8.9 Hz, 1H), 7.88-7.97 (m, 2H), 10.48 (br s, 1H).

[step 3] Using methyl 2-(methoxymethyl)-1H-benzo[d]imidazole-4-carboxylate (370 mg, 1.7 mmol) obtained in step 2, and in the same manner as in Reference Example 2H, step 1, [2-(methoxymethyl)-1H-benzo[d]imidazol-4-yl]methanol (203 mg, 63%) was obtained.

ESIMS m/z: 193 $(M+H)^+$; $^1H$ NMR (300 MHz, $CDCl_3$, δ): 3.45 (s, 3H), 4.66 (s, 2H), 5.06 (s, 2H), 7.07-7.14 (m, 1H), 7.20 (t, J=7.7 Hz, 1H), 7.43-7.58 (m, 1H).

[step 4] Using [2-(methoxymethyl)-1H-benzo[d]imidazol-4-yl]methanol (203 mg, 1.06 mmol) obtained in step 3 and (E)-2-[8-(bromomethyl)-3-fluorodibenzo[b,e]oxepin-11 (6H)-ylidene]propanenitrile (386 mg, 1.08 mmol) obtained in Reference Example 1, and in the same manner as in Reference Example 1A, the title compound (451 mg, 91%) was obtained.

ESIMS m/z: 470 $(M+H)^+$; $^1H$ NMR (300 MHz, $CDCl_3$, δ): 2.23 (s, 3H), 3.37 (s, 3H), 3.70-3.77 (m, 1H), 4.69 (s, 2H), 4.74 (d, J=12.5 Hz, 1H), 5.15 (d, J=6.2 Hz, 2H), 5.40 (d, J=12.5 Hz, 1H), 5.44-5.58 (m, 2H), 6.55 (dd, J=10.3, 2.6 Hz, 1H), 6.60-6.69 (m, 1H), 6.98-7.09 (m, 2H), 7.14-7.25 (m, 4H), 7.43 (d, J=7.7 Hz, 1H).

Reference Example 2J

(E)-2-(8-{[4-chloro-2-(methoxymethyl)-1H-benzo[d]imidazol-1-yl]methyl}-3-fluorodibenzo[b,e]oxepin-11(6H)-ylidene)propanenitrile

[step 1] 3-Chloro-2-nitroaniline (2.0 g, 11.6 mmol) was dissolved in dichloromethane, triethylamine (2.6 mL, 18.5 mmol) and 2-methoxyacetyl chloride (1.4 mL, 15.1 mmol) were added, and the mixture was stirred at 70° C. for 18 hr. To the mixture was added 1 mol/L hydrochloric acid, and the mixture was extracted 3 times with chloroform. The combined organic layers were washed with saturated aqueous sodium hydrogen carbonate and saturated brine, dried over anhydrous magnesium sulfate and concentrated under reduced pressure. The residue was purified by silica gel column chromatography (hexane/ethyl acetate=90/10 v/v-50/50 v/v) to give N-(3-chloro-2-nitrophenyl)-2-methoxyacetamide (1.7 g, 62%).

ESIMS m/z: 245 $(M+H)^+$; $^1H$ NMR (300 MHz, $CDCl_3$, δ): 3.51 (s, 3H), 4.03 (s, 2H), 7.29 (dd, J=8.2, 1.5 Hz, 1H), 7.45 (t, J=8.2 Hz, 1H), 8.31 (dd, J=8.2, 1.5 Hz, 1H), 9.19 (br s, 1H).

[step 2] Using N-(3-chloro-2-nitrophenyl)-2-methoxyacetamide (900 mg, 3.68 mmol) obtained in step 1, and in the same manner as in Reference Example 2A, step 2,4-chloro-2-(methoxymethyl)-1H-benzo[d]imidazole (710 mg, 98%) was obtained.

ESIMS m/z: 197 $(M+H)^+$; $^1H$ NMR (300 MHz, $CDCl_3$, δ): 3.53 (s, 3H), 4.81 (s, 2H), 7.21 (d, J=7.9 Hz, 1H), 7.25-7.30 (m, 1H), 7.50 (dd, J=7.9, 0.9 Hz, 1H).

[step 3] Using 4-chloro-2-(methoxymethyl)-1H-benzo[d]imidazole (50 mg, 0.25 mmol) obtained in step 2 and (E)-2-[8-(bromomethyl)-3-fluorodibenzo[b,e]oxepin-11(6H)-ylidene]propanenitrile (96 mg, 0.27 mmol) obtained in Reference Example 1, and in the same manner as in Reference Example 1A, the title compound (107 mg, 89%) was obtained.

ESIMS m/z: 474 $(M+H)^+$; $^1H$ NMR (300 MHz, $CDCl_3$, δ): 2.23 (s, 3H), 3.37 (s, 3H), 4.68-4.79 (m, 3H), 5.40 (d, J=12.8 Hz, 1H), 5.45-5.59 (m, 2H), 6.55 (dd, J=10.3, 2.6 Hz, 1H), 6.61-6.69 (m, 1H), 6.98-7.06 (m, 2H), 7.11-7.22 (m, 3H), 7.31 (dd, J=7.1, 1.6 Hz, 1H), 7.43 (d, J=8.1 Hz, 1H).

Reference Example 2K

(E)-2-(3-fluoro-8-{[4-(2-hydroxypropan-2-yl)-2-(methoxymethyl)-1H-benzo[d]imidazol-1-yl]methyl}dibenzo[b,e]oxepin-11(6H)-ylidene)propanenitrile

[step 1] Methyl 2-(methoxymethyl)-1H-benzo[d]imidazole-4-carboxylate (200 mg, 0.91 mmol) obtained in Reference Example 2I, step 2 was dissolved in THF (0.14 mL), 3 mol/L methylmagnesium chloride THF solution (3.0 mL, 9.1 mmol) was added at 0° C., and the mixture was stirred at room temperature for 1 hr. The reaction was discontinued with saturated aqueous sodium chloride solution, and the mixture was extracted with ethyl acetate, and the extract was dried over sodium sulfate and filtered. The filtrate was concentrated under reduced pressure, and the residue was crystallized from isopropyl ether to give 2-[2-(methoxymethyl)-1H-benzo[d]imidazol-4-yl]propan-2-ol (195 mg, 97%).

ESIMS m/z: 221 $(M+H)^+$; $^1H$ NMR (270 MHz, $CDCl_3$, δ): 1.72 (s, 6H), 3.51 (s, 3H), 4.75 (s, 2H), 7.06-7.09 (m, 1H), 7.17-7.23 (m, 1H), 7.26-7.27 (m, 1H).

[step 2] Using 2-[2-(methoxymethyl)-1H-benzo[d]imidazol-4-yl]propan-2-ol (74 mg, 0.34 mmol) obtained in step 1 and (E)-2-[8-(bromomethyl)-3-fluorodibenzo[b,e]oxepin-11 (6H)-ylidene]propanenitrile (120 mg, 0.335 mmol) obtained in Reference Example 1, and in the same manner as in Reference Example 1A, the title compound (166 mg, 99%) was obtained.

ESIMS m/z: 498 $(M+H)^+$; $^1H$ NMR (270 MHz, $CDCl_3$, δ): 1.70 (s, 6H), 2.22 (s, 3H), 3.38 (s, 3H), 4.69 (s, 2H), 4.74-4.77 (m, 1H), 5.35-5.45 (m, 3H), 6.54-6.67 (m, 2H), 7.01-7.22 (m, 6H), 7.42-7.44 (m, 1H).

Reference Example 2L

(E)-2-(8-{[2,4-bis(methoxymethyl)-1H-benzo[d]imidazol-1-yl]methyl}-3-fluorodibenzo[b,e]oxepin-11(6H)-ylidene)propanenitrile Using (E)-2-(3-fluoro-8-{[4-(hydroxymethyl)-2-(methoxymethyl)-1H-benzo[d]imidazol-1-yl]methyl}dibenzo[b,e]oxepin-11(6H)-ylidene)propanenitrile (150 mg, 0.32 mmol) obtained in Reference Example 2I, and in the same manner as in Reference Example 2A, step 6, the title compound (153 mg, 99%) was obtained.

ESIMS m/z: 484 $(M+H)^+$; $^1H$ NMR (400 MHz, $CDCl_3$, δ): 2.23 (s, 3H), 3.36 (s, 3H), 3.53 (s, 3H), 4.68-4.77 (m, 3H), 4.99 (s, 2H), 5.39 (d, J=12.7 Hz, 1H), 5.45-5.57 (m, 2H), 6.55 (dd, J=9.8, 2.9 Hz, 1H), 6.62-6.67 (m, 1H), 6.98-7.08 (m, 2H), 7.15-7.22 (m, 2H), 7.22-7.30 (m, 1H), 7.34 (d, J=6.8 Hz, 1H), 7.42 (d, J=7.8 Hz, 1H).

Reference Example 2M

(E)-2-(3-fluoro-8-{[2-(methoxymethyl)-4-(methylthio)-1H-benzo[d]imidazol-1-yl]methyl}dibenzo[b,e]oxepin-11(6H)-ylidene)propionitrile

[step 1] Commercially available 3-chloro-2-nitroaniline (3.0 g, 17 mmol) was dissolved in DMF (87 mL), sodium thiomethoxide (1.54 g, 21 mmol) was added, and the mixture was stirred at room temperature for 3 hr. The reaction was discontinued with water, and the mixture was extracted with ethyl acetate, and the extract was dried over sodium sulfate and filtered. The filtrate was concentrated under reduced pressure. The residue was crystallized from isopropyl ether to give 3-(methylthio)-2-nitroaniline (2.5 g, 78%).

ESIMS m/z: 185 $(M+H)^+$; $^1H$ NMR (270 MHz, $CDCl_3$, δ): 2.42 (s, 3H), 5.92 (br s, 2H), 6.55 (d, J=8.2 Hz, 2H), 7.21 (t, J=8.2 Hz, 1H).

[step 2] 3-(Methylthio)-2-nitroaniline (1.0 g, 5.4 mmol) obtained in step 1 was dissolved in DMA (5.4 mL), pyridine (0.44 mL, 5.4 mmol) and 2-methoxyacetyl chloride (1.49 mL, 16 mmol) were added, and the mixture was stirred at room temperature for 2 hr. To the reaction solution were added methanol and aqueous ammonia, and the mixture was stirred at room temperature for 30 min. Water was added, and the crystals were collected by filtration, and dried to give 2-methoxy-N-[3-(methylthio)-2-nitrophenyl]acetamide (1.26 g, 91%).

ESIMS m/z: 257 $(M+H)^+$; $^1H$ NMR (270 MHz, $CDCl_3$, δ): 2.42 (s, 3H), 3.37 (s, 3H), 4.31 (s, 2H), 7.01-7.06 (m, 1H), 7.22-7.38 (m, 1H), 8.17-8.36 (m, 1H).

[step 3]2-Methoxy-N-[3-(methylthio)-2-nitrophenyl]acetamide (215 mg, 0.84 mmol) obtained in step 2 was dissolved in THF (4.2 mL), and sodium hydride (60 mg, 2.5 mmol), and (E)-2-[8-(bromomethyl)-3-fluorodibenzo[b,e]oxepin-11(6H)-ylidene]propanenitrile (300 mg, 0.84 mmol) obtained in Reference Example 1 were added at 0° C., and the mixture was stirred for 5 hr. The reaction was discontinued with water, and the mixture was extracted with ethyl acetate, and the extract was dried over sodium sulfate and filtered. The filtrate was concentrated under reduced pressure. To the obtained residue were added ethanol (4.5 mL), reduced iron (0.12 g, 2.1 mmol), and acetic acid (4.5 mL), and the mixture was stirred at 130° C. for 1 hr and half. Furthermore, reduced iron (0.12 g, 2.1 mmol) was added, and the mixture was stirred at 130° C. for 1 hr, and filtered through celite. To the obtained filtrate was added saturated aqueous sodium hydrogen carbonate solution, and the mixture was extracted with ethyl acetate, and the extract was dried over sodium sulfate, and filtered. The filtrate was concentrated under reduced pressure. The residue was purified by silica gel column chromatography (chloroform/methanol=95/5 v/v) to give (E)-2-(3-fluoro-8-{[2-(methoxymethyl)-4-(methylthio)-1H-benzo[d]imidazol-1-yl]methyl}dibenzo[b,e]oxepin-11(6H)-ylidene)propionitrile (320 mg, 78%).

ESIMS m/z: 486 $(M+H)^+$; $^1H$ NMR (270 MHz, $CDCl_3$, δ): 2.23 (s, 3H), 2.63 (s, 3H), 3.35 (s, 3H), 4.73-4.75 (m, 2H), 5.32-5.44 (m, 2H), 5.50-5.51 (m, 2H), 6.54-6.57 (m, 1H), 6.60-6.72 (m, 2H), 6.97-7.11 (m, 5H), 7.40-7.43 (m, 1H).

Reference Example 2N

(E)-2-(3-fluoro-8-{[2-(methoxymethyl)-4-(methylsulfonyl)-1H-benzo[d]imidazol-1-yl]methyl}dibenzo[b,e]oxepin-11(6H)-ylidene)propionitrile (E)-2-(3-fluoro-8-{[2-(methoxymethyl)-4-(methylthio)-1H-benzo[d]imidazol-1-yl]methyl}dibenzo[b,e]oxepin-11(6H)-ylidene)propionitrile (120 mg, 0.25 mmol) obtained in Reference Example 2M was dissolved in methylene chloride (1.2 mL), m-chloroperbenzoic acid (227 mg, 0.989 mmol) was added at 0° C., and the mixture was stirred at room temperature for 4 hr. The reaction was discontinued with aqueous sodium thiosulfate solution, the mixture was extracted with chloroform, and the extract was dried over sodium sulfate and filtered. The filtrate was concentrated under reduced pressure. The obtained residue was purified by silica gel column chromatography (chloroform/methanol=10/1 v/v) to give (E)-2-(3-fluoro-8-{[2-(methoxymethyl)-4-(methylsulfonyl)-1H-benzo[d]imidazol-1-yl]methyl}dibenzo[b,e]oxepin-11(6H)-ylidene)propionitrile (79 mg, 62%).

ESIMS m/z: 518 $(M+H)^+$; $^1H$ NMR (270 MHz, $CDCl_3$, δ): 2.27 (s, 3H), 3.38 (s, 3H), 3.45 (s, 3H), 4.62-4.73 (m, 3H), 5.47-5.58 (m, 3H), 6.43-6.50 (m, 1H), 6.62-6.67 (m, 1H), 7.08-7.18 (m, 4H), 7.30-7.39 (m, 1H) 7.51-7.54 (m, 1H), 7.88-7.89 (m, 1H).

Reference Example 2P

(E)-2-{8-[(4-chloro-2-cyclopropyl-1H-benzo[d]imidazol-1-yl)methyl]-3-fluorodibenzo[b,e]oxepin-11(6H)-ylidene}propanenitrile Using 4-chloro-2-cyclopropyl-1H-benzo[d]imidazole (EP1988091; 64 mg, 0.34 mmol) and (E)-2-[8-(bromomethyl)-3-fluorodibenzo[b,e]oxepin-11(6H)-ylidene]propanenitrile (120 mg, 0.34 mmol) obtained in Reference Example 1, and in the same manner as in Reference Example 1A, the title compound (105 mg, 67%) was obtained.

ESIMS m/z: 470 $(M+H)^+$; $^1H$ NMR (300 MHz, $CDCl_3$, δ): 1.01-1.11 (m, 2H), 1.23-1.35 (m, 2H), 1.81-1.94 (m, 1H), 2.24 (s, 3H), 4.74 (d, J=12.8 Hz, 1H), 5.40 (d, J=12.8 Hz, 1H), 5.42-5.55 (m, 2H), 6.56 (dd, J=10.3, 2.6 Hz, 1H), 6.61-6.68 (m, 1H), 6.97-7.06 (m, 2H), 7.06-7.13 (m, 2H), 7.17-7.26 (m, 2H), 7.45 (d, J=7.7 Hz, 1H).

Reference Example 3A

(E)-2-{3-fluoro-8-[(2-propyl-1H-imidazo[4,5-c]pyridin-1-yl)methyl]dibenzo[b,e]oxepin-11(6H)-ylidene}propanenitrile Using 2-propyl-1H-imidazo[4,5-c]pyridine (135 mg, 0.838 mmol) and (E)-2-[8-(bromomethyl)-3-fluorodibenzo[b,e]oxepin-11(6H)-ylidene]propanenitrile (300 mg, 0.838 mmol) obtained in Reference Example 1, and in the same manner as in Reference Example 1A, the title compound (50 mg, 14%) was obtained.

ESIMS m/z: 439 $(M+H)^+$; $^1H$ NMR (270 MHz, $CDCl_3$, δ): 1.03 (t, J=7.4 Hz, 3H), 1.82-2.03 (m, 2H), 2.23 (s, 3H), 2.84 (t, J=7.4 Hz, 2H), 4.75 (d, J=12.8 Hz, 1H), 5.34-5.48 (m, 3H), 6.50-6.61 (m, 1H), 6.61-6.71 (m, 1H), 6.96-7.09 (m, 2H), 7.12-7.21 (m, 1H), 7.40-7.52 (m, 1H), 7.64-7.72 (m, 1H), 8.38-8.52 (m, 1H), 8.59-8.69 (m, 1H).

Reference Example 3B (E)-2-{8-[(4-chloro-2-cyclobutyl-1H-imidazo[4,5-c]pyridin-1-yl)methyl]-3-fluorodibenzo[b,e]oxepin-11(6H)-ylidene}propanenitrile

[step 1] 3,4-Diaminopyridine (2.0 g, 18.4 mmol) was mixed with polyphosphoric acid (20g), cyclobutanecarboxylic acid (2.63 mL, 27.5 mmol) was added, and the mixture was stirred with heating at 110° C. for 3 hr. The mixture was added dropwise to 5% aqueous ammonia solution under ice-cooling, and the mixture was extracted 3 times with chloroform. The combined organic layers were dried over anhydrous magnesium sulfate, and concentrated under reduced pressure. To the obtained residue was added ethyl acetate (7 mL), and the precipitated crystals were collected by suction filtration to give 2-cyclobutyl-1H-imidazo[4,5-c]pyridine (2.3 g, 73%).

ESIMS m/z: 174 $(M+H)^+$; $^1H$ NMR (270 MHz, $CDCl_3$, δ): 1.87-2.28 (m, 2H), 2.34-2.75 (m, 4H), 3.76-3.99 (m, 1H), 7.51 (d, J=5.5 Hz, 1H), 8.38 (d, J=5.5 Hz, 1H), 8.96 (s, 1H).

[step 2] 2-Cyclobutyl-1H-imidazo[4,5-c]pyridine (500 mg, 2.89 mmol) obtained in step 1 was dissolved in chloroform (10 mL), m-chloroperbenzoic acid (860 mg, 3.76 mmol) was added and the mixture was stirred at room temperature for 2 hr. To the mixture was added dichloromethane, and the mixture was washed twice with water. The combined aqueous layers were washed 3 times with ethyl acetate, and concentrated under reduced pressure to give a residue.

The obtained residue was dissolved in phosphorus oxychloride (2.5 mL), diisopropylethylamine (0.42 mL) was added, and the mixture was stirred with heating at 50° C. for 3 hr. The mixture was diluted with ethyl acetate, added dropwise to saturated aqueous sodium hydrogen carbonate solution under ice-cooling, and the mixture was extracted 3 times with ethyl acetate. The combined organic layers were dried over anhydrous magnesium sulfate, and concentrated under reduced pressure. The obtained residue was purified by silica gel column chromatography (chloroform/methanol=9/1 v/v) to give 4-chloro-2-cyclobutyl-1H-imidazo[4,5-c]pyridine (120 mg, 20%).

ESIMS m/z: 208 $(M+H)^+$; $^1H$ NMR (270 MHz, $CDCl_3$, δ): 1.84-2.19 (m, 2H), 2.31-2.74 (m, 4H), 3.83-4.06 (m, 1H), 7.45 (d, J=5.5 Hz, 1H), 8.15 (d, J=5.5 Hz, 1H).

[step 3] Using 4-chloro-2-cyclobutyl-1H-imidazo[4,5-c]pyridine (41 mg, 0.196 mmol) obtained in step 2 and (E)-2-[8-(bromomethyl)-3-fluorodibenzo[b,e]oxepin-11(6H)-ylidene]propanenitrile (70 mg, 0.196 mmol) obtained in Reference Example 1, and in the same manner as in Reference Example 1A, the title compound (87 mg, 91%) was obtained.

ESIMS m/z: 485 $(M+H)^+$; $^1H$ NMR (270 MHz, $CDCl_3$, δ): 1.92-2.16 (m, 2H), 2.18-2.44 (m, 5H), 2.50-2.77 (m, 2H), 3.53-3.76 (m, 1H), 4.73 (d, J=12.6 Hz, 1H), 5.28 (s, 2H), 5.40 (d, J=12.6 Hz, 1H), 6.53-6.70 (m, 2H), 6.88 (s, 1H), 6.97-7.16 (m, 3H), 7.43-7.48 (m, 1H), 8.10-8.15 (m, 1H).

Reference Example 3C (E)-2-{8-[(7-chloro-2-cyclopropyl-3H-imidazo[4,5-b]pyridin-3-yl)methyl]-3-fluorodibenzo[b,e]oxepin-11(6H)-ylidene}propanenitrile Using 7-chloro-2-cyclopropyl-3H-imidazo[4,5-b]pyridine (EP1988091, 81 mg, 0.419 mmol) and (E)-2-[8-(bromomethyl)-3-fluorodibenzo[b,e]oxepin-11(6H)-ylidene]propanenitrile (150 mg, 0.419 mmol) obtained in Reference Example 1, and in the same manner as in Reference Example 1A, the title compound (107 mg, 54%) was obtained.

ESIMS m/z: 471 $(M+H)^+$; $^1H$ NMR (270 MHz, $CDCl_3$, δ): 1.02-1.16 (m, 2H), 1.25-1.38 (m, 2H), 1.83-1.97 (m, 1H), 2.26 (s, 3H), 4.76 (d, J=12.8 Hz, 1H), 5.41 (d, J=12.8 Hz, 1H), 5.59-5.63 (m, 2H), 6.51-6.59 (m, 1H), 6.59-6.70 (m, 1H), 6.97-7.08 (m, 1H), 7.13-7.35 (m, 3H), 7.38-7.48 (m, 1H), 8.11-8.24 (m, 1H).

Reference Example 3D (E)-2-{8-[(7-chloro-2-cyclobutyl-3H-imidazo[4,5-b]pyridin-3-yl)methyl]-3-fluorodibenzo[b,e]oxepin-11(6H)-ylidene}propanenitrile Using 7-chloro-2-cyclobutyl-3H-imidazo[4,5-b]pyridine (WO2009/29592, 69 mg, 0.335 mmol) and (E)-2-[8-(bromomethyl)-3-fluorodibenzo[b,e]oxepin-11(6H)-ylidene]propanenitrile (120 mg, 0.335 mmol) obtained in Reference Example 1, and in the same manner as in Reference Example 1A, the title compound (102 mg, 62%) was obtained.

ESIMS m/z: 485 $(M+H)^+$; $^1H$ NMR (270 MHz, $CDCl_3$, δ): 1.92-2.12 (m, 2H), 2.17-2.35 (m, 5H), 2.51-2.73 (m, 2H), 3.54-3.70 (m, 1H), 4.74 (d, J=12.8 Hz, 1H), 5.35-5.47 (m, 3H), 6.50-6.60 (m, 1H), 6.60-6.70 (m, 1H), 6.93-7.07 (m, 2H), 7.14-7.21 (m, 1H), 7.23-7.29 (m, 1H), 7.40-7.49 (m, 1H), 8.12-8.24 (m, 1H).

Reference Example 3E (E)-2-{3-fluoro-8-[(2-propyl-3H-imidazo[4,5-b]pyridin-1-yl)methyl]dibenzo[b,e]oxepin-11(6H)-ylidene}propanenitrile (E)-2-[3-fluoro-8-(hydroxymethyl)dibenzo[b,e]oxepin-11(6H)-ylidene]propanenitrile (58 mg, 0.198 mmol) obtained in Reference Example 1, step 5 and 2-propyl-3H-imidazo[4,5-b]pyridine (Journal of Medicinal Chemistry, 1991, vol. 34, p 2919, 35 mg, 0.217 mmol) were dissolved in THF, triphenylphosphine polymer supported (3.02 mmol/g, 131 mg, 0.395 mmol), di-tert-butyl diazadicarboxylate (91 mg, 0.395 mmol) were added and the mixture was stirred at room temperature for 4 hr. The mixture was filtered through celite, and the filtrate was concentrated under reduced pressure. The obtained residue was purified by silica gel column chromatography (hexane/ethyl acetate=1/2 v/v) to give the title compound (44 mg, 51%).

ESIMS m/z: 439 $(M+H)^+$; $^1H$ NMR (270 MHz, $CDCl_3$, δ): 1.00 (t, J=7.4 Hz, 3H), 1.74-1.96 (m, 2H), 2.23 (s, 3H), 2.78 (t, J=7.4 Hz, 2H), 4.75 (d, J=12.8 Hz, 1H), 5.40 (d, J=12.8 Hz, 1H), 5.52 (s, 2H), 6.48-6.57 (m, 1H), 6.57-6.69 (m, 1H), 6.95-7.06 (m, 1H), 7.09-7.15 (m, 1H), 7.19-7.29 (m, 2H), 7.37-7.47 (m, 1H), 7.96-8.09 (m, 1H), 8.27-8.38 (m, 1H).

Reference Example 3G (E)-2-{3-fluoro-8-[(5-fluoro-2-propyl-3H-imidazo[4,5-b]pyridin-3-yl)methyl]dibenzo[b,e]oxepin-11(6H)-ylidene}propanenitrile

[step 1] 6-Fluoropyridin-3-amine (800 mg, 7.14 mmol) was suspended in butyric anhydride (3.5 mL, 21.4 mmol), fuming nitric acid (1.15 mL, 25.6 mmol) was added dropwise under ice-cooling, and the mixture was stirred at 0° C. for 4 hr. The mixture was allowed to warm to room temperature, and stirred for 4 hr. Water was added to the mixture, 4 mol/L aqueous sodium hydroxide solution was added dropwise to neutralize the mixture, and the mixture was extracted 3 times with ethyl acetate. The combined organic layers were dried over anhydrous magnesium sulfate and purified by silica gel column chromatography (hexane/ethyl acetate=2/1 v/v) to give N-(6-fluoro-2-nitropyridin-3-yl)butylamide (800 mg, 49%).

ESIMS m/z: 228 $(M+H)^+$; $^1H$ NMR (270 MHz, $CDCl_3$, δ): 1.05 (t, J=7.3 Hz, 3H), 1.71-1.90 (m, 2H), 2.51 (t, J=7.3 Hz, 2H), 7.35 (dd, J=8.8, 3.8 Hz, 1H), 9.46 (dd, J=8.8, 6.0 Hz, 1H), 10.13 (br s, 1H).

[step 2] N-(6-fluoro-2-nitropyridin-3-yl)butylamide (170 mg, 0.748 mmol) obtained in step 1 was dissolved in a mixed solvent of ethanol (1 mL)-ethyl acetate (1 mL), reduced iron (125 mg, 2.245 mmol) was added and the mixture was stirred at 100° C. overnight. The mixture was filtered through celite, and the filtrate was concentrated under reduced pressure. The obtained residue was purified by silica gel column chromatography (hexane/ethyl acetate=1/2 v/v) to give a residue (106 mg).

The obtained residue (106 mg) was dissolved in acetic acid (2 mL), and the mixture was stirred with heating under reflux overnight. The mixture was concentrated under reduced pressure, and the obtained residue was purified by silica gel column chromatography (hexane/ethyl acetate=1/1 v/v) to give 5-fluoro-2-propyl-3H-imidazo[4,5-b]pyridine (47 mg, 36%).

ESIMS m/z: 180 $(M+H)^+$; $^1H$ NMR (270 MHz, $CDCl_3$, δ): 1.03 (t, J=7.4 Hz, 3H), 1.68-1.90 (m, 2H), 2.38 (t, J=7.4 Hz, 2H), 6.27 (dd, J=7.7, 2.6 Hz, 1H), 6.94 (s, 1H), 7.44 (t, J=7.7 Hz, 1H).

[step 3] Using 5-fluoro-2-propyl-3H-imidazo[4,5-b]pyridine (47 mg, 0.262 mmol) obtained in step 2 and (E)-2-[3-fluoro-8-(hydroxymethyl)dibenzo[b,e]oxepin-11(6H)-ylidene]propanenitrile (70 mg, 0.238 mmol) obtained in Reference Example 1, step 5, and in the same manner as in Reference Example 3E, the title compound (46 mg, 42%) was obtained.

ESIMS m/z: 457 $(M+H)^+$; $^1H$ NMR (270 MHz, $CDCl_3$, δ): 0.99 (t, J=7.6 Hz, 3H), 1.80-1.91 (m, 2H), 2.23 (s, 3H), 2.76 (t, J=7.6 Hz, 2H), 4.77 (d, J=12.8 Hz, 1H), 5.35-5.51 (m, 3H), 6.50-6.59 (m, 1H), 6.59-6.70 (m, 1H), 6.80-6.91 (m, 1H), 6.96-7.08 (m, 1H), 7.09-7.17 (m, 1H), 7.17-7.27 (m, 1H), 7.41-7.54 (m, 1H), 7.98-8.12 (m, 1H).

Reference Example 3H

(E)-2-{3-fluoro-8-[(5-fluoro-2-propyl-1H-imidazo[4,5-b]pyridin-1-yl)methyl]dibenzo[b,e]oxepin-11(6H)-ylidene}propanenitrile

[step 1] Using N-(6-fluoro-2-nitropyridin-3-yl)butylamide (274 mg, 1.21 mmol) obtained in Reference Example 3G, step 1 and (E)-2-[8-(bromomethyl)-3-fluorodibenzo[b,e]oxepin-11(6H)-ylidene]propanenitrile (360 mg, 1.01 mmol) obtained in Reference Example 1, and in the same manner as in Reference Example 1A, (E)-N-{[11-(1-cyanoethylidene)-3-fluoro-6,11-dihydrodibenzo[b,e]oxepin-8-yl]methyl}-N-(6-fluoro-2-nitropyridin-3-yl)butylamide (390 mg, 78%) was obtained.

ESIMS m/z: 505 $(M+H)^+$; $^1H$ NMR (270 MHz, $CDCl_3$, δ): 0.78-0.95 (m, 3H), 1.59-1.73 (m, 2H), 1.95-2.08 (m, 2H), 2.24 (s, 3H), 3.84-4.02 (m, 1H), 4.71-4.91 (m, 1H), 5.29-5.51 (m, 1H), 5.69-5.85 (m, 1H), 6.54-6.63 (m, 1H), 6.63-6.72 (m, 1H), 7.00-7.16 (m, 4H), 7.24-7.35 (m, 1H), 7.38-7.51 (m, 1H).

[step 2] (E)-N-{[11-(1-cyanoethylidene)-3-fluoro-6,11-dihydrodibenzo[b,e]oxepin-8-yl]methyl}-N-(6-fluoro-2-nitropyridin-3-yl)butylamide (70 mg, 0.139 mmol) obtained in step 1 was dissolved in ethanol (2.5 mL), reduced iron (23 mg, 0.417 mmol) and acetic acid (0.5 mL) were added and the mixture was stirred with heating under reflux overnight. The mixture was filtered through celite, and the filtrate was concentrated under reduced pressure. The obtained residue was purified by silica gel column chromatography (hexane/ethyl acetate=1/2 v/v) to give the title compound (12 mg, 19%).

ESIMS m/z: 457 $(M+H)^+$; $^1H$ NMR (270 MHz, $CDCl_3$, δ): 1.01 (t, J=7.6 Hz, 3H), 1.79-2.00 (m, 2H), 2.25 (s, 3H), 2.85 (t, J=7.6 Hz, 2H), 4.71-4.79 (m, 1H), 5.35-5.48 (m, 3H), 6.53-6.62 (m, 1H), 6.60-6.71 (m, 1H), 6.71-6.83 (m, 1H), 6.92-6.98 (m, 1H), 6.98-7.09 (m, 1H), 7.09-7.17 (m, 1H), 7.38-7.56 (m, 2H).

Reference Example 3I

(E)-2-{8-[(2-cyclobutyl-5-fluoro-1H-imidazo[4,5-b]pyridin-1-yl)methyl]-3-fluorodibenzo[b,e]oxepin-11(6H)-ylidene}propanenitrile

[step 1] 6-Fluoropyridin-3-amine (600 mg, 5.35 mmol) was dissolved in dichloromethane (20 mL), triethylamine (1.49 mL, 10.7 mmol) and cyclobutanecarbonyl chloride (0.67 mL, 5.89 mmol) were added, and the mixture was stirred at room temperature overnight. Water was added to the mixture, and the mixture was extracted 3 times with ethyl acetate. The combined organic layers were dried over anhydrous magnesium sulfate, and concentrated under reduced pressure. To the obtained residue was added diisopropyl ether and the precipitated crystals were collected by suction filtration to give N-(6-fluoropyridin-3-yl)cyclobutanecarboxamide (899 mg, 86%).

ESIMS m/z: 195 $(M+H)^+$; $^1H$ NMR (270 MHz, $CDCl_3$, δ): 1.85-2.10 (m, 2H), 2.10-2.49 (m, 4H), 3.08-3.30 (m, 1H), 6.77-7.01 (m, 1H), 7.56 (br s, 1H), 8.17-8.35 (m, 2H).

[step 2] N-(6-fluoropyridin-3-yl)cyclobutanecarboxamide (800 mg, 4.12 mmol) obtained in step 1 was dissolved in acetic anhydride (4 mL), fuming nitric acid (0.7 mL, 15.7 mmol) was added under ice-cooling, and the mixture was stirred at room temperature for 3 hr. Under ice-cooling, 5 mol/L aqueous sodium hydroxide solution was added dropwise to the mixture, and the mixture was extracted 3 times with ethyl acetate. The combined organic layers were dried over anhydrous magnesium sulfate, and concentrated under reduced pressure. The obtained residue was purified by silica gel column chromatography (hexane/ethyl acetate=1/1 v/v) to give N-(6-fluoro-2-nitropyridin-3-yl)cyclobutanecarboxamide (348 mg, 35%).

ESIMS m/z: 240 $(M+H)^+$; $^1H$ NMR (270 MHz, $CDCl_3$, δ): 1.80-2.17 (m, 2H), 2.17-2.54 (m, 4H), 3.22-3.44 (m, 1H), 7.30-7.43 (m, 1H), 9.34-9.58 (m, 1H), 9.92-10.21 (m, 1H).

[step 3] Using N-(6-fluoro-2-nitropyridin-3-yl)cyclobutanecarboxamide (200 mg, 0.836 mmol) obtained in step 2 and (E)-2-[8-(bromomethyl)-3-fluorodibenzo[b,e]oxepin-11(6H)-ylidene]propanenitrile (250 mg, 0.697 mmol) obtained in Reference Example 1, and in the same manner as in Reference Example 1A, (E)-N-{[11-(1-cyanoethylidene)-3-fluoro-6,11-dihydrodibenzo[b,e]oxepin-8-yl]methyl}-N-(6-fluoro-2-nitropyridin-3-yl)cyclobutanecarboxamide (180 mg, 50%) was obtained.

ESIMS m/z: 517 $(M+H)^+$; $^1H$ NMR (270 MHz, $CDCl_3$, δ): 1.64-1.90 (m, 4H), 2.18-2.52 (m, 5H), 2.67-2.84 (m, 1H), 3.89-4.05 (m, 1H), 4.70-4.97 (m, 1H), 5.34-5.51 (m, 1H), 5.69-5.89 (m, 1H), 6.52-6.75 (m, 2H), 6.93-7.16 (m, 3H), 7.17-7.52 (m, 3H).

[step 4] Using (E)-N-{[11-(1-cyanoethylidene)-3-fluoro-6,11-dihydrodibenzo[b,e]oxepin-8-yl]methyl}-N-(6-fluoro-2-nitropyridin-3-yl)cyclobutanecarboxamide (180 mg, 0.349 mmol) obtained in step 3, and in the same manner as in Reference Example 3H, step 2, the title compound (100 mg, 61%) was obtained.

ESIMS m/z: 469 $(M+H)^+$; $^1H$ NMR (270 MHz, $CDCl_3$, δ): 1.97-2.16 (m, 2H), 2.24 (s, 3H), 2.29-2.46 (m, 2H), 2.54-2.78 (m, 2H), 3.55-3.76 (m, 1H), 4.72 (d, J=12.8 Hz, 1H), 5.27-5.30 (m, 2H), 5.41 (d, J=12.8 Hz, 1H), 6.50-6.61 (m, 1H), 6.61-6.71 (m, 1H), 6.71-6.81 (m, 1H), 6.87-6.94 (m, 1H), 6.99-7.08 (m, 1H), 7.08-7.16 (m, 1H), 7.39-7.55 (m, 2H).

Reference Example 3J

(E)-2-{3-fluoro-8-[(2-propyl-1H-imidazo[4,5-b]pyrazin-1-yl)methyl]dibenzo[b,e]oxepin-11(6H)-ylidene}propanenitrile

[step 1] Using pyrazine-2,3-diamine (1.0 g, 9.1 mmol) instead of 3,4-diaminopyridine, and butyric acid (1.2 mL, 13.6 mmol) instead of cyclobutanecarboxylic acid, and in the same manner as in Reference Example 3B, step 1,2-propyl-1H-imidazo[4,5-b]pyrazine (0.9 g, 60%) was obtained.

ESIMS m/z: 163 $(M+H)^+$; $^1H$ NMR (300 MHz, $CDCl_3$, δ): 0.96 (t, J=7.3 Hz, 3H), 1.75-1.91 (m, 2H), 2.88 (t, J=7.3 Hz, 2H), 8.31 (s, 2H), 13.21 (br s, 1H).

[step 2] Using 2-propyl-1H-imidazo[4,5-b]pyrazine (68 mg, 0.42 mmol) obtained in step 1 and (E)-2-[8-(bromomethyl)-3-fluorodibenzo[b,e]oxepin-11(6H)-ylidene]propanenitrile (153 mg, 0.43 mmol) obtained in Reference Example 1, and in the same manner as in Reference Example 1A, the title compound (136 mg, 74%) was obtained.

ESIMS m/z: 440 $(M+H)^+$; $^1H$ NMR (300 MHz, $CDCl_3$, δ): 1.01 (t, J=7.3 Hz, 3H), 1.84-1.98 (m, 2H), 2.23 (s, 3H), 2.79-2.89 (m, 2H), 4.76 (d, J=12.8 Hz, 1H), 5.41 (d, J=12.8 Hz, 1H), 5.43-5.56 (m, 2H), 6.56 (dd, J=10.3, 2.6 Hz, 1H), 6.60-6.69 (m, 1H), 7.02 (dd, J=8.8, 6.6 Hz, 1H), 7.10-7.14 (m, 1H), 7.21-7.26 (m, 1H), 7.45 (d, J=8.1 Hz, 1H), 8.27 (d, J=2.6 Hz, 1H), 8.51 (d, J=2.6 Hz, 1H).

Reference Example 4A

(E)-2-[8-({2-[(dimethylamino)methyl]-1H-benzo[d]imidazol-1-yl}methyl)-3-fluorodibenzo[b,e]oxepin-11(6H)-ylidene]propanenitrile

[step 1]2-Nitroaniline (0.7 g, 5.1 mmol) was dissolved in dichloromethane (25 mL), 2-[tert-butoxycarbonyl(methyl)amino]acetic acid (2.9 g, 15.2 mmol), N,N'-dicyclohexylcarbodiimide (3.1 g, 15.2 mmol) and N,N-dimethylaminopyridine (0.6 g, 5.1 mmol) were added, and the mixture was stirred at room temperature for 24 hr. The mixture was filtered to remove white solids, saturated aqueous sodium hydrogen carbonate was added to the obtained solution, and the mixture was extracted 3 times with chloroform. The combined organic layers were dried over anhydrous magnesium sulfate, and concentrated under reduced pressure. The residue was purified by silica gel column chromatography (hexane/ethyl acetate=100/0 v/v-60/40 v/v) to give tert-butyl methyl[2-(2-nitrophenylamino)-2-oxoethyl]carbamate (1.1 g, 69%).

ESIMS m/z: 310 $(M+H)^+$; $^1H$ NMR (300 MHz, $CDCl_3$, δ): 1.37-1.65 (m, 9H), 3.05 (s, 3H), 4.01-4.17 (m, 2H), 7.21 (t, J=7.3 Hz, 1H), 7.67 (t, J=7.3 Hz, 1H), 8.24 (d, J=8.4, 1.5 Hz, 1H), 8.78-8.90 (m, 1H), 10.94 (br s, 1H).

[step 2] tert-Butyl methyl[2-(2-nitrophenylamino)-2-oxoethyl]carbamate (400 mg, 1.29 mmol) obtained in step 1 was dissolved in THF (7.6 mL), sodium hydride (62 mg, 1.55 mmol) and (E)-2-[8-(bromomethyl)-3-fluorodibenzo[b,e]oxepin-11(6H)-ylidene]propanenitrile (468 mg, 1.31 mmol) obtained in Reference Example 1 were added under ice-cooling, and the mixture was stirred at room temperature for 36 hr. To the mixture was added water (20 mL), and the mixture was extracted 3 times with chloroform. The combined organic layers were dried over anhydrous magnesium sulfate, and concentrated under reduced pressure. The residue was purified by silica gel column chromatography (hexane/ethyl acetate=100/0 v/v-50/50 v/v) to give (E)-tert-butyl 2-({[11-(1-cyanoethylidene)-3-fluoro-6,11-dihydrodibenzo[b,e]oxepin-8-yl]methyl}(2-nitrophenyl)amino)-2-oxoethyl(methyl)carbamate (570 mg, 75%).

ESIMS m/z: 487 $(M+H)^+$ (-Boc); $^1H$ NMR (300 MHz, $CDCl_3$, δ): 1.34-1.50 (m, 9H), 2.24 (br s, 3H), 2.86-2.97 (m, 3H), 3.26-3.84 (m, 2H), 3.97-4.44 (m, 2H), 4.70-4.91 (m, 1H), 5.20-5.62 (m, 2H), 6.49-6.72 (m, 2H), 6.76-7.08 (m, 2H), 7.10-7.40 (m, 2H), 7.42-7.62 (m, 2H), 7.86-8.06 (m, 1H).

[step 3] Using (E)-tert-butyl 2-({[11-(1-cyanoethylidene)-3-fluoro-6,11-dihydrodibenzo[b,e]oxepin-8-yl]methyl}(2-nitrophenyl)amino)-2-oxoethyl(methyl)carbamate (570 mg, 0.97 mmol) obtained in step 2, and in the same manner as in Reference Example 2I, step 2, (E)-tert-butyl (1-{[11-(cyanoethylidene)-3-fluoro-6,11-dihydrodibenzo[b,e]oxepin-8-yl]methyl}-1H-benzo[d]imidazol-2-yl)methyl(methyl)carbamate (520 mg, 99%) was obtained.

ESIMS m/z: 539 $(M+H)^+$; $^1H$ NMR (300 MHz, $CDCl_3$, δ): 1.15-1.27 (m, 9H), 2.22 (s, 3H), 2.84 (s, 3H), 4.61-4.93 (m, 3H), 5.39 (d, J=12.8 Hz, 1H), 5.46-5.71 (m, 2H), 6.54 (dd, J=10.3, 2.6 Hz, 1H), 6.58-6.68 (m, 1H), 6.90-6.96 (m, 1H), 6.97-7.11 (m, 2H), 7.14-7.33 (m, 3H), 7.34-7.44 (m, 1H), 7.76-7.83 (m, 1H).

[step 4] (E)-tert-butyl (1-{[11-(cyanoethylidene)-3-fluoro-6,11-dihydrodibenzo[b,e]oxepin-8-yl]methyl}-1H-benzo[d]imidazol-2-yl)methyl(methyl)carbamate (400 mg, 0.74 mmol) obtained in step 3 was dissolved in dichloromethane (3.7 mL), trifluoroacetic acid (1.72 mL, 22.3 mol) was added, and the mixture was stirred at room temperature for 3 hr. To the mixture was added saturated aqueous sodium hydrogen carbonate was added, and the mixture was extracted 3 times with chloroform. The combined organic layers were dried over anhydrous magnesium sulfate, and concentrated under reduced pressure. The residue was purified by silica gel column chromatography (chloroform/methanol=100/0 v/v-90/10 v/v) to give (E)-2-[3-fluoro-8-({2-[(methylamino)methyl]-1H-benzo[d]imidazol-1-yl}methyl)dibenzo[b,e]oxepin-11(6H)-ylidene]propanenitrile (311 mg, 96%).

ESIMS m/z: 439 $(M+H)^+$; $^1H$ NMR (300 MHz, $CDCl_3$, δ): 2.23 (s, 3H), 2.47 (s, 3H), 3.97 (s, 2H), 4.73 (d, J=12.8 Hz, 1H), 5.39 (d, J=12.8 Hz, 1H), 5.47-5.62 (m, 2H), 6.54 (dd, J=10.3, 2.6 Hz, 1H), 6.60-6.66 (m, 1H), 6.99-7.06 (m, 2H), 7.14-7.21 (m, 1H), 7.21-7.32 (m, 3H), 7.42 (d, J=8.1 Hz, 1H), 7.76-7.82 (m, 1H).

[step 5] (E)-2-[3-fluoro-8-({2-[(methylamino)methyl]-1H-benzo[d]imidazol-1-yl}methyl)dibenzo[b,e]oxepin-11(6H)-ylidene]propanenitrile (215 mg, 0.49 mmol) obtained in step 4 was dissolved in acetonitrile (9.8 mL), formaldehyde (0.26 mL, 3.43 mmol) and sodium cyanoborohydride (62 mg, 0.98 mmol) were added, and the mixture was stirred at room temperature for 6 hr. To the mixture was added saturated aqueous sodium hydrogen carbonate, and the mixture was extracted 3 times with chloroform. The combined organic layers were dried over anhydrous magnesium sulfate, and concentrated under reduced pressure. The residue was purified by silica gel column chromatography (hexane/ethyl acetate=100/0 v/v-0/100 v/v) to quantitatively give the title compound (222 mg).

ESIMS m/z: 453 $(M+H)^+$; $^1H$ NMR (300 MHz, $CDCl_3$, δ): 2.23 (s, 3H), 2.26 (s, 6H), 3.60-3.73 (m, 2H), 4.72 (d, J=12.8 Hz, 1H), 5.39 (d, J=12.8 Hz, 1H), 5.54-5.70 (m, 2H), 6.55 (dd, J=10.3, 2.6 Hz, 1H), 6.60-6.69 (m, 1H), 6.98-7.06 (m, 2H), 7.15-7.31 (m, 4H), 7.42 (d, J=7.7 Hz, 1H), 7.76-7.81 (m, 1H).

Reference Example 4B (E)-tert-butyl [1-({3-fluoro-11-[1-(5-oxo-4,5-dihydro-1,2,4-oxadiazol-3-yl)ethylidene]-6,11-dihydrodibenzo[b,e]oxepin-8-yl}methyl)-1H-benzo[d]imidazol-2-yl]methyl(methyl)carbamate Using (E)-tert-butyl (1-{[11-(cyanoethylidene)-3-fluoro-6,11-dihydrodibenzo[b,e]oxepin-8-yl]methyl}-1H-benzo[d]imidazol-2-yl)methyl(methyl)carbamate (80 mg, 0.15 mmol) obtained in Reference Example 4A, step 3, and in the same manner as in Example 1, the title compound (48 mg, 54%) was obtained.

ESIMS m/z: 598 $(M+H)^+$; $^1H$ NMR (300 MHz, $CDCl_3$, δ): 1.21-1.41 (m, 9H), 2.27 (s, 3H), 2.80-2.96 (m, 3H), 4.63-4.80 (m, 3H), 5.42-5.71 (m, 3H), 6.52 (dd, J=10.3, 2.6 Hz, 1H), 6.60-6.70 (m, 1H), 6.93-7.01 (m, 1H), 7.02-7.16 (m, 3H), 7.22-7.38 (m, 3H), 7.78-7.87 (m, 1H).

Reference Example 4C (E)-2-(8-{[2-(azetidin-1-yl)-1H-benzo[d]imidazol-1-yl]methyl}-3-fluorodibenzo[b,e]oxepin-11(6H)-ylidene)propanenitrile

[step 1] Commercially available 2-chloro-1H-benzo[d]imidazole (200 mg, 1.31 mmol) was dissolved in THF (1.9 mL), azetidine (0.27 mL, 3.93 mmol) and water (0.27 mL, 0.015 mmol) were added, and the mixture was stirred with heating in an Emrys Optimizer microwave synthesizer at 180° C. for 3 hr. Water was added to the mixture, and the mixture was extracted 3 times with chloroform. The combined organic layers were dried over anhydrous magnesium sulfate, and concentrated under reduced pressure. The residue was purified by silica gel column chromatography (chloroform/methanol=100/0 v/v-90/10 v/v) to give 2-(azetidin-1-yl)-1H-benzo[d]imidazole (40 mg, 18%).

ESIMS m/z: 174 $(M+H)^+$; $^1H$ NMR (300 MHz, DMSO-$d_6$, δ): 2.28-2.43 (m, 2H), 3.98-4.07 (m, 4H), 6.81-6.99 (m, 2H), 7.08-7.24 (m, 2H), 11.28 (br s, 1H).

[step 2] Using 2-(azetidin-1-yl)-1H-benzo[d]imidazole (40 mg, 0.23 mmol) obtained in step 1 and (E)-2-[8-(bromomethyl)-3-fluorodibenzo[b,e]oxepin-11(6H)-ylidene] propanenitrile (84 mg, 0.24 mmol) obtained in Reference Example 1, and in the same manner as in Reference Example 1A, the title compound (61 mg, 59%) was obtained.

ESIMS m/z: 451 $(M+H)^+$; $^1H$ NMR (300 MHz, $CDCl_3$, δ): 2.24 (s, 3H), 2.30-2.42 (m, 2H), 4.14 (t, J=7.5 Hz, 4H), 4.75 (d, J=12.5 Hz, 1H), 5.09-5.23 (m, 2H), 5.41 (d, J=12.5 Hz, 1H), 6.56 (dd, J=10.3, 2.6 Hz, 1H), 6.60-6.69 (m, 1H), 6.93-6.99 (m, 1H), 6.99-7.10 (m, 3H), 7.13-7.20 (m, 1H), 7.19-7.25 (m, 1H), 7.43 (d, J=7.7 Hz, 1H), 7.56 (d, J=7.7 Hz, 1H).

Reference Example 4D (E)-2-(3-fluoro-8-{[2-(pyrrolidin-1-yl)-1H-benzo[d]imidazol-1-yl]methyl}dibenzo[b,e]oxepin-11(6H)-ylidene)propanenitrile Using commercially available 2-(pyrrolidin-1-yl)-1H-benzo[d]imidazole (63 mg, 0.34 mmol) and (E)-2-[8-(bromomethyl)-3-fluorodibenzo[b,e]oxepin-11(6H)-ylidene] propanenitrile (120 mg, 0.34 mmol) obtained in Reference Example 1, and in the same manner as in Reference Example 1A, the title compound (141 mg, 91%) was obtained.

ESIMS m/z: 465 $(M+H)^+$; $^1H$ NMR (270 MHz, $CDCl_3$, δ): 1.86-1.97 (m, 4H), 2.24 (s, 3H), 3.46-3.60 (m, 4H), 4.76 (d, J=12.8 Hz, 1H), 5.24-5.32 (m, 2H), 5.42 (d, J=12.8 Hz, 1H), 6.57 (dd, J=10.2, 2.6 Hz, 1H), 6.61-6.70 (m, 1H), 6.91-7.08 (m, 3H), 7.09-7.19 (m, 2H), 7.22-7.27 (m, 1H), 7.45 (d, J=7.6 Hz, 1H), 7.54 (d, J=7.6 Hz, 1H).

Reference Example 4E (E)-2-(3-fluoro-8-{[2-(piperidin-1-yl)-1H-benzo[d]imidazol-1-yl]methyl}dibenzo[b,e]oxepin-11(6H)-ylidene)propanenitrile Using commercially available 2-(piperidin-1-yl)-1H-benzo[d]imidazole (67 mg, 0.34 mmol) and (E)-2-[8-(bromomethyl)-3-fluorodibenzo[b,e]oxepin-11(6H)-ylidene] propanenitrile (120 mg, 0.34 mmol) obtained in Reference Example 1, and in the same manner as in Reference Example 1A, the title compound (125 mg, 78%) was obtained.

ESIMS m/z: 479 $(M+H)^+$; $^1H$ NMR (270 MHz, $CDCl_3$, δ): 1.49-1.73 (m, 6H), 2.24 (s, 3H), 3.12-3.24 (m, 4H), 4.76 (d, J=12.5 Hz, 1H), 5.12-5.29 (m, 2H), 5.42 (d, J=12.5 Hz, 1H), 6.57 (dd, J=10.2, 2.6 Hz, 1H), 6.61-6.69 (m, 1H), 6.94-7.11 (m, 3H), 7.12-7.22 (m, 2H), 7.23-7.30 (m, 1H), 7.45 (d, J=7.9 Hz, 1H), 7.63 (d, J=7.9 Hz, 1H).

Reference Example 4F (E)-2-(8-{[2-(dimethylamino)-1H-benzo[d]imidazol-1-yl]methyl}-3-fluorodibenzo[b,e]oxepin-11(6H)-ylidene)propanenitrile

[step 1] Commercially available 2-chloro-1H-benzo[d]imidazole (250 mg, 1.64 mmol) was dissolved in DMF (4.7 mL), dimethylamine (50% aqueous solution, 0.50 mL, 4.92 mmol) was added, and the mixture was stirred with heating at 200° C. for 30 min in an Emrys Optimizer microwave synthesizer. Water was added to the mixture, and the precipitated crystals were collected by suction filtration to give N,N-dimethyl-1H-benzo[d]imidazole-2-amine (234 mg, 89%).

ESIMS m/z: 162 $(M+H)^+$; $^1H$ NMR (270 MHz, DMSO-$d_6$, δ): 3.03 (s, 6H), 6.79-6.97 (m, 2H), 7.07-7.20 (m, 2H), 11.17 (br s, 1H).

[step 2] Using N,N-dimethyl-1H-benzo[d]imidazole-2-amine (57 mg, 0.35 mmol) obtained in step 1 and (E)-2-[8-(bromomethyl)-3-fluorodibenzo[b,e]oxepin-11(6H)-ylidene]propanenitrile (129 mg, 0.36 mmol) obtained in Reference Example 1, and in the same manner as in Reference Example 1A, the title compound (103 mg, 66%) was obtained.

ESIMS m/z: 439 $(M+H)^+$; $^1H$ NMR (270 MHz, $CDCl_3$, δ): 2.24 (s, 3H), 2.92 (s, 6H), 4.77 (d, J=12.9 Hz, 1H), 5.20-5.30 (m, 2H), 5.43 (d, J=12.9 Hz, 1H), 6.57 (dd, J=10.2, 2.6 Hz,

1H), 6.61-6.70 (m, 1H), 6.94-7.11 (m, 3H), 7.14-7.23 (m, 2H), 7.24-7.30 (m, 1H), 7.46 (d, J=7.9 Hz, 1H), 7.60-7.65 (m, 1H).

Reference Example 4G (E)-2-cyclopropyl-2-{3-fluoro-8-[(2-propyl-1H-benzo[d]imidazol-1-yl)methyl]dibenzo[b,e]oxepin-11(6H)-ylidene)acetonitrile Using 2-propyl-1H-benzo[d]imidazole (Synthetic Communication, 2002, vol. 32, p 3703, 55 mg, 0.33 mmol) and (E)-2-(8-bromomethyl-3-fluorodibenzo[b,e]oxepin-11(6H)-ylidene)-2-cyclopropylacetonitrile (120 mg, 0.31 mmol) obtained in Reference Example 6, and in the same manner as in Reference Example 1A, the title compound (132 mg, 92%) was obtained.

ESIMS m/z: 464 $(M+H)^+$; $^1H$ NMR (270 MHz, $CDCl_3$, δ): 0.84-1.09 (m, 7H), 1.84-2.00 (m, 3H), 2.80 (t, J=7.7 Hz, 2H), 4.72 (d, J=12.2 Hz, 1H), 5.36 (s, 2H), 5.45 (d, J=12.2 Hz, 1H), 6.53-6.57 (m, 1H), 6.61-6.68 (m, 1H), 6.94-6.95 (m, 1H), 7.12-7.21 (m, 4H), 7.32-7.43 (m, 2H), 7.77-7.79 (m, 1H).

Reference Example 4H (E)-2-cyclopropyl-2-{8-[(2-cyclopropyl-1H-benzo[d]imidazol-1-yl)methyl]-3-fluorodibenzo[b,e]oxepin-11(6H)-ylidene)acetonitrile Using 2-cyclopropyl-1H-benzo[d]imidazole (European Journal of Organic Chemistry, 2000, p 1229, 58 mg, 0.33 mmol) and (E)-2-(8-bromomethyl-3-fluorodibenzo[b,e]oxepin-11(6H)-ylidene)-2-cyclopropylacetonitrile (120 mg, 0.31 mmol) obtained in Reference Example 6, and in the same manner as in Reference Example 1A, the title compound (133 mg, 93%) was obtained.

ESIMS m/z: 462 $(M+H)^+$; $^1H$ NMR (270 MHz, $CDCl_3$, δ): 0.86-1.26 (m, 8H), 1.84-2.02 (m, 2H), 4.74 (d, J=12.5 Hz, 1H), 5.44-5.48 (m, 3H), 6.53-6.57 (m, 1H), 6.62-6.68 (m, 1H), 7.03-7.04 (m, 1H), 7.19-7.22 (m, 4H), 7.32-7.44 (m, 2H), 7.70-7.73 (m, 1H).

Reference Example 4I (E)-2-cyclopropyl-2-(8-{[2-(3,3-difluorocyclobutyl)-1H-benzo[d]imidazol-1-yl]methyl}-3-fluorodibenzo[b,e]oxepin-11(6H)-ylidene)acetonitrile Using 2-(3,3-difluorocyclobutyl)-1H-benzo[d]imidazole (65 mg, 0.31 mmol) obtained in Reference Example 1J, step 2 and (E)-2-(8-bromomethyl-3-fluorodibenzo[b,e]oxepin-11(6H)-ylidene)-2-cyclopropylacetonitrile (120 mg, 0.31 mmol) obtained in Reference Example 6, and in the same manner as in Reference Example 1A, the title compound (152 mg, 95%) was obtained.

ESIMS m/z: 512 $(M+H)^+$; $^1H$ NMR (270 MHz, $CDCl_3$, δ): 0.85-1.31 (m, 4H), 1.92-2.06 (m, 1H), 2.78-2.96 (m, 2H), 3.05-3.24 (m, 2H), 3.37-3.47 (m, 1H), 4.72 (d, J=13.2 Hz, 1H), 5.32 (s, 2H), 5.45 (d, J=13.2 Hz, 1H), 6.53-6.58 (m, 1H), 6.62-6.68 (m, 1H), 6.93-6.94 (m, 1H), 7.07-7.11 (m, 1H), 7.23-7.43 (m, 5H), 7.80-7.84 (m, 1H).

Reference Example 4J (E)-2-cyclopropyl-2-(3-fluoro-8-{[4-(2-hydroxypropan-2-yl)-2-(methoxymethyl)-1H-benzo[d]imidazol-1-yl]methyl}dibenzo[b,e]oxepin-11(6H)-ylidene) acetonitrile Using 2-[(2-(methoxymethyl)-1H-benzo[d]imidazol-4-yl]propan-2-ol (65 mg, 0.31 mmol) obtained in Reference Example 2K, step 1 and (E)-2-(8-bromomethyl-3-fluorodibenzo[b,e]oxepin-11(6H)-ylidene)-2-cyclopropylacetonitrile (120 mg, 0.31 mmol) obtained in Reference Example 6, and in the same manner as in Reference Example 1A, the title compound (164 mg, 85%) was obtained.

ESIMS m/z: 524 $(M+H)^+$; $^1H$ NMR (270 MHz, $CDCl_3$, δ): 0.85-1.09 (m, 4H), 1.74 (s, 6H), 1.92-2.00 (m, 1H), 3.36 (s, 3H), 4.68-4.78 (m, 3H), 5.43-5.49 (m, 3H), 6.33 (s, 1H), 6.53-6.68 (m, 2H), 7.08-7.24 (m, 4H), 7.32-7.42 (m, 2H).

Reference Example 4K (E)-2-{8-[(4-chloro-2-cyclopropyl-1H-benzo[d]imidazol-1-yl)methyl]-3-fluorodibenzo[b,e]oxepin-11(6H)-ylidene}-2-cyclopropylacetonitrile Using 4-chloro-2-cyclopropyl-1H-benzo[d]imidazole (EP1988091, 60 mg, 0.31 mmol) and (E)-2-(8-bromomethyl-3-fluorodibenzo[b,e]oxepin-11(6H)-ylidene)-2-cyclopropylacetonitrile (120 mg, 0.31 mmol) obtained in Reference Example 6, and in the same manner as in Reference Example 1A, the title compound (115 mg, 74%) was obtained.

ESIMS m/z: 496 $(M+H)^+$; $^1H$ NMR (270 MHz, $CDCl_3$, δ): 0.85-1.33 (m, 8H), 1.77-1.87 (m, 1H), 1.96-2.04 (m, 1H), 4.70 (d, J=13.2 Hz, 1H), 5.42-5.48 (m, 3H), 6.52-6.56 (m, 1H), 6.62-6.68 (m, 1H), 6.90-6.92 (m, 1H), 7.07-7.18 (m, 5H), 7.40-7.45 (m, 1H).

Reference Example 4L (E)-2-(3-fluoro-8-{[2-(methoxymethyl)-1H-benzo[d]imidazol-1-yl]methyl}dibenzo[b,e]oxepin-11(6H)-ylidene)butanenitrile Using 2-(methoxymethyl)-1H-benzo[d]imidazole (61 mg, 0.376 mmol) and (E)-2-[8-(bromomethyl)-3-fluorodibenzo[b,e]oxepin-11(6H)-ylidene]butanenitrile (140 mg, 0.376 mmol) obtained in Reference Example 8, and in the same manner as in Reference Example 1A, the title compound (171 mg, 100%) was obtained.

ESIMS m/z: 454 $(M+H)^+$; $^1H$ NMR (270 MHz, $CDCl_3$, δ): 1.23-1.37 (m, 3H), 2.48-2.74 (m, 2H), 3.38 (s, 3H), 4.61-4.81 (m, 3H), 5.33-5.58 (m, 3H), 6.49-6.71 (m, 2H), 6.95-7.12 (m, 2H), 7.15-7.37 (m, 4H), 7.37-7.52 (m, 1H), 7.75-7.92 (m, 1H).

Reference Example 5A (E)-2-{1,3-difluoro-8-[(2-propyl-1H-benzo[d]imidazol-1-yl)methyl]dibenzo[b,e]oxepin-11(6H)-ylidene}propanenitrile Using 2-propyl-1H-benzo[d]imidazole (Synthetic Communication, 2002, vol. 32, p 3703; 67 mg, 0.42 mmol) and (E)-2-[8-(bromomethyl)-1,3-difluorodibenzo[b,e]oxepin-11(6H)-ylidene]propanenitrile (160 mg, 0.43 mmol) obtained in Reference Example 2, and in the same manner as in Reference Example 1A, the title compound (184 mg, 97%) was obtained.

ESIMS m/z: 456 $(M+H)^+$; $^1H$ NMR (300 MHz, $CDCl_3$, δ): 1.02 (t, J=7.3 Hz, 3H), 1.81-1.96 (m, 2H), 2.09 (d, J=4.0 Hz, 3H), 2.75-2.84 (m, 2H), 4.73 (d, J=12.8 Hz, 1H), 5.32-5.40 (m, 2H), 5.46 (d, J=12.8 Hz, 1H), 6.35-6.50 (m, 2H), 6.91-6.95 (m, 1H), 7.15-7.22 (m, 3H), 7.22-7.29 (m, 1H), 7.44 (d, J=7.7 Hz, 1H), 7.75-7.81 (m, 1H).

Reference Example 6A (E)-2-{2,3-difluoro-8-[(2-propyl-1H-benzo[d]imidazol-1-yl)methyl]dibenzo[b,e]oxepin-11(6H)-ylidene}propanenitrile Using 2-propyl-1H-benzo[d]imidazole (Synthetic Communication, 2002, vol. 32, p 3703; 51 mg, 0.32 mmol) and (E)-2-[8-(bromomethyl)-2,3-difluorodibenzo[b,e]oxepin-11(6H)-ylidene]propanenitrile (120 mg, 0.32 mmol) obtained in Reference Example 3, and in the same manner as in Reference Example 1A, the title compound (132 mg, 91%) was obtained.

ESIMS m/z: 456 $(M+H)^+$

Reference Example 7A (E)-2-{3,4-difluoro-8-[(2-propyl-1H-benzo[d]imidazol-1-yl)methyl]dibenzo[b,e]oxepin-11(6H)-ylidene}propanenitrile Using 2-propyl-1H-benzo[d]imidazole (Synthetic Communication, 2002, vol. 32, p 3703; 17 mg, 0.10 mmol) and (E)-2-[8-(bromomethyl)-3,4-difluorodibenzo[b,e]oxepin-11(6H)-ylidene]propanenitrile (40 mg, 0.12 mmol) obtained in Reference Example 4, and in the same manner as in Reference Example 1A, the title compound (41 mg, 87%) was obtained.

ESIMS m/z: 456 $(M+H)^+$; $^1H$ NMR (300 MHz, $CDCl_3$, δ): 1.02 (t, J=7.3 Hz, 3H), 1.82-1.96 (m, 2H), 2.23 (s, 3H), 2.76-2.85 (m, 2H), 4.90 (d, J=12.8 Hz, 1H), 5.29-5.44 (m, 2H), 5.46 (d, J=12.8 Hz, 1H), 6.69-6.82 (m, 2H), 7.01-7.04 (m, 1H), 7.11-7.16 (m, 1H), 7.17-7.22 (m, 2H), 7.23-7.29 (m, 1H), 7.42 (d, J=8.1 Hz, 1H), 7.75-7.80 (m, 1H).

Reference Example 8A (E)-2-{8-[(8-chloro-2-cyclopropylimidazo[1,2-a]pyridin-3-yl)methyl]-3-fluorodibenzo[b,e]oxepin-11(6H)-ylidene}propanenitrile

[step 1] 3-Chloropyridin-2-amine (15 g, 117 mmol) was dissolved in ethanol (117 mL), 2-bromo-1-cyclopropylethanone (22.8 g, 140 mmol) was added, and the mixture was stirred with heating under reflux for 3 hr. The mixture was concentrated under reduced pressure, ethyl acetate (60 mL) was added to the obtained residue, and the resulting precipitate was collected by suction filtration to give white crystals (27.2 g). The obtained crystals were dissolved in water (300 mL), saturated aqueous sodium hydrogen carbonate solution (100 mL) was added, and the precipitated crystals were collected by suction filtration to give 8-chloro-2-cyclopropylimidazo[1,2-a]pyridine (16g, 71.4%).

ESIMS m/z: 193 $(M+H)^+$; $^1H$ NMR (270 MHz, $CDCl_3$, δ): 0.84-0.93 (m, 2H), 0.93-1.06 (m, 2H), 2.01-2.17 (m, 1H), 6.64 (t, J=7.2 Hz, 1H), 7.17 (dd, J=7.2, 1.4 Hz, 1H), 7.33 (s, 1H), 7.94 (dd, J=7.2, 1.4 Hz, 1H).

[step 2] 8-Chloro-2-cyclopropylimidazo[1,2-a]pyridine (2.23 g, 11.6 mmol) obtained in step 1 was dissolved in DMF (23 mL), N-iodosuccinimide (2.36 g, 12.7 mmol) was added, and the mixture was stirred at room temperature for 2 hr. To the mixture was added water (100 mL), and the precipitated crystals were collected by suction filtration to give 8-chloro-2-cyclopropyl-3-iodoimidazo[1,2-a]pyridine (3.46 g, 94%).

ESIMS m/z: 319 $(M+H)^+$; $^1H$ NMR (270 MHz, $CDCl_3$, δ): 0.97-1.12 (m, 2H), 1.12-1.26 (m, 2H), 1.97-2.14 (m, 1H), 6.72-6.88 (m, 1H), 7.20-7.32 (m, 1H), 7.99-8.04 (m, 1H).

[step 3]8-Chloro-2-cyclopropyl-3-iodoimidazo[1,2-a]pyridine (3.0 g, 9.42 mmol) obtained in step 2 was dissolved in THF (18 mL), cooled to −70° C. in a dry ice-acetone bath. A 2 mol/L isopropylmagnesium chloride THF solution (4.93 mL, 9.89 mmol) was added and the mixture was gradually warmed to −50° C. The mixture was cooled again to −70° C. in a dry ice-acetone bath, a solution (5 mL) of (E)-2-(3-fluoro-8-formyldibenzo[b,e]oxepin-11(6H)-ylidene)propanenitrile (1.38 g, 4.71 mmol) obtained in Reference Example 5 in THF was added, and the mixture was gradually warmed and stirred at −20° C. for 1 hr. To the mixture was added aqueous ammonium chloride solution, and the mixture was extracted 3 times with ethyl acetate. The combined organic layers were dried over anhydrous magnesium sulfate, and concentrated under reduced pressure. To the obtained residue was added a mixed solution of hexane (10 mL)-ethyl acetate (10 mL), and the precipitated crystals were collected by suction filtration to give (E)-2-{8-[(8-chloro-2-cyclopropylimidazo[1,2-a]pyridin-3-yl)(hydroxy)methyl]-3-fluorodibenzo[b,e]oxepin-11(6H)-ylidene}propanenitrile (1.84 g, 80%).

ESIMS m/z: 486 $(M+H)^+$; $^1H$ NMR (270 MHz, $CDCl_3$, δ): 0.77-1.07 (m, 4H), 2.06-2.24 (m, 4H), 4.92-5.09 (m, 1H), 5.42-5.61 (m, 1H), 6.37-6.54 (m, 2H), 6.61-6.89 (m, 3H), 7.20-7.72 (m, 4H), 8.16-8.26 (m, 1H).

[step 4] Sodium iodide (4.63 g, 30.9 mmol) was suspended in a mixed solution of dichloromethane (15 mL)-acetone (15 mL), dichlorodimethylsilane (1.84 mL, 15.4 mmol) was added under ice-cooling, and the mixture was stirred for 15 min. Under ice-cooling, a solution (15 mL) of (E)-2-{8-[(8-chloro-2-cyclopropylimidazo[1,2-a]pyridin-3-yl)(hydroxy)methyl]-3-fluorodibenzo[b,e]oxepin-11(6H)-ylidene}propanenitrile (1.5 g, 3.09 mmol) obtained in step 3 in dichloromethane was added, and the mixture was stirred at room temperature for 30 min. To the mixture were added 10% aqueous sodium thiosulfate solution (50 mL) and saturated aqueous sodium hydrogen carbonate solution (100 mL), and the mixture was extracted 3 times with ethyl acetate. The combined organic layers were dried over anhydrous magnesium sulfate, and concentrated under reduced pressure. To the obtained residue was added isopropylalcohol (15 mL)-diisopropyl ether (15 mL), and the precipitated crystals were collected by suction filtration to give the title compound (1.4 g, 97%).

ESIMS m/z: 470 $(M+H)^+$; $^1H$ NMR (270 MHz, $CDCl_3$, δ): 0.92-1.09 (m, 2H), 1.09-1.28 (m, 2H), 1.93-2.10 (m, 1H), 2.23 (s, 3H), 4.24-4.52 (m, 2H), 4.75 (d, J=12.6 Hz, 1H), 5.40 (d, J=12.6 Hz, 1H), 6.45-6.73 (m, 3H), 6.95-7.31 (m, 4H), 7.40 (d, J=7.8 Hz, 1H), 7.55 (d, J=7.8 Hz, 1H).

Reference Example 8B (E)-2-{8-[(2-cyclopropylimidazo[1,2-a]pyridin-3-yl)methyl]-3-fluorodibenzo[b,e]oxepin-11(6H)-ylidene}propanenitrile 2-Aminopyridine (136 mg, 1.44 mmol) was dissolved in toluene (7 mL), 2-(8-ethynyl-3-fluorodibenzo[b,e]oxepin-11(6H)-ylidene)propanenitrile (500 mg, 1.73 mmol) obtained in Reference Example 9, copper trifluoromethanesulfonate (36 mg, 0.101 mmol), coprous chloride (10 mg, 0.101 mol) and cyclopropanecarboxyaldehyde (0.16 mL, 2.16 mmol) were added, and the mixture was stirred with heating under reflux for 6 hr. The mixture was filtered through celite, saturated aqueous sodium hydrogen carbonate solution was added to the filtrate and the mixture was extracted 3 times with ethyl acetate. The combined organic layers were dried over anhydrous magnesium sulfate, and concentrated under reduced pressure. The obtained residue was purified by silica gel column chromatography (hexane/ethyl acetate=1/3 v/v) to give the title compound (205 mg, 32%).

ESIMS m/z: 436 $(M+H)^+$; $^1H$ NMR (270 MHz, $CDCl_3$, δ): 0.92-1.08 (m, 2H), 1.08-1.18 (m, 2H), 1.91-2.09 (m, 1H), 2.23 (s, 3H), 4.24-4.51 (m, 2H), 4.76 (d, J=12.8 Hz, 1H), 5.41 (d, J=12.8 Hz, 1H), 6.50-6.70 (m, 3H), 6.94-7.15 (m, 3H), 7.21-7.30 (m, 1H), 7.35-7.46 (m, 1H), 7.49-7.58 (m, 1H), 7.58-7.66 (m, 1H).

Reference Example 8C (E)-2-{3-fluoro-8-[(2-isopropylimidazo[1,2-a]pyridin-3-yl)methyl]dibenzo[b,e]oxepin-11(6H)-ylidene}propanenitrile

[step 1] Using 2-aminopyridine (517 mg, 5.51 mmol) and 2-bromo-1-isopropylethanone (1.0 g, 6.06 mmol), and in the same manner as in Reference Example 8A, step 1,2-isopropylimidazo[1,2-a]pyridine (868 mg, 98%) was obtained.

ESIMS m/z: 161 $(M+H)^+$; $^1H$ NMR (270 MHz, $CDCl_3$, δ): 1.32-1.45 (m, 6H), 3.02-3.17 (m, 1H), 6.65-6.78 (m, 1H), 7.03-7.21 (m, 1H), 7.33 (s, 1H), 7.51-7.63 (m, 1H), 7.97-8.15 (m, 1H).

[step 2] Using 2-isopropylimidazo[1,2-a]pyridine (814 mg, 5.09 mmol) obtained in step 1, and in the same manner as in Reference Example 8A, step 2,2-isopropyl-3-iodoimidazo[1,2-a]pyridine (1.05 g, 72%) was obtained.

ESIMS m/z: 287 $(M+H)^+$; $^1H$ NMR (270 MHz, $CDCl_3$, δ): 1.38 (d, J=7.0 Hz, 6H), 3.10-3.25 (m, 1H), 6.80-6.92 (m, 1H), 7.14-7.22 (m, 1H), 7.52-7.64 (m, 1H), 8.03-8.16 (m, 1H).

[step 3] Using 2-isopropyl-3-iodoimidazo[1,2-a]pyridine (366 mg, 1.28 mmol) obtained in step 2 and (E)-2-(3-fluoro-8-formyldibenzo[b,e]oxepin-11(6H)-ylidene)propanenitrile (250 mg, 0.853 mmol) obtained in Reference Example 5, and in the same manner as in Reference Example 8A, step 3, (E)-2-{3-fluoro-8-[hydroxy(2-isopropylimidazo[1,2-a]pyridin-3-yl)methyl]dibenzo[b,e]oxepin-11(6H)-ylidene}propanenitrile (175 mg, 45%) was obtained.

ESIMS m/z: 454 $(M+H)^+$; $^1H$ NMR (270 MHz, $CDCl_3$, δ): 1.18-1.52 (m, 6H), 2.28 (s, 3H), 3.06-3.31 (m, 1H), 4.73-4.91 (m, 1H), 5.40-5.53 (m, 1H), 6.40-6.48 (m, 1H), 6.48-6.78 (m, 3H), 6.98-7.15 (m, 2H), 7.36-7.57 (m, 4H), 7.87-8.11 (m, 1H).

[step 4] Using (E)-2-{3-fluoro-8-[hydroxy(2-isopropylimidazo[1,2-a]pyridin-3-yl)methyl]dibenzo[b,e]oxepin-11(6H)-ylidene}propanenitrile (173 mg, 0.382 mmol) obtained in step 3, and in the same manner as in Reference Example 8A, step 4, the title compound (108 mg, 31%) was obtained.

ESIMS m/z: 438 $(M+H)^+$; $^1H$ NMR (270 MHz, $CDCl_3$, δ): 1.30-1.48 (m, 6H), 2.21 (s, 3H), 3.12-3.30 (m, 1H), 4.20-4.39 (m, 2H), 4.73 (d, J=12.8 Hz, 1H), 5.40 (d, J=12.8 Hz, 1H), 6.48-6.69 (m, 3H), 6.94-7.22 (m, 4H), 7.35-7.46 (m, 1H), 7.56-7.66 (m, 2H).

Reference Example 8D (E)-2-{8-[(2-cyclobutylimidazo[1,2-a]pyridin-3-yl)methyl]-3-fluorodibenzo[b,e]oxepin-11(6H)-ylidene}propanenitrile Using cyclobutanecarboxyaldehyde (0.127 mg, 1.51 mmol) and 2-(8-ethynyl-3-fluorodibenzo[b,e]oxepin-11(6H)-ylidene)propanenitrile (320 mg, 1.11 mmol) obtained in Reference Example 9, and in the same manner as in Reference Example 8B, the title compound (130 mg, 29%) was obtained.

ESIMS m/z: 450 $(M+H)^+$; $^1H$ NMR (270 MHz, $CDCl_3$, δ): 1.92-2.14 (m, 2H), 2.23 (s, 3H), 2.27-2.42 (m, 2H), 2.52-2.71 (m, 2H), 3.64-3.85 (m, 1H), 4.17-4.34 (m, 2H), 4.73 (d, J=12.8 Hz, 1H), 5.40 (d, J=12.8 Hz, 1H), 6.51-6.72 (m, 3H), 6.97-7.05 (m, 2H), 7.08-7.22 (m, 2H), 7.35-7.45 (m, 1H), 7.57-7.68 (m, 2H).

Reference Example 8E (E)-2-{8-[(2-cyclopentylimidazo[1,2-a]pyridin-3-yl)methyl]-3-fluorodibenzo[b,e]oxepin-11(6H)-ylidene}propanenitrile Using cyclopentanecarboxyaldehyde (106 mg, 1.08 mmol) and 2-(8-ethynyl-3-fluorodibenzo[b,e]oxepin-11(6H)-ylidene)propanenitrile (250 mg, 0.864 mmol) obtained in Reference Example 9, and in the same manner as in Reference Example 8B, the title compound (94 mg, 28%) was obtained.

ESIMS m/z: 464 $(M+H)^+$; $^1H$ NMR (270 MHz, $CDCl_3$, δ): 1.58-2.13 (m, 8H), 2.22 (s, 3H), 3.11-3.35 (m, 1H), 4.20-4.40 (m, 2H), 4.74 (d, J=12.8 Hz, 1H), 5.41 (d, J=12.8 Hz, 1H), 6.44-6.71 (m, 3H), 6.95-7.22 (m, 4H), 7.32-7.44 (m, 1H), 7.56-7.67 (m, 2H).

Reference Example 8F (E)-2-(3-fluoro8-{[2-(methoxymethyl)imidazo[1,2-a]pyridin-3-yl]methyl}dibenzo[b,e]oxepin-11(6H)-ylidene)propanenitrile

[step 1] To commercially available 2-aminopyridine (5.0 g, 53 mmol) were added dimethoxyethane (14 mL) and 1,3-dichloropropanone (7.4 g, 58 mmol), and the mixture was stirred at room temperature overnight. The obtained white crystals were collected by filtration, ethanol (140 mL) was added, and the mixture was stirred with heating under reflux for 1 hr. The reaction was discontinued with saturated aqueous sodium hydrogen carbonate, and the mixture was extracted with chloroform and the extract was dried over sodium sulfate. Filtration and concentration under reduced pressure gave 2-(chloromethyl)imidazo[1,2-a]pyridine (5.5 g, 62%).

ESIMS m/z: 167 $(M+H)^+$; $^1H$ NMR (270 MHz, $CDCl_3$, δ): 4.78 (s, 2H), 6.78-6.82 (m, 1H), 7.17-7.21 (m, 1H), 7.57-7.62 (m, 2H), 8.07-8.09 (m, 1H).

[step 2] To 2-(chloromethyl)imidazo[1,2-a]pyridine (4.04 g, 24 mmol) obtained in step 1 were added methanol (121 mL) and sodium methoxide (3.93 g, 73 mmol), and the mixture was stirred at 50° C. for 6 hr. The reaction was discontinued with water, and the mixture was extracted with chloroform and the extract was dried over sodium sulfate. Filtration and concentration under reduced pressure gave 2-(methoxymethyl)imidazo[1,2-a]pyridine (3.45 g, 88%).

ESIMS m/z: 163 $(M+H)^+$; $^1H$ NMR (270 MHz, $CDCl_3$, δ): 3.49 (s, 3H), 4.65 (s, 2H), 6.74-6.84 (m, 1H), 7.13-7.18 (m, 1H), 7.55-7.62 (m, 2H), 8.08-8.10 (m, 1H).

[step 3] To 2-(methoxymethyl)imidazo[1,2-a]pyridine (1.8 g, 11 mmol) obtained in step 2 were added DMF (22 mL) and N-iodosuccinimide (2.75 g, 12 mmol), and the mixture was stirred at room temperature for 3 hr. The reaction was discontinued with saturated aqueous sodium hydrogen carbonate solution, and the mixture was extracted with ethyl acetate and the extract was dried over sodium sulfate. Filtration, concentration under reduced pressure and purification by silica gel column chromatography (chloroform/methanol=10/1 v/v) gave 3-iodo-2-(methoxymethyl)imidazo[1,2-a]pyridine (3.1 g, 99%).

ESIMS m/z: 289 $(M+H)^+$; $^1H$ NMR (270 MHz, $CDCl_3$, δ): 3.47 (s, 3H), 4.65 (s, 2H), 6.92-6.95 (m, 1H), 7.23-7.28 (m, 1H), 7.58-7.60 (m, 1H), 8.12-8.14 (m, 1H).

[step 4]3-Iodo-2-(methoxymethyl)imidazo[1,2-a]pyridine (500 mg, 1.74 mmol) obtained in step 3 was dissolved in THF (1 mL), and the mixture was cooled to −78° C. Isopropylmagnesium chloride (0.87 mL, 1.7 mmol) was added, and the mixture was stirred at −50° C. for 30 min. The mixture was cooled to −78° C. again. (E)-2-(3-fluoro-8-formyldibenzo[b,e]oxepin-11(6H)-ylidene)propanenitrile (255 mg, 0.868 mmol) obtained in Reference Example 5 was dissolved in THF (2.4 mL), and the solution was added dropwise thereto. The mixture was allowed to warm to −20° C., and stirred for 1 hr. The reaction was discontinued with saturated aqueous ammonium chloride, and the mixture was extracted with chloroform and the extract was dried over sodium sulfate. Filtration, concentration under reduced pressure and purification by silica gel column chromatography (chloroform/methanol=10/1 v/v) gave (E)-2-(3-fluoro8-{hydroxy[2-(methoxymethyl)imidazo[1,2-a]pyridin-3-yl]methyl}dibenzo[b,e]oxepin-11(6H)-ylidene)propanenitrile (395 mg, 92%).

ESIMS m/z: 456 $(M+H)^+$; $^1H$ NMR (270 MHz, $CDCl_3$, δ): 2.24 (s, 3H), 3.43 (s, 3H), 4.54-4.73 (m, 2H), 4.81 (d, J=13.7 Hz, 1H), 5.42-5.46 (m, 1H), 6.39-6.42 (m, 1H), 6.54-6.59 (m, 1H), 6.62-6.72 (m, 2H), 7.00-7.05 (m, 1H), 7.15-7.20 (m, 1H), 7.40-7.46 (m, 3H), 7.57-7.59 (m, 1H), 7.91-7.98 (m, 1H).

[step 5] To sodium iodide (197 mg, 1.32 mmol) were added trimethylchlorosilane (165 mL, 1.32 mmol) and acetonitrile (69 mL, 1.3 mmol), and the mixture was stirred at room temperature for 15 min. To the reaction mixture was added hexane (0.22 mL). Furthermore, (E)-2-(3-fluoro8-{hydroxy[2-(methoxymethyl)imidazo[1,2-a]pyridin-3-yl]methyl}dibenzo[b,e]oxepin-11(6H)-ylidene)propanenitrile (100 mg, 0.22 mmol) obtained in step 4 was added, and the mixture was stirred for 1 hr. The reaction was discontinued with water, and the mixture was extracted with chloroform, the extract was washed with saturated sodium thiosulfate aqueous solution, dried over sodium sulfate and filtered. The filtrate was concentrated under reduced pressure and the obtained reaction residue was purified by silica gel column chromatography (chloroform/methanol=10/1 v/v) to give the title compound (60 mg, 62%).

ESIMS m/z: 440 $(M+H)^+$; $^1H$ NMR (270 MHz, $CDCl_3$, δ): 2.23 (s, 3H), 3.47 (s, 3H), 4.32-4.44 (m, 2H), 4.71-4.75 (m, 3H), 5.40 (d, J=12.7 Hz, 1H), 6.53-6.57 (m, 1H), 6.61-6.65 (m, 1H), 6.70-6.74 (m, 1H), 7.00-7.04 (m, 1H), 7.12-7.31 (m, 3H), 7.38-7.40 (m, 1H), 7.60-7.63 (m, 1H), 7.68-7.70 (m, 1H).

Reference Example 8G

(E)-2-[3-fluoro-8-({2-[(methoxy-$d_3$)-methyl]imidazo[1,2-a]pyridin-3-yl}methyl)dibenzo[b,e]oxepin-11(6H)-ylidene]propanenitrile

[step 1] Under ice-cooling, sodium hydride (1.46 g, 36.6 mmol) was suspended in deuterated methanol (24 mL), and the mixture was stirred at room temperature for 30 min. To the mixture was added 2-(chloromethyl)imidazo[1,2-a]pyridine (1.22 g, 7.32 mmol) obtained in Reference Example 8F, step 1, and the mixture was stirred at room temperature for 24 hr. Water was added to the mixture, and the mixture was extracted 3 times with chloroform. The combined organic layers were dried over anhydrous magnesium sulfate, and concentrated under reduced pressure. The residue was purified by silica gel column chromatography (hexane/ethyl acetate=100/0 v/v-0/100 v/v) to give 2-(methoxy-$d_3$-methyl)imidazo[1,2-a]pyridine (1.10 g, 91%).

ESIMS m/z: 166 $(M+H)^+$; $^1H$ NMR (300 MHz, $CDCl_3$, δ): 4.65 (s, 2H), 6.76 (d, J=6.8 Hz, 1H), 7.10-7.20 (m, 1H), 7.51-7.60 (m, 2H), 8.08 (d, J=6.8 Hz, 1H).

[step 2] Using 2-(methoxy-$d_3$-methyl)imidazo[1,2-a]pyridine (1.1 g, 6.66 mmol) obtained in step 1, and in the same manner as in Reference Example 8A, step 2,3-iodo-2-(methoxy-$d_3$-methyl)imidazo[1,2-a]pyridine (1.5 g, 77%) was obtained.

ESIMS m/z: 292 $(M+H)^+$; $^1H$ NMR (300 MHz, $CDCl_3$, δ): 4.65 (s, 2H), 6.88-6.97 (m, 1H), 7.20-7.29 (m, 1H), 7.54-7.62 (m, 1H), 8.09-8.10 (m, 1H).

[step 3] Using 3-iodo-2-(methoxy-$d_3$-methyl)imidazo[1,2-a]pyridine (500 mg, 1.72 mmol) obtained in step 2 and (E)-2-(3-fluoro-8-formyldibenzo[b,e]oxepin-11(6H)-ylidene)propanenitrile (252 mg, 0.86 mmol) obtained in Reference Example 5, and in the same manner as in Reference Example 8A, step 3, (E)-2-(3-fluoro-8-{hydroxy[2-(methoxy-$d_3$-methyl)imidazo[1,2-a]pyridin-3-yl]methyl}dibenzo[b,e]oxepin-11(6H)-ylidene)propanenitrile (354 mg, 79%) was obtained.

ESIMS m/z: 459 $(M+H)^+$; $^1H$ NMR (300 MHz, $CDCl_3$, δ): 2.23 (s, 3H), 4.41-4.67 (m, 3H), 4.80 (d, J=12.5 Hz, 1H), 5.38-5.48 (m, 1H), 6.33-6.43 (m, 1H), 6.50-6.80 (m, 3H), 6.98-7.07 (m, 1H), 7.10-7.21 (m, 1H), 7.37-7.61 (m, 4H), 7.91-8.11 (m, 1H).

[step 4] Using (E)-2-(3-fluoro-8-{hydroxy[2-(methoxy-$d_3$-methyl)imidazo[1,2-a]pyridin-3-yl]methyl}dibenzo[b,e]oxepin-11(6H)-ylidene)propanenitrile (200 mg, 0.44 mmol) obtained in step 3, and in the same manner as in Reference Example 8A, step 4, the title compound (110 mg, 65%) was obtained.

ESIMS m/z: 443 $(M+H)^+$; $^1H$ NMR (300 MHz, $CDCl_3$, δ): 2.23 (s, 3H), 4.29-4.46 (m, 2H), 4.70 (s, 2H), 4.74 (d, J=12.5 Hz, 1H), 5.40 (d, J=12.5 Hz, 1H), 6.55 (dd, J=10.3, 2.6 Hz, 1H), 6.60-6.67 (m, 1H), 6.68-6.75 (m, 1H), 7.02 (dd, J=8.8, 6.6 Hz, 1H), 7.09-7.26 (m, 3H), 7.39 (d, J=7.7 Hz, 1H), 7.59-7.64 (m, 1H), 7.66-7.71 (m, 1H).

Reference Example 8H

(E)-2-{8-[(8-chloro-2-isopropylimidazo[1,2-a]pyridin-3-yl)methyl]-3-fluorodibenzo[b,e]oxepin-11(6H)-ylidene}propanenitrile

[step 1] Using 8-chloro-2-isopropylimidazo[1,2-a]pyridine (WO2009086123; 1.02 g, 5.24 mmol), and in the same manner as in Reference Example 8A, step 2,8-chloro-3-iodo-2-isopropylimidazo[1,2-a]pyridine (1.58 g, 94%) was obtained.

ESIMS m/z: 321 $(M+H)^+$; $^1H$ NMR (300 MHz, $CDCl_3$, δ): 1.40 (d, J=7.0 Hz, 6H), 3.14-3.30 (m, 1H), 6.77-6.86 (m, 1H), 7.24-7.31 (m, 1H), 8.02-8.09 (m, 1H).

[step 2] Using 8-chloro-3-iodo-2-isopropylimidazo[1,2-a]pyridine (393 mg, 1.23 mmol) obtained in step 1 and (E)-2-(3-fluoro-8-formyldibenzo[b,e]oxepin-11(6H)-ylidene)propanenitrile (300 mg, 1.02 mmol) obtained in Reference Example 5, and in the same manner as in Reference Example 8A, step 3, (E)-2-{8-[(8-chloro2-isopropylimidazo[1,2-a]pyridin-3-yl)(hydroxy)methyl]-3-fluorodibenzo[b,e]oxepin-11(6H)-ylidene}propanenitrile (254 mg, 51%) was obtained.

ESIMS m/z: 488 $(M+H)^+$; $^1$H NMR (300 MHz, $CDCl_3$, δ): 1.38-1.51 (m, 6H), 2.24 (s, 3H), 3.19-3.34 (m, 1H), 4.75-4.86 (m, 1H), 5.39-5.49 (m, 1H), 6.36-6.43 (m, 1H), 6.47-6.69 (m, 3H), 7.00-7.08 (m, 1H), 7.15-7.23 (m, 1H), 7.29-7.47 (m, 4H), 7.87-8.95 (m, 1H).

[step 3] Using (E)-2-{8-[(8-chloro2-isopropylimidazo[1,2-a]pyridin-3-yl)(hydroxy)methyl]-3-fluorodibenzo[b,e]oxepin-11(6H)-ylidene}propanenitrile (150 mg, 0.31 mmol) obtained in step 2, and in the same manner as in Reference Example 8A, step 4, the title compound (131 mg, 90%) was obtained.

ESIMS m/z: 472 $(M+H)^+$; $^1$H NMR (300 MHz, $CDCl_3$, δ): 1.37-1.49 (m, 6H), 2.23 (s, 3H), 3.18-3.30 (m, 1H), 4.23-4.39 (m, 2H), 4.73 (d, J=12.5 Hz, 1H), 5.40 (d, J=12.5 Hz, 1H), 6.51-6.69 (m, 3H), 6.98-7.06 (m, 2H), 7.12-7.22 (m, 2H), 7.39 (d, J=7.7 Hz, 1H), 7.51-7.57 (m, 1H).

Reference Example 8I

(E)-2-{3-fluoro-8-[(2-propylimidazo[1,2-a]pyridin-3-yl)methyl]dibenzo[b,e]oxepin-11(6H)-ylidene}propanenitrile

[step 1] Using pyridin-2-amine (0.985 g, 10.2 mmol) and 1-bromopenta-2-one (2.00 g, 7.27 mmol), and in the same manner as in Reference Example 8A, step 1,2-propylimidazo[1,2-a]pyridine (0.650g, 56%) was obtained.

ESIMS m/z: 161 $(M+H)^+$; $^1$H NMR (400 MHz, $CDCl_3$, δ): 1.01 (t, J=7.3 Hz, 3H), 1.74-1.85 (m, 2H), 2.76 (t, J=7.3 Hz, 2H), 6.71 (t, J=6.8 Hz, 1H), 7.08-7.13 (m, 1H), 7.34 (s, 1H), 7.52 (d, J=8.8, 1H), 8.04 (d, J=6.8, 1H).

[step 2] Using 2-propylimidazo[1,2-a]pyridine (0.650 g, 4.06 mmol) obtained in step 1, and in the same manner as in Reference Example 8A, step 2,3-iodo-2-propylimidazo[1,2-a]pyridine (1.07 g, 92%) was obtained.

ESIMS m/z: 287 $(M+H)^+$; $^1$H NMR (400 MHz, $CDCl_3$, δ): 1.00 (t, J=7.3 Hz, 3H), 1.75-1.88 (m, 2H), 2.78 (t, J=7.8 Hz, 2H), 6.81 (t, J=6.8 Hz, 1H), 7.17-7.23 (m, 1H), 7.52 (d, J=8.8, 1H), 8.08 (d, J=6.8, 1H).

[step 3] Using 3-iodo-2-propylimidazo[1,2-a]pyridine (585 mg, mmol) obtained in step 2, and in the same manner as in Reference Example 8A, step 3, (E)-2-{3-fluoro-8-[hydroxy(2-propylimidazo[1,2-a]pyridin-3-yl)methyl]dibenzo[b,e]oxepin-11(6H)-ylidene}propanenitrile (250 mg, 54%) was obtained.

ESIMS m/z: 454 $(M+H)^+$; $^1$H NMR (300 MHz, DMSO-$d_6$, δ): 0.89 (t, J=7.3 Hz, 3H), 1.61-1.75 (m, 2H), 2.16 (s, 3H), 2.64 (td, J=7.3, 4.2 Hz, 2H), 5.00 (dd, J=12.6, 6.0 Hz, 1H), 5.48 (dd, J=12.6, 2.2 Hz, 1H), 6.25-6.36 (m, 2H), 6.64-6.86 (m, 3H), 7.11-7.18 (m, 1H), 7.24-7.31 (m, 1H), 7.33-7.64 (m, 4H), 8.15-8.22 (m, 1H).

[step 4] Using (E)-2-{3-fluoro-8-[hydroxy(2-propylimidazo[1,2-a]pyridin-3-yl)methyl]dibenzo[b,e]oxepin-11(6H)-ylidene}propanenitrile (75 mg, 0.165 mmol) obtained in step 3, and in the same manner as in Reference Example 8A, step 4, the title compound (60 mg, 83%) was obtained.

ESIMS m/z: 438 $(M+H)^+$; $^1$H NMR (400 MHz, $CDCl_3$, δ): 1.04 (t, J=7.3 Hz, 3H), 1.89-2.02 (m, 2H), 2.24 (s, 3H), 2.93 (t, J=7.8 Hz, 2H), 4.31 (d, J=17.6 Hz, 1H), 4.38 (d, J=17.6 Hz, 1H), 4.77 (d, J=12.6 Hz, 1H), 5.42 (d, J=12.6 Hz, 1H), 6.52-6.70 (m, 2H), 7.00-7.10 (m, 3H), 7.19-7.22 (m, 1H), 7.42-7.47 (m, 1H), 7.52-7.57 (m, 1H), 7.82 (d, J=5.9 Hz, 1H), 8.22 (d, J=8.8 Hz, 1H).

Reference Example 8J

(E)-2-{8-[(8-chloro-2-cyclobutylimidazo[1,2-a]pyridin-3-yl)methyl]-3-fluorodibenzo[b,e]oxepin-11(6H)-ylidene}propanenitrile Using cyclobutylcarboxyaldehyde (153 mg, 1.12 mmol), 3-chloropyridin-2-amine (171 mg, 1.33 mmol) and 2-(8-ethynyl-3-fluorodibenzo[b,e]oxepin-11(6H)-ylidene)propanenitrile (350 mg, 1.21 mmol) obtained in Reference Example 9, and in the same manner as in Reference Example 8B, the title compound (84 mg, 14%) was obtained.

ESIMS m/z: 484 $(M+H)^+$; $^1$H NMR (270 MHz, $CDCl_3$, δ): 1.87-2.13 (m, 2H), 2.13-2.45 (m, 5H), 2.48-2.77 (m, 2H), 3.65-3.89 (m, 1H), 4.14-4.39 (m, 2H), 4.63-4.81 (m, 1H), 5.31-5.48 (m, 1H), 6.49-6.70 (m, 3H), 6.93-7.09 (m, 2H), 7.11-7.23 (m, 1H), 7.35-7.58 (m, 2H), 7.93-8.06 (m, 1H).

Reference Example 8K

(E)-2-(8-{8-chloro-[2-(methoxymethyl)imidazo[1,2-a]pyridin-3-yl]methyl}-3-fluorodibenzo[b,e]oxepin-11(6H)-ylidene)propanenitrile

[step 1] Using commercially available 3-chloro-2-aminopyridine (2.5 g, 19 mmol), and in the same manner as in Reference Example 8F, step 1,8-chloro-2-(chloromethyl)imidazo[1,2-a]pyridine (3.25 g, 83%) was obtained.

ESIMS m/z: 201 $(M+H)^+$; $^1$H NMR (270 MHz, $CDCl_3$, δ): 4.78 (s, 2H), 6.78-6.82 (m, 1H), 7.17-7.21 (m, 1H), 7.57-7.62 (m, 1H), 8.07-8.09 (m, 1H).

[step 2] Using 8-chloro-2-(chloromethyl)imidazo[1,2-a]pyridine (1.79 g, 8.9 mmol) obtained in step 1, and in the same manner as in Reference Example 8F, step 2,8-chloro-2-(methoxymethyl)imidazo[1,2-a]pyridine (1.6 g, 91%) was obtained.

ESIMS m/z: 197 $(M+H)^+$; $^1$H NMR (270 MHz, $CDCl_3$, δ): 3.50 (s, 3H), 4.71 (s, 2H), 6.71-6.78 (m, 1H), 7.24-7.29 (m, 1H), 7.64-7.72 (m, 1H), 8.03-8.05 (m, 1H).

[step 3] Using 8-chloro-2-(methoxymethyl)imidazo[1,2-a]pyridine (1.6 g, 8.2 mmol) obtained in step 2, and in the same manner as in Reference Example 8F, step 3,8-chloro-3-iodo-2-(methoxymethyl)imidazo[1,2-a]pyridine (1.8 g, 69%) was obtained.

ESIMS m/z: 322 $(M+H)^+$; $^1$H NMR (270 MHz, $CDCl_3$, δ): 3.47 (s, 3H), 4.68 (s, 2H), 6.87-6.91 (m, 1H), 7.34-7.36 (m, 1H), 8.08-8.14 (m, 1H).

[step 4] Using 8-chloro-3-iodo-2-(methoxymethyl)imidazo[1,2-a]pyridine (500 mg, 1.55 mmol) obtained in step 3 and (E)-2-(3-fluoro-8-formyldibenzo[b,e]oxepin-11(6H)-ylidene)propanenitrile (227 mg, 0.775 mmol) obtained in Reference Example 5, and in the same manner as in Reference Example 8F, step 4, (E)-2-(8-{[8-chloro-2-(methoxymethyl)imidazo[1,2-a]pyridin-3-yl](hydroxy)methyl}-3-fluorodibenzo[b,e]oxepin-11(6H)-ylidene)propanenitrile (205 mg, 54%) was obtained.

ESIMS m/z: 490 $(M+H)^+$; $^1$H NMR (270 MHz, $CDCl_3$, δ): 2.22 (s, 3H), 3.34 (s, 3H), 4.64-4.74 (m, 2H), 4.82 (d, J=12.7 Hz, 1H), 5.42-5.47 (m, 1H), 6.41 (s, 1H), 6.53-6.59 (m, 1H), 6.63-6.67 (m, 2H), 7.03-7.08 (m, 1H), 7.26-7.32 (m, 2H), 7.41-7.52 (m, 3H).

[step 5] Using (E)-2-(8-{[8-chloro-2-(methoxymethyl)imidazo[1,2-a]pyridin-3-yl](hydroxy)methyl}-3-fluorodibenzo[b,e]oxepin-11(6H)-ylidene)propanenitrile (200 mg, 0.408 mmol) obtained in step 4, and in the same manner as in Reference Example 8F, step 5, the title compound (100 mg, 52%) was obtained.

ESIMS m/z: 474 $(M+H)^+$; $^1H$ NMR (270 MHz, $CDCl_3$, δ): 2.23 (s, 3H), 3.47 (s, 3H), 4.33-4.46 (m, 2H), 4.76 (s, 3H), 5.39 (d, J=12.7 Hz, 1H), 6.53-6.57 (m, 1H), 6.62-6.68 (m, 2H), 7.00-7.04 (m, 1H), 7.10-7.11 (m, 1H), 7.23-7.30 (m, 2H), 7.39-7.41 (m, 1H), 7.62-7.64 (m, 1H).

Reference Example 8L (E)-2-{8-[(8-chloro-2-cyclopropylimidazo[1,2-a]pyridin-3-yl)methyl]-3-fluorodibenzo[b,e]oxepin-11(6H)-ylidene}acetonitrile Using (E)-2-(8-ethynyl-3-fluoro-dibenzo[b,e]oxepin-11(6H)-ylidene)acetonitrile (270 mg, 0.981 mmol) obtained in Reference Example 11 and 3-chloropyridin-2-amine (126 mg, 0.981 mmol), and in the same manner as in Reference Example 8B, the title compound (225 mg, 50%) was obtained.

ESIMS m/z: 456 $(M+H)^+$; $^1H$ NMR (300 MHz, $CDCl_3$, δ): 0.99-1.06 (m, 2H), 1.17-1.24 (m, 2H), 1.99-2.09 (m, 1H), 4.39 (s, 2H), 5.05 (s, 2H), 5.79 (s, 1H), 6.54-6.74 (m, 3H), 7.09-7.11 (m, 1H), 7.15-7.19 (m, 1H), 7.25-7.31 (m, 2H), 7.49-7.59 (m, 2H).

Reference Example 8M (E)-2-{8-[(2-cyclopropyl-8-methoxyimidazo[1,2-a]pyridin-3-yl)methyl]-3-fluorodibenzo[b,e]oxepin-11(6H)-ylidene}acetonitrile Using (E)-2-(8-ethynyl-3-fluoro-dibenzo[b,e]oxepin-11(6H)-ylidene)acetonitrile (270 mg, 0.981 mmol) obtained in Reference Example 11 and 3-methoxypyridin-2-amine (122 mg, 0.981 mmol), and in the same manner as in Reference Example 8B, the title compound (132 mg, 30%) was obtained.

ESIMS m/z: 452 $(M+H)^+$; $^1H$ NMR (300 MHz, $CDCl_3$, δ): 1.14-1.22 (m, 2H), 1.32-1.44 (m, 2H), 1.98-2.07 (m, 1H), 4.09 (s, 3H), 4.43 (br s, 2H), 5.08 (s, 2H), 5.81 (s, 1H), 6.54-6.59 (m, 1H), 6.62-6.74 (m, 2H), 6.78-6.84 (m, 1H), 7.11 (br s, 1H), 7.21-7.32 (m, 3H), 7.53 (d, J=8.1 Hz, 1H).

Reference Example 8N (Z)-2-{8-[(8-chloro-2-cyclopropylimidazo[1,2-a]pyridin-3-yl)methyl]-3-fluorodibenzo[b,e]oxepin-11(6H)-ylidene}-2-fluoroacetonitrile Using cyclopropanecarboxyaldehyde (93 mg, 1.33 mmol), 3-chloropyridin-2-amine (125 mg, 0.975 mmol) and 2-(8-ethynyl-3-fluorodibenzo[b,e]oxepin-11(6H)-ylidene)-2-fluoroacetonitrile (260 mg, 0.887 mmol) obtained in Reference Example 12, and in the same manner as in Reference Example 8B, the title compound (44 mg, 11%) was obtained.

ESIMS m/z: 474 $(M+H)^+$; $^1H$ NMR (270 MHz, $CDCl_3$, δ): 0.90-1.08 (m, 2H), 1.09-1.23 (m, 2H), 1.87-2.08 (m, 1H), 4.25-4.47 (m, 2H), 4.75-5.46 (m, 2H), 6.45-6.78 (m, 3H), 7.04-7.59 (m, 6H).

Reference Example 9A (E)-2-{8-[(2-cyclopropyl-8-methoxyimidazo[1,2-a]pyridin-3-yl)methyl]-3-fluorodibenzo[b,e]oxepin-11(6H)-ylidene}propanenitrile Using cyclopropanecarboxyaldehyde (330 mg, 4.71 mmol), 3-methoxypyridin-2-amine (390 mg, 3.14 mmol) and 2-(8-ethynyl-3-fluorodibenzo[b,e]oxepin-11(6H)-ylidene)propanenitrile (1.0 g, 3.46 mmol) obtained in Reference Example 9, and in the same manner as in Reference Example 8B, the title compound (240 mg, 16%) was obtained.

ESIMS m/z: 466 $(M+H)^+$; $^1H$ NMR (270 MHz, $CDCl_3$, δ): 0.93-1.06 (m, 2H), 1.13-1.24 (m, 2H), 1.90-2.06 (m, 1H), 2.25 (s, 3H), 3.98 (s, 3H), 4.25-4.46 (m, 2H), 4.76 (d, J=12.8 Hz, 1H), 5.40 (d, J=12.8 Hz, 1H), 6.35-6.43 (m, 1H), 6.50-6.68 (m, 3H), 6.98-7.15 (m, 2H), 7.16-7.27 (m, 2H), 7.32-7.41 (m, 1H).

Reference Example 9B (E)-2-{8-[(2-cyclopropyl-8-ethoxyimidazo[1,2-a]pyridin-3-yl)methyl]-3-fluorodibenzo[b,e]oxepin-11(6H)-ylidene}propanenitrile Using cyclopropanecarboxyaldehyde (0.2 mL, 2.66 mmol), 3-ethoxypyridin-2-amine (220 mg, 1.77 mmol) and 2-(8-ethynyl-3-fluorodibenzo[b,e]oxepin-11(6H)-ylidene)propanenitrile (564 mg, 1.95 mmol) obtained in Reference Example 9, and in the same manner as in Reference Example 8B, the title compound (120 mg, 9%) was obtained.

ESIMS m/z: 480 $(M+H)^+$; $^1H$ NMR (270 MHz, $CDCl_3$, δ): 0.85-1.00 (m, 2H), 1.08-1.25 (m, 2H), 1.50-1.61 (m, 3H), 1.83-2.13 (m, 1H), 2.24 (s, 3H), 4.14-4.48 (m, 4H), 4.63-4.82 (m, 1H), 5.29-5.46 (m, 1H), 6.33-6.42 (m, 1H), 6.49-6.69 (m, 3H), 6.98-7.07 (m, 2H), 7.19-7.30 (m, 2H), 7.34-7.43 (m, 1H).

Reference Example 9C (E)-2-(8-{[2-cyclopropyl-8-(difluoromethoxy)imidazo[1,2-a]pyridin-3-yl]methyl}-3-fluorodibenzo[b,e]oxepin-11(6H)-ylidene)propanenitrile

[step 1]2-Nitropyridin-3-ol (600 mg, 4.28 mmol) was dissolved in DMF (50 mL), sodium 2-chloro-2,2-difluoroacetate (1.96 g, 12.9 mmol), and cesium carbonate (4.2 g, 12.9 mmol) were added, and the mixture was stirred with heating at 60° C. for 4 hr. To the mixture was added saturated aqueous ammonium chloride solution, and the mixture was extracted 3 times with ethyl acetate. The combined organic layers were dried over anhydrous magnesium sulfate, and concentrated under reduced pressure. The obtained residue was purified by column chromatography (hexane/ethyl acetate=1/3) to give 3-(difluoromethoxy)-2-nitropyridine (452 mg, 56%).

ESIMS m/z: 191 $(M+H)^+$; $^1H$ NMR (270 MHz, $CDCl_3$, δ): 6.65 (t, J=71.5 Hz, 1H), 7.61-7.70 (m, 1H), 7.87-7.98 (m, 1H), 8.38-8.53 (m, 1H).

[step 2] 3-(Difluoromethoxy)-2-nitropyridine (450 mg, 2.37 mmol) obtained in step 1 was dissolved in ethanol (2 mL)-acetic acid (2 mL), reduced iron (397 mg, 7.10 mmol) was added, and the mixture was stirred at 100° C. overnight. Since the starting material did not disappear, reduced iron (397 mg, 7.10 mmol) was added, and the mixture was further stirred at 100° C. overnight. The mixture was filtered through celite, and the filtrate was concentrated under reduced pressure. To the obtained residue was added saturated aqueous sodium hydrogen carbonate solution, and the mixture was extracted 3 times with ethyl acetate. The combined organic layers were dried over anhydrous magnesium sulfate, and purified by silica gel column chromatography (chloroform/methanol=9/1 v/v) to give 3-(difluoromethoxy)pyridin-2-amine (250 mg, 66%).

ESIMS m/z: 161 $(M+H)^+$; $^1$H NMR (270 MHz, $CDCl_3$, δ): 4.79 (br s, 2H), 6.14-6.80 (m, 2H), 7.19-7.35 (m, 1H), 7.85-7.98 (m, 1H).

[step 3] Using cyclopropanecarboxyaldehyde (0.216 mL, 2.12 mmol), 3-(difluoromethoxy)pyridin-2-amine (250 mg, 1.56 mmol) obtained in step 2 and 2-(8-ethynyl-3-fluorodibenzo[b,e]oxepin-11(6H)-ylidene)propanenitrile (410 mg, 1.42 mmol) obtained in Reference Example 9, and in the same manner as in Reference Example 8B, the title compound (440 mg, 29%) was obtained.

ESIMS m/z: 502 $(M+H)^+$; $^1$H NMR (270 MHz, $CDCl_3$, δ): 0.96-1.08 (m, 2H), 1.09-1.21 (m, 2H), 1.95-2.12 (m, 1H), 2.22 (s, 3H), 4.24-4.49 (m, 2H), 4.76 (d, J=12.8 Hz, 1H), 5.42 (d, J=12.8 Hz, 1H), 6.48-6.72 (m, 3H), 6.81-6.90 (m, 1H), 6.97-7.08 (m, 1H), 7.08-7.14 (m, 1H), 7.19-7.88 (m, 4H).

Reference Example 9D (E)-2-{3-fluoro-8-[(2-isopropyl-8-methoxyimidazo[1,2-a]pyridin-3-yl)methyl]dibenzo[b,e]oxepin-11(6H)-ylidene}propanenitrile

[step 1] Commercially available 3-methoxypyridin-2-amine (1.0 g, 8.06 mmol) was dissolved in ethanol (8.1 mL), 1-bromo-3-methylbutan-2-one (Organic Syntheses, 1976, vol. 55, p 24; 1.46 g, 8.86 mmol) was added, and the mixture was stirred at 110° C. for 13 hr. To the mixture was added saturated aqueous sodium hydrogen carbonate, and the mixture was extracted 3 times with chloroform. The combined organic layers were dried over anhydrous magnesium sulfate, and concentrated under reduced pressure. The residue was purified by silica gel column chromatography (hexane/ethyl acetate=100/0 v/v-30/70 v/v) to give 2-isopropyl-8-methoxyimidazo[1,2-a]pyridine (746 mg, 49%).

ESIMS m/z: 191 $(M+H)^+$; $^1$H NMR (300 MHz, $CDCl_3$, δ): 1.37 (d, J=7.0 Hz, 6H), 3.05-3.20 (m, 1H), 3.99 (s, 3H), 6.35-6.41 (m, 1H), 6.56-6.65 (m, 1H), 7.26-7.31 (m, 1H), 7.64-7.72 (m, 1H).

[step 2] Using 2-isopropyl-8-methoxyimidazo[1,2-a]pyridine (745 mg, 3.92 mmol) obtained in step 1, and in the same manner as in Reference Example 8A, step 2,3-iodo-2-isopropyl-8-methoxyimidazo[1,2-a]pyridine (1.19 g, 96%) was obtained.

ESIMS m/z: 317 $(M+H)^+$; $^1$H NMR (300 MHz, $CDCl_3$, δ): 1.39 (d, J=7.0 Hz, 6H), 3.10-3.27 (m, 1H), 4.01 (s, 3H), 6.47-6.53 (m, 1H), 6.75-6.82 (m, 1H), 7.73-7.78 (m, 1H).

[step 3] Using 3-iodo-2-isopropyl-8-methoxyimidazo[1,2-a]pyridine (600 mg, 1.90 mmol) obtained in step 2 and (E)-2-(3-fluoro-8-formyldibenzo[b,e]oxepin-11(6H)-ylidene)propanenitrile (278 mg, 0.95 mmol) obtained in Reference Example 5, and in the same manner as in Reference Example 8A, step 3, (E)-2-{3-fluoro-8-[hydroxy(2-isopropyl-8-methoxyimidazo[1,2-a]pyridin-3-yl)methyl]dibenzo[b,e]oxepin-11(6H)-ylidene}propanenitrile (159 mg, 35%) was obtained.

ESIMS m/z: 484 $(M+H)^+$; $^1$H NMR (300 MHz, $CDCl_3$, δ): 1.36-1.49 (m, 6H), 2.23 (s, 3H), 3.11-3.30 (m, 1H), 3.92-3.99 (m, 3H), 4.74-4.84 (m, 1H), 5.37-5.49 (m, 1H), 6.35-6.69 (m, 5H), 6.99-7.07 (m, 1H), 7.28-7.46 (m, 3H), 7.51-7.57 (m, 1H).

[step 4] Using (E)-2-{3-fluoro-8-[hydroxy(2-isopropyl-8-methoxyimidazo[1,2-a]pyridin-3-yl)methyl]dibenzo[b,e]oxepin-11(6H)-ylidene}propanenitrile (152 mg, 0.31 mmol) obtained in step 3, and in the same manner as in Reference Example 8A, step 4, the title compound (112 mg, 76%) was obtained.

ESIMS m/z: 468 $(M+H)^+$; $^1$H NMR (300 MHz, $CDCl_3$, δ): 1.36-1.47 (m, 6H), 2.23 (s, 3H), 3.10-3.26 (m, 1H), 4.00 (s, 3H), 4.20-4.36 (m, 2H), 4.71 (d, J=12.8 Hz, 1H), 5.39 (d, J=12.8 Hz, 1H), 6.36-6.43 (m, 1H), 6.51-6.68 (m, 3H), 6.96-7.06 (m, 2H), 7.12-7.19 (m, 1H), 7.23-7.28 (m, 1H), 7.38 (d, J=8.1 Hz, 1H).

Reference Example 9E (E)-2-(3-fluoro-8-{[8-methoxy-2-(methoxymethyl)imidazo[1,2-a]pyridin-3-yl]methyl}dibenzo[b,e]oxepin-11(6H)-ylidene)propanenitrile

[step 1] Using commercially available 3-methoxy-2-aminopyridine (1.0 g, 8.1 mmol), and in the same manner as in Reference Example 8F, step 1,2-(chloromethyl)-8-methoxyimidazo[1,2-a]pyridine (1.5 g, 99%) was obtained.

ESIMS m/z: 197 $(M+H)^+$; $^1$H NMR (270 MHz, $CDCl_3$, δ): 4.01 (s, 3H), 4.76 (s, 2H), 6.46 (d, J=7.8 Hz, 1H), 6.69-6.72 (m, 1H), 7.60 (s, 1H), 7.71-7.72 (m, 1H).

[step 2] Using 2-(chloromethyl)-8-methoxyimidazo[1,2-a]pyridine (1.58 g, 8.1 mmol) obtained in step 1, and in the same manner as in Reference Example 8F, step 2,8-methoxy-2-(methoxymethyl)imidazo[1,2-a]pyridine (0.79 g, 51%) was obtained.

ESIMS m/z: 193 $(M+H)^+$; $^1$H NMR (270 MHz, $CDCl_3$, δ): 3.47 (s, 3H), 4.00 (s, 3H), 4.67 (s, 2H), 6.43 (d, J=6.8 Hz, 1H), 6.65-6.69 (m, 1H), 7.54 (s, 1H), 7.71-7.73 (m, 1H).

[step 3] Using 8-methoxy-2-(methoxymethyl)imidazo[1,2-a]pyridine (0.786 g, 4.1 mmol) obtained in step 2, and in the same manner as in Reference Example 8F, step 3,8-methoxy-3-iodo-2-(methoxymethyl)imidazo[1,2-a]pyridine (1.24 g, 95%) was obtained.

ESIMS m/z: 318 $(M+H)^+$; $^1$H NMR (270 MHz, $CDCl_3$, δ): 3.43 (s, 3H), 4.02 (s, 3H), 4.65 (s, 2H), 6.57 (d, J=7.7 Hz, 1H), 6.83-6.88 (m, 1H), 7.77-7.80 (m, 1H).

[step 4] Using 8-methoxy-3-iodo-2-(methoxymethyl)imidazo[1,2-a]pyridine (500 mg, 1.57 mmol) obtained in step 3 and (E)-2-(3-fluoro-8-formyldibenzo[b,e]oxepin-11(6H)-ylidene)propanenitrile (230 mg, 0.786 mmol) obtained in Reference Example 5, and in the same manner as in Reference Example 8F, step 4, (E)-2-(3-fluoro-8-{hydroxy[8-methoxy-2-(methoxymethyl)imidazo[1,2-a]pyridin-3-yl]methyl}dibenzo[b,e]oxepin-11(6H)-ylidene)propanenitrile (250 mg, 66%) was obtained.

ESIMS m/z: 486 $(M+H)^+$; $^1$H NMR (270 MHz, $CDCl_3$, δ): 2.23 (s, 3H), 3.40 (s, 3H), 3.99 (s, 3H), 4.53-4.82 (m, 4H), 5.41-5.45 (m, 1H), 6.33-6.47 (m, 2H), 6.54-6.67 (m, 2H), 6.71 (s, 1H), 7.00-7.06 (m, 1H), 7.37-7.60 (m, 3H).

[step 5] Using (E)-2-(3-fluoro-8-{hydroxy[8-methoxy-2-(methoxymethyl)imidazo[1,2-a]pyridin-3-yl]methyl}dibenzo[b,e]oxepin-11(6H)-ylidene)propanenitrile (180 mg, 0.37 mmol) obtained in step 4, and in the same manner as in Reference Example 8F, step 5, the title compound (77 mg, 44%) was obtained.

ESIMS m/z: 470 $(M+H)^+$; $^1$H NMR (270 MHz, $CDCl_3$, δ): 2.22 (s, 3H), 3.43 (s, 3H), 4.00 (s, 3H), 4.30-4.43 (m, 2H), 4.71-4.75 (m, 3H), 5.39 (d, J=12.8 Hz, 1H), 6.42-6.44 (m, 1H), 6.53-6.66 (m, 2H), 6.99-7.04 (m, 1H), 7.09-7.10 (m, 1H), 7.09-7.10 (m, 1H), 7.21-7.24 (m, 1H), 7.31-7.39 (m, 2H).

Reference Example 9F (E)-2-(3-fluoro-8-{[2-isopropyl-8-(methoxy-$d_3$)-imidazo[1,2-a]pyridin-3-yl]methyl}dibenzo[b,e]oxepin-11(6H)-ylidene)propanenitrile

[step 1] Using commercially available 2-nitropyridin-3-ol (2.7 g, 19.3 mmol), and in the same manner as in Reference Example 2A, step 5,3-(methoxy-$d_3$)-2-nitropyridine (2.7 g, 88%) was obtained.

ESIMS m/z: 158 $(M+H)^+$; $^1$H NMR (300 MHz, $CDCl_3$, δ): 7.47-7.59 (m, 2H), 8.05-8.14 (m, 1H).

[step 2] 3-(Methoxy-$d_3$)-2-nitropyridine (2.7 g, 16.9 mmol) obtained in step 1 was dissolved in ethanol (46 mL), 10% Pd—C (359 mg) was added, the reaction system was purged with hydrogen gas, and the mixture was stirred at room temperature for 3 hr. After completion of the reaction, the reaction mixture was filtered through celite, and the solution was concentrated under reduced pressure to quantitatively give 3-(methoxy-$d_3$)-pyridin-2-amine (2.14 g).

ESIMS m/z: 128 $(M+H)^+$; $^1$H NMR (300 MHz, $CDCl_3$, δ): 4.29-4.84 (m, 2H), 6.62 (dd, J=7.7, 5.1 Hz, 1H), 6.90 (dd, J=7.7, 1.5 Hz, 1H), 7.66 (dd, J=5.1, 1.5 Hz, 1H).

[step 3] Using 3-(methoxy-$d_3$)-pyridin-2-amine (700 mg, 5.5 mmol) obtained in step 2, and in the same manner as in Reference Example 9D, step 1,2-isopropyl-8-(methoxy-$d_3$)-imidazo[1,2-a]pyridine (776 mg, 73%) was obtained.

ESIMS m/z: 194 $(M+H)^+$; $^1$H NMR (300 MHz, $CDCl_3$, δ): 1.37 (d, J=7.0 Hz, 6H), 3.05-3.21 (m, 1H), 6.35-6.41 (m, 1H), 6.57-6.65 (m, 1H), 7.28-7.31 (m, 1H), 7.65-7.70 (m, 1H).

[step 4] Using 2-isopropyl-8-(methoxy-$d_3$)-imidazo[1,2-a]pyridine (745 mg, 3.85 mmol) obtained in step 3, and in the same manner as in Reference Example 8A, step 2,3-iodo-2-isopropyl-8-(methoxy-$d_3$)-imidazo[1,2-a]pyridine (1.13 g, 92%) was obtained.

ESIMS m/z: 320 $(M+H)^+$; $^1$H NMR (300 MHz, $CDCl_3$, δ): 1.39 (d, J=7.0 Hz, 6H), 3.11-3.24 (m, 1H), 6.48-6.53 (m, 1H), 6.75-6.82 (m, 1H), 7.73-7.78 (m, 1H).

[step 5] Using 3-iodo-2-isopropyl-8-(methoxy-$d_3$)-imidazo[1,2-a]pyridine (653 mg, 2.05 mmol) obtained in step 4 and (E)-2-(3-fluoro-8-formyldibenzo[b,e]oxepin-11(6H)-ylidene)propanenitrile (300 mg, 1.02 mmol) obtained in Reference Example 5, and in the same manner as in Reference Example 8A, step 3, (E)-2-(3-fluoro-8-{hydroxy[2-isopropyl-8-(methoxy-$d_3$)-imidazo[1,2-a]pyridin-3-yl]methyl}dibenzo[b,e]oxepin-11(6H)-ylidene)propanenitrile (228 mg, 46%) was obtained.

ESIMS m/z: 487 $(M+H)^+$; $^1$H NMR (300 MHz, $CDCl_3$, δ): 1.38-1.49 (m, 6H), 2.23 (s, 3H), 3.11-3.30 (m, 1H), 4.72-4.83 (m, 1H), 5.38-5.49 (m, 1H), 6.35-6.70 (m, 5H), 6.98-7.07 (m, 1H), 7.29-7.47 (m, 3H), 7.50-7.57 (m, 1H).

[step 6] Using (E)-2-(3-fluoro-8-{hydroxy[2-isopropyl-8-(methoxy-$d_3$)-imidazo[1,2-a]pyridin-3-yl]methyl}dibenzo[b,e]oxepin-11(6H)-ylidene)propanenitrile (220 mg, 0.45 mmol) obtained in step 5, and in the same manner as in Reference Example 8A, step 4, the title compound (129 mg, 61%) was obtained.

ESIMS m/z: 471 $(M+H)^+$; $^1$H NMR (300 MHz, $CDCl_3$, δ): 1.37-1.46 (m, 6H), 2.23 (s, 3H), 3.13-3.25 (m, 1H), 4.20-4.35 (m, 2H), 4.71 (d, J=12.8 Hz, 1H), 5.39 (d, J=12.8 Hz, 1H), 6.37-6.42 (m, 1H), 6.51-6.67 (m, 3H), 6.98-7.06 (m, 2H), 7.12-7.19 (m, 1H), 7.23-7.27 (m, 1H), 7.38 (d, J=8.1 Hz, 1H).

Reference Example 9G

(E)-2-(8-{[8-(difluoromethoxy)-2-isopropylimidazo[1,2-a]pyridin-3-yl]methyl}-3-fluorodibenzo[b,e]oxepin-11(6H)-ylidene)propanenitrile

[step 1] Using 3-(difluoromethoxy)pyridin-2-amine (700 mg, 4.37 mmol) obtained in Reference Example 9C, step 2, and in the same manner as in Reference Example 9D, step 1,8-(difluoromethoxy)-2-isopropylimidazo[1,2-a]pyridine (766 mg, 77%) was obtained.

ESIMS m/z: 227 $(M+H)^+$; $^1$H NMR (300 MHz, $CDCl_3$, δ): 1.36 (d, J=7.0 Hz, 6H), 3.04-3.20 (m, 1H), 6.60-6.70 (m, 1H), 6.86-6.91 (m, 1H), 7.36-7.39 (m, 1H), 7.39 (t, J=74.6 Hz, 1H), 7.88-7.93 (m, 1H).

[step 2] Using 8-(difluoromethoxy)-2-isopropylimidazo[1,2-a]pyridine (745 mg, 3.29 mmol) obtained in step 1, and in the same manner as in Reference Example 8A, step 2, 8-(difluoromethoxy)-3-iodo-2-isopropylimidazo[1,2-a]pyridine (1.1 g, 95%) was obtained.

ESIMS m/z: 353 $(M+H)^+$; $^1$H NMR (300 MHz, $CDCl_3$, δ): 1.37 (d, J=7.0 Hz, 6H), 3.10-3.26 (m, 1H), 6.78-6.86 (m, 1H), 6.97-7.04 (m, 1H), 7.47 (t, J=74.6 Hz, 1H), 7.95-8.01 (m, 1H).

[step 3] Using 8-(difluoromethoxy)-3-iodo-2-isopropylimidazo[1,2-a]pyridine (600 mg, 1.71 mmol) obtained in step 2 and (E)-2-(3-fluoro-8-formyldibenzo[b,e]oxepin-11(6H)-ylidene)propanenitrile (250 mg, 0.85 mmol) obtained in Reference Example 5, and in the same manner as in Reference Example 8A, step 3, (E)-2-(8-{[8-(difluoromethoxy)-2-isopropylimidazo[1,2-a]pyridin-3-yl](hydroxy)methyl}-3-fluorodibenzo[b,e]oxepin-11(6H)-ylidene)propanenitrile (426 mg, 96%) was obtained.

ESIMS m/z: 520 $(M+H)^+$; $^1$H NMR (300 MHz, $CDCl_3$, δ): 1.33-1.45 (m, 6H), 2.19-2.27 (m, 3H), 3.13-3.29 (m, 1H), 4.71-4.90 (m, 1H), 5.40-5.51 (m, 1H), 6.40-6.71 (m, 4H), 6.84-6.93 (m, 1H), 6.99-7.07 (m, 1H), 7.19-7.72 (m, 4H), 7.74-7.82 (m, 1H).

[step 4] Using (E)-2-(8-{[8-(difluoromethoxy)-2-isopropylimidazo[1,2-a]pyridin-3-yl](hydroxy)methyl}-3-fluorodibenzo[b,e]oxepin-11(6H)-ylidene)propanenitrile (200 mg, 0.39 mmol) obtained in step 3, and in the same manner as in Reference Example 8A, step 4, the title compound (151 mg, 78%) was obtained.

ESIMS m/z: 504 $(M+H)^+$; $^1$H NMR (300 MHz, $CDCl_3$, δ): 1.32-1.45 (m, 6H), 2.23 (s, 3H), 3.14-3.26 (m, 1H), 4.22-4.37 (m, 2H), 4.74 (d, J=12.8 Hz, 1H), 5.41 (d, J=12.8 Hz, 1H), 6.51-6.69 (m, 3H), 6.86-6.91 (m, 1H), 6.98-7.06 (m, 2H), 7.13-7.19 (m, 1H), 7.39 (d, J=7.7 Hz, 1H), 7.44-7.49 (m, 1H), 7.56 (d, J=74.6 Hz, 1H).

Reference Example 9H

(E)-2-(8-{[2-cyclopropyl-8-(methoxy-$d_3$)-imidazo[1,2-a]pyridin-3-yl]methyl}-3-fluorodibenzo[b,e]oxepin-11(6H)-ylidene)propanenitrile Using 2-(8-ethynyl-3-fluorodibenzo[b,e]oxepin-11(6H)-ylidene)propanenitrile (400 mg, 1.38 mmol, E/Z=1/1) obtained in Reference Example 9,3-(methoxy-$d_3$)-pyridin-2-amine (193 mg, 1.52 mmol) obtained in Reference Example 9F, step 2 and cyclopropanecarbaldehyde (0.16 mL, 2.07 mmol), and in the same manner as in Reference Example 8B, the title compound (220 mg, 34%) was obtained.

ESIMS m/z: 469 $(M+H)^+$; $^1$H NMR (300 MHz, $CDCl_3$, δ): 0.90-1.01 (m, 2H), 1.15-1.22 (m, 2H), 1.93-2.05 (m, 1H), 2.23 (s, 3H), 4.25-4.43 (m, 2H), 4.73 (d, J=12.8 Hz, 1H), 5.40 (d, J=12.8 Hz, 1H), 6.35-6.41 (m, 1H), 6.51-6.59 (m, 2H), 6.59-6.67 (m, 1H), 6.98-7.05 (m, 1H), 7.05-7.09 (m, 1H), 7.20-7.30 (m, 2H), 7.39 (d, J=8.1 Hz, 1H).

Reference Example 9I

(E)-2-{8-[(2-cyclopropyl-8-fluoroimidazo[1,2-a]pyridin-3-yl)methyl]-3-fluorodibenzo[b,e]oxepin-11(6H)-ylidene}propanenitrile Using cyclopropanecarboxyaldehyde (0.156 mL, 2.07 mmol), 3-fluoropyridin-2-amine (171 mg, 1.52 mmol) and 2-(8-ethynyl-3-fluorodibenzo[b,e]oxepin-11(6H)-ylidene) propanenitrile (400 mg, 1.38 mmol) obtained in Reference Example 9, and in the same manner as in Reference Example 8B, the title compound (179 mg, 29%) was obtained.

ESIMS m/z: 454 $(M+H)^+$; $^1H$ NMR (270 MHz, $CDCl_3$, δ): 0.90-1.09 (m, 2H), 1.13-1.32 (m, 2H), 1.95-2.10 (m, 1H), 2.24 (s, 3H), 4.26-4.50 (m, 2H), 4.77 (d, J=12.8 Hz, 1H), 5.41 (d, J=12.8 Hz, 1H), 6.47-6.70 (m, 3H), 6.74-6.88 (m, 1H), 6.99-7.18 (m, 2H), 7.22-7.33 (m, 1H), 7.37-7.56 (m, 2H).

Reference Example 9J (E)-2-(8-{[8-(difluoromethoxy)-2-(methoxymethyl) imidazo[1,2-a]pyridin-3-yl]methyl}-3-fluorodibenzo [b,e]oxepin-11(6H)-ylidene)propanenitrile

[step 1] Using 3-(difluoromethoxy)pyridin-2-amine (1.0 g, 6.3 mmol) obtained in Reference Example 9C, step 2, and in the same manner as in Reference Example 8F, step 1,2-(chloromethyl)-8-(difluoromethoxy)imidazo[1,2-a]pyridine (1.5 g, 99%) was obtained.

ESIMS m/z: 233 $(M+H)^+$; $^1H$ NMR (270 MHz, $CDCl_3$, δ): 4.78 (s, 2H), 6.24-7.05 (m, 4H), 7.92-7.97 (m, 1H).

[step 2] Using 2-(chloromethyl)-8-(difluoromethoxy)imidazo[1,2-a]pyridine (1.45 g, 6.25 mmol) obtained in step 1, and in the same manner as in Reference Example 8F, step 2, 8-(difluoromethoxy)-2-(methoxymethyl)imidazo[1,2-a]pyridine (1.33 g, 93%) was obtained.

ESIMS m/z: 229$(M+H)^+$; $^1H$ NMR (270 MHz, $CDCl_3$, δ): 3.49 (s, 3H), 4.66 (s, 2H), 6.24-7.06 (m, 4H), 7.92-7.97 (m, 1H).

[step 3] Using 8-(difluoromethoxy)-2-(methoxymethyl) imidazo[1,2-a]pyridine (1.33 g, 5.8 mmol) obtained in step 2, and in the same manner as in Reference Example 8F, step 3,8-(difluoromethoxy)-3-iodo-2-(methoxymethyl)imidazo [1,2-a]pyridine (1.66 g, 80%) was obtained.

ESIMS m/z: 355 $(M+H)^+$; $^1H$ NMR (270 MHz, $CDCl_3$, δ): 3.46 (s, 3H), 4.65 (s, 2H), 6.24-7.06 (m, 3H), 7.92-7.97 (m, 1H).

[step 4] Using 8-(difluoromethoxy)-3-iodo-2-(methoxymethyl)imidazo[1,2-a]pyridine (700 mg, 1.98 mmol) obtained in step 3 and (E)-2-(3-fluoro-8-formyldibenzo[b,e]oxepin-11 (6H)-ylidene)propanenitrile (290 mg, 0.988 mmol) obtained in Reference Example 5, and in the same manner as in Reference Example 8F, step 4, (E)-2-(8-{[8-(difluoromethoxy)-2-(methoxymethyl)imidazo[1,2-a]pyridin-3-yl](hydroxy) methyl}-3-fluorodibenzo[b,e]oxepin-11(6H)-ylidene) propanenitrile (400 mg, 78%) was obtained.

ESIMS m/z: 522 $(M+H)^+$; $^1H$ NMR (270 MHz, $CDCl_3$, δ): 2.24 (s, 3H), 3.43 (s, 3H), 4.61-4.83 (m, 3H), 5.43-5.46 (m, 1H), 6.41-6.43 (m, 1H), 6.56-6.65 (m, 3H), 6.95-7.03 (m, 3H), 7.42-7.45 (m, 3H), 7.76-7.83 (m, 1H).

[step 5] Using (E)-2-(8-{[8-(difluoromethoxy)-2-(methoxymethyl)imidazo[1,2-a]pyridin-3-yl](hydroxy)methyl}-3-fluorodibenzo[b,e]oxepin-11(6H)-ylidene)propanenitrile (193 mg, 0.37 mmol) obtained in step 4, and in the same manner as in Reference Example 8F, step 5, the title compound (60 mg, 32%) was obtained.

ESIMS m/z: 506 $(M+H)^+$; $^1H$ NMR (270 MHz, $CDCl_3$, δ): 2.23 (s, 3H), 3.47 (s, 3H), 4.33-4.44 (m, 2H), 4.72-4.77 (m, 1H), 5.39-5.42 (m, 1H), 6.54-6.57 (m, 1H), 6.62-6.69 (m, 2H), 6.93-7.04 (m, 3H), 7.12-7.14 (m, 1H), 7.23-7.25 (m, 1H), 7.30-7.33 (m, 1H), 7.39-7.41 (m, 1H), 7.51-7.57 (m, 1H).

Reference Example 9K (E)-2-{3-fluoro-8-[(8-methoxy-2-cyclopropylimidazo[1,2-a]pyridin-3-yl)methyl]dibenzo[b,e]oxepin-11(6H)-ylidene}propanenitrile Using 2-(8-ethynyl-3-fluorodibenzo[b,e]oxepin-11(6H)-ylidene)propanenitrile (200 mg, 0.691 mmol, E/Z=1/1) obtained in Reference Example 9, 2-amino-3-methoxypyridine (112 mg, 0.899 mmol) and butylaldehyde (100 mg, 1.38 mmol), and in the same manner as in Reference Example 8B, the title compound (75 mg, 15%) was obtained.

ESIMS m/z: 468 $(M+H)^+$; $^1H$ NMR (270 MHz, $CDCl_3$, δ): 0.98 (t, J=7.3 Hz, 3H), 1.79-2.02 (m, 2H), 2.23 (s, 3H), 2.79 (t, J=7.8 Hz, 2H), 4.01 (s, 3H), 4.23 (d, J=17.6 Hz, 1H), 4.29 (d, J=17.6 Hz, 1H), 4.72 (d, J=12.7 Hz, 1H), 5.40 (d, J=12.7 Hz, 1H), 6.42-6.46 (m, 1H), 6.53-6.67 (m, 3H), 7.00-7.05 (m, 2H), 7.18 (d, J=7.8 Hz, 1H), 7.24-7.28 (m, 1H), 7.39 (d, J=7.8 Hz, 1H).

Reference Example 9L (E)-2-(8-{[8-chloro-2-(methoxy-$d_3$-methyl)imidazo [1,2-a]pyridin-3-yl]methyl}-3-fluorodibenzo[b,e] oxepin-11(6H)-ylidene)propanenitrile

[step 1] Using 8-chloro-2-(chloromethyl)imidazo[1,2-a] pyridine obtained in Reference Example 8K, step 1,8-chloro-3-iodo-2-(methoxy-$d_3$-methyl)imidazo[1,2-a]pyridine (496 mg, 1.52 mmol) synthesized according to Reference Example 8G, step 1 and step 2 and (E)-2-(3-fluoro-8-formyldibenzo[b,e]oxepin-11(6H)-ylidene)propanenitrile (223 mg, 0.76 mmol) obtained in Reference Example 5, and in the same manner as in Reference Example 8A, step 3, (E)-2-(8-{[8-chloro-2-(methoxy-$d_3$-methyl)imidazo[1,2-a]pyridin-3-yl] (hydroxy)methyl}-3-fluorodibenzo[b,e]oxepin-11(6H)-ylidene)propanenitrile (334 mg, 89%) was obtained.

ESIMS m/z: 493 $(M+H)^+$; $^1H$ NMR (300 MHz, DMSO-$d_6$, δ): 2.16 (s, 3H), 4.59-4.64 (m, 2H), 4.93-5.04 (m, 1H), 5.43-5.52 (m, 1H), 6.40-6.54 (m, 2H), 6.76-6.91 (m, 3H), 7.23-7.31 (m, 1H), 7.37-7.45 (m, 2H), 7.50-7.58 (m, 1H), 8.23-8.28 (m, 1H), 8.49-8.55 (m, 1H).

[step 2] Using (E)-2-(8-{[8-chloro-2-(methoxy-$d_3$-methyl)imidazo[1,2-a]pyridin-3-yl](hydroxy)methyl}-3-fluorodibenzo[b,e]oxepin-11(6H)-ylidene)propanenitrile (323 mg, 0.66 mmol) obtained in step 1, and in the same manner as in Reference Example 8A, step 4, the title compound (137 mg, 44%) was obtained.

ESIMS m/z: 477 $(M+H)^+$; $^1H$ NMR (300 MHz, $CDCl_3$, δ): 2.23 (s, 3H), 4.31-4.48 (m, 2H), 4.69-4.78 (m, 3H), 5.40 (d, J=12.5 Hz, 1H), 6.55 (dd, J=10.3, 2.6 Hz, 1H), 6.60-6.70 (m, 2H), 6.98-7.06 (m, 1H), 7.08-7.13 (m, 1H), 7.20-7.26 (m, 2H), 7.40 (d, J=8.1 Hz, 1H), 7.60-7.66 (m, 1H).

Reference Example 10A (E)-2-{8-[(7-chloro-2-cyclopropylimidazo[1,2-a] pyridin-3-yl)methyl]-3-fluorodibenzo[b,e]oxepin-11 (6H)-ylidene}propanenitrile Using 2-(8-ethynyl-3-fluorodibenzo[b,e]oxepin-11(6H)-ylidene)propanenitrile (350 mg, 1.21 mmol, E/Z=1/1) obtained in Reference Example 9 and 2-amino-4-chloropyridine (156 mg, 1.21 mmol), and in the same manner as in Reference Example 8B, the title compound (73 mg, 13%) was obtained.

ESIMS m/z: 470 $(M+H)^+$; $^1H$ NMR (300 MHz, $CDCl_3$, δ): 0.98-1.05 (m, 2H), 1.08-1.15 (m, 2H), 1.94-2.03 (m, 1H), 2.23 (s, 3H), 4.30 (d, J=17.2 Hz, 1H), 4.38 (d, J=17.2 Hz, 1H), 4.76 (d, J=12.8 Hz, 1H), 5.41 (d, J=12.8 Hz, 1H), 6.53-6.59 (m, 1H), 6.61-6.68 (m, 2H), 6.99-7.06 (m, 1H), 7.08-7.10 (m, 1H), 7.20-7.24 (m, 1H), 7.41 (d, J=7.7 Hz, 1H), 7.50-7.54 (m, 2H).

Reference Example 10B

(E)-2-{8-[(6-chloro-2-cyclopropylimidazo[1,2-a]pyridin-3-yl)methyl]-3-fluorodibenzo[b,e]oxepin-11(6H)-ylidene}propanenitrile Using 2-(8-ethynyl-3-fluorodibenzo[b,e]oxepin-11(6H)-ylidene)propanenitrile (400 mg, 1.38 mmol) obtained in Reference Example 9 and 2-amino-5-chloropyridine (178 mg, 1.38 mmol), and in the same manner as in Reference Example 8B, the title compound (88 mg, 14%) was obtained.

ESIMS m/z: 470 $(M+H)^+$; $^1H$ NMR (300 MHz, $CDCl_3$, δ): 0.99-1.04 (m, 2H), 1.09-1.15 (m, 2H), 1.95-2.02 (m, 1H), 2.24 (s, 3H), 4.30-4.35 (m, 2H), 4.78 (d, J=12.7 Hz, 1H), 5.43 (d, J=12.7 Hz, 1H), 6.54-6.58 (m, 1H), 6.62-6.67 (m, 1H), 7.01-7.07 (m, 2H), 7.11 (br s, 1H), 7.23 (d, J=7.8 Hz, 1H), 7.42 (d, J=7.8 Hz, 1H), 7.46 (d, J=9.8 Hz, 1H), 7.67 (d, J=2.0 Hz, 1H).

Reference Example 10C

(E)-2-{8-[(2-cyclopropyl-7-fluoroimidazo[1,2-a]pyridin-3-yl)methyl]-3-fluorodibenzo[b,e]oxepin-11(6H)-ylidene}propanenitrile Using cyclopropanecarboxyaldehyde (0.129 mL, 1.77 mmol), 4-fluoropyridin-2-amine (141 mg, 1.26 mmol) and 2-(8-ethynyl-3-fluorodibenzo[b,e]oxepin-11(6H)-ylidene)propanenitrile (330 mg, 1.14 mmol) obtained in Reference Example 9, and in the same manner as in Reference Example 8B, the title compound (25 mg, 5%) was obtained.

ESIMS m/z: 454 $(M+H)^+$; $^1H$ NMR (270 MHz, $CDCl_3$, δ): 0.90-1.18 (m, 4H), 1.92-2.07 (m, 1H), 2.23 (s, 3H), 4.21-4.44 (m, 2H), 4.75 (d, J=12.8 Hz, 1H), 5.43 (d, J=12.8 Hz, 1H), 6.43-6.74 (m, 3H), 6.99-7.31 (m, 4H), 7.33-7.62 (m, 2H).

Reference Example 10D

(E)-2-{8-[(2-cyclopropyl-6-fluoroimidazo[1,2-a]pyridin-3-yl)methyl]-3-fluorodibenzo[b,e]oxepin-11(6H)-ylidene}propanenitrile Using 2-(8-ethynyl-3-fluorodibenzo[b,e]oxepin-11(6H)-ylidene)propanenitrile (400 mg, 1.38 mmol, E/Z=1/1) obtained in Reference Example 9, commercially available 5-fluoropyridin-2-amine (155 mg, 1.38 mmol) and cyclopropanecarbaldehyde (0.16 mL, 2.07 mmol), and in the same manner as in Reference Example 8B, the title compound (151 mg, 24%) was obtained.

ESIMS m/z: 454 $(M+H)^+$; $^1H$ NMR (400 MHz, $CDCl_3$, δ): 0.95-1.14 (m, 4H), 1.96-2.07 (m, 1H), 2.24 (s, 3H), 4.27-4.39 (m, 2H), 4.78 (d, J=12.7 Hz, 1H), 5.42 (d, J=12.7 Hz, 1H), 6.56 (dd, J=10.2, 2.4 Hz, 1H), 6.61-6.68 (m, 1H), 6.96-7.06 (m, 2H), 7.08-7.14 (m, 1H), 7.20-7.25 (m, 1H), 7.42 (d, J=7.8 Hz, 1H), 7.45-7.51 (m, 1H), 7.52-7.57 (m, 1H).

Reference Example 10E

(E)-2-(8-{[7-chloro-2-(methoxymethyl)imidazo[1,2-a]pyridin-3-yl]methyl}-3-fluorodibenzo[b,e]oxepin-11(6H)-ylidene)propanenitrile

[step 1] Using commercially available 4-chloro-2-aminopyridine (2.5 g, 19 mmol), and in the same manner as in Reference Example 8F, step 1,7-chloro-2-(chloromethyl)imidazo[1,2-a]pyridine (3.9 g, 99%) was obtained.

ESIMS m/z: 201 $(M+H)^+$; $^1H$ NMR (270 MHz, $CDCl_3$, δ): 4.74 (s, 2H), 6.78-6.81 (m, 1H), 7.57-7.60 (m, 2H), 7.99-8.02 (m, 1H).

[step 2] Using 7-chloro-2-(chloromethyl)imidazo[1,2-a]pyridine (3.9 g, 19 mmol) obtained in step 1, and in the same manner as in Reference Example 8F, step 2,7-chloro-2-(methoxymethyl)imidazo[1,2-a]pyridine (3.8 g, 99%) was obtained.

ESIMS m/z: 197$(M+H)^+$; $^1H$ NMR (270 MHz, $CDCl_3$, δ): 3.49 (s, 3H), 4.63 (s, 2H), 6.76-6.78 (m, 1H), 7.54-7.56 (m, 2H), 8.00-8.02 (m, 1H).

[step 3] Using 7-chloro-2-(methoxymethyl)imidazo[1,2-a]pyridine (3.8 g, 19 mmol) obtained in step 2, and in the same manner as in Reference Example 8F, step 3,7-chloro-3-iodo-2-(methoxymethyl)imidazo[1,2-a]pyridine (5.1 g, 81%) was obtained.

ESIMS m/z: 323 $(M+H)^+$; $^1H$ NMR (270 MHz, $CDCl_3$, δ): 3.46 (s, 3H), 4.61 (s, 2H), 6.90-6.92 (m, 1H), 7.55-7.58 (m, 1H), 8.04-8.06 (m, 1H).

[step 4] Using 7-chloro-3-iodo-2-(methoxymethyl)imidazo[1,2-a]pyridine (700 mg, 2.17 mmol) obtained in step 3 and (E)-2-(3-fluoro-8-formyldibenzo[b,e]oxepin-11(6H)-ylidene)propanenitrile (318 mg, 1.09 mmol) obtained in Reference Example 5, and in the same manner as in Reference Example 8F, step 4, (E)-2-(8-{[7-chloro-2-(methoxymethyl)imidazo[1,2-a]pyridin-3-yl](hydroxy)methyl}-3-fluorodibenzo[b,e]oxepin-11(6H)-ylidene)propanenitrile (400 mg, 75%) was obtained.

ESIMS m/z: 490 $(M+H)^+$; $^1H$ NMR (270 MHz, $CDCl_3$, δ): 2.24 (s, 3H), 3.44 (s, 3H), 4.55-4.70 (m, 2H), 4.78-4.82 (m, 1H), 5.42-5.46 (m, 1H), 6.39-6.42 (m, 1H), 6.54-6.59 (m, 1H), 6.62-6.68 (m, 2H), 7.01-7.05 (m, 1H), 7.35-7.46 (m, 3H), 7.53-7.55 (m, 1H), 7.85-7.89 (m, 1H).

[step 5] Using (E)-2-(8-{[7-chloro-2-(methoxymethyl)imidazo[1,2-a]pyridin-3-yl](hydroxy)methyl}-3-fluorodibenzo[b,e]oxepin-11(6H)-ylidene)propanenitrile (200 mg, 0.41 mmol) obtained in step 4, and in the same manner as in Reference Example 8F, step 5, the title compound (72 mg, 37%) was obtained.

ESIMS m/z: 474 $(M+H)^+$; $^1H$ NMR (270 MHz, $CDCl_3$, δ): 2.23 (s, 3H), 3.47 (s, 3H), 4.35-4.37 (m, 1H), 4.63-4.76 (m, 4H), 5.38-5.42 (m, 1H), 6.53-6.71 (m, 3H), 7.00-7.10 (m, 2H), 7.20-7.24 (m, 2H), 7.39-7.42 (m, 1H), 7.58-7.60 (m, 1H).

Reference Example 10G

(E)-2-{8-[(2-cyclopropyl-7-methoxyimidazo[1,2-a]pyridin-3-yl)methyl]-3-fluorodibenzo[b,e]oxepin-11(6H)-ylidene}propanenitrile Using 2-(8-ethynyl-3-fluorodibenzo[b,e]oxepin-11(6H)-ylidene)propanenitrile (400 mg, 1.38 mmol, E/Z=1/1) obtained in Reference Example 9, commercially available 4-methoxypyridin-2-amine (172 mg, 1.38 mmol) and cyclopropanecarbaldehyde (0.16 mL, 2.07 mmol), and in the same manner as in Reference Example 8B, the title compound (172 mg, 27%) was obtained.

ESIMS m/z: 466 $(M+H)^+$; $^1$H NMR (300 MHz, $CDCl_3$, δ): 0.93-1.17 (m, 4H), 1.89-2.03 (m, 1H), 2.23 (s, 3H), 3.81 (s, 3H), 4.22-4.41 (m, 2H), 4.76 (d, J=12.8 Hz, 1H), 5.41 (d, J=12.8 Hz, 1H), 6.38 (d, J=7.3 Hz, 1H), 6.55 (dd, J=10.3, 2.6 Hz, 1H), 6.59-6.68 (m, 1H), 6.81-6.91 (m, 1H), 7.02 (dd, J=8.8, 6.6 Hz, 1H), 7.02-7.12 (m, 1H), 7.20-7.26 (m, 1H), 7.35-7.53 (m, 2H).

Reference Example 10H (E)-2-(3-fluoro-8-{[2-methyl-8-(trifluoromethyl)imidazo[1,2-a]pyridin-3-yl]methyl}dibenzo[b,e]oxepin-11(6H)-ylidene)propanenitrile

[step 1] Using commercially available 3-trifluoromethyl-2-aminopyridine (2.0 g, 12 mmol), and in the same manner as in Reference Example 8F, step 1,2-(chloromethyl)-8-(trifluoromethyl)imidazo[1,2-a]pyridine (2.78 g, 96%) was obtained.

ESIMS m/z: 235 $(M+H)^+$; $^1$H NMR (270 MHz, $CDCl_3$, δ): 4.78 (s, 2H), 6.72-6.75 (m, 1H), 7.52-7.67 (m, 1H), 7.70-8.76 (m, 2H).

[step 2] Using 2-(chloromethyl)-8-(trifluoromethyl)imidazo[1,2-a]pyridine (2.78 g, 12 mmol) obtained in step 1, and in the same manner as in Reference Example 8F, step 2, 2-(methoxymethyl)-8-(trifluoromethyl)imidazo[1,2-a]pyridine (2.25 g, 82%) was obtained.

ESIMS m/z: 231 $(M+H)^+$; $^1$H NMR (270 MHz, $CDCl_3$, δ): 3.57 (s, 3H), 4.73 (s, 2H), 6.71-6.87 (m, 1H), 7.51-7.53 (m, 1H), 7.68-7.72 (m, 1H), 8.25-8.26 (m, 1H).

[step 3] Using 2-(methoxymethyl)-8-(trifluoromethyl)imidazo[1,2-a]pyridine (2.25 g, 9.8 mmol) obtained in step 2, and in the same manner as in Reference Example 8F, step 3,3-iodo-2-(methoxymethyl)-8-(trifluoromethyl)imidazo[1,2-a]pyridine (1.32 g, 38%) was obtained.

ESIMS m/z: 357 $(M+H)^+$; $^1$H NMR (270 MHz, $CDCl_3$, δ): 3.47 (s, 3H), 4.69 (s, 2H), 7.00 (t, J=6.9 Hz, 1H), 7.62 (d, J=6.9 Hz, 1H), 8.32 (d, J=6.9 Hz, 1H).

[step 4] Using 3-iodo-2-(methoxymethyl)-8-(trifluoromethyl)imidazo[1,2-a]pyridine (700 mg, 1.97 mmol) obtained in step 3 and (E)-2-(3-fluoro-8-formyldibenzo[b,e]oxepin-11(6H)-ylidene)propanenitrile (288 mg, 0.98 mmol) obtained in Reference Example 5, and in the same manner as in Reference Example 8F, step 4, (E)-2-(3-fluoro-8-{hydroxy[2-(methoxymethyl)-8-(trifluoromethyl)imidazo[1,2-a]pyridin-3-yl]methyl}dibenzo[b,e]oxepin-11(6H)-ylidene)propanenitrile (420 mg, 82%) was obtained.

ESIMS m/z: 524 $(M+H)^+$; $^1$H NMR (270 MHz, $CDCl_3$, δ): 2.24 (s, 3H), 3.45 (s, 3H), 4.62-4.83 (m, 3H), 5.41-5.47 (m, 1H), 6.43-6.87 (m, 4H), 7.01-7.06 (m, 1H), 7.41-7.53 (m, 4H), 8.07-8.26 (m, 1H).

[step 5] Using (E)-2-(3-fluoro-8-{hydroxy[2-(methoxymethyl)-8-(trifluoromethyl)imidazo[1,2-a]pyridin-3-yl]methyl}dibenzo[b,e]oxepin-11(6H)-ylidene)propanenitrile (400 mg, 0.76 mmol) obtained in step 4, and in the same manner as in Reference Example 8F, step 5, the title compound (74 mg, 20%) was obtained.

ESIMS m/z: 478 $(M+H)^+$; $^1$H NMR (270 MHz, $CDCl_3$, δ): 2.26 (s, 3H), 2.58 (s, 3H), 4.29-4.31 (m, 2H), 4.73-4.77 (m, 1H), 5.38-5.42 (m, 1H), 6.53-6.77 (m, 3H), 7.00-7.06 (m, 2H), 7.18-7.22 (m, 1H), 7.40-7.49 (m, 2H), 7.77-7.79 (m, 1H).

Reference Example 10I (E)-2-{8-[(8-bromo-2-cyclopropylimidazo[1,2-a]pyridin-3-yl)methyl]-3-fluorodibenzo[b,e]oxepin-11(6H)-ylidene}propanenitrile Using 2-(8-ethynyl-3-fluorodibenzo[b,e]oxepin-11(6H)-ylidene)propanenitrile (1.5 g, 5.18 mmol, E/Z=1/1) obtained in Reference Example 9, commercially available 3-bromopyridin-2-amine (0.9 g, 5.18 mmol) and cyclopropanecarbaldehyde (0.6 mL, 7.78 mmol), and in the same manner as in Reference Example 8B, the title compound (332 mg, 12%) was obtained.

ESIMS m/z: 514 $(M+H)^+$; $^1$H NMR (400 MHz, $CDCl_3$, δ): 0.97-1.05 (m, 2H), 1.13-1.22 (m, 2H), 1.98-2.08 (m, 1H), 2.23 (s, 3H), 4.28-4.44 (m, 2H), 4.75 (d, J=12.7 Hz, 1H), 5.40 (d, J=12.7 Hz, 1H), 6.52-6.58 (m, 2H), 6.60-6.67 (m, 1H), 6.99-7.09 (m, 2H), 7.20-7.25 (m, 1H), 7.35-7.43 (m, 2H), 7.57-7.62 (m, 1H).

Reference Example 10J (E)-2-(8-{[7-chloro-2-methylimidazo[1,2-a]pyridin-3-yl]methyl}-3-fluorodibenzo[b,e]oxepin-11(6H)-ylidene)propanenitrile

[step 1] Using commercially available 4-chloro-2-aminopyridine (2.0 g, 16 mmol) and 1-chloro-2-propanone (1.37 mL, 17 mmol), and in the same manner as in Reference Example 8F, step 1,7-chloro-2-methylimidazo[1,2-a]pyridine (2.59 g, 41%) was obtained.

ESIMS m/z: 167 $(M+H)^+$; $^1$H NMR (270 MHz, $CDCl_3$, δ): 2.51 (s, 3H), 6.92 (d, J=6.8 Hz, 1H), 7.35 (s, 1H), 7.82 (s, 1H), 8.04 (d, J=6.8 Hz, 1H).

[step 2] Using 7-chloro-2-methylimidazo[1,2-a]pyridine (1.06 g, 6.4 mmol) obtained in step 1, and in the same manner as in Reference Example 8F, step 3,7-chloro-3-iodo-2-methylimidazo[1,2-a]pyridine (1.71 g, 92%) was obtained.

ESIMS m/z: 293 $(M+H)^+$; $^1$H NMR (270 MHz, $CDCl_3$, δ): 2.53 (s, 3H), 7.02 (d, J=6.8 Hz, 1H), 7.77 (s, 1H), 8.04 (d, J=6.8 Hz, 1H).

[step 3] Using 7-chloro-3-iodo-2-methylimidazo[1,2-a]pyridine (700 mg, 2.39 mmol) obtained in step 2 and (E)-2-(3-fluoro-8-formyldibenzo[b,e]oxepin-11(6H)-ylidene)propanenitrile (351 mg, 1.20 mmol) obtained in Reference Example 5, and in the same manner as in Reference Example 8F, step 4, (E)-2-(8-{[7-chloro-2-methylimidazo[1,2-a]pyridin-3-yl](hydroxy)methyl}-3-fluorodibenzo[b,e]oxepin-11(6H)-ylidene)propanenitrile (471 mg, 86%) was obtained.

ESIMS m/z: 460 $(M+H)^+$; $^1$H NMR (270 MHz, $CDCl_3$, δ): 2.22 (s, 3H), 2.53 (s, 3H), 4.77-4.85 (m, 2H), 5.38-5.46 (m, 1H), 6.52-6.66 (m, 2H), 6.83-6.86 (m, 1H), 6.98-7.04 (m, 1H), 7.29-7.63 (m, 4H), 8.09-8.14 (m, 1H).

[step 4] Using (E)-2-(8-{[7-chloro-2-methylimidazo[1,2-a]pyridin-3-yl](hydroxy)methyl}-3-fluorodibenzo[b,e]oxepin-11(6H)-ylidene)propanenitrile (470 mg, 0.76 mmol) obtained in step 3, and in the same manner as in Reference Example 8F, step 5, the title compound (368 mg, 71%) was obtained.

ESIMS m/z: 444 $(M+H)^+$; $^1$H NMR (270 MHz, $CDCl_3$, δ): 2.23 (s, 3H), 2.70 (s, 3H), 4.22-4.36 (m, 2H), 4.74-4.77 (m, 1H), 5.38-5.41 (m, 1H), 6.54-6.57 (m, 1H), 6.63-6.66 (m, 1H), 6.97-7.04 (m, 2H), 7.12-7.18 (m, 2H), 7.45-7.50 (m, 1H), 7.74-7.75 (m, 1H), 8.31-8.32 (m, 1H).

Reference Example 10K (E)-2-{8-[(2-cyclopropyl-8-methylimidazo[1,2-a]pyridin-3-yl)methyl]-3-fluorodibenzo[b,e]oxepin-11(6H)-ylidene}propanenitrile Using 2-(8-ethynyl-3-fluorodibenzo[b,e]oxepin-11(6H)-ylidene)propanenitrile (400 mg, 1.38 mmol, E/Z=1/1) obtained in Reference Example 9, commercially available 3-methylpyridin-2-amine (150 mg, 1.38 mmol) and cyclopropanecarbaldehyde (0.16 mL, 2.07 mmol), and in the same manner as in Reference Example 8B, the title compound (189 mg, 30%) was obtained.

ESIMS m/z: 450 $(M+H)^+$; $^1$H NMR (270 MHz, $CDCl_3$, δ): 0.94-1.03 (m, 2H), 1.05-1.13 (m, 2H), 1.96-2.08 (m, 1H), 2.23 (s, 3H), 2.57 (s, 3H), 4.24-4.44 (m, 2H), 4.74 (d, J=12.5 Hz, 1H), 5.40 (d, J=12.5 Hz, 1H), 6.51-6.67 (m, 3H), 6.84-6.90 (m, 1H), 6.97-7.10 (m, 2H), 7.19-7.25 (m, 1H), 7.38 (d, J=7.6 Hz, 1H), 7.45-7.51 (m, 1H).

Reference Example 10L (E)-2-{8-[(7-chloro-2-ethylimidazo[1,2-a]pyridin-3-yl)methyl]-3-fluorodibenzo[b,e]oxepin-11(6H)-ylidene}propanenitrile

[step 1] Using 4-chloropyridin-2-amine (2.0 g, 15.6 mmol) and 1-bromobutan-2-one (1.75 mL, 17.1 mmol), and in the same manner as in Reference Example 8A, step 1,7-chloro-2-ethylimidazo[1,2-a]pyridine (1.08 g, 38%) was obtained.

ESIMS m/z: 182 $(M+H)^+$; $^1$H NMR (270 MHz, $CDCl_3$, δ): 1.34 (t, J=7.6 Hz, 3H), 2.81 (q, J=7.6 Hz, 2H), 6.66-6.77 (m, 1H), 7.32 (s, 1H), 7.46-7.60 (m, 1H), 7.90-8.01 (m, 1H).

[step 2] Using 7-chloro-2-ethylimidazo[1,2-a]pyridine (1.08 g, 5.94 mmol) obtained in step 1, and in the same manner as in Reference Example 8A, step 2,7-chloro-2-ethyl-3-iodoimidazo[1,2-a]pyridine (1.58 g, 87%) was obtained.

ESIMS m/z: 308 $(M+H)^+$; $^1$H NMR (270 MHz, $CDCl_3$, δ): 1.31 (t, J=7.6 Hz, 3H), 2.78 (q, J=7.6 Hz, 2H), 6.86 (d, J=7.0 Hz, 1H), 7.53 (s, 1H), 7.99 (d, J=7.0 Hz, 1H).

[step 3] Using 7-chloro-2-ethyl-3-iodoimidazo[1,2-a]pyridine (700 mg, 2.28 mmol) obtained in step 2 and (E)-2-(3-fluoro-8-formyldibenzo[b,e]oxepin-11(6H)-ylidene)propanenitrile (335 mg, 1.14 mmol) obtained in Reference Example 5, and in the same manner as in Reference Example 8A, step 3, (E)-2-{3-fluoro-8-[(7-chloro-2-ethylimidazo[1,2-a]pyridin-3-yl)(hydroxy)methyl]dibenzo[b,e]oxepin-11(6H)-ylidene}propanenitrile (480 mg, 89%) was obtained.

ESIMS m/z: 474 $(M+H)^+$; $^1$H NMR (270 MHz, DMSO-$d_6$, δ): 1.13-1.30 (m, 3H), 2.10-2.26 (m, 3H), 2.65-2.82 (m, 2H), 4.95-5.09 (m, 1H), 5.38-5.54 (m, 1H), 6.28-6.39 (m, 2H), 6.60-6.78 (m, 1H), 6.78-6.93 (m, 2H), 7.22-7.67 (m, 4H), 8.12-8.26 (m, 1H).

[step 4] Using (E)-2-{3-fluoro-8-[(7-chloro-2-ethylimidazo[1,2-a]pyridin-3-yl)(hydroxy)methyl]dibenzo[b,e]oxepin-11(6H)-ylidene}propanenitrile (478 mg, 1.01 mmol) obtained in step 3, and in the same manner as in Reference Example 8A, step 4, the title compound (462 mg, 100%) was obtained.

ESIMS m/z: 458 $(M+H)^+$; $^1$H NMR (270 MHz, $CDCl_3$, δ): 1.36 (t, J=7.6 Hz, 3H), 2.24 (s, 3H), 2.82 (q, J=7.6 Hz, 2H), 4.16-4.36 (m, 2H), 4.74 (d, J=12.8 Hz, 1H), 5.40 (d, J=12.8 Hz, 1H), 6.52-6.59 (m, 1H), 6.61-6.69 (m, 2H), 6.99-7.07 (m, 2H), 7.14-7.20 (m, 1H), 7.37-7.42 (m, 1H), 7.50-7.55 (m, 1H), 7.55-7.61 (m, 1H).

Reference Example 11A (E)-2-{8-[(8-chloro-2-methylimidazo[1,2-a]pyridin-3-yl)methyl]-3-fluorodibenzo[b,e]oxepin-11(6H)-ylidene}propanenitrile

[step 1] Using 3-chloropyridin-2-amine (1.0 g, 7.78 mmol) and 1-chloropropan-2-one (2.0 g, 21.6 mmol), and in the same manner as in Reference Example 8A, step 1,8-chloro-2-methylimidazo[1,2-a]pyridine (700 mg, 54%) was obtained.

ESIMS m/z: 167 $(M+H)^+$; $^1$H NMR (270 MHz, DMSO-$d_6$, δ): 2.50 (s, 3H), 7.40 (t, J=7.4 Hz, 1H), 8.03 (d, J=7.4 Hz, 1H), 8.18-8.22 (m, 1H), 8.85 (d, J=7.4 Hz, 1H).

[step 2] Using 8-chloro-2-methylimidazo[1,2-a]pyridine (600 mg, 3.60 mmol) obtained in step 1, and in the same manner as in Reference Example 8A, step 2,8-chloro-2-methyl-3-iodoimidazo[1,2-a]pyridine (1.01 g, 97%) was obtained.

ESIMS m/z: 293 $(M+H)^+$; $^1$H NMR (270 MHz, $CDCl_3$, δ): 2.54 (s, 3H), 6.83 (t, J=6.9 Hz, 1H), 7.30 (dd, J=6.9, 1.2 Hz, 1H), 8.01 (dd, J=6.9, 1.2 Hz, 1H).

[step 3] Using 8-chloro-2-methyl-3-iodoimidazo[1,2-a]pyridine (598 mg, 2.05 mmol) obtained in step 2 and (E)-2-(3-fluoro-8-formyldibenzo[b,e]oxepin-11(6H)-ylidene)propanenitrile (300 mg, 1.02 mmol) obtained in Reference Example 5, and in the same manner as in Reference Example 8A, step 3, (E)-2-{3-fluoro-8-[(8-chloro-2-methylimidazo[1,2-a]pyridin-3-yl)(hydroxy)methyl]dibenzo[b,e]oxepin-11(6H)-ylidene}propanenitrile (430 mg, 91%) was obtained.

ESIMS m/z: 474 $(M+H)^+$; $^1$H NMR (270 MHz, DMSO-$d_6$, δ): 2.16 (s, 3H), 2.39 (s, 3H), 4.89-5.10 (m, 1H), 5.40-5.53 (m, 1H), 6.26-6.43 (m, 2H), 6.58-6.92 (m, 3H), 7.20-7.65 (m, 4H), 8.10-8.28 (m, 1H).

[step 4] Using (E)-2-{3-fluoro-8-[(8-chloro-2-methylimidazo[1,2-a]pyridin-3-yl)(hydroxy)methyl]dibenzo[b,e]oxepin-11(6H)-ylidene}propanenitrile (430 mg, 0.935 mmol) obtained in step 3, and in the same manner as in Reference Example 8A, step 4, the title compound (329 mg, 79%) was obtained.

ESIMS m/z: 444 $(M+H)^+$; $^1$H NMR (270 MHz, $CDCl_3$, δ): 2.26 (s, 3H), 2.55 (s, 3H), 4.13-4.41 (m, 2H), 4.72 (d, J=12.8 Hz, 1H), 5.39 (d, J=12.8 Hz, 1H), 6.50-6.68 (m, 3H), 6.93-7.07 (m, 2H), 7.14-7.34 (m, 2H), 7.35-7.44 (m, 1H), 7.49-7.64 (m, 1H).

Reference Example 11B (E)-2-(3-fluoro-8-{[2-methyl-7-(trifluoromethyl)imidazo[1,2-a]pyridin-3-yl]methyl}dibenzo[b,e]oxepin-11(6H)-ylidene)propanenitrile

[step 1] Using commercially available 4-(trifluoromethyl)-2-aminopyridine (1.0 g, 6.2 mmol) and 1-chloro-2-propanone (0.54 mL, 6.8 mmol), and in the same manner as in Reference Example 8F, step 1,2-methyl-7-(trifluoromethyl)imidazo[1,2-a]pyridine (1.0 g, 81%) was obtained.

ESIMS m/z: 201 $(M+H)^+$; $^1$H NMR (270 MHz, $CDCl_3$, δ): 2.48 (s, 3H), 6.90-6.92 (m, 1H), 7.46 (s, 1H), 7.85 (s, 1H), 8.09-8.16 (m, 1H).

[step 2] Using 2-methyl-7-(trifluoromethyl)imidazo[1,2-a]pyridine (1.0 g, 5.0 mmol) obtained in step 1, and in the same manner as in Reference Example 8F, step 3,3-iodo-2-methyl-7-(trifluoromethyl)imidazo[1,2-a]pyridine (0.75 g, 46%) was obtained.

ESIMS m/z: 327 $(M+H)^+$; $^1$H NMR (270 MHz, $CDCl_3$, δ): 2.54 (s, 3H), 7.06 (dd, J=6.8, 2.0 Hz, 1H), 7.80 (s, 1H), 8.16 (d, J=6.8 Hz, 1H).

[step 3] Using 3-iodo-2-methyl-7-(trifluoromethyl)imidazo[1,2-a]pyridine (730 mg, 2.24 mmol) obtained in step 2 and (E)-2-(3-fluoro-8-formyldibenzo[b,e]oxepin-11(6H)-ylidene)propanenitrile (328 mg, 1.12 mmol) obtained in Reference Example 5, and in the same manner as in Reference Example 8F, step 4, (E)-2-(3-fluoro-8-{hydroxy[2-methyl-7-(trifluoromethyl)imidazo[1,2-a]pyridin-3-yl]methyl}dibenzo[b,e]oxepin-11(6H)-ylidene)propanenitrile (550 mg, 99%) was obtained.

ESIMS m/z: 494 $(M+H)^+$; $^1$H NMR (270 MHz, $CDCl_3$, δ): 2.22 (s, 3H), 2.43 (s, 3H), 4.80-4.84 (m, 1H), 5.43-5.47 (m, 1H), 6.39 (br s, 1H), 6.54-6.67 (m, 2H), 6.79-6.81 (m, 1H), 7.00-7.05 (m, 1H), 7.32-7.35 (m, 1H), 7.42-7.52 (m, 2H), 7.79-7.80 (m, 1H), 8.10-8.16 (m, 1H).

[step 4] Using (E)-2-(3-fluoro-8-{hydroxy[2-methyl-7-(trifluoromethyl)imidazo[1,2-a]pyridin-3-yl]methyl}dibenzo[b,e]oxepin-11(6H)-ylidene)propanenitrile (550 mg, 1.12 mmol) obtained in step 3, and in the same manner as in Reference Example 8F, step 5, the title compound (464 mg, 84%) was obtained.

ESIMS m/z: 478 $(M+H)^+$; $^1$H NMR (270 MHz, $CDCl_3$, δ): 2.27 (s, 3H), 2.58 (s, 3H), 4.25-4.36 (m, 2H), 4.73-4.76 (m, 1H), 5.39-5.42 (m, 1H), 6.54-6.57 (m, 1H), 6.62-6.67 (m, 1H), 6.85-6.87 (m, 1H), 7.00-7.04 (m, 2H), 7.16-7.18 (m, 1H), 7.40-7.42 (m, 1H), 7.73-7.74 (m, 1H), 7.84-7.85 (m, 1H).

Reference Example 11C

(E)-2-(8-{[2-cyclopropyl-8-(2-hydroxypropan-2-yl)imidazo[1,2-a]pyridin-3-yl]methyl}-3-fluorodibenzo[b,e]oxepin-11(6H)-ylidene)propanenitrile

[step 1] (E)-2-{8-[(8-bromo-2-cyclopropylimidazo[1,2-a]pyridin-3-yl)methyl]-3-fluorodibenzo[b,e]oxepin-11(6H)-ylidene}propanenitrile (1.0 g, 1.94 mmol) obtained in Reference Example 10I was dissolved in a mixed solvent of DMF (5.3 mL) and n-propanol (5.3 mL), and 1,1'-bis(diphenylphosphino)ferrocene-palladium (II) dichloride-dichloromethane complex (318 mg, 0.39 mmol), 1,1'-bis(diphenylphosphino)ferrocene (431 mg, 0.78 mmol) and triethylamine (2.7 mL, 19.44 mmol) were added. After purging with nitrogen using a vacuum line, CO gas was filled and the mixture was stirred at 80° C. in the presence of CO gas for 5 hr. After completion of the reaction, the mixture was filtered through celite, saturated aqueous ammonium chloride solution was added to the solution, and the mixture was extracted 3 times with ethyl acetate. The combined organic layers were washed with water, dried over anhydrous magnesium sulfate and concentrated under reduced pressure. The residue was purified by silica gel column chromatography (hexane/ethyl acetate=100/0 v/v-60/40 v/v) to give (E)-propyl 3-{[11-(1-cyanoethylidene)-3-fluoro-6,11-dihydrodibenzo[b,e]oxepin-8-yl]methyl}-2-cyclopropylimidazo[1,2-a]pyridine-8-carboxylate (847 mg, 84%).

ESIMS m/z: 522 $(M+H)^+$; $^1$H NMR (300 MHz, $CDCl_3$, δ): 0.97-1.04 (m, 2H), 1.13 (t, J=7.3 Hz, 3H), 1.18-1.29 (m, 2H), 1.79-1.93 (m, 2H), 1.99-2.09 (m, 1H), 2.23 (s, 3H), 4.29-4.48 (m, 4H), 4.72 (d, J=12.5 Hz, 1H), 5.39 (d, J=12.5 Hz, 1H), 6.55 (dd, J=10.3, 2.6 Hz, 1H), 6.60-6.68 (m, 1H), 6.68-6.75 (m, 1H), 6.98-7.07 (m, 2H), 7.20-7.27 (m, 1H), 7.40 (d, J=7.7 Hz, 1H), 7.75 (dd, J=7.1, 1.3 Hz, 1H), 7.85 (dd, J=7.1, 1.3 Hz, 1H).

[step 2] (E)-propyl 3-{[11-(1-cyanoethylidene)-3-fluoro-6,11-dihydrodibenzo[b,e]oxepin-8-yl]methyl}-2-cyclopropylimidazo[1,2-a]pyridine-8-carboxylate (350 mg, 0.55 mmol) obtained in step 1 was dissolved in THF (4.1 mL), methylmagnesium chloride (3 mol/L THF solution, 0.73 mL, 2.20 mmol) was added at −30° C., and the mixture was stirred at −20° C. for 2 hr. To the mixture was added saturated aqueous ammonium chloride solution, and the mixture was extracted 3 times with ethyl acetate. The combined organic layers were dried over anhydrous magnesium sulfate, and concentrated under reduced pressure. The residue was purified by silica gel column chromatography (hexane/ethyl acetate=100/0 v/v-70/30 v/v) to give the title compound (244 mg, 90%).

ESIMS m/z: 494 $(M+H)^+$; $^1$H NMR (300 MHz, $CDCl_3$, δ): 0.93-1.02 (m, 2H), 1.05-1.15 (m, 2H), 1.67 (s, 6H), 1.92-2.06 (m, 1H), 2.23 (s, 3H), 4.25-4.43 (m, 2H), 4.78 (d, J=12.5 Hz, 1H), 5.41 (d, J=12.5 Hz, 1H), 6.51-6.68 (m, 3H), 6.89-6.98 (m, 2H), 6.98-7.06 (m, 1H), 7.08-7.14 (m, 1H), 7.21-7.26 (m, 1H), 7.36-7.43 (m, 1H), 7.48-7.53 (m, 1H).

Reference Example 11D

(E)-2-(8-{[2-cyclopropyl-8-(trifluoromethyl)imidazo[1,2-a]pyridin-3-yl]methyl}-3-fluorodibenzo[b,e]oxepin-11(6H)-ylidene)propanenitrile

[step 1] Using 3-(trifluoromethyl)pyridin-2-amine (700 mg, 4.32 mmol), and in the same manner as in Reference Example 8A, step 1,2-cyclopropyl-8-(trifluoromethyl)imidazo[1,2-a]pyridine (710 mg, 73%) was obtained.

ESIMS m/z: 227 $(M+H)^+$; $^1$H NMR (300 MHz, $CDCl_3$, δ): 0.83-0.95 (m, 2H), 0.95-1.07 (m, 2H), 2.05-2.19 (m, 1H), 6.76 (t, J=6.8 Hz, 1H), 7.35 (s, 1H), 7.40-7.47 (m, 1H), 8.15 (d, J=6.8 Hz, 1H).

[step 2] Using 2-cyclopropyl-8-(trifluoromethyl)imidazo[1,2-a]pyridine (710 mg, 3.14 mmol) obtained in step 1, and in the same manner as in Reference Example 8A, step 2,2-cyclopropyl-3-iodo-8-(trifluoromethyl)imidazo[1,2-a]pyridine (1.06 g, 96%) was obtained.

ESIMS m/z: 353 $(M+H)^+$; $^1$H NMR (270 MHz, $CDCl_3$, δ): 0.88-1.27 (m, 4H), 1.95-2.15 (m, 1H), 6.88 (t, J=6.9 Hz, 1H), 7.49 (d, J=6.9 Hz, 1H), 8.20 (d, J=6.9 Hz, 1H).

[step 3] Using 2-cyclopropyl-3-iodo-8-(trifluoromethyl)imidazo[1,2-a]pyridine (480 mg, 1.36 mmol) obtained in step 2 and (E)-2-(3-fluoro-8-formyldibenzo[b,e]oxepin-11(6H)-ylidene)propanenitrile (200 mg, 0.68 mmol) obtained in Reference Example 5, and in the same manner as in Reference Example 8A, step 3, (E)-2-(8-{[2-cyclopropyl-8-(trifluoromethyl)imidazo[1,2-a]pyridin-3-yl](hydroxy)methyl}-3-fluorodibenzo[b,e]oxepin-11(6H)-ylidene)propanenitrile (356 mg) was obtained quantitatively.

ESIMS m/z: 520 $(M+H)^+$; $^1$H NMR (270 MHz, $CDCl_3$, δ): 0.79-1.09 (m, 4H), 1.65-1.82 (m, 1H), 2.23 (s, 3H), 4.77-4.88 (m, 1H), 5.38-5.50 (m, 1H), 6.41-6.49 (m, 1H), 6.50-6.70 (m, 3H), 6.98-7.07 (m, 1H), 7.36-7.50 (m, 4H), 8.08-8.15 (m, 1H).

[step 4] Using (E)-2-(8-{[2-cyclopropyl-8-(trifluoromethyl)imidazo[1,2-a]pyridin-3-yl](hydroxy)methyl}-3-fluorodibenzo[b,e]oxepin-11(6H)-ylidene)propanenitrile (345 mg, 0.66 mmol) obtained in step 3, and in the same manner as in Reference Example 8A, step 4, the title compound (305 mg, 91%) was obtained.

ESIMS m/z: 504 $(M+H)^+$; $^1$H NMR (270 MHz, $CDCl_3$, δ): 0.96-1.06 (m, 2H), 1.11-1.21 (m, 2H), 1.98-2.09 (m, 1H), 2.23 (s, 3H), 4.29-4.48 (m, 2H), 4.76 (d, J=12.5 Hz, 1H), 5.41 (d, J=12.5 Hz, 1H), 6.56 (dd, J=10.2, 2.6 Hz, 1H), 6.60-6.73

(m, 2H), 6.99-7.06 (m, 1H), 7.06-7.11 (m, 1H), 7.21-7.26 (m, 1H), 7.37-7.44 (m, 2H), 7.70-7.76 (m, 1H).

Reference Example 11E

(E)-2-{8-[(2-cyclopropylimidazo[1,2-b]pyridazin-3-yl)methyl]-3-fluorodibenzo[b,e]oxepin-11(6H)-ylidene}propanenitrile

[step 1] Using pyridazin-3-amine (300 mg, 3.15 mmol), and in the same manner as in Reference Example 8A, step 1, 2-cyclopropylimidazo[1,2-b]pyridazine (157 mg, 31%) was obtained.

ESIMS m/z: 160 $(M+H)^+$; $^1H$ NMR (400 MHz, $CDCl_3$, δ): 0.95-1.05 (m, 4H), 2.05-2.12 (m, 1H), 6.95 (dd, J=9.0, 4.0 Hz, 1H), 7.77 (s, 1H), 7.81 (d, J=9.0 Hz, 1H), 8.21 (d, J=4.0 Hz, 1H).

[step 2] Using 2-cyclopropylimidazo[1,2-b]pyridazine (120 mg, 0.754 mmol) obtained in step 1, and in the same manner as in Reference Example 8A, step 2,2-cyclopropyl-3-iodoimidazo[1,2-b]pyridazine (164 mg, 76%) was obtained.

ESIMS m/z: 286 $(M+H)^+$; $^1H$ NMR (300 MHz, $CDCl_3$, δ): 1.03-1.17 (m, 4H), 2.09-2.19 (m, 1H), 6.98-7.05 (m, 1H), 7.76 (d, J=9.2, 2.0 Hz, 1H), 8.35-8.39 (m, 1H).

[step 3] Using 2-cyclopropyl-3-iodoimidazo[1,2-b]pyridazine (164 mg, 0.575 mmol) obtained in step 2, and in the same manner as in Reference Example 8A, step 3, (E)-2-{8-[(2-cyclopropylimidazo[1,2-b]pyridazin-3-yl)(hydroxy)methyl]-3-fluorodibenzo[b,e]oxepin-11(6H)-ylidene}propanenitrile (65 mg, 42%) was obtained.

ESIMS m/z: 453 $(M+H)^+$; $^1H$ NMR (400 MHz, $CDCl_3$, δ): 0.94-1.13 (m, 4H), 1.87-2.02 (m, 1H), 2.24 (s, 3H), 4.25 (dd, J=18.5, 8.8 Hz, 1H), 4.84 (d, J=12.7, 1H), 5.46 (dd, J=12.7, 2.9 Hz, 1H), 6.47-6.67 (m, 3H), 6.94-7.05 (m, 2H), 7.40-7.53 (m, 3H), 8.17-8.21 (m, 1H).

[step 4] Using (E)-2-{8-[(2-cyclopropylimidazo[1,2-b]pyridazin-3-yl)(hydroxy)methyl]-3-fluorodibenzo[b,e]oxepin-11(6H)-ylidene}propanenitrile (65 mg, 0.144 mmol) obtained in step 3, and in the same manner as in Reference Example 8A, step 4, the title compound (40 mg, 64%) was obtained.

ESIMS m/z: 437 $(M+H)^+$; $^1H$ NMR (300 MHz, $CDCl_3$, δ): 0.99-1.08 (m, 2H), 1.09-1.16 (m, 2H), 1.99-2.10 (m, 1H), 2.22 (s, 3H), 4.46 (s, 2H), 4.78 (d, J=12.5 Hz, 1H), 5.42 (d, J=12.5 Hz, 1H), 6.51-6.66 (m, 2H), 6.90-7.05 (m, 2H), 7.26-7.28 (m, 1H), 7.31-7.40 (m, 2H), 7.78-7.83 (m, 1H), 8.22 (dd, J=4.6, 1.6 Hz, 1H).

Reference Example 11F

(E)-2-{3-fluoro-8-[(2-isopropyl-7-methoxyimidazo[1,2-a]pyrimidin-3-yl)methyl]dibenzo[b,e]oxepin-11(6H)-ylidene}propanenitrile

[step 1]4-Chloropyrimidin-2-amine (200 mg, 1.54 mmol) was dissolved in methanol (2 mL), and the mixture was stirred with heating at 110° C. for 1 hr in a microwave synthesizer. Saturated aqueous sodium hydrogen carbonate solution was added to the mixture, and the mixture was extracted 3 times with chloroform. The combined organic layers were dried over anhydrous magnesium sulfate, and concentration under reduced pressure to give 4-methoxypyrimidin-2-amine (140 mg, 73%).

ESIMS m/z: 126 $(M+H)^+$; $^1H$ NMR (270 MHz, $CDCl_3$, δ): 3.88 (s, 3H), 4.96 (br s, 2H), 6.04-6.17 (m, 1H), 7.93-8.10 (m, 1H).

[step 2] Using 4-methoxypyrimidin-2-amine (100 mg, 0.799 mmol) and 1-bromo-3-methylbutan-2-one (158 mg, 0.959 mmol), and in the same manner as in Reference Example 8A, step 1,2-isopropyl-7-methoxyimidazo[1,2-a]pyrimidine (67 mg, 44%) was obtained.

ESIMS m/z: 192 $(M+H)^+$; $^1H$ NMR (270 MHz, $CDCl_3$, δ): 1.30-1.37 (m, 6H), 2.94-3.10 (m, 1H), 4.01-4.03 (m, 3H), 6.26-6.39 (m, 1H), 7.03 (s, 1H), 8.03-8.09 (m, 1H).

[step 3] Using 2-isopropyl-7-methoxyimidazo[1,2-a]pyrimidine (67 mg, 0.35 mmol) obtained in step 2, and in the same manner as in Reference Example 8A, step 2,3-iodo-2-isopropyl-7-methoxyimidazo[1,2-a]pyrimidine (66 mg, 59%) was obtained.

ESIMS m/z: 318 $(M+H)^+$; $^1H$ NMR (270 MHz, $CDCl_3$, δ): 1.35 (d, J=7.2 Hz, 6H), 2.85-3.18 (m, 1H), 4.06 (s, 3H), 6.44 (d, J=7.4 Hz, 1H), 7.99 (d, J=7.4 Hz, 1H).

[step 4] Using 3-iodo-2-isopropyl-7-methoxyimidazo[1,2-a]pyrimidine (649 mg, 2.05 mmol) obtained in step 3 and (E)-2-(3-fluoro-8-formyldibenzo[b,e]oxepin-11(6H)-ylidene)propanenitrile (300 mg, 1.02 mmol) obtained in Reference Example 5, and in the same manner as in Reference Example 8A, step 3, (E)-2-{3-fluoro-8-[(hydroxy) (2-isopropyl-7-methoxyimidazo[1,2-a]pyrimidin-3-yl)methyl]dibenzo[b,e]oxepin-11(6H)-ylidene}propanenitrile (310 mg, 63%) was obtained.

ESIMS m/z: 485 $(M+H)^+$; $^1H$ NMR (270 MHz, $CDCl_3$, δ): 1.31-1.47 (m, 6H), 2.24 (s, 3H), 3.05-3.25 (m, 1H), 3.91-4.09 (m, 3H), 4.75-4.88 (m, 1H), 5.35-5.51 (m, 1H), 6.13-6.22 (m, 1H), 6.32-6.41 (m, 1H), 6.49-6.72 (m, 2H), 6.94-7.09 (m, 1H), 7.22-7.55 (m, 3H), 7.83-8.02 (m, 1H).

[step 5] Using (E)-2-{3-fluoro-8-[(hydroxy) (2-isopropyl-7-methoxyimidazo[1,2-a]pyrimidin-3-yl)methyl]dibenzo[b,e]oxepin-11(6H)-ylidene}propanenitrile (310 mg, 0.64 mmol) obtained in step 4, and in the same manner as in Reference Example 8A, step 4, the title compound (300 mg, 100%) was obtained.

ESIMS m/z: 469 $(M+H)^+$; $^1H$ NMR (270 MHz, $CDCl_3$, δ): 1.34-1.53 (m, 6H), 2.23 (s, 3H), 3.00-3.29 (m, 1H), 4.03 (s, 3H), 4.17-4.35 (m, 2H), 4.77 (d, J=12.8 Hz, 1H), 5.41 (d, J=12.8 Hz, 1H), 6.26-6.42 (m, 1H), 6.48-6.72 (m, 2H), 6.90-7.12 (m, 2H), 7.14-7.23 (m, 1H), 7.39-7.50 (m, 1H), 7.67-7.80 (m, 1H).

Reference Example 11G

(E)-2-{8-[(2-cyclopropylimidazo[1,2-a]pyrazin-3-yl)methyl]-3-fluorodibenzo[b,e]oxepin-11(6H)-ylidene}propanenitrile

[step 1] Using 2-(8-ethynyl-3-fluorodibenzo[b,e]oxepin-11(6H)-ylidene)propanenitrile (1.00 g, 3.46 mmol, E/Z=1/1) obtained in Reference Example 9 and 2-amino-pyrazine (493 mg, 5.18 mmol), and in the same manner as in Reference Example 8B, the title compound (28 mg, 1.9%) was obtained.

ESIMS m/z: 437 $(M+H)^+$; $^1H$ NMR (300 MHz, $CDCl_3$, δ): 1.01-1.20 (m, 4H), 2.00-2.09 (m, 1H), 2.23 (s, 3H), 4.34 (d, J=17.6 Hz, 1H), 4.42 (d, J=17.6 Hz, 1H), 4.76 (d, J=12.8 Hz, 1H), 5.42 (d, J=12.8 Hz, 1H), 6.52-6.68 (m, 2H), 6.99-7.10 (m, 2H), 7.22 (d, J=8.1 Hz, 1H), 7.42 (d, J=8.1 Hz, 1H), 7.57-7.60 (m, 1H), 7.74 (d, J=4.8 Hz, 1H), 8.95 (d, J=1.1, 1H).

Reference Example 11H

(E)-2-(8-{[2-cyclopropyl-7-(trifluoromethyl)imidazo[1,2-a]pyrimidin-3-yl]methyl}-3-fluorodibenzo[b,e]oxepin-11(6H)-ylidene)propanenitrile Using cyclopropanecarboxyaldehyde (0.586 mL, 7.74 mmol), 4-trifluoromethylpyrimidin-2-amine (930 mg, 5.7 mmol) and 2-(8-ethynyl-3-fluorodibenzo[b,e]oxepin-11(6H)-ylidene)propanenitrile (1.5 g, 5.18 mmol) obtained in Reference Example 9, and in the same manner as in Reference Example 8B, the title compound (150 mg, 6%) was obtained.

ESIMS m/z: 505 $(M+H)^+$; $^1H$ NMR (270 MHz, $CDCl_3$, δ): 1.02-1.39 (m, 4H), 1.97-2.12 (m, 1H), 2.17-2.29 (m, 3H), 4.30-4.56 (m, 2H), 4.69-5.00 (m, 1H), 5.31-5.55 (m, 1H), 6.46-6.81 (m, 3H), 6.98-7.18 (m, 1H), 7.26-7.62 (m, 3H), 7.97-8.11 (m, 1H).

Reference Example 11I

(E)-2-{8-[(2-cyclopropyl-8-methoxyimidazo[1,2-a]pyrazin-3-yl)methyl]-3-fluorodibenzo[b,e]oxepin-11(6H)-ylidene}propanenitrile Using cyclopropanecarboxyaldehyde (0.586 mL, 7.74 mmol), 3-chloropyrazin-2-amine (739 mg, 5.7 mmol) and 2-(8-ethynyl-3-fluorodibenzo[b,e]oxepin-11(6H)-ylidene)propanenitrile (1.5 g, 5.18 mmol) obtained in Reference Example 9, and in the same manner as in Reference Example 8B, 2-{8-[(8-chloro-2-cyclopropylimidazo[1,2-a]pyrazin-3-yl)methyl]-3-fluorodibenzo[b,e]oxepin-11(6H)-ylidene}propanenitrile was obtained. Successively, the obtained 2-{8-[(8-chloro-2-cyclopropylimidazo[1,2-a]pyrazin-3-yl)methyl]-3-fluorodibenzo[b,e]oxepin-11(6H)-ylidene}propanenitrile was dissolved in methanol (1 mL), 28% sodium methoxide (0.3 mL, 0.425 mmol) was added, and the mixture was stirred with heating at 60° C. Water was added to the mixture, and the mixture was extracted 3 times with ethyl acetate. The combined organic layers were dried over anhydrous magnesium sulfate, and concentrated under reduced pressure. The residue was purified by silica gel column chromatography (hexane/ethyl acetate=1/1 v/v) to give the title compound (25 mg, 1%).

ESIMS m/z: 467 $(M+H)^+$; $^1H$ NMR (270 MHz, $CDCl_3$, δ): 0.89-1.05 (m, 2H), 1.11-1.30 (m, 2H), 1.89-2.09 (m, 1H), 2.23 (s, 3H), 4.11 (s, 3H), 4.25-4.40 (m, 2H), 4.76 (d, J=12.8 Hz, 1H), 5.41 (d, J=12.8 Hz, 1H), 6.51-6.61 (m, 1H), 6.60-6.71 (m, 1H), 6.96-7.11 (m, 2H), 7.16-7.29 (m, 3H), 7.37-7.47 (m, 1H).

Reference Example 11J

(E)-2-{8-[(2-cyclopropylimidazo[1,2-a]pyrimidin-3-yl)methyl]-3-fluorodibenzo[b,e]oxepin-11(6H)-ylidene}propanenitrile

[step 1] Using pyrimidin-2-amine (500 mg, 5.26 mmol), and in the same manner as in Reference Example 8A, step 1, 2-cyclopropylimidazo[1,2-a]pyrimidine (294 mg, 35%) was obtained.

ESIMS m/z: 160 $(M+H)^+$; $^1H$ NMR (300 MHz, $CDCl_3$, δ): 0.96-1.11 (m, 4H), 1.99-2.08 (m, 1H), 6.78 (dd, J=6.8, 4.2 Hz, 1H), 7.32 (s, 1H), 8.30 (dd, J=6.8, 2.0 Hz, 1H), 8.44 (dd, J=4.2, 2.0 Hz, 1H).

[step 2] Using 2-cyclopropylimidazo[1,2-a]pyrimidine (280 mg, 1.76 mmol) obtained in step 1, and in the same manner as in Reference Example 8A, step 2,2-cyclopropyl-3-iodoimidazo[1,2-a]pyrimidine (366 mg, 73%) was obtained.

ESIMS m/z: 286 $(M+H)^+$; $^1H$ NMR (300 MHz, $CDCl_3$, δ): 1.02-1.09 (m, 2H), 1.21-1.27 (m, 2H), 2.00-2.09 (m, 1H), 6.91 (dd, J=6.8, 4.0 Hz, 1H), 8.32 (dd, J=6.8, 2.0 Hz, 1H), 8.42 (dd, J=4.0, 2.0 Hz, 1H).

[step 3] Using 2-cyclopropyl-3-iodoimidazo[1,2-a]pyrimidine (350 mg, 1.23 mmol) obtained in step 2, and in the same manner as in Reference Example 8A, step 3, (E)-2-{8-[(2-cyclopropylimidazo[1,2-a]pyrimidin-3-yl)(hydroxy)methyl]-3-fluorodibenzo[b,e]oxepin-11(6H)-ylidene}propanenitrile (168 mg, 61%) was obtained.

ESIMS m/z: 453 $(M+H)^+$; $^1H$ NMR (400 MHz, $CDCl_3$, δ): 0.55-1.01 (m, 4H), 1.72-1.83 (m, 1H), 2.23 (s, 3H), 4.83 (dd, J=12.7, 3.9 Hz, 1H), 5.44 (d, J=12.7, 4.9, 1H), 5.78 (br s, 1H), 6.51-6.68 (m, 4H), 7.03 (d, J=8.8, 6.8, 1H), 7.40-7.55 (m, 3H), 8.26-8.37 (m, 2H).

[step 4] Using (E)-2-{8-[(2-cyclopropylimidazo[1,2-a]pyrimidin-3-yl)(hydroxy)methyl]3-fluorodibenzo[b,e]oxepin-11(6H)-ylidene}propanenitrile (147 mg, 0.325 mmol) obtained in step 3, and in the same manner as in Reference Example 8A, step 4, the title compound (118 mg, 83%) was obtained.

ESIMS m/z: 437 $(M+H)^+$; $^1H$ NMR (300 MHz, $CDCl_3$, δ): 1.00-1.07 (m, 2H), 1.24-1.30 (m, 2H), 1.98-2.06 (m, 1H), 2.24 (s, 3H), 4.32 (d, J=17.6 Hz, 1H), 4.42 (d, J=17.6 Hz, 1H), 4.76 (d, J=12.5 Hz, 1H), 5.41 (d, J=12.5 Hz, 1H), 6.53-6.73 (m, 3H), 7.00-7.06 (m, 1H), 7.09-7.11 (m, 1H), 7.42 (d, J=7.4 Hz, 1H), 7.88 (dd, J=7.4, 2.0 Hz, 1H), 7.74 (d, J=4.8 Hz, 1H), 8.41 (dd, J=4.2, 2.0 Hz, 1H).

Reference Example 12A

(E)-2-({8-[(8-chloro-2-cyclopropylimidazo[1,2-a]pyridin-3-yl)methyl]3-fluorodibenzo[b,e]oxepin-11(6H)-ylidene}-2-cyclopropylacetonitrile Using 2-cyclopropyl-2-(8-ethynyl-3-fluorodibenzo[b,e]oxepin-11(6H)-ylidene)acetonitrile (300 mg, 0.95 mmol) obtained in Reference Example 10, and in the same manner as in Reference Example 8B, the title compound (66 mg, 17%) was obtained.

ESIMS m/z: 496 $(M+H)^+$; $^1H$ NMR (270 MHz, $CDCl_3$, δ): 0.86-1.26 (m, 8H), 1.96-2.05 (m, 2H), 4.30-4.42 (m, 2H), 4.73-4.76 (m, 1H), 5.44-5.48 (m, 1H), 6.54-6.67 (m, 4H), 7.06-7.23 (m, 2H), 7.33-7.40 (m, 1H), 7.48-7.55 (m, 2H).

Reference Example 12B

(E)-2-cyclopropyl-2-{3-fluoro-8-[(2-isopropylimidazo[1,2-a]pyridin-3-yl)methyl]dibenzo[b,e]oxepin-11(6H)-ylidene}acetonitrile Using 2-cyclopropyl-2-(8-ethynyl-3-fluorodibenzo[b,e]oxepin-11(6H)-ylidene)acetonitrile (250 mg, 0.793 mmol) obtained in Reference Example 10, and in the same manner as in Reference Example 8B, the title compound (75 mg, 25%) was obtained.

ESIMS m/z: 464 $(M+H)^+$; $^1H$ NMR (270 MHz, $CDCl_3$, δ): 0.84-1.06 (m, 4H), 1.39-1.43 (m, 6H), 1.92-2.05 (m, 1H), 3.14-3.22 (m, 1H), 4.29-4.31 (m, 2H), 4.71-4.75 (m, 1H), 5.43-5.49 (m, 1H), 6.53-6.69 (m, 4H), 7.03-7.19 (m, 3H), 7.34-7.39 (m, 1H), 7.60-7.64 (m, 2H).

Reference Example 12C

(E)-2-cyclopropyl-2-{8-[(2-cyclopropylimidazo[1,2-a]pyridin-3-yl)methyl]-3-fluorodibenzo[b,e]oxepin-11(6H)-ylidene}acetonitrile Using 2-cyclopropyl-2-(8-ethynyl-3-fluorodibenzo[b,e]oxepin-11(6H)-ylidene)acetonitrile (300 mg, 0.951 mmol)

obtained in Reference Example 10, and in the same manner as in Reference Example 8B, the title compound (51 mg, 14%) was obtained.

ESIMS m/z: 462 $(M+H)^+$; $^1$H NMR (270 MHz, $CDCl_3$, δ): 0.69-1.28 (m, 8H), 1.97-2.05 (m, 2H), 4.35-4.37 (m, 2H), 4.74-4.80 (m, 1H), 5.44-5.50 (m, 1H), 6.49-6.69 (m, 3H), 7.06-7.25 (m, 3H), 7.31-7.45 (m, 2H), 7.51-7.55 (m, 1H), 7.61-7.65 (m, 1H).

Reference Example 12D

(E)-2-cyclopropyl-2-{3-fluoro-8-[(2-(methoxymethyl)imidazo[1,2-a]pyridin-3-yl)methyl]dibenzo[b,e]oxepin-11(6H)-ylidene}acetonitrile

[step 1] Using 3-iodo-2-methoxymethylimidazo[1,2-a]pyridine (700 mg, 2.43 mmol) obtained in Reference Example 8F, step 3 and (E)-2-cyclopropyl-2-(3-fluoro-8-formyldibenzo[b,e]oxepin-11(6H)-ylidene)acetonitrile (388 mg, 1.22 mmol) obtained in Reference Example 7, and in the same manner as in Reference Example 8F, step 4, (E)-2-cyclopropyl-2-{3-fluoro-8-[hydroxy(2-(methoxymethyl)imidazo[1,2-a]pyridin-3-yl)methyl]dibenzo[b,e]oxepin-11(6H)-ylidene}acetonitrile (360 mg, 62%) was obtained.

ESIMS m/z: 482 $(M+H)^+$; $^1$H NMR (270 MHz, $CDCl_3$, δ): 0.89-1.14 (m, 4H), 1.97-2.01 (m, 1H), 3.42 (s, 3H), 4.53-4.72 (m, 2H), 4.79-4.82 (m, 1H), 5.48-5.51 (m, 1H), 6.39-6.71 (m, 4H), 7.15-7.25 (m, 1H), 7.34-7.44 (m, 4H), 7.57-7.59 (m, 1H), 7.92-7.98 (m, 1H).

[step 2] Using (E)-2-cyclopropyl-2-(3-fluoro-8-{hydroxy[2-(methoxymethyl)imidazo[1,2-a]pyridin-3-yl]methyl}dibenzo[b,e]oxepin-11(6H)-ylidene)acetonitrile (114 mg, 0.24 mmol) obtained in step 1, and in the same manner as in Reference Example 8F, step 5, the title compound (75 mg, 68%) was obtained.

ESIMS m/z: 466 $(M+H)^+$; $^1$H NMR (270 MHz, $CDCl_3$, δ): 0.86-1.30 (m, 4H), 1.91-2.00 (m, 1H), 3.47 (s, 3H), 4.31-4.37 (m, 2H), 4.66-4.74 (m, 3H), 5.38-5.46 (m, 1H), 6.529-6.77 (m, 3H), 7.10-7.36 (m, 5H), 7.55-7.69 (m, 2H).

Reference Example 12E

(E)-2-{8-[(8-chloro-2-(methoxymethyl)imidazo[1,2-a]pyridin-3-yl)methyl]-3-fluorodibenzo[b,e]oxepin-11(6H)-ylidene}-2-cyclopropylacetonitrile

[step 1] Using 8-chloro-3-iodo-2-methoxymethylimidazo[1,2-a]pyridine (700 mg, 2.17 mmol) obtained in Reference Example 8K, step 3 and (E)-2-cyclopropyl-2-(3-fluoro-8-formyldibenzo[b,e]oxepin-11(6H)-ylidene)acetonitrile (347 mg, 1.09 mmol) obtained in Reference Example 7, and in the same manner as in Reference Example 8F, step 4, (E)-2-{8-[(8-chloro-2-(methoxymethyl)imidazo[1,2-a]pyridin-3-yl)(hydroxy)methyl]-3-fluorodibenzo[b,e]oxepin-11(6H)-ylidene}-2-cyclopropylacetonitrile (470 mg, 84%) was obtained.

ESIMS m/z: 516 $(M+H)^+$; $^1$H NMR (270 MHz, $CDCl_3$, δ): 0.71-1.10 (m, 4H), 1.89-2.05 (m, 1H), 3.39 (s, 3H), 4.55-4.72 (m, 2H), 4.79-4.82 (m, 1H), 5.47-5.54 (m, 1H), 6.41-6.43 (m, 1H), 6.54-6.74 (m, 3H), 7.23-7.25 (m, 2H), 7.34-7.63 (m, 3H), 7.89-8.14 (m, 1H).

[step 2] Using (E)-2-{8-[(8-chloro-2-(methoxymethyl)imidazo[1,2-a]pyridin-3-yl)(hydroxy)methyl]-3-fluorodibenzo[b,e]oxepin-11(6H)-ylidene}-2-cyclopropylacetonitrile (269 mg, 0.52 mmol) obtained in step 1, and in the same manner as in Reference Example 8F, step 5, the title compound (39 mg, 15%) was obtained.

ESIMS m/z: 500 $(M+H)^+$; $^1$H NMR (270 MHz, $CDCl_3$, δ): 0.85-1.09 (m, 4H), 1.91-2.05 (m, 1H), 3.45 (s, 3H), 4.31-4.47 (m, 2H), 4.71-4.75 (m, 3H), 5.45 (d, J=12.8 Hz, 1H), 6.53-6.68 (m, 3H), 7.09-7.10 (m, 1H), 7.20-7.27 (m, 2H), 7.32-7.39 (m, 2H), 7.61-7.64 (m, 1H).

Reference Example 12F

(E)-2-{8-[(7-chloro-2-methylimidazo[1,2-a]pyridin-3-yl)methyl]-3-fluorodibenzo[b,e]oxepin-11(6H)-ylidene}-2-cyclopropylacetonitrile

[step 1] Using 7-chloro-3-iodo-2-methylimidazo[1,2-a]pyridine (700 mg, 2.39 mmol) obtained in Reference Example 10J, step 2 and (E)-2-cyclopropyl-2-(3-fluoro-8-formyldibenzo[b,e]oxepin-11(6H)-ylidene)acetonitrile (382 mg, 1.20 mmol) obtained in Reference Example 7, and in the same manner as in Reference Example 8F, step 4, (E)-2-{8-[(7-chloro-2-methylimidazo[1,2-a]pyridin-3-yl)(hydroxy)methyl]-3-fluorodibenzo[b,e]oxepin-11(6H)-ylidene}-2-cyclopropylacetonitrile (550 mg, 95%) was obtained.

ESIMS m/z: 486 $(M+H)^+$; $^1$H NMR (270 MHz, $CDCl_3$, δ): 0.85-1.04 (m, 4H), 1.92-2.02 (m, 1H), 2.52 (s, 1.5H), 2.57 (s, 1.5H), 4.78-4.84 (m, 1H), 5.45-5.53 (m, 1H), 6.38 (br s, 1H), 6.53-6.66 (m, 2H), 6.84-6.85 (m, 1H), 7.27-7.35 (m, 2H), 7.38-7.42 (m, 2H), 7.50-7.53 (m, 1H), 8.10-8.14 (m, 1H).

[step 2] Using (E)-2-{8-[(7-chloro-2-methylimidazo[1,2-a]pyridin-3-yl)(hydroxy)methyl]-3-fluorodibenzo[b,e]oxepin-11(6H)-ylidene}-2-cyclopropylacetonitrile (550 mg, 1.13 mmol) obtained in step 1, and in the same manner as in Reference Example 8F, step 5, the title compound (424 mg, 80%) was obtained.

ESIMS m/z: 470 $(M+H)^+$; $^1$H NMR (270 MHz, $CDCl_3$, δ): 0.81-1.08 (m, 4H), 1.94-2.02 (m, 1H), 2.50 (s, 3H), 4.19-4.30 (m, 2H), 4.76 (d, J=12.7 Hz, 1H), 5.46 (d, J=12.7 Hz, 1H), 7.00-7.10 (m, 1H), 7.15-7.17 (m, 1H), 7.32-7.40 (m, 2H), 7.52-7.58 (m, 3H), 7.86-8.18 (m, 2H).

Reference Example 12G

(E)-2-{8-[(7-chloro-2-(methoxymethyl)imidazo[1,2-a]pyridin-3-yl)methyl]-3-fluorodibenzo[b,e]oxepin-11(6H)-ylidene}-2-cyclopropylacetonitrile

[step 1] Using 7-chloro-3-iodo-2-methoxymethylimidazo[1,2-a]pyridine (700 mg, 2.17 mmol) obtained in Reference Example 10E, step 3 and (E)-2-cyclopropyl-2-(3-fluoro-8-formyldibenzo[b,e]oxepin-11(6H)-ylidene)acetonitrile (347 mg, 1.09 mmol) obtained in Reference Example 7, and in the same manner as in Reference Example 8F, step 4, (E)-2-{8-[(7-chloro-2-(methoxymethyl)imidazo[1,2-a]pyridin-3-yl)(hydroxy)methyl]-3-fluorodibenzo[b,e]oxepin-11(6H)-ylidene}-2-cyclopropylacetonitrile (203 mg, 36%) was obtained.

ESIMS m/z: 516 $(M+H)^+$; $^1$H NMR (270 MHz, $CDCl_3$, δ): 0.84-1.09 (m, 4H), 1.93-2.03 (m, 1H), 3.44-3.51 (m, 3H), 4.69-5.01 (m, 3H), 5.43-5.52 (m, 1H), 6.52-6.66 (m, 3H), 6.99-7.02 (m, 1H), 7.30-7.64 (m, 4H), 7.83-7.93 (m, 1H), 8.27-8.30 (m, 1H).

[step 2] Using (E)-2-(8-{[7-chloro-2-(methoxymethyl)imidazo[1,2-a]pyridin-3-yl](hydroxy)methyl}-3-fluorodibenzo[b,e]oxepin-11(6H)-ylidene)-2-cyclopropylacetonitrile (200 mg, 0.39 mmol) obtained in step 1, and in the same manner as in Reference Example 8F, step 5, the title compound (81 mg, 42%) was obtained.

ESIMS m/z: 500 $(M+H)^+$; $^1$H NMR (270 MHz, $CDCl_3$, δ): 0.86-1.08 (m, 4H), 1.93-2.02 (m, 1H), 3.52 (s, 3H), 4.07-4.13

(m, 2H), 4.28-4.50 (m, 2H), 4.70-4.77 (m, 1H), 5.41-5.47 (m, 1H), 6.52-6.67 (m, 2H), 6.98-7.16 (m, 2H), 7.28-7.44 (m, 3H), 7.80-7.88 (m, 1H), 8.31-8.32 (m, 1H).

Reference Example 12H

(E)-2-cyclopropyl-2-(3-fluoro-8-{[2-(methoxy-$d_3$methyl)imidazo[1,2-a]pyridin-3-yl]methyl}dibenzo[b,e]oxepin-11(6H)-ylidene)acetonitrile

[step 1] Using 3-iodo-2-(methoxy-$d_3$-methyl)imidazo[1,2-a]pyridine (700 mg, 2.41 mmol) obtained in Reference Example 8G, step 2 and (E)-2-cyclopropyl-2-(3-fluoro-8-formyldibenzo[b,e]oxepin-11(6H)-ylidene)acetonitrile (384 mg, 1.20 mmol) obtained in Reference Example 7, and in the same manner as in Reference Example 8F, step 4, (E)-2-cyclopropyl-2-(8-hydroxy{[2-(methoxy-$d_3$methyl)imidazo[1,2-a]pyridin-3-yl]methyl}-3-fluorodibenzo[b,e]oxepin-11(6H)-ylidene)acetonitrile (580 mg, 99%) was obtained.

ESIMS m/z: 485 $(M+H)^+$; $^1$H NMR (270 MHz, $CDCl_3$, δ): 0.86-1.08 (m, 4H), 1.95-2.04 (m, 1H), 4.45-4.67 (m, 2H), 4.72-4.82 (m, 1H), 5.47-5.51 (m, 1H), 6.38-6.41 (m, 1H), 6.53-6.70 (m, 2H), 6.75-6.79 (m, 1H), 7.13-7.17 (m, 1H), 7.34-7.47 (m, 2H), 7.53-7.59 (m, 2H), 7.95-8.00 (m, 2H).

[step 2] Using (E)-2-cyclopropyl-2-(8-hydroxy{[2-(methoxy-$d_3$ methyl)imidazo[1,2-a]pyridin-3-yl]methyl}-3-fluorodibenzo[b,e]oxepin-11(6H)-ylidene)acetonitrile (200 mg, 0.39 mmol) obtained in step 1, and in the same manner as in Reference Example 8F, step 5, the title compound (81 mg, 42%) was obtained.

ESIMS m/z: 469 $(M+H)^+$; $^1$H NMR (270 MHz, $CDCl_3$, δ): 0.83-1.26 (m, 4H), 1.93-2.05 (m, 1H), 4.31-4.42 (m, 2H), 4.65-4.79 (m, 3H), 5.44-5.47 (m, 1H), 6.53-6.57 (m, 3H), 7.10-7.17 (m, 3H), 7.33-7.38 (m, 2H), 7.59-7.69 (m, 2H).

Reference Example 13A

(E)-2-{3-fluoro-8-[(2-methyl-1H-indol-3-yl)methyl]dibenzo[b,e]oxepin-11(6H)-ylidene}propanenitrile Commercially available 2-methyl-1H-indole (100 mg, 0.76 mmol) and (E)-2-(3-fluoro-8-formyldibenzo[b,e]oxepin-11(6H)-ylidene)propanenitrile (246 mg, 0.84 mmol) obtained in Reference Example 5 were dissolved in methylene chloride (3.8 mL), TFA (88 mL, 1.1 mmol), and triethylsilane (365 mL, 2.29 mmol) were added at 0° C., and the mixture was stirred at room temperature overnight. The reaction mixture was adjusted to pH=8 with 2 mol/L sodium hydroxide solution, extracted with chloroform, and the extract was dried over sodium sulfate and filtered. The filtrate was concentrated under reduced pressure and the obtained residue was purified by silica gel column chromatography (hexane/ethyl acetate=1/1 v/v) to give the target compound (107 mg, 34%).

ESIMS m/z: 409 $(M+H)^+$; $^1$H NMR (270 MHz, $CDCl_3$, δ): 2.22 (s, 3H), 2.38 (s, 3H), 4.08 (s, 2H), 4.75 (d, J=12.7 Hz, 1H), 5.40 (d, J=12.7 Hz, 1H), 6.52-6.55 (m, 1H), 6.59-6.64 (m, 1H), 6.99-7.05 (m, 2H), 7.09-7.16 (m, 2H), 7.21-7.39 (m, 4H), 7.83 (br s, 1H).

Reference Example 13B

(E)-2-{3-fluoro-8-[(2-propyl-1H-indol-3-yl)methyl]dibenzo[b,e]oxepin-11(6H)-ylidene}propanenitrile

[step 1] Commercially available 2-nitrophenol (1.0 g, 7.2 mmol) was dissolved in methylene chloride (36 mL), and the solution was cooled to 0° C. Triethylamine (1.2 mL, 8.6 mmol) and trifluoromethanesulfonic anhydride (1.2 mL, 8.6 mmol) were added, and the mixture was stirred at 0° C. for 30 min. The reaction was discontinued with aqueous saturated ammonium chloride, and the mixture was extracted with chloroform, and the extract was dried over sodium sulfate. Filtration and concentration under reduced pressure gave 2-nitrophenyl trifluoromethanesulfonate (1.71 g, 88%).

ESIMS m/z: 272 $(M+H)^+$; $^1$H NMR (270 MHz, $CDCl_3$, δ): 7.39-7.52 (m, 1H), 7.58-7.62 (m, 1H), 7.75-7.79 (m, 1H), 8.17-8.20 (m, 1H).

[step 2] Using 2-nitrophenyl trifluoromethanesulfonate (3.0 g, 11 mmol) obtained in step 1 and 1-pentyne (2.15 mL, 22 mmol), and in the same manner as in Reference Example 10, step 1,1-nitro-2-(pent-1-ynyl)benzene (2.01 g, 96%) was obtained.

ESIMS m/z: 190 $(M+H)^+$; $^1$H NMR (270 MHz, $CDCl_3$, δ): 1.08 (t, J=7.4 Hz, 3H), 1.60-1.74 (m, 2H), 2.46 (t, J=7.2 Hz, 2H), 7.36-7.42 (m, 1H), 7.49-7.60 (m, 2H), 7.95-7.98 (m, 1H).

[step 3]1-Nitro-2-(pent-1-ynyl)benzene (1.0 g, 5.3 mmol) obtained in step 2 was dissolved in pyrrolidine (8.68 mL, 106 mmol), and the mixture was stirred at room temperature for 2 hr. The mixture was cooled to 0° C., and the reaction was discontinued with 1 mmol/L hydrochloric acid. The reaction mixture was extracted with chloroform, the extract was dried over sodium sulfate, filtered, and the filtrate was concentrated under reduced pressure to give 1-(2-nitrophenyl)pentan-2-one (0.61 g, 56%).

ESIMS m/z: 208 $(M+H)^+$; $^1$H NMR (270 MHz, $CDCl_3$, δ): 0.96 (t, J=7.3 Hz, 3H), 1.64-1.72 (m, 2H), 2.59 (t, J=7.3 Hz, 2H), 4.10 (s, 2H), 7.26-7.30 (m, 1H), 7.44-7.47 (m, 1H), 7.57-7.61 (m, 1H), 8.11 (d, J=9.8 Hz, 1H).

[step 4]1-(2-Nitrophenyl)pentan-2-one (0.31 g, 1.5 mmol) obtained in step 3 was dissolved in ethanol (3.0 mL), 10% palladium carbon (0.032 mg, 0.30 mmol) was added, and the mixture was stirred at room temperature overnight under a hydrogen atmosphere. The reaction solution was filtered through celite, and the filtrate was concentrated under reduced pressure. The obtained reaction residue was purified by silica gel column chromatography (hexane/ethyl acetate=10/1 v/v) to give 2-propyl-1H-indole (100 mg, 42%).

ESIMS m/z: 160 $(M+H)^+$; $^1$H NMR (270 MHz, $CDCl_3$, δ): 1.03 (t, J=7.3 Hz, 3H), 1.71-1.80 (m, 2H), 2.74 (t, J=7.3 Hz, 2H), 6.21 (br s, 1H), 7.04-7.12 (m, 2H), 7.30 (d, J=7.8 Hz, 1H), 7.52 (d, J=7.8 Hz, 1H), 7.86 (br s, 1H).

[step 5] Using 2-propyl-1H-indole (100 mg, 0.64 mmol) obtained in step 4 and (E)-2-(3-fluoro-8-formyldibenzo[b,e]oxepin-11(6H)-ylidene)propanenitrile (153 mg, 0.52 mmol) obtained in Reference Example 5, and in the same manner as in Reference Example 13A, the target compound (125 mg, 55%) was obtained.

ESIMS m/z: 437 $(M+H)^+$; $^1$H NMR (270 MHz, $CDCl_3$, δ): 0.94 (t, J=7.5 Hz, 3H), 1.61-1.70 (m, 2H), 2.22 (s, 3H), 2.69-2.72 (m, 2H), 4.09 (s, 2H), 4.74 (d, J=12.7 Hz, 1H), 5.40 (d, J=12.7 Hz, 1H), 6.52-6.55 (m, 1H), 6.59-6.64 (m, 1H), 6.99-7.04 (m, 2H), 7.06-7.10 (m, 2H), 7.23-7.37 (m, 4H), 7.85 (br s, 1H).

Reference Example 13C

(E)-2-{8-[(4,5-dichloro-2-isopropyl-1H-imidazol-1-yl)methyl]-3-fluorodibenzo[b,e]oxepin-11(6H)-ylidene}propanenitrile

[step 1]2-Isopropyl-1H-imidazole (600 mg, 5.45 mmol) was dissolved in 1,4-dioxane (6 mL)-2-methoxyethanol (6 mL), N-chlorosuccinimide (1.0 g, 7.51 mmol) was added, and the mixture was heated at room temperature for 30 min. N-chlorosuccinimide (450 mg, 3.38 mmol) was further added, and the mixture was stirred at room temperature for 1 hr. Water was added to the mixture, and the precipitated crystals were collected by suction filtration to give 4,5-dichloro-2-isopropyl-1H-imidazole (477 mg, 49%).

ESIMS m/z: 179 $(M+H)^+$; $^1H$ NMR (270 MHz, $CDCl_3$, δ): 1.32 (d, J=7.2 Hz, 6H), 2.89-3.11 (m, 1H).

[step 2] Using 4,5-dichloro-2-isopropyl-1H-imidazole (68 mg, 0.381 mmol) obtained in step 1 and (E)-2-[8-(bromomethyl)-3-fluorodibenzo[b,e]oxepin-11(6H)-ylidene]propanenitrile (130 mg, 0.363 mmol) obtained in Reference Example 1, and in the same manner as in Reference Example 1A, the title compound (150 mg, 91%) was obtained.

ESIMS m/z: 456 $(M+H)^+$; $^1H$ NMR (270 MHz, $CDCl_3$, δ): 1.12-1.31 (m, 6H), 2.24 (s, 3H), 2.77-2.93 (m, 1H), 4.80 (d, J=12.8 Hz, 1H), 5.06-5.17 (m, 2H), 5.43 (d, J=12.8 Hz, 1H), 6.48-6.74 (m, 2H), 6.94-7.17 (m, 3H), 7.40-7.53 (m, 1H).

Reference Example 13D (E)-2-(3-fluoro-8-{[2-(methoxymethyl)-1H-thieno[3,4-d]imidazol-1-yl]methyl}dibenzo[b,e]oxepin-11(6H)-ylidene)propanenitrile

[step 1] 3,4-Diaminothiophene dihydrochloride (300 mg, 1.60 mmol) was suspended in ethanol (12 mL), triethylamine (0.45 mL, 3.21 mmol) and ethyl 2-methoxyacetimidate monohydrochloride (Journal of Medicinal Chemistry, 1991, vol. 34, p 2468; 906 mg, 4.01 mmol) were added, and the mixture was stirred at room temperature for 70 hr. To the mixture was added saturated aqueous sodium hydrogen carbonate, and the mixture was extracted 3 times with chloroform. The combined organic layers were dried over anhydrous magnesium sulfate, and concentrated under reduced pressure. The residue was purified by silica gel column chromatography (hexane/ethyl acetate=100/0 v/v-0/100 v/v) to give 2-(methoxymethyl)-1H-thieno[3,4-d]imidazole (156 mg, 58%).

ESIMS m/z: 169 $(M+H)^+$; $^1H$ NMR (300 MHz, $CDCl_3$, δ): 3.49 (s, 3H), 4.64 (s, 2H), 6.33-7.16 (m, 2H), 8.89 (br s, 1H).

[step 2] Using 2-(methoxymethyl)-1H-thieno[3,4-d]imidazole (65 mg, 0.39 mmol) obtained in step 1 and (E)-2-[8-(bromomethyl)-3-fluorodibenzo[b,e]oxepin-11(6H)-ylidene]propanenitrile (141 mg, 0.39 mmol) obtained in Reference Example 1, and in the same manner as in Reference Example 1A, the title compound (167 mg, 97%) was obtained.

ESIMS m/z: 446 $(M+H)^+$; $^1H$ NMR (300 MHz, $CDCl_3$, δ): 2.24 (s, 3H), 3.39 (s, 3H), 4.60 (s, 2H), 4.79 (d, J=12.8 Hz, 1H), 5.19-5.35 (m, 2H), 5.43 (d, J=12.8 Hz, 1H), 6.32 (d, J=2.6 Hz, 1H), 6.57 (dd, J=10.3, 2.6 Hz, 1H), 6.61-6.69 (m, 1H), 7.04 (dd, J=8.8, 6.6 Hz, 1H), 7.10 (d, J=2.6 Hz, 1H), 7.17-7.22 (m, 1H), 7.27-7.33 (m, 1H), 7.45 (d, J=7.7 Hz, 1H).

Reference Example 13E (E)-2-{8-[(2-cyclopropyl-1H-thieno[3,4-d]imidazol-1-yl)methyl]-3-fluorodibenzo[b,e]oxepin-11(6H)-ylidene}propanenitrile

[step 1] 3,4-Diaminothiophene dihydrochloride (300 mg, 1.60 mmol) was suspended in ethanol (12 mL), triethylamine (0.45 mL, 3.21 mmol) and ethyl cyclopropanecarboimidate monohydrochloride (WO200970485; 528 mg, 3.53 mmol) were added, and the mixture was stirred at room temperature for 70 hr. To the mixture was added saturated aqueous sodium hydrogen carbonate, and the mixture was extracted 3 times with chloroform. The combined organic layers were dried over anhydrous magnesium sulfate, and concentrated under reduced pressure. The residue was purified by silica gel column chromatography (hexane/ethyl acetate=100/0 v/v-0/100 v/v) to give 2-cyclopropyl-1H-thieno[3,4-d]imidazole (84 mg, 32%).

ESIMS m/z: 165 $(M+H)^+$; $^1H$ NMR (300 MHz, DMSO-$d_6$, δ): 0.94-1.08 (m, 4H), 1.87-2.00 (m, 1H), 6.61-6.91 (m, 2H), 11.46 (br s, 1H).

[step 2] Using 2-cyclopropyl-1H-thieno[3,4-d]imidazole (65 mg, 0.40 mmol) obtained in step 1 and (E)-2-[8-(bromomethyl)-3-fluorodibenzo[b,e]oxepin-11(6H)-ylidene]propanenitrile (145 mg, 0.40 mmol) obtained in Reference Example 1, and in the same manner as in Reference Example 1A, the title compound (166 mg, 95%) was obtained.

ESIMS m/z: 442 $(M+H)^+$; $^1H$ NMR (300 MHz, $CDCl_3$, δ): 1.00-1.09 (m, 2H), 1.18-1.26 (m, 2H), 1.73-1.84 (m, 1H), 2.25 (s, 3H), 4.80 (d, J=12.8 Hz, 1H), 5.19-5.35 (m, 2H), 5.43 (d, J=12.8 Hz, 1H), 6.29 (d, J=2.6 Hz, 1H), 6.57 (dd, J=9.9, 2.6 Hz, 1H), 6.61-6.69 (m, 1H), 6.94 (d, J=2.6 Hz, 1H), 7.04 (d, J=8.8, 6.6 Hz, 1H), 7.16-7.19 (m, 1H), 7.27-7.32 (m, 1H), 7.47 (d, J=8.1 Hz, 1H).

Reference Example 13F (E)-2-{8-[(2-ethyl-4-phenyl-1H-imidazol-1-yl)methyl]-3-fluorodibenzo[b,e]oxepin-11(6H)-ylidene}propanenitrile Using 2-ethyl-4-phenyl-1H-imidazole (Tetrahedron Letters, 1967, p 265, 47 mg, 0.273 mmol) and (E)-2-[8-(bromomethyl)-3-fluorodibenzo[b,e]oxepin-11(6H)-ylidene]propanenitrile (90 mg, 0.273 mmol) obtained in Reference Example 1, and in the same manner as in Reference Example 1A, the title compound (114 mg, 92%) was obtained.

ESIMS m/z: 450 $(M+H)^+$; $^1H$ NMR (270 MHz, $CDCl_3$, δ): 1.32 (t, J=7.6 Hz, 3H), 2.24 (s, 3H), 2.70 (q, J=7.6 Hz, 2H), 4.79 (d, J=12.8 Hz, 1H), 5.14 (s, 2H), 5.43 (d, J=12.8 Hz, 1H), 6.52-6.61 (m, 1H), 6.61-6.73 (m, 1H), 7.00-7.10 (m, 2H), 7.11 (s, 1H), 7.14-7.30 (m, 2H), 7.30-7.39 (m, 2H), 7.38-7.51 (m, 1H), 7.73-7.80 (m, 2H).

Reference Example 13G (E)-2-(8-{[4-(azetidin-1-yl)-2-methyl-6-propylpyrimidin-5-yl]methyl}-3-fluorodibenzo[b,e]oxepin-11(6H)-ylidene)propanenitrile

[step 1] Ethyl 3-oxohexanoate (883 mg, 5.58 mmol) was dissolved in THF (9 mL), sodium hydride (60% w/w, 190 mg, 4.75 mmol) was added, and the mixture was stirred at room temperature for 30 min. To the mixture was added dropwise a solution (9 mL) of (E)-2-[8-(bromomethyl)-3-fluorodibenzo[b,e]oxepin-11(6H)-ylidene]propanenitrile (1.0 g, 2.79 mmol) obtained in Reference Example 1 in tetrahydrofuran, and the mixture was stirred at room temperature overnight. Water was added to the mixture, and the mixture was extracted 3 times with ethyl acetate. The combined organic layers were dried over anhydrous magnesium sulfate, and concentrated under reduced pressure. The residue was purified by silica gel column chromatography (hexane/ethyl acetate=4/1 v/v) to give (E)-ethyl 2-{[11-(1-cyanoethylidene)-3-fluoro-6,11-dihydrodibenzo[b,e]oxepin-8-yl]methyl}-3-oxohexanoate (1.19 g, 98%).

ESIMS m/z: 436 $(M+H)^+$; $^1H$ NMR (270 MHz, $CDCl_3$, δ): 0.75-0.89 (m, 3H), 1.18 (t, J=7.2 Hz, 3H), 1.49-1.62 (m, 2H), 2.16-2.43 (m, 4H), 2.43-2.62 (m, 1H), 3.11-3.22 (m, 2H), 3.70-3.82 (m, 1H), 4.13 (q, J=7.2 Hz, 2H), 4.80 (d, J=12.8 Hz, 1H), 5.44 (d, J=12.8 Hz, 1H), 6.54-6.69 (m, 2H), 6.96-7.08 (m, 1H), 7.17-7.27 (m, 2H), 7.33-7.45 (m, 1H).

[step 2] (E)-ethyl 2-{[11-(1-cyanoethylidene)-3-fluoro-6,11-dihydrodibenzo[b,e]oxepin-8-yl]methyl}-3-oxohexanoate (1.18 g, 2.71 mmol) obtained in step 1 was dissolved in methanol (14 mL), acetimidamide hydrochloride (640 mg, 6.77 mmol) and 28% sodium methoxide methanol solution (1.83 mL, 9.48 mmol) were added, and the mixture was stirred at room temperature for 2 hr. The mixture was concentrated under reduced pressure, methanol was added to the obtained residue, and the precipitated crystals were collected by suction filtration to give (E)-2-{3-fluoro-8-[(2-methyl-6-oxo-4-propyl-1,6-dihydropyrimidin-5-yl)methyl]dibenzo[b,e]oxepin-11(6H)-ylidene}propanenitrile (960 mg, 82%).

ESIMS m/z: 430 $(M+H)^+$; $^1H$ NMR (270 MHz, $CDCl_3$, δ): 0.83-0.98 (m, 3H), 1.43-1.76 (m, 2H), 2.21 (s, 3H), 2.28-2.42 (m, 3H), 2.50-2.59 (m, 2H), 3.90 (s, 2H), 4.81 (d, J=12.8 Hz, 1H), 5.40 (d, J=12.8 Hz, 1H), 6.44-6.70 (m, 2H), 6.95-7.12 (m, 1H), 7.23-7.44 (m, 3H), 12.92 (s, 1H).

[step 3] (E)-2-{3-fluoro-8-[(2-methyl-6-oxo-4-propyl-1,6-dihydropyrimidin-5-yl)methyl]dibenzo[b,e]oxepin-11(6H)-ylidene}propanenitrile (960 mg, 2.23 mmol) obtained in step 2 was dissolved in phosphorus oxychloride (2.5 mL, 26.8 mmol), and the mixture was stirred at 100° C. for 2 hr. The mixture was concentrated under reduced pressure, and the obtained residue was purified by silica gel column chromatography (hexane/ethyl acetate=1/1 v/v) to give (E)-2-{8-[(4-chloro-2-methyl-6-propylpyrimidin-5-yl)methyl]-3-fluorodibenzo[b,e]oxepin-11(6H)-ylidene}propanenitrile (970 mg, 97%).

ESIMS m/z: 448 $(M+H)^+$; $^1H$ NMR (270 MHz, $CDCl_3$, δ): 0.74-0.98 (m, 3H), 1.48-1.77 (m, 2H), 2.24 (s, 3H), 2.59-2.72 (m, 5H), 4.03-4.25 (m, 2H), 4.77 (d, J=12.8 Hz, 1H), 5.42 (d, J=12.8 Hz, 1H), 6.51-6.70 (m, 2H), 6.94-7.10 (m, 2H), 7.13-7.20 (m, 1H), 7.38-7.47 (m, 1H).

[step 4] (E)-2-{8-[(4-chloro-2-methyl-6-propylpyrimidin-5-yl)methyl]-3-fluorodibenzo[b,e]oxepin-11(6H)-ylidene}propanenitrile (140 mg, 3.13 mmol) obtained in step 3 was dissolved in ethanol (3 mL), azetidine (0.148 mL, 2.19 mmol) was added, and the mixture was stirred with heating at 50° C. for 2 hr. The mixture was concentrated under reduced pressure, and the obtained residue was purified by silica gel column chromatography (hexane/ethyl acetate=1/2 v/v) to give the title compound (145 mg, 99%).

ESIMS m/z: 469 $(M+H)^+$; $^1H$ NMR (270 MHz, $CDCl_3$, δ): 0.77-0.97 (m, 3H), 1.49-1.76 (m, 2H), 2.11-2.30 (m, 5H), 2.38-2.58 (m, 5H), 3.79-4.00 (m, 2H), 4.02-4.18 (m, 4H), 4.78 (d, J=12.8 Hz, 1H), 5.42 (d, J=12.8 Hz, 1H), 6.51-6.61 (m, 1H), 6.61-6.72 (m, 1H), 6.97-7.10 (m, 2H), 7.10-7.20 (m, 1H), 7.34-7.46 (m, 1H).

Reference Example 13H

(E)-2-(8-{[4-(dimethylamino)-6-(methoxymethyl)-2-methylpyrimidin-5-yl]methyl}-3-fluorodibenzo[b,e]oxepin-11(6H)-ylidene)propanenitrile

[step 1] Using methyl 4-methoxy-3-oxobutanoate (816 mg, 5.58 mmol) and (E)-2-[8-(bromomethyl)-3-fluorodibenzo[b,e]oxepin-11(6H)-ylidene]propanenitrile (1.0 g, 2.79 mmol) obtained in Reference Example 1, and in the same manner as in Reference Example 13G, step 1, (E)-methyl 2-{[11-(1-cyanoethylidene)-3-fluoro-6,11-dihydrodibenzo[b,e]oxepin-8-yl]methyl}-4-methoxy-3-oxobutanoate (977 mg, 83%) was obtained.

ESIMS m/z: 424 $(M+H)^+$; $^1H$ NMR (270 MHz, $CDCl_3$, δ): 2.27 (s, 3H), 3.04-3.43 (m, 5H), 3.71 (s, 3H), 3.83-4.15 (m, 3H), 4.83 (d, J=12.8 Hz, 1H), 5.43 (d, J=12.8 Hz, 1H), 6.40-6.72 (m, 2H), 6.97-7.12 (m, 1H), 7.17-7.48 (m, 3H).

[step 2] Using (E)-methyl 2-{[11-(1-cyanoethylidene)-3-fluoro-6,11-dihydrodibenzo[b,e]oxepin-8-yl]methyl}-4-methoxy-3-oxobutanoate (977 mg, 2.31 mmol) obtained in step 1, and in the same manner as in Reference Example 13G, step 2, (E)-2-(3-fluoro-8-{[4-(methoxymethyl)-2-methyl-6-oxo-1,6-dihydropyrimidin-5-yl]methyl}dibenzo[b,e]oxepin-11(6H)-ylidene)propanenitrile (926 mg, 93%) was obtained.

ESIMS m/z: 432 $(M+H)^+$; $^1H$ NMR (270 MHz, $CDCl_3$, δ): 2.22 (s, 3H), 2.42 (s, 3H), 3.42 (s, 3H), 3.93 (s, 2H), 4.35 (s, 2H), 4.78 (d, J=12.8 Hz, 1H), 5.42 (d, J=12.8 Hz, 1H), 6.46-6.71 (m, 2H), 6.93-7.07 (m, 1H), 7.18-7.45 (m, 3H), 12.66 (s, 1H).

[step 3] Using (E)-2-(3-fluoro-8-{[4-(methoxymethyl)-2-methyl-6-oxo-1,6-dihydropyrimidin-5-yl]methyl}dibenzo[b,e]oxepin-11(6H)-ylidene)propanenitrile (924 mg, 2.14 mmol) obtained in step 2, and in the same manner as in Reference Example 13G, step 3, (E)-2-(8-{[4-chloro-6-(methoxymethyl)-2-methylpyrimidin-5-yl]methyl}-3-fluorodibenzo[b,e]oxepin-11(6H)-ylidene)propanenitrile (487 mg, 51%) was obtained.

ESIMS m/z: 450 $(M+H)^+$; $^1H$ NMR (270 MHz, $CDCl_3$, δ): 2.19-2.27 (m, 3H), 2.73 (s, 3H), 3.38 (s, 3H), 4.25 (s, 2H), 4.45 (s, 2H), 4.78 (d, J=12.8 Hz, 1H), 5.42 (d, J=12.8 Hz, 1H), 6.53-6.59 (m, 1H), 6.60-6.67 (m, 1H), 6.99-7.05 (m, 1H), 7.06-7.09 (m, 1H), 7.15-7.20 (m, 1H), 7.32-7.42 (m, 1H).

[step 4] Using (E)-2-(8-{[4-chloro-6-(methoxymethyl)-2-methylpyrimidin-5-yl]methyl}-3-fluorodibenzo[b,e]oxepin-11(6H)-ylidene)propanenitrile (164 mg, 0.365 mmol) obtained in step 3 and 2 mol/L dimethylamine methanol solution (1.28 mL, 2.55 mmol), and in the same manner as in Reference Example 13G, step 4, the title compound (96 mg, 56%) was obtained.

ESIMS m/z: 459 $(M+H)^+$; $^1H$ NMR (270 MHz, $CDCl_3$, δ): 2.24 (s, 3H), 2.57 (s, 3H), 2.92 (s, 6H), 3.30 (s, 3H), 4.13 (s, 2H), 4.23 (s, 2H), 4.77 (d, J=12.8 Hz, 1H), 5.43 (d, J=12.8 Hz, 1H), 6.54-6.60 (m, 1H), 6.61-6.69 (m, 1H), 6.98-7.08 (m, 2H), 7.12-7.19 (m, 1H), 7.36-7.41 (m, 1H).

Reference Example 14A

(E)-2-{8-[(2-cyclopropyl-8-methylimidazo[1,2-a]pyrazin-3-yl)methyl]-3-fluorodibenzo[b,e]oxepin-11(6H)-ylidene}propanenitrile

[step 1] 3-Methylpyrazin-2-amine (16 g, 147 mmol) was dissolved in 1,2-dimethoxyethane (122 mL) and THF (61 mL), 2-bromo-1-cyclopropylethanone (36 g, 220 mmol) was added, and the mixture was stirred at room temperature for 70 hr. Saturated aqueous sodium hydrogen carbonate solution was added to the mixture, and the mixture was extracted 3 times with chloroform. The combined organic layers were dried over anhydrous magnesium sulfate, and concentrated under reduced pressure. The residue was purified by silica gel column chromatography (chloroform/methanol=100/0 v/v-85/15 v/v) to give 2-cyclopropyl-8-methylimidazo[1,2-a]pyrazine (11g, 43%).

ESIMS m/z: 174 $(M+H)^+$; $^1$H NMR (300 MHz, $CDCl_3$, δ): 0.87-0.95 (m, 2H), 0.96-1.08 (m, 2H), 2.04-2.17 (m, 1H), 2.84 (s, 3H), 7.34 (s, 1H), 7.67 (d, J=4.4 Hz, 1H), 7.82 (d, J=4.4 Hz, 1H).

[step 2] Using 2-cyclopropyl-8-methylimidazo[1,2-a]pyrazine (11 g, 66 mmol) obtained in step 1, and in the same manner as in Reference Example 8A, step 2,2-cyclopropyl-3-iodo-8-methylimidazo[1,2-a]pyrazine (17g, 85%) was obtained.

ESIMS m/z: 300 $(M+H)^+$; $^1$H NMR (300 MHz, $CDCl_3$, δ): 1.00-1.18 (m, 4H), 2.02-2.14 (m, 1H), 2.82 (s, 3H), 7.79 (d, J=4.8 Hz, 1H), 7.84 (d, J=4.8 Hz, 1H).

[step 3]2-Cyclopropyl-3-iodo-8-methylimidazo[1,2-a]pyrazine (14 g, 45 mmol) obtained in step 2 was suspended in THF (100 mL), and the suspension was cooled to −20±10° C. in a dry ice-acetone bath. A 1.3 mol/L isopropylmagnesium chloride lithium chloride complex THF solution (39 mL, 51 mmol) was added dropwise, and the mixture was stirred at −10±10° C. for 1 hr. A solution (40 mL) of (E)-2-(3-fluoro-8-formyldibenzo[b,e]oxepin-11(6H)-ylidene)propanenitrile (8.3 g, 28 mmol) obtained in Reference Example 5 in THF was added, and the mixture was stirred at −10±10° C. for 1.5 hr. To the mixture was added aqueous ammonium chloride solution, and the mixture was extracted 3 times with ethyl acetate. The combined organic layers were dried over anhydrous magnesium sulfate, and concentrated under reduced pressure. The residue was purified by silica gel column chromatography (chloroform/methanol=100/0 v/v-85/15 v/v) to give (E)-2-{8-[(2-cyclopropyl-8-methylimidazo[1,2-a]pyrazin-3-yl)(hydroxy)methyl]-3-fluorodibenzo[b,e]oxepin-11(6H)-ylidene}propanenitrile (21g, quantitative).

ESIMS m/z: 467 $(M+H)^+$; $^1$H NMR (400 MHz, $CDCl_3$, δ): 0.86-1.06 (m, 3H), 1.16-1.27 (m, 1H), 1.75-1.92 (m, 1H), 2.23 (s, 3H), 2.72-2.81 (m, 3H), 3.76-3.93 (m, 1H), 4.75-4.89 (m, 1H), 5.45 (d, J=12.7 Hz, 1H), 6.42 (d, J=9.8 Hz, 1H), 6.50-6.61 (m, 1H), 6.61-6.68 (m, 1H), 7.03 (dd, J=8.8, 6.8 Hz, 1H), 7.30-7.37 (m, 1H), 7.39-7.53 (m, 3H), 7.72-7.29 (m, 1H).

[step 4] (E)-2-{8-[(2-cyclopropyl-8-methylimidazo[1,2-a]pyrazin-3-yl)(hydroxy)methyl]-3-fluorodibenzo[b,e]oxepin-11(6H)-ylidene}propanenitrile (18 g, 39 mmol) obtained in step 3 was dissolved in trifluoroacetic acid (181 mL, 2.3 mol), triethylsilane (31 mL, 0.19 mol) was added, and the mixture was stirred with heating at 60° C. for 1 hr. The mixture was concentrated under reduced pressure, saturated aqueous sodium hydrogen carbonate solution (100 mL) was added to the obtained residue, and the mixture was extracted 3 times with a mixed solvent of chloroform-methanol. The combined organic layers were dried over anhydrous magnesium sulfate, and concentrated under reduced pressure. To the obtained residue was added isopropylalcohol (133 mL), and the mixture was stirred at room temperature for 4 hr and further for 1 hr under ice-cooling. The precipitated crystals were collected by suction filtration to give the title compound (13g, 72%).

ESIMS m/z: 451 $(M+H)^+$; $^1$H NMR (300 MHz, $CDCl_3$, δ): 0.97-1.08 (m, 2H), 1.08-1.18 (m, 2H), 1.97-2.09 (m, 1H), 2.23 (s, 3H), 2.83 (s, 3H), 4.27-4.44 (m, 2H), 4.75 (d, J=12.8 Hz, 1H), 5.41 (d, J=12.8 Hz, 1H), 6.55 (dd, J=9.9, 2.6 Hz, 1H), 6.60-6.68 (m, 1H), 7.03 (dd, J=8.6, 6.4 Hz, 1H), 7.05-7.09 (m, 1H), 7.18-7.24 (m, 1H), 7.41 (d, J=7.7 Hz, 1H), 7.46 (d, J=4.8 Hz, 1H), 7.61 (d, J=4.8 Hz, 1H).

Reference Example 14B

(E)-3-{[11(6H)-(1-cyanoethylidene)-3-fluorodibenzo[b,e]oxepin-8-yl]methyl}-2-cyclopropylimidazo[1,2-a]pyridine-7-carboxamide

[step 1]4-Bromopyridin-2-amine (10 g, 58 mmol) was dissolved in ethanol (58 mL), 2-bromo-1-cyclopropylethanone (14 g, 87 mmol) was added, and the mixture was heated under reflux for 5.5 hr. To the mixture was added saturated aqueous sodium hydrogen carbonate, and the mixture was extracted twice with ethyl acetate. The combined organic layers were dried over anhydrous magnesium sulfate, and concentrated under reduced pressure. The residue was purified by silica gel column chromatography (heptane/ethyl acetate=100/0 v/v-10/90 v/v) to give 7-bromo-2-cyclopropylimidazo[1,2-a]pyridine (5.6 g, 41%).

ESIMS m/z: 237 $(M+H)^+$; $^1$H NMR (300 MHz, $CDCl_3$, δ): 0.87-1.02 (m, 4H), 1.94-2.06 (m, 1H), 6.81 (dd, J=7.1, 2.0 Hz, 1H), 7.32 (s, 1H), 7.67 (d, J=2.0 Hz, 1H), 7.86 (d, J=7.1 Hz, 1H).

[step 2] Using 7-bromo-2-cyclopropylimidazo[1,2-a]pyridine (3.1 g, 13 mmol) obtained in step 1, and in the same manner as in Reference Example 8A, step 2,7-bromo-2-cyclopropyl-3-iodoimidazo[1,2-a]pyridine (4.6 g, 95%) was obtained.

ESIMS m/z: 363 $(M+H)^+$; $^1$H NMR (400 MHz, $CDCl_3$, δ): 0.96-1.14 (m, 4H), 1.96-2.07 (m, 1H), 6.94 (dd, J=6.8, 2.0 Hz, 1H), 7.64 (s, 1H), 7.91 (d, J=6.8 Hz, 1H).

[step 3] Using 7-bromo-2-cyclopropyl-3-iodoimidazo[1,2-a]pyridine (4.6 g, 13 mmol) obtained in step 2 and (E)-2-(3-fluoro-8-formyldibenzo[b,e]oxepin-11(6H)-ylidene)propanenitrile (2.3 g, 7.9 mmol) obtained in Reference Example 5, and in the same manner as in Reference Example 14A, step 3, (E)-2-{8-[(7-bromo-2-cyclopropylimidazo[1,2-a]pyridin-3-yl)(hydroxy)methyl]-3-fluorodibenzo[b,e]oxepin-11(6H)-ylidene}propanenitrile (4.1 g, 98%) was obtained.

ESIMS m/z: 530 $(M+H)^+$; $^1$H NMR (400 MHz, DMSO-$d_6$, δ): 0.78-1.00 (m, 4H), 2.05-2.19 (m, 1H), 2.16 (s, 3H), 4.97-5.07 (m, 1H), 5.48 (d, J=12.7 Hz, 1H), 6.40-6.51 (m, 2H), 6.66-6.76 (m, 1H), 6.78-6.86 (m, 1H), 6.88-6.95 (m, 1H), 7.22-7.32 (m, 1H), 7.34-7.52 (m, 2H), 7.53-7.67 (m, 1H), 7.69-7.78 (m, 1H), 8.14 (d, J=7.8 Hz, 1H).

[step 4] Using (E)-2-{8-[(7-bromo-2-cyclopropylimidazo[1,2-a]pyridin-3-yl)(hydroxy)methyl]-3-fluorodibenzo[b,e]oxepin-11(6H)-ylidene}propanenitrile (4.1 g, 7.7 mmol) obtained in step 3, and in the same manner as in Reference Example 14A, step 4, (E)-2-{8-[(7-bromo-2-cyclopropylimidazo[1,2-a]pyridin-3-yl)methyl]-3-fluorodibenzo[b,e]oxepin-11(6H)-ylidene}propanenitrile (3.3 g, 83%) was obtained.

ESIMS m/z: 514 $(M+H)^+$; $^1$H NMR (400 MHz, DMSO-$d_6$, δ): 0.89-0.98 (m, 4H), 2.13-2.21 (m, 1H), 2.16 (s, 3H), 4.39-4.52 (m, 2H), 4.94 (d, J=12.7 Hz, 1H), 5.45 (d, J=12.7 Hz, 1H), 6.67-6.73 (m, 1H), 6.77-6.85 (m, 1H), 6.92-6.98 (m, 1H), 7.21-7.30 (m, 2H), 7.34-7.40 (m, 2H), 7.74 (s, 1H), 8.10 (d, J=6.8 Hz, 1H).

[step 5] (E)-2-{8-[(7-bromo-2-cyclopropylimidazo[1,2-a]pyridin-3-yl)methyl]-3-fluorodibenzo[b,e]oxepin-11(6H)-ylidene}propanenitrile (2.5 g, 4.8 mmol) obtained in step 4 was dissolved in DMF (26 mL), water (6.8 mL), 1,3-bis(diphenylphosphino)propane (0.60 g, 1.5 mmol), potassium carbonate (0.80 g, 5.8 mmol) and palladium acetate (0.33 g, 1.5 mmol) were added. After purging 3 times with carbon monoxide under reduced pressure, the mixture was stirred with heating at 80° C. for 7 hr. The reaction mixture was filtered through celite, activated carbon (0.75 g) was added to the obtained filtrate, and the mixture was stirred with heating at 60° C. for 1.5 hr. The mixture was filtered again through celite, 2 mol/L hydrochloric acid was added to the filtrate, and the mixture was extracted 3 times with a mixed solvent of chloroform-methanol. The combined organic layers were washed 3 times with water, dried over anhydrous magnesium sulfate and concentrated under reduced pressure. To the obtained residue were added isopropylalcohol (25 mL) and ethanol (20 mL), and the mixture was stirred at 80° C. for 1 hr and further at room temperature for 1 hr. The precipitated crystals were collected by suction filtration to give (E)-3-{[11(6H)-(1-cyanoethylidene)-3-fluorodibenzo[b,e]oxepin-8-yl]methyl}-2-cyclopropylimidazo[1,2-a]pyridine-7-carboxylic acid (2.4 g, quantitative).

ESIMS m/z: 480 $(M+H)^+$; $^1$H NMR (300 MHz, DMSO-$d_6$, δ): 0.90-1.01 (m, 4H), 2.15 (s, 3H), 2.17-2.29 (m, 1H), 4.48-4.55 (m, 2H), 4.94 (d, J=12.7 Hz, 1H), 5.45 (d, J=12.7 Hz, 1H), 6.69 (dd, J=10.6, 2.6 Hz, 1H), 6.76-6.85 (m, 1H), 7.18-7.30 (m, 3H), 7.33-7.41 (m, 2H), 7.97 (s, 1H), 8.24 (d, J=7.1 Hz, 1H).

[step 6] (E)-3-{[11(6H)-(1-cyanoethylidene)-3-fluorodibenzo[b,e]oxepin-8-yl]methyl}-2-cyclopropylimidazo[1,2-a]pyridine-7-carboxylic acid (2.4 g, 5.1 mmol) obtained in step 5 was suspended in THF (25 mL), 1,1'-carbonyldiimidazole (4.1 g, 25 mmol) was added, and the mixture was stirred with heating at 60° C. for 1.5 hr. To the reaction mixture was added 25% aqueous ammonia solution (4.4 mL, 51 mmol), and the mixture was stirred at room temperature for 15 min. To the mixture was added 2 mol/L hydrochloric acid, and the mixture was stirred at room temperature for 1.5 hr. The precipitated crystals were collected by suction filtration, and dried at 50° C. under reduced pressure. The obtained residue was purified by silica gel column chromatography (chloroform/methanol=100/0 v/v-10/90 v/v) to give the title compound (2.1 g, 86%).

ESIMS m/z: 479 $(M+H)^+$; $^1$H NMR (400 MHz, DMSO-$d_6$, δ): 0.90-1.03 (m, 4H), 2.16 (s, 3H), 2.16-2.25 (m, 1H), 4.47-4.54 (m, 2H), 4.94 (d, J=12.7 Hz, 1H), 5.45 (d, J=12.7 Hz, 1H), 6.70 (dd, J=10.7, 2.9 Hz, 1H), 6.77-6.85 (m, 1H), 7.21-7.31 (m, 3H), 7.35-7.41 (m, 2H), 7.49-7.56 (m, 1H), 7.98-8.08 (m, 2H), 8.23 (d, J=7.8 Hz, 1H).

Reference Example 14C

(E)-3-{[11(6H)-(1-cyanoethylidene)-3-fluorodibenzo[b,e]oxepin-8-yl]methyl}-2-cyclopropylimidazo[1,2-a]pyridine-8-carboxamide

[step 1] Using 3-bromopyridin-2-amine (2.0 g, 12 mmol) and 2-bromo-1-cyclopropylethanone (2.6 g, 16 mmol), and in the same manner as in Reference Example 8A, step 1,8-bromo-2-cyclopropylimidazo[1,2-a]pyridine (2.4 g, 89%) was obtained.

ESIMS m/z: 237 $(M+H)^+$; $^1$H NMR (270 MHz, $CDCl_3$, δ): 0.82-0.91 (m, 2H), 0.92-1.05 (m, 2H), 2.05-2.18 (m, 1H), 6.57 (t, J=7.1 Hz, 1H), 7.31-7.38 (m, 2H), 7.98 (d, J=6.6 Hz, 1H).

[step 2] Using 8-bromo-2-cyclopropylimidazo[1,2-a]pyridine (2.4 g, 10 mmol) obtained in step 1, and in the same manner as in Reference Example 8A, step 2,8-bromo-2-cyclopropyl-3-iodoimidazo[1,2-a]pyridine (3.4 g, 90%) was obtained.

ESIMS m/z: 363 $(M+H)^+$; $^1$H NMR (270 MHz, $CDCl_3$, δ): 0.95-1.07 (m, 2H), 1.10-1.20 (m, 2H), 1.97-2.11 (m, 1H), 6.66-6.77 (m, 1H), 7.38-7.46 (m, 1H), 8.00-8.09 (m, 1H).

[step 3] Using 8-bromo-2-cyclopropyl-3-iodoimidazo[1,2-a]pyridine (2.2 g, 5.9 mmol) obtained in step 2 and (E)-2-(3-fluoro-8-formyldibenzo[b,e]oxepin-11(6H)-ylidene)propanenitrile (1.1 g, 3.7 mmol) obtained in Reference Example 5, and in the same manner as in Reference Example 14A, step 3, (E)-2-{8-[(8-bromo-2-cyclopropylimidazo[1,2-a]pyridin-3-yl)(hydroxy)methyl]-3-fluorodibenzo[b,e]oxepin-11(6H)-ylidene}propanenitrile (1.6 g, 80%) was obtained.

ESIMS m/z: 530 $(M+H)^+$; $^1$H NMR (400 MHz, DMSO-$d_6$, δ): 0.84-1.05 (m, 4H), 2.13-2.22 (m, 1H), 2.16 (s, 3H), 4.97-5.06 (m, 1H), 5.45-5.53 (m, 1H), 6.40-6.52 (m, 2H), 6.63-6.77 (m, 2H), 6.77-6.88 (m, 1H), 7.24-7.31 (m, 1H), 7.38-7.65 (m, 4H), 8.23 (d, J=5.9 Hz, 1H).

[step 4] Using (E)-2-{8-[(8-bromo-2-cyclopropylimidazo[1,2-a]pyridin-3-yl)(hydroxy)methyl]-3-fluorodibenzo[b,e]oxepin-11(6H)-ylidene}propanenitrile (1.6 g, 3.0 mmol) obtained in step 3, and in the same manner as in Reference Example 14A, step 4, (E)-2-{8-[(8-bromo-2-cyclopropylimidazo[1,2-a]pyridin-3-yl)methyl]-3-fluorodibenzo[b,e]oxepin-11(6H)-ylidene}propanenitrile (1.4 g, 92%) was obtained.

ESIMS m/z: 514 $(M+H)^+$; $^1$H NMR (270 MHz, $CDCl_3$, δ): 0.96-1.95 (m, 2H), 1.12-1.21 (m, 2H), 1.96-2.07 (m, 1H), 2.23 (s, 3H), 4.26-4.45 (m, 2H), 4.74 (d, J=12.8 Hz, 1H), 5.40 (d, J=12.8 Hz, 1H), 6.49-6.58 (m, 2H), 6.60-6.68 (m, 1H), 6.99-7.08 (m, 2H), 7.19-7.25 (m, 1H), 7.34 (dd, J=7.2, 1.0 Hz, 1H), 7.40 (d, J=7.6 Hz, 1H), 7.58 (dd, J=6.9, 1.0 Hz, 1H).

[step 5] Using (E)-2-{8-[(8-bromo-2-cyclopropylimidazo[1,2-a]pyridin-3-yl)methyl]-3-fluorodibenzo[b,e]oxepin-11(6H)-ylidene}propanenitrile (1.3 g, 2.5 mmol) obtained in step 4, and in the same manner as in Reference Example 14B, step 5, (E)-3-{[11(6H)-(1-cyanoethylidene)-3-fluorodibenzo[b,e]oxepin-8-yl]methyl}-2-cyclopropylimidazo[1,2-a]pyridine-8-carboxylic acid (1.0 g, 83%) was obtained.

ESIMS m/z: 480 $(M+H)^+$; $^1$H NMR (400 MHz, $CDCl_3$, δ): 1.02-1.19 (m, 4H), 1.98-2.09 (m, 1H), 2.24 (s, 3H), 4.32-4.48 (m, 2H), 4.78 (d, J=12.7 Hz, 1H), 5.42 (d, J=12.7 Hz, 1H), 6.56 (dd, J=10.2, 2.4 Hz, 1H), 6.61-6.69 (m, 1H), 6.89 (t, J=7.3 Hz, 1H), 7.03 (d, J=8.8, 6.8 Hz, 1H), 7.10-7.16 (m, 1H), 7.21-7.26 (m, 1H), 7.43 (d, J=7.8 Hz, 1H), 7.82 (d, J=6.8 Hz, 1H), 8.06 (d, J=7.8 Hz, 1H).

[step 6] Using (E)-3-{[11(6H)-(1-cyanoethylidene)-3-fluorodibenzo[b,e]oxepin-8-yl]methyl}-2-cyclopropylimidazo[1,2-a]pyridine-8-carboxylic acid (0.80 g, 1.7 mmol) obtained in step 5, and in the same manner as in Reference Example 14B, step 6, the title compound (0.62 g, 77%) was obtained.

ESIMS m/z: 479 $(M+H)^+$; $^1$H NMR (400 MHz, $CDCl_3$, δ): 0.99-1.08 (m, 2H), 1.09-1.16 (m, 2H), 1.98-2.07 (m, 1H), 2.24 (s, 3H), 4.31-4.46 (m, 2H), 4.77 (d, J=12.7 Hz, 1H), 5.42 (d, J=12.7 Hz, 1H), 5.89-5.97 (m, 1H), 6.55 (dd, J=10.2, 2.4 Hz, 1H), 6.61-6.68 (m, 1H), 6.82 (t, J=6.8 Hz, 1H), 6.99-7.07 (m, 1H), 7.09-7.13 (m, 1H), 7.21-7.26 (m, 1H), 7.42 (d, J=7.8 Hz, 1H), 7.76 (d, J=6.8 Hz, 1H), 8.11 (d, J=6.8 Hz, 1H), 10.05 (br s, 1H).

Reference Example 14D

(E)-2-{3-fluoro-8-[(8-methyl-2-propylimidazo[1,2-a]pyrazin-3-yl)methyl]dibenzo[b,e]oxepin-11(6H)-ylidene}propanenitrile

[step 1] Using 3-methylpyrazin-2-amine (1.0 g, 9.2 mmol) and 1-bromopentan-2-one (3.9 g, 18 mmol), and in the same manner as in Reference Example 14A, step 1,8-methyl-2-propylimidazo[1,2-a]pyrazine (1.2 g, 73%) was obtained.

ESIMS m/z: 176 $(M+H)^+$; $^1$H NMR (400 MHz, $CDCl_3$, δ): 1.02 (t, J=7.3 Hz, 3H), 1.72-1.85 (m, 2H), 2.82 (t, J=7.3 Hz, 2H), 2.88 (s, 3H), 7.42 (s, 1H), 7.69 (d, J=3.9 Hz, 1H), 7.87 (d, J=3.9 Hz, 1H).

[step 2] Using 8-methyl-2-propylimidazo[1,2-a]pyrazine (1.2 g, 6.7 mmol) obtained in step 1, and in the same manner as in Reference Example 8A, step 2,3-iodo-8-methyl-2-propylimidazo[1,2-a]pyrazine (1.7 g, 85%) was obtained.

ESIMS m/z: 302 $(M+H)^+$; $^1H$ NMR (400 MHz, $CDCl_3$, δ): 1.01 (t, J=7.3 Hz, 3H), 1.74-1.86 (m, 2H), 2.82 (t, J=7.3 Hz, 2H), 2.89 (s, 3H), 7.83 (d, J=4.9 Hz, 1H), 7.87 (d, J=4.9 Hz, 1H).

[step 3] Using 3-iodo-8-methyl-2-propylimidazo[1,2-a] pyrazine (0.5 g, 1.7 mmol) obtained in step 2 and (E)-2-(3-fluoro-8-formyldibenzo[b,e]oxepin-11(6H)-ylidene)propanenitrile (0.3 g, 1.0 mmol) obtained in Reference Example 5, and in the same manner as in Reference Example 14A, step 3, (E)-2-{3-fluoro-8-[hydroxy(8-methyl-2-propylimidazo[1,2-a]pyrazin-3-yl)methyl]dibenzo[b,e]oxepin-11(6H)-ylidene}propanenitrile (0.51 g, quantitative) was obtained.

ESIMS m/z: 469 $(M+H)^+$; $^1H$ NMR (300 MHz, $CDCl_3$, δ): 0.89-1.03 (m, 3H), 1.68-1.84 (m, 2H), 2.24 (s, 3H), 2.64-2.75 (m, 2H), 2.80-2.87 (m, 3H), 3.15-3.34 (m, 1H), 4.74-4.87 (m, 1H), 5.45 (d, J=12.8 Hz, 1H), 6.34 (br d, J=4.8 Hz, 1H), 6.50-6.70 (m, 2H), 7.03 (dd, J=8.8, 6.2 Hz, 1H), 7.28-7.36 (m, 1H), 7.39-7.49 (m, 2H), 7.52 (d, J=4.4 Hz, 1H), 7.71-7.80 (m, 1H).

[step 4] Using (E)-2-{3-fluoro-8-[hydroxy(8-methyl-2-propylimidazo[1,2-a]pyrazin-3-yl)methyl]dibenzo[b,e]oxepin-11(6H)-ylidene}propanenitrile (0.5 g, 1.1 mmol) obtained in step 3, and in the same manner as in Reference Example 14A, step 4, the title compound (0.35 g, 73%) was obtained.

ESIMS m/z: 453 $(M+H)^+$; $^1H$ NMR (400 MHz, $CDCl_3$, δ): 1.00 (t, J=7.3 Hz, 3H), 1.73-1.85 (m, 2H), 2.23 (s, 3H), 2.83 (t, J=7.3 Hz, 2H), 2.90 (s, 3H), 4.21-4.35 (m, 2H), 4.74 (d, J=12.7 Hz, 1H), 5.41 (d, J=12.7 Hz, 1H), 6.55 (dd, J=10.2, 2.4 Hz, 1H), 6.61-6.68 (m, 1H), 6.98-7.06 (m, 2H), 7.13-7.18 (m, 1H), 7.41 (d, J=7.8 Hz, 1H), 7.46 (d, J=3.9 Hz, 1H), 7.63 (d, J=4.9 Hz, 1H).

Reference Example 14E

(E)-2-(8-{[2-cyclopropyl-8-(dimethylamino)imidazo[1,2-a]pyrazin-3-yl]methyl}-3-fluorodibenzo[b,e]oxepin-11(6H)-ylidene)propanenitrile

[step 1] Using 3-methoxypyrazin-2-amine (9.7 g, 78 mmol) and 2-bromo-1-cyclopropylethanone (16 g, 101 mmol), and in the same manner as in Reference Example 14A, step 1,2-cyclopropyl-8-methoxyimidazo[1,2-a]pyrazine (7.4 g, 50%) was obtained.

ESIMS m/z: 190 $(M+H)^+$; $^1H$ NMR (400 MHz, $CDCl_3$, δ): 0.94-1.04 (m, 4H), 1.99-2.10 (m, 1H), 4.12 (s, 3H), 7.30 (d, J=4.9 Hz, 1H), 7.37 (s, 1H), 7.60 (d, J=4.9 Hz, 1H).

[step 2] Using 2-cyclopropyl-8-methoxyimidazo[1,2-a] pyrazine (7.1 g, 37 mmol) obtained in step 1, and in the same manner as in Reference Example 8A, step 2,2-cyclopropyl-3-iodo-8-methoxyimidazo[1,2-a]pyrazine (9.2 g, 78%) was obtained.

ESIMS m/z: 316 $(M+H)^+$; $^1H$ NMR (400 MHz, $CDCl_3$, δ): 0.96-1.08 (m, 2H), 1.13-1.21 (m, 2H), 2.00-2.11 (m, 1H), 4.14 (s, 3H), 7.44 (d, J=4.8 Hz, 1H), 7.64 (d, J=4.8 Hz, 1H).

[step 3] Using 2-cyclopropyl-3-iodo-8-methoxyimidazo[1,2-a]pyrazine (9.2 g, 29 mmol) obtained in step 2 and (E)-2-(3-fluoro-8-formyldibenzo[b,e]oxepin-11(6H)-ylidene) propanenitrile (5.3 g, 18 mmol) obtained in Reference Example 5, and in the same manner as in Reference Example 14A, step 3, (E)-2-{8-[(2-cyclopropyl-8-methoxyimidazo[1,2-a]pyrazin-3-yl)(hydroxy)methyl]-3-fluorodibenzo[b,e]oxepin-11(6H)-ylidene}propanenitrile (9.1 g, quantitative) was obtained.

ESIMS m/z: 483 $(M+H)^+$; $^1H$ NMR (300 MHz, DMSO-$d_6$, δ): 0.77-1.00 (m, 4H), 2.10-2.21 (m, 1H), 2.16 (s, 3H), 3.96 (s, 3H), 4.96-5.05 (m, 1H), 5.44-5.53 (m, 1H), 6.41-6.53 (m, 2H), 6.65-6.76 (m, 1H), 6.77-6.87 (m, 1H), 7.23-7.32 (m, 2H), 7.39-7.53 (m, 2H), 7.54-7.65 (m, 1H), 7.90 (d, J=4.8 Hz, 1H).

[step 4] Using (E)-2-{8-[(2-cyclopropyl-8-methoxyimidazo[1,2-a]pyrazin-3-yl)(hydroxy)methyl]-3-fluorodibenzo[b,e]oxepin-11(6H)-ylidene}propanenitrile (9.1 g, 19 mmol) obtained in step 3, and in the same manner as in Reference Example 8A, step 4, (E)-2-{8-[(2-cyclopropyl-8-hydroxyimidazo[1,2-a]pyrazin-3-yl)methyl]-3-fluorodibenzo[b,e]oxepin-11(6H)-ylidene}propanenitrile (8.9 g, quantitative) was obtained.

ESIMS m/z: 453 $(M+H)^+$; $^1H$ NMR (300 MHz, DMSO-$d_6$, δ): 0.93-1.07 (m, 4H), 2.13-2.24 (m, 1H), 2.17 (s, 3H), 4.41-4.54 (m, 2H), 4.94 (d, J=12.8 Hz, 1H), 5.48 (d, J=12.8 Hz, 1H), 6.71 (dd, J=10.6, 2.6 Hz, 1H), 6.78-6.87 (m, 1H), 7.14-7.23 (m, 1H), 7.27 (dd, J=8.8, 6.6 Hz, 1H), 7.31-7.43 (m, 3H), 7.46-7.53 (m, 1H), 11.90-12.13 (m, 1H).

[step 5] To (E)-2-{8-[(2-cyclopropyl-8-hydroxyimidazo[1,2-a]pyrazin-3-yl)methyl]-3-fluorodibenzo[b,e]oxepin-11(6H)-ylidene}propanenitrile (3.8 g, 8.3 mmol) obtained in step 4 was added phosphorus oxychloride (19 mL, 207 mmol), and the mixture was stirred with heating at 110° C. for 4 hr. The mixture was concentrated under reduced pressure, saturated aqueous sodium hydrogen carbonate solution was added to the residue, and the mixture was extracted 3 times with ethyl acetate. The combined organic layers were dried over anhydrous magnesium sulfate and concentrated under reduced pressure to give (E)-2-{8-[(8-chloro-2-cyclopropylimidazo[1,2-a]pyrazin-3-yl)methyl]-3-fluorodibenzo[b,e]oxepin-11(6H)-ylidene}propanenitrile (3.7 g, 96%).

ESIMS m/z: 471 $(M+H)^+$; $^1H$ NMR (400 MHz, $CDCl_3$, δ): 1.04-1.11 (m, 2H), 1.17-1.25 (m, 2H), 2.00-2.09 (m, 1H), 2.24 (s, 3H), 4.31-4.46 (m, 2H), 4.77 (d, J=12.7 Hz, 1H), 5.42 (d, J=12.7 Hz, 1H), 6.56 (dd, J=10.2, 2.4 Hz, 1H), 6.61-6.69 (m, 1H), 7.03 (dd, J=8.8, 6.8 Hz, 1H), 7.06-7.09 (m, 1H), 7.19-7.24 (m, 1H), 7.43 (d, J=7.8 Hz, 1H), 7.52-7.57 (m, 2H).

[step 6] (E)-2-{8-[(8-chloro-2-cyclopropylimidazo[1,2-a]pyrazin-3-yl)methyl]-3-fluorodibenzo[b,e]oxepin-11(6H)-ylidene}propanenitrile (0.2 g, 0.43 mmol) obtained in step 5 was dissolved in THF (1.4 mL), and 2 mol/L dimethylamine THF solution (1.7 mL, 3.4 mmol) was added. The mixture was stirred with heating at 100° C. for 1.5 hr in an Emrys Optimizer microwave synthesizer. Water was added to the mixture, and the mixture was extracted 3 times with ethyl acetate. The combined organic layers were dried over anhydrous magnesium sulfate, and concentrated under reduced pressure. The residue was purified by silica gel column chromatography (heptane/ethyl acetate=100/0 v/v-50/50 v/v) to give the title compound (0.18 g, 87%).

ESIMS m/z: 480 $(M+H)^+$; $^1H$ NMR (400 MHz, $CDCl_3$, δ): 0.91-0.99 (m, 2H), 1.01-1.11 (m, 2H), 1.90-2.00 (m, 1H), 2.23 (s, 3H), 3.51 (s, 6H), 4.15-4.36 (m, 2H), 4.75 (d, J=12.7 Hz, 1H), 5.41 (d, J=12.7 Hz, 1H), 6.55 (dd, J=10.2, 2.4 Hz, 1H), 6.60-6.67 (m, 1H), 6.97 (d, J=3.9 Hz, 1H), 7.02 (dd, J=8.8, 5.9 Hz, 1H), 7.04-7.07 (m, 1H), 7.18-7.24 (m, 2H), 7.39 (d, J=7.8 Hz, 1H).

Reference Example 14F

(E)-2-(8-{[2-cyclopropyl-8-(dimethylamino)imidazo[1,2-a]pyridin-3-yl]methyl}-3-fluorodibenzo[b,e]oxepin-11(6H)-ylidene)propanenitrile (E)-2-{8-[(8-bromo-2-cyclopropylimidazo[1,2-a]pyridin-3-yl)methyl]-3-fluorodibenzo[b,e]oxepin-11(6H)-ylidene}propanenitrile (0.36 g, 0.69 mmol) obtained in Reference Example 14C, step 4 was dissolved in toluene (14 mL), $Pd_2(dba)_3$ (0.13 g, 0.14 mmol), 2-(di-tert-butylphosphino)biphenyl (0.04 g, 0.14 mmol), sodium tert-butoxide (0.13 g, 1.4 mmol) and 2 mol/L dimethylamine THF solution (4.5 mL, 9.0 mmol) were added, and the mixture was stirred with heating at 120° C. for 2.5 hr in an Emrys Optimizer microwave synthesizer. The mixture was filtered through celite, the filtrate was concentrated under reduced pressure, and the obtained residue was purified by silica gel column chromatography (heptane/ethyl acetate=100/0 v/v-70/30 v/v) to give the title compound (0.10 g, 29%).

ESIMS m/z: 479 $(M+H)^+$; $^1H$ NMR (270 MHz, $CDCl_3$, δ): 0.87-0.98 (m, 2H), 1.09-1.18 (m, 2H), 1.91-2.03 (m, 1H), 2.23 (s, 3H), 3.15 (s, 6H), 4.22-4.40 (m, 2H), 4.74 (d, J=12.8 Hz, 1H), 5.40 (d, J=12.8 Hz, 1H), 6.22 (d, J=7.2 Hz, 1H), 6.48-6.58 (m, 2H), 6.58-6.67 (m, 1H), 7.01 (dd, J=8.7, 6.4 Hz, 1H), 7.06-7.11 (m, 1H), 7.17-7.23 (m, 2H), 7.38 (d, J=7.9 Hz, 1H).

Reference Example 14G (E)-2-{8-[(7-cyclopropyl-2-methylimidazo[1,2-a]pyridin-3-yl)methyl]-3-fluorodibenzo[b,e]oxepin-11(6H)-ylidene}propanenitrile

[step 1] Using 2-amino-4-bromopyridine (1.5 g, 8.7 mmol) and bromoacetone (1.58 g, 10 mmol), and in the same manner as in Reference Example 8A, step 1,7-bromo-2-methylimidazo[1,2-a]pyridine (1.5 g, 82%) was obtained.

ESIMS m/z: 211 $(M+H)^+$; $^1H$ NMR (270 MHz, $CDCl_3$, δ): 2.45 (s, 3H), 6.84 (dd, J=8.2, 2.0 Hz, 1H), 7.33 (s, 1H), 7.70 (d, J=2.0 Hz, 1H), 7.91 (d, J=8.2 Hz, 1H).

[step 2] Using 7-bromo-2-methylimidazo[1,2-a]pyridine (2.0 g, 9.5 mmol) obtained in step 1, and in the same manner as in Reference Example 8A, step 2,7-bromo-3-iodo-2-methylimidazo[1,2-a]pyridine (3.2 g, 99%) was obtained.

ESIMS m/z: 337 $(M+H)^+$; $^1H$ NMR (270 MHz, $CDCl_3$, δ): 2.51 (s, 3H), 6.80-7.11 (m, 1H), 7.58-7.82 (m, 1H), 7.83-8.02 (m, 1H).

[step 3] Using 7-bromo-3-iodo-2-methylimidazo[1,2-a]pyridine (3.2 g, 9.5 mmol) obtained in step 2 and (E)-2-(3-fluoro-8-formyldibenzo[b,e]oxepin-11(6H)-ylidene)propanenitrile (1.7 g, 5.9 mmol) obtained in Reference Example 5, and in the same manner as in Reference Example 14A, step 3, (E)-2-{3-fluoro-8-[hydroxy(7-bromo-2-methylimidazo[1,2-a]pyridin-3-yl)methyl]dibenzo[b,e]oxepin-11(6H)-ylidene}propanenitrile (3.0 g, 99%) was obtained.

ESIMS m/z: 504 $(M+H)^+$; $^1H$ NMR (270 MHz, $CDCl_3$, δ): 2.22 (s, 3H), 2.35-2.44 (m, 3H), 4.76-4.87 (m, 1H), 5.39-5.51 (m, 1H), 6.27-6.39 (m, 1H), 6.48-6.79 (m, 3H), 6.95-7.07 (m, 1H), 7.29-7.53 (m, 3H), 7.62-7.72 (m, 1H), 7.76-7.92 (m, 1H).

[step 4] Using (E)-2-{3-fluoro-8-[hydroxy(7-bromo-2-methylimidazo[1,2-a]pyridin-3-yl)methyl]dibenzo[b,e]oxepin-11(6H)-ylidene}propanenitrile (3.0 g, 5.9 mmol) obtained in step 3, and in the same manner as in Reference Example 14A, step 4, (E)-2-{3-fluoro-8-[(7-bromo-2-methylimidazo[1,2-a]pyridin-3-yl)methyl]dibenzo[b,e]oxepin-11(6H)-ylidene}propanenitrile (2.2 g, 75%) was obtained.

ESIMS m/z: 488 $(M+H)^+$; $^1H$ NMR (270 MHz, $CDCl_3$, δ): 2.24 (s, 3H), 2.49 (s, 3H), 4.13-4.36 (m, 2H), 4.74 (d, J=12.0 Hz, 1H), 5.40 (d, J=12.0 Hz, 1H), 6.52-6.60 (m, 1H), 6.60-6.70 (m, 1H), 6.72-6.82 (m, 1H), 6.97-7.07 (m, 2H), 7.11-7.21 (m, 1H), 7.35-7.44 (m, 1H), 7.44-7.52 (m, 1H), 7.68-7.77 (m, 1H).

[step 5] (E)-2-{3-fluoro-8-[(7-bromo-2-methylimidazo[1,2-a]pyridin-3-yl)methyl]dibenzo[b,e]oxepin-11(6H)-ylidene}propanenitrile (350 mg, 0.72 mmol) obtained in step 4 was dissolved in toluene (4.0 mL), cyclopropylboronic acid (123 mg, 1.4 mmol), tricyclohexylphosphine (80 mg, 0.29 mmol), palladium acetate (32 mg, 0.14 mmol), potassium phosphate (532 mg, 2.5 mmol) and water (13 mg, 0.72 mmol) were added, and the mixture was stirred with heating at 100° C. for 3 hr. The reaction mixture was filtered through celite, and the filtrate was concentrated under reduced pressure. The obtained residue was purified by silica gel column chromatography (chloroform/methanol=19/1 v/v) to give the title compound (280 mg, 87%).

ESIMS m/z: 450 $(M+H)^+$; $^1H$ NMR (270 MHz, $CDCl_3$, δ): 0.66-0.75 (m, 2H), 0.87-1.07 (m, 2H), 1.80-2.00 (m, 1H), 2.24 (s, 3H), 2.46 (s, 3H), 4.15-4.32 (m, 2H), 4.75 (d, J=12.0 Hz, 1H), 5.39 (d, J=12.0 Hz, 1H), 6.35-6.43 (m, 1H), 6.49-6.72 (m, 2H), 6.97-7.10 (m, 2H), 7.15-7.24 (m, 2H), 7.34-7.43 (m, 1H), 7.44-7.55 (m, 1H).

Reference Example 14H (E)-2-{8-[(7-ethynyl-2-methylimidazo[1,2-a]pyridin-3-yl)methyl]-3-fluorodibenzo[b,e]oxepin-11(6H)-ylidene}propanenitrile

[step 1] To a mixture of (E)-2-{3-fluoro-8-[(7-bromo-2-methylimidazo[1,2-a]pyridin-3-yl)methyl]dibenzo[b,e]oxepin-11(6H)-ylidene}propanenitrile (400 mg, 0.82 mmol) obtained in Reference Example 14G, step 4, trimethylsilylacetylene (0.23 mL, 1.6 mmol), triethylamine (0.34 mL, 2.5 mmol), bis(triphenylphosphine)dichloropalladium (II) (29 mg, 0.04 mmol) and triphenylphosphine (54 mg, 0.21 mmol) were added THF (4.0 mL), copper (I) iodide (1.6 mg, 0.008 mmol), and the mixture was stirred with heating at 60° C. for 3 hr. The reaction mixture was filtered through celite, and the filtrate was concentrated under reduced pressure. The obtained residue was purified by silica gel column chromatography (heptane/ethyl acetate=1/2 v/v) to give (E)-2-{8-[(2-methyl-7-trimethylsilylethynylimidazo[1,2-a]pyridin-3-yl)methyl]-3-fluorodibenzo[b,e]oxepin-11(6H)-ylidene}propanenitrile (340 mg, 82%).

ESIMS m/z: 506 $(M+H)^+$; $^1H$ NMR (270 MHz, $CDCl_3$, δ): 0.23 (s, 9H), 2.24 (s, 3H), 2.49 (s, 3H), 4.19-4.36 (m, 2H), 4.75 (d, J=12.4 Hz, 1H), 5.41 (d, J=12.4 Hz, 1H), 6.49-6.77 (m, 3H), 6.96-7.09 (m, 2H), 7.14-7.23 (m, 1H), 7.36-7.45 (m, 1H), 7.49-7.60 (m, 1H), 7.62-7.70 (m, 1H).

[step 2] (E)-2-{8-[(2-methyl-7-trimethylsilylethynylimidazo[1,2-a]pyridin-3-yl)methyl]-3-fluorodibenzo[b,e]oxepin-11(6H)-ylidene}propanenitrile (340 mg, 0.62 mmol) obtained in step 1 was dissolved in THF (3 ml), 1 mmol/L tetrabutylammonium fluoride THF solution (0.81 ml, 0.81 mmol) was added, and the mixture was stirred at room temperature for 4 hr. Water was added to the reaction mixture and the mixture was extracted 3 times with ethyl acetate. The combined organic layers were dried over anhydrous magnesium sulfate, and concentrated under reduced pressure. The obtained residue was purified by silica gel column chromatography (heptane/ethyl acetate=1/2 v/v) to give the title compound (152 mg, 53%).

ESIMS m/z: 434 $(M+H)^+$; $^1H$ NMR (270 MHz, $CDCl_3$, δ): 2.25 (s, 3H), 2.52 (s, 3H), 3.16-3.24 (m, 1H), 4.17-4.40 (m, 2H), 4.75 (d, J=12.4 Hz, 1H), 5.41 (d, J=12.4 Hz, 1H), 6.50-6.80 (m, 3H), 6.96-7.08 (m, 2H), 7.13-7.23 (m, 1H), 7.36-7.47 (m, 1H), 7.51-7.63 (m, 1H), 7.63-7.78 (m, 1H).

Reference Example 14I (E)-3-({11(6H)-[1-(cyanoethylidene)]-3-fluorodibenzo[b,e]oxepin}methyl)-7-fluoroimidazo[1,2-a]pyridine-2-carboxamide

[step 1] Using 2-amino-4-fluoropyridine (3.2 g, 28.5 mmol) and ethyl bromopyruvate (4.3 ml, 34.3 mmol), and in the same manner as in Reference Example 8A, step 1, ethyl 7-fluoroimidazo[1,2-a]pyridine-2-carboxylate (3.5 g, 59%) was obtained.

ESIMS m/z: 209 $(M+H)^+$; $^1$H NMR (270 MHz, $CDCl_3$, δ): 1.44 (t, J=7.3 Hz, 3H), 4.46 (q, J=7.3 Hz, 2H), 6.74-6.86 (m, 1H), 7.21-7.36 (m, 1H), 8.06-8.14 (m, 1H), 8.18 (s, 1H).

[step 2] Using ethyl 7-fluoroimidazo[1,2-a]pyridine-2-carboxylate (2.8 g, 13.5 mmol) obtained in step 1, and in the same manner as in Reference Example 8A, step 2, ethyl 7-fluoro-3-iodo-imidazo[1,2-a]pyridine-2-carboxylate (2.6 g, 57%) was obtained.

ESIMS m/z: 335 $(M+H)^+$; $^1$H NMR (270 MHz, $CDCl_3$, δ): 1.46 (t, J=7.3 Hz, 3H), 4.51 (q, J=7.3 Hz, 2H), 6.83-7.00 (m, 1H), 7.23-7.43 (m, 1H), 8.11-8.35 (m, 1H).

[step 3] Using ethyl 7-fluoro-3-iodo-imidazo[1,2-a]pyridine-2-carboxylate (4.5 g, 13.5 mmol) obtained in step 2 and (E)-2-(3-fluoro-8-formyldibenzo[b,e]oxepin-11(6H)-ylidene)propanenitrile (2.5 g, 8.4 mmol) obtained in Reference Example 5, and in the same manner as in Reference Example 14A, step 3, (E)-ethyl 3-({11(6H)-[1-(cyanoethylidene)]-3-fluorodibenzo[b,e]oxepin}(hydroxy)methyl)-7-fluoroimidazo[1,2-a]pyridine-2-carboxylate (1.8 g, 76%) was obtained.

ESIMS m/z: 502 $(M+H)^+$; $^1$H NMR (270 MHz, $CDCl_3$, δ): 1.46 (t, J=7.3 Hz, 3H), 2.24 (s, 3H), 4.48 (q, J=7.3 Hz, 2H), 4.73-4.86 (m, 1H), 5.28-5.49 (m, 1H), 6.47-6.72 (m, 3H), 6.94-7.13 (m, 2H), 7.19-7.29 (m, 1H), 7.36-7.55 (m, 3H), 8.03-8.20 (m, 1H).

[step 4] Using (E)-ethyl 3-({11(6H)-[1-(cyanoethylidene)]-3-fluorodibenzo[b,e]oxepin}(hydroxy)methyl)-7-fluoroimidazo[1,2-a]pyridine-2-carboxylate (2.0 g, 8.9 mmol) obtained in step 3, and in the same manner as in Reference Example 14A, step 4, (E)-ethyl 3-({11(6H)-[1-(cyanoethylidene)]-3-fluorodibenzo[b,e]oxepin}methyl)-7-fluoroimidazo[1,2-a]pyridine-2-carboxylate (1.4 g, 74%) was obtained.

ESIMS m/z: 486 $(M+H)^+$; $^1$H NMR (270 MHz, $CDCl_3$, δ): 1.45 (t, J=7.3 Hz, 3H), 2.22 (s, 3H), 4.49 (q, J=7.3 Hz, 2H), 4.62-4.88 (m, 3H), 5.39 (d, J=12.4 Hz, 1H), 6.39-6.78 (m, 3H), 6.98-7.06 (m, 2H), 7.22-7.34 (m, 2H), 7.37-7.44 (m, 1H), 7.72-7.79 (m, 1H).

[step 5] (E)-ethyl 3-({11(6H)-[1-(cyanoethylidene)]-3-fluorodibenzo[b,e]oxepin}methyl)-7-fluoroimidazo[1,2-a]pyridine-2-carboxylate (350 mg, 0.72 mmol) obtained in step 4 was dissolved in THF (5 mL)-ethanol (2.5 mL), lithium hydroxide (26 mg, 1.1 mmol) was added, and the mixture was stirred at room temperature for 7 hr. To the reaction mixture was added 1 mol/L hydrochloric acid (1.5 mL), and precipitated crystals were collected by suction filtration.

The obtained crystals (330 mg) were dissolved in THF (5 mL), carbonyldiimidazole (585 mg, 3.6 mmol) was added, and the mixture was stirred at room temperature for 1 hr. To the reaction mixture was added 25% aqueous ammonia solution (0.63 mL, 7.2 mmol), and the mixture was further stirred for 1 hr. To the reaction mixture was added 5% aqueous citric acid solution, and the mixture was extracted 3 times with chloroform. The combined organic layers were dried over anhydrous magnesium sulfate, and concentrated under reduced pressure. The obtained residue was purified by silica gel column chromatography (chloroform/methanol=9/1 v/v) to give the title compound (253 mg, 77%).

ESIMS m/z: 457 $(M+H)^+$; $^1$H NMR (270 MHz, $CDCl_3$, δ): 2.22 (s, 3H), 4.67-4.85 (m, 3H), 5.39 (d, J=12.4 Hz, 1H), 5.49-5.57 (m, 1H), 6.49-6.59 (m, 1H), 6.59-6.73 (m, 2H), 6.95-7.07 (m, 1H), 7.16-7.24 (m, 2H), 7.24-7.32 (m, 1H), 7.32-7.43 (m, 2H), 7.72-7.82 (m, 1H).

Reference Example 14J

(E)-2-(8-{[7-fluoro-2-(tetrahydrofuran-3-yl)imidazo[1,2-a]pyridin-3-yl]methyl}-3-fluorodibenzo[b,e]oxepin-11(6H)-ylidene)propanenitrile

[step 1] Using 2-amino-4-fluoropyridine (294 mg, 2.6 mmol) and 3-bromoacetyltetrahydrofuran (WO2002/046198, 607 mg, 3.1 mmol), and in the same manner as in Reference Example 8A, step 1,7-fluoro-2-(tetrahydrofuran-3-yl)imidazo[1,2-a]pyridine (150 mg, 27%) was obtained.

ESIMS m/z: 207 $(M+H)^+$; $^1$H NMR (270 MHz, $CDCl_3$, δ): 2.12-2.27 (m, 1H), 2.31-2.47 (m, 1H), 3.54-3.68 (m, 1H), 3.87-3.99 (m, 2H), 3.99-4.11 (m, 1H), 4.12-4.23 (m, 1H), 6.56-6.70 (m, 1H), 7.13-7.25 (m, 1H), 7.38 (s, 1H), 7.86-8.07 (m, 1H).

[step 2] Using 7-fluoro-2-(tetrahydrofuran-3-yl)imidazo[1,2-a]pyridine (150 mg, 0.73 mmol) obtained in step 1, and in the same manner as in Reference Example 8A, step 2,7-fluoro-3-iodo-2-(tetrahydrofuran-3-yl)imidazo[1,2-a]pyridine (180 mg, 75%) was obtained.

ESIMS m/z: 333 $(M+H)^+$; $^1$H NMR (270 MHz, $CDCl_3$, δ): 2.25-2.47 (m, 2H), 3.54-3.68 (m, 1H), 3.83-4.07 (m, 2H), 4.11-4.23 (m, 2H), 6.71-6.84 (m, 1H), 7.17-7.34 (m, 1H), 8.00-8.17 (m, 1H).

[step 3] Using 7-fluoro-3-iodo-2-(tetrahydrofuran-3-yl)imidazo[1,2-a]pyridine (180 mg, 0.54 mmol) obtained in step 2 and (E)-2-(3-fluoro-8-formyldibenzo[b,e]oxepin-11(6H)-ylidene)propanenitrile (99 mg, 0.34 mmol) obtained in Reference Example 5, and in the same manner as in Reference Example 14A, step 3, (E)-2-(3-fluoro-8-{[7-fluoro-2-(tetrahydrofuran-3-yl)(hydroxy)imidazo[1,2-a]pyridin-3-yl]methyl}dibenzo[b,e]oxepin-11(6H)-ylidene)propanenitrile (137 mg, 81%) was obtained.

ESIMS m/z: 500 $(M+H)^+$; $^1$H NMR (270 MHz, $CDCl_3$, δ): 2.20-2.48 (m, 5H), 3.46-3.70 (m, 1H), 3.83-4.01 (m, 2H), 4.01-4.23 (m, 2H), 4.73-4.89 (m, 1H), 5.37-5.54 (m, 1H), 6.33-6.45 (m, 1H), 6.45-6.71 (m, 3H), 6.97-7.10 (m, 1H), 7.10-7.23 (m, 1H), 7.32-7.54 (m, 3H), 7.86-8.02 (m, 1H).

[step 4] Using (E)-2-(3-fluoro-8-{[7-fluoro-2-(tetrahydrofuran-3-yl)(hydroxy)imidazo[1,2-a]pyridin-3-yl]methyl}dibenzo[b,e]oxepin-11(6H)-ylidene)propanenitrile (137 mg, 0.27 mmol) obtained in step 3, and in the same manner as in Reference Example 14A, step 4, (E)-2-(3-fluoro-8-{[7-fluoro-2-(tetrahydrofuran-3-yl)imidazo[1,2-a]pyridin-3-yl]methyl}dibenzo[b,e]oxepin-11(6H)-ylidene)propanenitrile (104 mg, 78%) was obtained.

ESIMS m/z: 484 $(M+H)^+$; $^1$H NMR (270 MHz, $CDCl_3$, δ): 2.16-2.52 (m, 5H), 3.50-3.69 (m, 1H), 3.88-4.05 (m, 2H), 4.07-4.22 (m, 2H), 4.22-4.37 (m, 2H), 4.63-4.83 (m, 1H), 5.33-5.50 (m, 1H), 6.52-6.72 (m, 3H), 6.98-7.11 (m, 2H), 7.10-7.18 (m, 1H), 7.21-7.32 (m, 1H), 7.39-7.47 (m, 1H), 7.51-7.63 (m, 1H).

Reference Example 14K

(E)-2-{8-[(2-chloroimidazo[1,2-a]pyridin-3-yl)methyl]-3-fluorodibenzo[b,e]oxepin-11(6H)-ylidene}propanenitrile

[step 1]2-chloro-iodoimidazo[1,2-a]pyridine

By reference to Journal of Medicinal Chemistry (J. Med. Chem.) 2003, 46, 1449-1455, 2-chloro-3-iodoimidazo[1,2-a]pyridine (2.3 g, 33%) was obtained in 3 steps using pyridin-2-amine (2.5 g, 26 mmol).

ESIMS m/z: 279 $(M+H)^+$; $^1H$ NMR (270 MHz, $CDCl_3$, δ): 6.95-7.00 (m, 1H), 7.26-7.32 (m, 1H), 7.51-7.55 (m, 1H), 8.04-8.08 (m, 1H).

[step 2] Using 2-chloro-3-iodoimidazo[1,2-a]pyridine (500 mg, 1.80 mmol) obtained in step 1 and (E)-2-(3-fluoro-8-formyldibenzo[b,e]oxepin-11(6H)-ylidene)propanenitrile (263 mg, 0.90 mmol) obtained in Reference Example 5, and in the same manner as in Reference Example 8F, step 4, (E)-2-{8-[(2-chloroimidazo[1,2-a]pyridin-3-yl)(hydroxy)methyl]-3-fluorodibenzo[b,e]oxepin-11(6H)-ylidene}propanenitrile (179 mg, 45%) was obtained.

ESIMS m/z: 446 $(M+H)^+$; $^1H$ NMR (270 MHz, $CDCl_3$, δ): 2.24 (s, 3H), 4.81-4.85 (m, 1H), 5.41-5.47 (m, 1H), 6.46-6.72 (m, 4H), 7.00-7.05 (m, 1H), 7.19-7.23 (m, 1H), 7.40-7.56 (m, 4H), 8.01-8.03 (m, 1H).

[step 3] Using (E)-2-{8-[(2-chloroimidazo[1,2-a]pyridin-3-yl)(hydroxy)methyl]-3-fluorodibenzo[b,e]oxepin-11(6H)-ylidene}propanenitrile (170 mg, 0.38 mmol) obtained in step 2, and in the same manner as in Reference Example 8F, step 5, the title compound (66 mg, 40%) was obtained.

ESIMS m/z: 430 $(M+H)^+$; $^1H$ NMR (270 MHz, $CDCl_3$, δ): 2.23 (s, 3H), 4.29-4.34 (m, 2H), 4.73-4.97 (m, 1H), 5.38-5.54 (m, 1H), 6.52-6.79 (m, 4H), 6.99-7.05 (m, 1H), 7.39-7.42 (m, 1H), 7.52-7.62 (m, 2H), 7.65-7.73 (m, 1H), 7.77-7.82 (m, 1H).

Reference Example 14L

(E)-2-(3-fluoro-8-{[2-methoxy-7-(trifluoromethyl)imidazo[1,2-a]pyridin-3-yl]methyl}-dibenzo[b,e]oxepin-11(6H)-ylidene)propanenitrile

[step 1] By reference to Journal of Medicinal Chemistry (J. Med. Chem.) 2003, 46, 1449-1455, 2-chloro-3-iodo-7-(trifluoromethyl)imidazo[1,2-a]pyridine (0.5 g, 16%) was obtained in 3 steps using 4-(trifluoromethyl)pyridin-2-amine (0.81 g, 8.6 mmol).

ESIMS m/z: 347 $(M+H)^+$; $^1H$ NMR (270 MHz, $CDCl_3$, δ): 7.14-7.17 (m, 1H), 7.84-7.85 (m, 1H), 8.17-8.19 (m, 1H).

[step 2] Using 2-chloro-3-iodo-7-(trifluoromethyl)imidazo[1,2-a]pyridine (1.81 g, 5.22 mmol) obtained in step 1 and (E)-2-(3-fluoro-8-formyldibenzo[b,e]oxepin-11(6H)-ylidene)propanenitrile (0.77 g, 2.6 mmol) obtained in Reference Example 5, and in the same manner as in Reference Example 8F, step 4, (E)-2-{8-[(2-chloro-7-(trifluoromethyl)imidazo[1,2-a]pyridin-3-yl)(hydroxy)methyl]-3-fluorodibenzo[b,e]oxepin-11(6H)-ylidene}propanenitrile (1.21 g, 90%) was obtained.

ESIMS m/z: 514 $(M+H)^+$; $^1H$ NMR (270 MHz, $CDCl_3$, δ): 2.25 (s, 3H), 4.82-4.86 (m, 1H), 5.41-5.48 (m, 1H), 6.43-6.68 (m, 3H), 6.88-6.92 (m, 1H), 7.01-7.06 (m, 1H), 7.38-7.56 (m, 3H), 7.80-7.82 (m, 1H), 8.23-8.30 (m, 1H).

[step 3] (E)-2-{8-[(2-chloro-7-(trifluoromethyl)imidazo[1,2-a]pyridin-3-yl)(hydroxy)methyl]-3-fluorodibenzo[b,e]oxepin-11(6H)-ylidene}propanenitrile (0.985 g, 1.92 mmol) obtained in step 2 was dissolved in methylene chloride (9.6 mL), Dess-Martin periodinane (0.976 g, 2.30 mmol) was added at 0° C., and the mixture was stirred for 30 min. To the mixture was added saturated aqueous sodium hydrogen carbonate solution and the reaction was discontinued with saturated aqueous sodium thiosulfate solution. The mixture was extracted 3 times with chloroform. The combined organic layers were dried over anhydrous magnesium sulfate, and concentrated under reduced pressure. The obtained residue was re-slurried with isopropyl ether to give (E)-2-{8-[(2-chloro-7-(trifluoromethyl)imidazo[1,2-a]pyridine-3-carbonyl]-3-fluorodibenzo[b,e]oxepin-11(6H)-ylidene}propanenitrile (0.98 g, 100%).

ESIMS m/z: 512 $(M+H)^+$; $^1H$ NMR (270 MHz, $CDCl_3$, δ): 2.29 (s, 3H), 4.94-4.99 (m, 1H), 5.51-5.56 (m, 1H), 6.60-6.74 (m, 2H), 7.06-7.12 (m, 1H), 7.31-7.34 (m, 1H), 7.61-7.64 (m, 1H), 7.81-8.00 (m, 2H), 7.99-8.01 (m, 1H), 9.48-9.51 (m, 1H).

[step 4] (E)-2-{8-[(2-chloro-7-(trifluoromethyl)imidazo[1,2-a]pyridine-3-carbonyl]-3-fluorodibenzo[b,e]oxepin-11(6H)-ylidene}propanenitrile (0.300 g, 0.59 mmol) obtained in step 3 was dissolved in 28% sodium methoxide methanol solution (0.93 mL, 4.7 mmol), and the mixture was stirred with heating under reflux for 3 hr. Water was added to the mixture, and the residue collected by filtration was purified by silica gel column chromatography (hexane/ethyl acetate=70/30 v/v) to give (E)-2-{3-fluoro-8-[2-methoxy-7-(trifluoromethyl)imidazo[1,2-a]pyridine-3-carbonyl)dibenzo[b,e]oxepin-11(6H)-ylidene}propanenitrile (0.21 g, 71%).

ESIMS m/z: 508 $(M+H)^+$; $^1H$ NMR (270 MHz, $CDCl_3$, δ): 2.29 (s, 3H), 4.00 (s, 3H), 4.93-4.97 (m, 1H), 5.51-5.55 (m, 1H), 6.60-6.72 (m, 2H), 7.06-7.11 (m, 1H), 7.55-7.64 (m, 1H), 7.77-7.86 (m, 4H), 9.80-9.82 (m, 1H).

[step 5] (E)-2-{3-fluoro-8-[2-methoxy-7-(trifluoromethyl)imidazo[1,2-a]pyridine-3-carbonyl)dibenzo[b,e]oxepin-11(6H)-ylidene}propanenitrile (0.100 g, 0.197 mmol) obtained in step 4 was dissolved in ethanol (0.985 mL) and THF (0.985 mL), lithium borohydride (0.44 g, 1.2 mmol) was added, and the mixture was stirred at room temperature for 3 hr. The reaction was discontinued with water, and the mixture was extracted 3 times with chloroform. The combined organic layers were dried over anhydrous magnesium sulfate, and concentrated under reduced pressure to give (E)-2-(3-fluoro-8-{hydroxy[2-methoxy-7-(trifluoromethyl)imidazo[1,2-a]pyridin-3-yl]methyl}dibenzo[b,e]oxepin-11(6H)-ylidene)propanenitrile (100 mg, 100%).

ESIMS m/z: 510 $(M+H)^+$; $^1H$ NMR (270 MHz, $CDCl_3$, δ): 2.24 (s, 3H), 4.14 (s, 3H), 4.81-4.86 (m, 1H), 5.42-5.48 (m, 1H), 6.38-6.42 (m, 1H), 6.52-6.68 (m, 2H), 6.83-6.86 (m, 1H), 7.00-7.06 (m, 1H), 7.40-7.53 (m, 3H), 7.74-7.76 (m, 1H), 7.98-8.04 (m, 1H).

[step 6] Using (E)-2-(3-fluoro-8-{hydroxy[2-methoxy-7-(trifluoromethyl)imidazo[1,2-a]pyridin-3-yl]methyl}dibenzo[b,e]oxepin-11(6H)-ylidene)propanenitrile (100 mg, 0.20 mmol) obtained in step 5, and in the same manner as in Reference Example 8F, step 5, the title compound (89 mg, 92%) was obtained.

ESIMS m/z: 494 $(M+H)^+$; $^1H$ NMR (270 MHz, $CDCl_3$, δ): 2.24 (s, 3H), 4.14 (s, 3H), 4.23-4.25 (m, 2H), 4.75-4.79 (m, 1H), 5.39-5.43 (m, 1H), 6.53-6.67 (m, 2H), 6.90-6.94 (m, 1H), 6.99-7.05 (m, 1H), 7.10-7.11 (m, 1H), 7.21-7.24 (m, 1H), 7.38-7.41 (m, 1H), 7.69-7.79 (m, 2H).

Reference Example 1

(E)-2-[8-(bromomethyl)-3-fluorodibenzo[b,e]oxepin-11(6H)-ylidene]propanenitrile

[step 1]5-Bromoisobenzofuran-1(3H)-one (18.0 g, 84.5 mmol) was dissolved in DMF (18 mL), and 3-fluorophenol (11.5 mL, 126.8 mmol) and sodium methoxide (28% methanol solution, 24g, 126.8 mmol) were added. A trap bulb of an evaporator was connected, a nitrogen balloon was set, and the mixture was refluxed under heating at 130° C. for 10 hr. The reaction mixture was allowed to cool to room temperature, water (100 mL) and 4 mol/L aqueous sodium hydroxide solution (30 mL) were added, and the mixture was washed once with each of diethyl ether (200 mL) and toluene (550 mL). The aqueous layer was adjusted to pH 1-2 by adding 4 mol/L hydrochloric acid (about 20 mL), ethanol (70 mL) was added to a dark-brown aqueous solution, and the mixture was stirred at room temperature overnight. The precipitated crystals were collected by suction filtration with a Hirsch funnel, and washed twice with a mixed solvent of ethanol/water=1/1 (20 ml) to give 4-bromo-2-[(3-fluorophenoxy)methyl]benzoic acid (20.5 g, 75%).

ESIMS m/z: 323, 325 $(M-H)^-$; $^1H$ NMR (270 MHz, $CDCl_3$, δ): 5.48 (s, 2H), 6.66-6.86 (m, 3H), 7.21-7.32 (m, 1H), 7.58 (dd, J=8.5, 2.0 Hz, 1H), 7.99 (d, J=2.0 Hz, 1H), 8.03 (d, J=8.5 Hz, 1H).

[step 2] 4-Bromo-2-[(3-fluorophenoxy)methyl]benzoic acid (18.8 g, 57.8 mmol) obtained in step 1 was dissolved in dichloromethane (193 mL), trifluoroacetic anhydride (16.0 mL, 115.6 mmol) and trifluoroborane diethyl ether complex (7.3 mL, 57.8 mmol) were added, and the mixture was stirred at room temperature for 3 hr. To the mixture were added 2 mol/L aqueous sodium hydroxide solution (150 mL) and saturated aqueous sodium hydrogen carbonate solution (50 mL), and the mixture was extracted 3 times with dichloromethane (200 mL). The combined organic layers were dried over anhydrous magnesium sulfate, and concentrated under reduced pressure. The obtained brown solid (18.7 g) was suspended in chloroform (100 mL), and the suspension was stirred at room temperature for 1 hr. The suspension was suction filtered to give a first crop of crystals (9.42 g). The filtrate was concentrated under reduced pressure, chloroform (50 mL) was added to the obtained residue, and the mixture was stirred for 1 hr and suction filtered again to give a second crop of crystals (2.47 g). The first crop of crystals and the second crop of crystals were combined, and dried under reduced pressure to give 8-bromo-3-fluorodibenzo[b,e]oxepin-11(6H)-one (11.9 g, 67%).

$^1H$ NMR (270 MHz, $CDCl_3$, δ): 5.16 (s, 2H), 6.76 (dd, J=9.8, 2.5 Hz, 1H), 6.83-6.93 (m, 1H), 7.54 (d, J=1.7 Hz, 1H), 7.63 (dd, J=8.5, 1.7 Hz, 1H), 7.80 (d, J=8.5 Hz, 1H), 8.28 (dd, J=10.8, 8.1 Hz, 1H).

[step 3] Commercially available diethyl 1-cyanoethylphosphonate (38.0 g, 199 mmol) was dissolved in THF (170 mL), LDA (99.0 mL, 199 mmol, 2.0 mol/L heptane/THF/ethylbenzene solution) was added dropwise at 0° C., and the mixture was stirred at 0° C. for 1 hr. 8-Bromo-3-fluorodibenzo[b,e]oxepin-11(6H)-one (30.5 g, 99.0 mmol) obtained in step 2 and dissolved in THF (120 ml) was added to the reaction system, and the mixture was stirred at room temperature for 1 hr. To the mixture was added saturated aqueous ammonium chloride solution (500 mL), and the mixture was extracted 3 times with ethyl acetate. The combined organic layers were washed with saturated brine, dried over anhydrous magnesium sulfate, and concentrated under reduced pressure. The residue was purified by silica gel column chromatography (hexane/ethyl acetate=100/0 v/v-80/20 v/v) to give 2-(8-bromo-3-fluorodibenzo[b,e]oxepin-11(6H)-ylidene)propanenitrile (31.4 g, 92%, E/Z=1/1).

$^1H$ NMR (300 MHz, $CDCl_3$, δ): 2.01 (s, 1.5H), 2.24 (s, 1.5H), 4.74-4.88 (m, 1H), 5.42 (d, J=12.8 Hz, 1H), 6.51-6.62 (m, 1H), 6.62-6.74 (m, 1H), 6.99-7.08 (m, 1H), 7.35 (d, J=8.1 Hz, 1H), 7.48 (dd, J=8.8, 6.6 Hz, 1H), 7.51-7.60 (m, 1H).

[step 4]2-(8-Bromo-3-fluorodibenzo[b,e]oxepin-11(6H)-ylidene)propanenitrile (5.0 g, 14.5 mmol, E/Z=1/1) obtained in step 3 was dissolved in DMF (37 mL) and n-propanol (19 mL), cesium carbonate (5.7 g, 17.4 mmol) was added, and the mixture was stirred at 50° C. for 45 min under a nitrogen stream. The reaction mixture was allowed to cool to room temperature, palladium (II) acetate (163 mg, 0.73 mmol) and 1,3-bis(diphenylphosphino)propane (300 mg, 0.73 mmol) were added, and the mixture was stirred at 70° C. for 3 hr in the presence of CO gas. The mixture was filtered through celite, water (50 mL) was added to the filtrate, and the mixture was extracted 3 times with ethyl acetate. The combined organic layers were washed with water, dried over anhydrous magnesium sulfate and concentrated under reduced pressure. The residue was purified by silica gel column chromatography (hexane/ethyl acetate=100/0 v/v-70/30 v/v) to give propyl 11-(1-cyanoethylidene)-3-fluoro-6,11-dihydrodibenzo[b,e]oxepin-8-carboxylate (4.2 g, 83%, E/Z=1/1).

$^1H$ NMR (300 MHz, $CDCl_3$, δ): 0.96-1.09 (m, 3H), 1.72-1.87 (m, 2H), 2.02 (s, 1.5H), 2.27 (s, 1.5H), 4.22-4.36 (m, 2H), 4.87-5.00 (m, 1H), 5.49 (d, J=12.7 Hz, 1H), 6.50-6.63 (m, 1H), 6.63-6.75 (m, 1H), 7.06 (dd, J=8.8, 5.9 Hz, 0.5H), 7.26 (d, J=7.8 Hz, 0.5H), 7.50 (dd, J=8.8, 5.9 Hz, 0.5H), 7.55 (d, J=7.8 Hz, 0.5H), 8.00-8.16 (m, 2H).

[step 5] Propyl 11-(1-cyanoethylidene)-3-fluoro-6,11-dihydrodibenzo[b,e]oxepin-8-carboxylate (15.5 g, 44.1 mmol, E/Z=1/1) obtained in step 4 was dissolved in THF (220 mL), lithium borohydride (4.8 g, 221 mmol) was added, and the mixture was stirred at 60° C. for 3 hr. Under ice-cooling, the mixture was added dropwise to 2 mol/L hydrochloric acid, and the mixture was extracted 3 times with chloroform (550 mL). The combined organic layers were dried over anhydrous magnesium sulfate, and concentrated under reduced pressure. The residue was purified 3 times by silica gel column chromatography (hexane/ethyl acetate=100/0 v/v-40/60 v/v) to give (E)-2-[3-fluoro-8-(hydroxymethyl)dibenzo[b,e]oxepin-11(6H)-ylidene]propanenitrile (6.06 g, 47%).

ESIMS m/z: 296 $(M+H)^+$; $^1H$ NMR (300 MHz, $CDCl_3$, δ): 1.71 (t, J=6.0 Hz, 1H), 2.25 (s, 3H), 4.73 (d, J=6.0 Hz, 2H), 4.88 (d, J=12.8 Hz, 1H), 5.48 (d, J=12.8 Hz, 1H), 6.58 (dd, J=10.8, 2.6 Hz, 1H), 6.61-6.69 (m, 1H), 7.04 (dd, J=8.8, 6.6 Hz, 1H), 7.38-7.50 (m, 3H).

[step 6] (E)-2-[3-fluoro-8-(hydroxymethyl)dibenzo[b,e]oxepin-11(6H)-ylidene]propanenitrile (13.3 g, 45.0 mmol) obtained in step 5 was dissolved in THF (450 mL), methanesulfonic anhydride (19.6 g, 112.6 mmol), lithium bromide (23.5 g, 270.2 mmol) and 2,6-lutidine (31.5 mL, 270.2 mmol) were added, and the mixture was stirred at room temperature for 13 hr. To the mixture was added water (200 mL), and the mixture was extracted 3 times with ethyl acetate. The combined organic layers were washed with 1 mol/L hydrochloric acid (100 mL), saturated aqueous sodium hydrogen carbonate solution (100 mL) and saturated brine (100 mL), dried over anhydrous magnesium sulfate, and concentrated under reduced pressure. The residue was purified by silica gel column chromatography (chloroform/methanol=100/0 v/v-97/3 v/v) to give the title compound (13.4 g, 83%).

$^1H$ NMR (270 MHz, $CDCl_3$, δ): 2.25 (s, 3H), 4.48 (s, 2H), 4.86 (d, J=12.9 Hz, 1H), 5.45 (d, J=12.9 Hz, 1H), 6.58 (dd, J=10.2, 2.6 Hz, 1H), 6.61-6.70 (m, 1H), 7.04 (dd, J=8.6, 6.6 Hz, 1H), 7.39-7.49 (m, 3H).

Reference Example 2

(E)-2-[8-(bromomethyl)-1,3-difluorodibenzo[b,e]oxepin-11(6H)-ylidene]propanenitrile

[step 1] Using 5-bromoisobenzofuran-1(3H)-one (10.0 g, 46.9 mmol) and 3,5-difluorophenol (18.3 g, 140.7 mmol), and in the same manner as in Reference Example 1, step 1,4-bromo-2-[(3,5-difluorophenoxy)methyl]benzoic acid (14.4 g, 90%) was obtained.

ESIMS m/z: 341, 343 (M−H)$^-$; $^1$H NMR (270 MHz, DMSO-$d_6$, δ): 5.45 (s, 2H), 6.75-6.88 (m, 3H), 7.69 (dd, J=8.4, 2.1 Hz, 1H), 7.83 (br d, J=2.1 Hz, 1H), 7.87 (d, J=8.4 Hz, 1H).

[step 2] 4-Bromo-2-[(3,5-difluorophenoxy)methyl]benzoic acid (11.4 g, 33.2 mmol) obtained in step 1 was dissolved in dichloromethane (111 mL), trifluoroacetic anhydride (9.4 mL, 66.4 mmol) and trifluoroborane diethyl ether complex (4.2 mL, 33.2 mmol) were added, and the mixture was stirred at room temperature for 4 hr. To the mixture were added 2 mol/L aqueous sodium hydroxide solution (100 mL) and saturated aqueous sodium hydrogen carbonate solution (30 mL), and the mixture was extracted 3 times with dichloromethane (300 mL). The combined organic layers were dried over anhydrous magnesium sulfate, and concentrated under reduced pressure. The obtained brown solid (12.6 g) was suspended in isopropylalcohol (100 mL), and the suspension was stirred at room temperature for 13 hr. The suspension was suction filtered, and the obtained solid was dried under reduced pressure to give 8-bromo-1,3-difluorodibenzo[b,e]oxepin-11(6H)-one (9.3 g, 86%).

$^1$H NMR (270 MHz, $CDCl_3$, δ): 5.17 (s, 2H), 6.56-6.69 (m, 2H), 7.48 (br d, J=1.6 Hz, 1H), 7.62 (dd, J=8.6, 1.6 Hz, 1H), 7.75 (d, J=8.6 Hz, 1H).

[step 3] Using 8-bromo-1,3-difluorodibenzo[b,e]oxepin-11(6H)-one (8.3 g, 25.4 mmol) obtained in step 2, and in the same manner as in Reference Example 1, step 3,2-(8-bromo-1,3-difluorodibenzo[b,e]oxepin-11(6H)-ylidene)propanenitrile (4.6 g, 50%, E/Z=1/1) was obtained.

$^1$H NMR (270 MHz, $CDCl_3$, δ): 2.02 (s, 1.5H), 2.11 (d, J=4.3 Hz, 1.5H), 4.76-4.88 (m, 1H), 5.49 (d, J=12.8 Hz, 1H), 6.34-6.46 (m, 1H), 6.46-6.58 (m, 1H), 7.11 (d, J=8.9 Hz, 0.5H), 7.35 (d, J=8.2 Hz, 0.5H), 7.48-7.63 (m, 2H).

[step 4] Using 2-(8-bromo-1,3-difluorodibenzo[b,e]oxepin-11(6H)-ylidene)propanenitrile (4.2 g, 11.5 mmol) obtained in step 3, and in the same manner as in Reference Example 1, step 4, (E)-propyl 11-(1-cyanoethylidene)-1,3-difluoro-6,11-dihydrodibenzo[b,e]oxepin-8-carboxylate (1.3 g, 31%) was obtained.

$^1$H NMR (300 MHz, $CDCl_3$, δ): 1.03 (t, J=7.5 Hz, 3H), 1.72-1.87 (m, 2H), 2.13 (d, J=4.0 Hz, 3H), 4.30 (td, J=6.7, 1.0 Hz, 2H), 4.96 (d, J=12.8 Hz, 1H), 5.56 (d, J=12.8 Hz, 1H), 6.38-6.52 (m, 2H), 7.55 (d, J=7.7 Hz, 1H), 8.07 (br d, J=1.5 Hz, 1H), 8.13 (dd, J=7.9, 1.6 Hz, 1H).

[step 5] Using (E)-propyl 11-(1-cyanoethylidene)-1,3-difluoro-6,11-dihydrodibenzo[b,e]oxepin-8-carboxylate (1.3 g, 3.5 mmol) obtained in step 4, and in the same manner as in Reference Example 1, step 5, (E)-2-[1,3-difluoro-8-(hydroxymethyl)dibenzo[b,e]oxepin-11(6H)-ylidene]propanenitrile (0.85 g, 77%) was obtained.

ESIMS m/z: 314 (M+H)$^+$; $^1$H NMR (300 MHz, $CDCl_3$, δ): 1.72 (t, J=5.9 Hz, 1H), 2.11 (d, J=4.0 Hz, 3H), 4.73 (d, J=5.9 Hz, 2H), 4.89 (d, J=12.8 Hz, 1H), 5.55 (d, J=12.8 Hz, 1H), 6.36-6.52 (m, 2H), 7.37-7.50 (m, 3H).

[step 6] Using (E)-2-[1,3-difluoro-8-(hydroxymethyl)dibenzo[b,e]oxepin-11(6H)-ylidene]propanenitrile (0.85 g, 2.7 mmol) obtained in step 5, and in the same manner as in Reference Example 1, step 6, the title compound (0.78 g, 76%) was obtained.

$^1$H NMR (300 MHz, $CDCl_3$, δ): 2.11 (d, J=3.7 Hz, 3H), 4.43-4.53 (m, 2H), 4.88 (d, J=12.8 Hz, 1H), 5.53 (d, J=12.8 Hz, 1H), 6.37-6.52 (m, 2H), 7.38-7.50 (m, 3H).

Reference Example 3

(E)-2-[8-(bromomethyl)-2,3-difluorodibenzo[b,e]oxepin-11(6H)-ylidene]propanenitrile

[step 1] Using 5-bromoisobenzofuran-1(3H)-one (15.0 g, 70.4 mmol) and 3,4-difluorophenol (27.5 g, 211 mmol), and in the same manner as in Reference Example 1, step 1,4-bromo-2-[(3,4-difluorophenoxy)methyl]benzoic acid (18.8 g, 78%) was obtained.

ESIMS m/z: 341, 343 (M−H)$^-$; $^1$H NMR (300 MHz, DMSO-$d_6$, δ): 5.42 (s, 2H), 6.79-6.89 (m, 1H), 7.11-7.22 (m, 1H), 7.31-7.45 (m, 1H), 7.68 (dd, J=8.2, 2.0 Hz, 1H), 7.83 (br d, J=2.2 Hz, 1H), 7.86 (d, J=8.4 Hz, 1H), 13.31 (br s, 1H).

[step 2] Using 4-bromo-2-[(3,4-difluorophenoxy)methyl]benzoic acid (18.8 g, 54.9 mmol) obtained in step 1, and in the same manner as in Reference Example 2, step 2,8-bromo-2,3-difluorodibenzo[b,e]oxepin-11(6H)-one (13.2 g, 74%) was obtained.

$^1$H NMR (300 MHz, $CDCl_3$, δ): 5.15 (s, 2H), 6.89 (dd, J=10.6, 6.2 Hz, 1H), 7.54 (br d, J=1.8 Hz, 1H), 7.64 (dd, J=8.4, 1.8 Hz, 1H), 7.82 (d, J=8.4 Hz, 1H), 8.07 (dd, J=11.5, 9.3 Hz, 1H).

[step 3] Using 8-bromo-2,3-difluorodibenzo[b,e]oxepin-11(6H)-one (9.3 g, 28.6 mmol) obtained in step 2, and in the same manner as in Reference Example 1, step 3,2-(8-bromo-2,3-difluorodibenzo[b,e]oxepin-11(6H)-ylidene)propanenitrile (9.8 g, 95%, E/Z=1/1) was obtained.

$^1$H NMR (300 MHz, $CDCl_3$, δ): 2.01 (s, 1.5H), 2.26 (s, 1.5H), 4.72-4.87 (m, 1H), 5.38 (d, J=12.8 Hz, 1H), 6.60-6.75 (m, 1H), 6.89 (dd, J=10.6, 8.8 Hz, 0.5H), 7.05 (d, J=8.1 Hz, 0.5H), 7.29-7.38 (m, 1H), 7.50-7.61 (m, 2H).

[step 4] Using 2-(8-bromo-2,3-difluorodibenzo[b,e]oxepin-11(6H)-ylidene)propanenitrile (9.8 g, 27.0 mmol) obtained in step 3, and in the same manner as in Reference Example 1, step 4, propyl 11-(1-cyanoethylidene)-2,3-difluoro-6,11-dihydrodibenzo[b,e]oxepin-8-carboxylate (7.6 g, 76%) was obtained.

$^1$H NMR (300 MHz, $CDCl_3$, δ): 0.97-1.09 (m, 3H), 1.71-1.87 (m, 2H), 2.02 (s, 1.5H), 2.28 (s, 1.5H), 4.24-4.36 (m, 2H), 4.86-4.99 (m, 1H), 5.45 (d, J=12.8 Hz, 1H), 6.60-6.75 (m, 1H), 6.92 (dd, J=10.6, 8.6 Hz, 0.5H), 7.22-7.28 (m, 0.5H), 7.31-7.42 (m, 0.5H), 7.55 (d, J=7.9 Hz, 0.5H), 8.01-8.18 (m, 2H).

[step 5] Using propyl 11-(1-cyanoethylidene)-2,3-difluoro-6,11-dihydrodibenzo[b,e]oxepin-8-carboxylate (7.6 g, 20.6 mmol) obtained in step 4, and in the same manner as in Reference Example 1, step 5, (E)-2-[2,3-difluoro-8-(hydroxymethyl)dibenzo[b,e]oxepin-11(6H)-ylidene]propanenitrile (2.7 g, 41%) was obtained.

ESIMS m/z: 314 (M+H)$^+$; $^1$H NMR (300 MHz, $CDCl_3$, δ): 1.83 (t, J=5.9 Hz, 1H), 2.26 (s, 3H), 4.72 (d, J=5.9 Hz, 2H), 4.86 (d, J=12.8 Hz, 1H), 5.44 (d, J=12.8 Hz, 1H), 6.68 (dd, J=11.4, 7.0 Hz, 1H), 6.90 (dd, J=10.8, 8.6 Hz, 1H), 7.36-7.48 (m, 3H).

[step 6] Using (E)-2-[2,3-difluoro-8-(hydroxymethyl)dibenzo[b,e]oxepin-11(6H)-ylidene]propanenitrile (2.1 g, 6.8 mmol) obtained in step 5, and in the same manner as in Reference Example 1, step 6, the title compound (2.2 g, 84%) was obtained.

$^1$H NMR (300 MHz, $CDCl_3$, δ): 2.26 (s, 3H), 4.48 (s, 2H), 4.86 (d, J=12.8 Hz, 1H), 5.42 (d, J=12.8 Hz, 1H), 6.69 (dd, J=11.4, 7.0 Hz, 1H), 6.90 (dd, J=10.6, 8.4 Hz, 1H), 7.38-7.48 (m, 3H).

Reference Example 4

(E)-2-[8-(bromomethyl)-3,4-difluorodibenzo[b,e]oxepin-11(6H)-ylidene]propanenitrile

[step 1] Using 5-bromoisobenzofuran-1(3H)-one (20.0 g, 93.9 mmol) and 2,3-difluorophenol (36.6 g, 282 mmol), and in the same manner as in Reference Example 1, step 1,4-bromo-2-[(2,3-difluorophenoxy)methyl]benzoic acid (6.6 g, 20%) was obtained.

ESIMS m/z: 341, 343 $(M-H)^-$; $^1$H NMR (300 MHz, DMSO-$d_6$, δ): 5.54 (s, 2H), 7.00-7.09 (m, 2H), 7.10-7.19 (m, 1H), 7.70 (dd, J=8.4, 2.2 Hz, 1H), 7.83-7.90 (m, 2H).

[step 2] Using 4-bromo-2-[(2,3-difluorophenoxy)methyl]benzoic acid (6.5 g, 18.9 mmol) obtained in step 1, and in the same manner as in Reference Example 2, step 2,8-bromo-3,4-difluorodibenzo[b,e]oxepin-11(6H)-one (4.4 g, 72%) was obtained.

$^1$H NMR (300 MHz, $CDCl_3$, δ): 5.26 (s, 2H), 6.91-7.02 (m, 1H), 7.57 (br d, J=1.8 Hz, 1H), 7.65 (dd, J=8.4, 1.8 Hz, 1H), 7.80 (d, J=8.4 Hz, 1H), 7.98-8.07 (m, 1H).

[step 3] Using 8-bromo-3,4-difluorodibenzo[b,e]oxepin-11(6H)-one (4.0 g, 12.4 mmol) obtained in step 2, and in the same manner as in Reference Example 1, step 3,2-(8-bromo-3,4-difluorodibenzo[b,e]oxepin-11(6H)-ylidene)propanenitrile (4.3 g, 96%, E/Z=1/1) was obtained.

$^1$H NMR (300 MHz, $CDCl_3$, δ): 2.03 (s, 1.5H), 2.24 (s, 1.5H), 4.93-5.03 (m, 1H), 5.48 (d, J=12.5 Hz, 1H), 6.70-6.87 (m, 1.5H), 7.06 (d, J=8.1 Hz, 0.5H), 7.19-7.26 (m, 0.5H), 7.35 (d, J=8.1 Hz, 0.5H), 7.54-7.66 (m, 2H).

[step 4] Using 2-(8-bromo-3,4-difluorodibenzo[b,e]oxepin-11(6H)-ylidene)propanenitrile (4.3 g, 11.8 mmol) obtained in step 3, and in the same manner as in Reference Example 1, step 4, propyl 11-(1-cyanoethylidene)-3,4-difluoro-6,11-dihydrodibenzo[b,e]oxepin-8-carboxylate (3.0 g, 69%) was obtained.

$^1$H NMR (270 MHz, $CDCl_3$, δ): 0.98-1.08 (m, 3H), 1.71-1.88 (m, 2H), 2.03 (s, 1.5H), 2.27 (s, 1.5H), 4.22-4.36 (m, 2H), 5.04-5.17 (m, 1H), 5.54 (d, J=12.6 Hz, 1H), 6.70-6.87 (m, 1.5H), 7.22-7.26 (m, 0.5H), 7.26-7.30 (m, 0.5H), 7.56 (d, J=7.9 Hz, 0.5H), 8.06-8.17 (m, 2H).

[step 5] Using propyl 11-(1-cyanoethylidene)-3,4-difluoro-6,11-dihydrodibenzo[b,e]oxepin-8-carboxylate (3.0 g, 8.1 mmol) obtained in step 4, and in the same manner as in Reference Example 1, step 5, (E)-2-[3,4-difluoro-8-(hydroxymethyl)dibenzo[b,e]oxepin-11(6H)-ylidene]propanenitrile (1.0 g, 40%) was obtained.

ESIMS m/z: 314 $(M+H)^+$; $^1$H NMR (300 MHz, $CDCl_3$, δ): 1.76 (t, J=5.9 Hz, 1H), 2.25 (s, 3H), 4.74 (d, J=5.9 Hz, 2H), 5.04 (d, J=12.8 Hz, 1H), 5.54 (d, J=12.8 Hz, 1H), 6.67-6.85 (m, 2H), 7.40-7.50 (m, 3H).

[step 6] Using (E)-2-[3,4-difluoro-8-(hydroxymethyl)dibenzo[b,e]oxepin-11(6H)-ylidene]propanenitrile (1.0 g, 3.2 mmol) obtained in step 5, and in the same manner as in Reference Example 1, step 6, the title compound (1.1 g, 88%) was obtained.

$^1$H NMR (270 MHz, $CDCl_3$, δ): 2.25 (s, 3H), 4.49 (s, 2H), 5.03 (d, J=12.8 Hz, 1H), 5.51 (d, J=12.8 Hz, 1H), 6.68-6.85 (m, 2H), 7.42-7.51 (m, 3H).

Reference Example 5

(E)-2-(3-fluoro-8-formyldibenzo[b,e]oxepin-11(6H)-ylidene)propanenitrile (E)-2-[3-fluoro-8-(hydroxymethyl)dibenzo[b,e]oxepin-11(6H)-ylidene]propanenitrile (6.2 g, 21.0 mmol) obtained in Reference Example 1, step 5 was dissolved in dichloromethane (93 mL), Dess-Martin periodinane (10.7 g, 25.2 mmol) was added under ice-cooling, and the mixture was stirred at room temperature for 1 hr. To the mixture were added saturated aqueous sodium hydrogen carbonate solution (300 mL) and saturated aqueous sodium thiosulfate solution (300 mL), and the mixture was extracted twice with dichloromethane. The combined organic layers were washed with water, dried over anhydrous sodium sulfate, and concentrated under reduced pressure. The obtained amorphous form (6.9 g) was suspended in diisopropyl ether, the precipitated crystals were suction filtered, and the solid was dried under reduced pressure to give the title compound (5.5 g, 90%).

$^1$H NMR (400 MHz, $CDCl_3$, δ): 2.28 (s, 3H), 4.99 (d, J=12.7 Hz, 1H), 5.51 (d, J=12.7 Hz, 1H), 6.61 (dd, J=9.8, 2.9 Hz, 1H), 6.65-6.72 (m, 1H), 7.07 (dd, J=8.8, 6.8 Hz, 1H), 7.66 (d, J=7.8 Hz, 1H), 7.90-7.98 (m, 2H), 10.04 (s, 1H).

Reference Example 6

(E)-2-[8-(bromomethyl)-3-fluorodibenzo[b,e]oxepin-11(6H)-ylidene]-2-cyclopropylacetonitrile

[step 1] LDA (65 mL, 130 mmol, 2.0 mol/L heptane/THF/ethylbenzene solution) was dissolved in THF (300 mL), and cooled to −78° C. Commercially available 2-cyclopropylacetonitrile (6.0 mL, 65 mmol) dissolved in THF (50 mL) was added, and the mixture was stirred at −78° C. for 30 min. Diethyl chloroformate phosphate (9.3 mL, 78 mmol) dissolved in THF (50 mL) was added, and the mixture was stirred at −78° C. for 30 min. The reaction was discontinued with 1 mol/L hydrochloric acid at 0° C., and the mixture was extracted with chloroform. The organic layer was dried over anhydrous sodium sulfate and concentrated under reduced pressure to give diethyl cyano(cyclopropyl)methylphosphonate (14g, 99%).

ESIMS m/z: 218 $(M+H)^+$; $^1$H NMR (300 MHz, $CDCl_3$, δ): 0.53-1.29 (m, 4H), 1.35-1.44 (m, 6H), 2.61-2.82 (m, 1H), 4.05-4.17 (m, 1H), 4.21-4.33 (m, 4H).

[step 2] Diethyl cyano(cyclopropyl)methylphosphonate (2.8 g, 13 mmol) obtained in step 1 was dissolved in THF (20 mL), LDA (6.5 mL, 13 mmol, 2.0 mol/L heptane/THF/ethylbenzene solution) was added dropwise at 0° C., and the mixture was stirred at room temperature for 1 hr. A solution of 8-bromo-3-fluorodibenzo[b,e]oxepin-11(6H)-one (2.0 g, 6.5 mmol) obtained in Reference Example 1, step 2 in DMF (6.5 mL) was added to the reaction system, and the mixture was stirred at 80° C. for 2 hr. To the mixture was added saturated aqueous ammonium chloride solution (500 mL), and the mixture was extracted 3 times with ethyl acetate. The combined organic layers were washed with saturated brine, dried over anhydrous magnesium sulfate, and concentrated under reduced pressure. The residue was purified by silica gel column chromatography (hexane/ethyl acetate=4/1 v/v) to give 2-(8-bromo-3-fluorodibenzo[b,e]oxepin-11(6H)-ylidene)-2-cyclopropylacetonitrile (1.96 g, 82%, E/Z=1/1).

$^1$H NMR (300 MHz, $CDCl_3$, δ): 0.73-1.13 (m, 4H), 1.94-2.04 (m, 1H), 4.82 (d, J=12.9 Hz, 1H), 5.48 (d, J=12.9 Hz, 1H), 6.52-6.61 (m, 1H), 6.63-6.72 (m, 1H), 7.21-7.47 (m, 2H), 7.53-7.59 (m, 2H).

[step 3] Using 2-(8-bromo-3-fluorodibenzo[b,e]oxepin-11(6H)-ylidene)-2-cyclopropylacetonitrile (3.0 g, 8.1 mmol, E/Z=1/1) obtained in step 2, and in the same manner as in Reference Example 1, step 4, propyl 11-[1-cyano(cyclopropyl)methylene]-3-fluoro-6,11-dihydrodibenzo[b,e]oxepin-8-carboxylate (1.3 g, 43%, E/Z=1/1) was obtained.

$^1$H NMR (300 MHz, $CDCl_3$, δ):0.90-1.27 (m, 7H), 1.75-1.83 (m, 2H), 1.95-2.05 (m, 1H), 4.27-4.33 (m, 2H), 4.95 (d, J=12.5 Hz, 1H), 5.54 (d, J=12.5 Hz, 1H), 6.52-6.70 (m, 2H), 7.34-7.55 (m, 2H), 8.07-8.11 (m, 2H).

[step 4] Using propyl 11-[1-cyano(cyclopropyl)methylene]-3-fluoro-6,11-dihydrodibenzo[b,e]oxepin-8-carboxylate (5.22 g, 13.8 mmol, E/Z=1/1) obtained in step 3, and in the same manner as in Reference Example 1, step 5, (E)-2- cyclopropyl-2-[3-fluoro-8-(hydroxymethyl)dibenzo[b,e]oxepin-11(6H)-ylidene]acetonitrile (1.6 g, 36%) was obtained.

ESIMS m/z: 322 $(M+H)^+$; $^1$H NMR (300 MHz, $CDCl_3$, δ): 0.90-1.28 (m, 4H), 1.73 (t, J=6.3 Hz, 1H), 1.96-2.05 (m, 1H), 4.73 (s, 2H), 4.88 (d, J=12.7 Hz, 1H), 5.54 (d, J=12.7 Hz, 1H), 6.56-6.59 (m, 1H), 6.63-6.68 (m, 1H), 7.35-7.52 (m, 4H).

[step 5] Using (E)-2-cyclopropyl-2-[3-fluoro-8-(hydroxymethyl)dibenzo[b,e]oxepin-11(6H)-ylidene]acetonitrile (1.62 g, 5.07 mmol) obtained in step 4, and in the same manner as in Reference Example 1, step 6, the title compound (1.6 g, 84%) was obtained.

$^1$H NMR (270 MHz, $CDCl_3$, δ): 0.87-1.08 (m, 4H), 1.95-2.04 (m, 1H), 4.42 (s, 2H), 4.87 (d, J=12.5 Hz, 1H), 5.51 (d, J=12.5 Hz, 1H), 6.56-6.69 (m, 2H), 7.33-7.44 (m, 4H).

Reference Example 7

(E)-2-cyclopropyl-2-(3-fluoro-8-formyldibenzo[b,e]oxepin-11(6H)-ylidene)acetonitrile Using (E)-2-cyclopropyl-2-[3-fluoro-8-(hydroxymethyl)dibenzo[b,e]oxepin-11(6H)-ylidene]acetonitrile (1.0 g, 3.11 mmol) obtained in Reference Example 6, step 4, and in the same manner as in Reference Example 5, the title compound (680 mg, 69%) was obtained.

$^1$H NMR (400 MHz, $CDCl_3$, δ): 0.96-1.14 (m, 4H), 2.01-2.04 (m, 1H), 4.99 (d, J=12.7 Hz, 1H), 5.56 (d, J=12.5 Hz, 1H), 6.59-6.71 (m, 2H), 7.36-7.40 (m, 1H), 7.64-7.65 (m, 1H), 7.92-7.96 (m, 2H), 10.0 (s, 1H).

Reference Example 8

(E)-2-[8-(bromomethyl)-3-fluorodibenzo[b,e]oxepin-11(6H)-ylidene]butanenitrile

[step 1] Using 8-bromo-3-fluorodibenzo[b,e]oxepin-11(6H)-one (5.0 g, 16 mmol) obtained in Reference Example 1, step 2, and in the same manner as in Reference Example 1, step 3,2-(8-bromo-3-fluorodibenzo[b,e]oxepin-11(6H)-ylidene)butanenitrile (3.5 g, 60%) was obtained.

$^1$H NMR (270 MHz, $CDCl_3$, δ): 1.13-1.23 (m, 1.5H), 1.23-1.35 (m, 1.5H), 2.20-2.35 (m, 1H), 2.49-2.65 (m, 1H), 4.71-4.88 (m, 1H), 5.34-5.49 (m, 1H), 6.50-6.61 (m, 1H), 6.62-6.74 (m, 1H), 6.96-7.06 (m, 1H), 7.32-7.38 (m, 0.5H), 7.43-7.49 (m, 0.5H), 7.51-7.60 (m, 2H).

[step 2] Using (E)-2-(8-bromo-3-fluorodibenzo[b,e]oxepin-11(6H)-ylidene)butanenitrile (20 g, 57 mmol) obtained in step 1, and in the same manner as in Reference Example 1, step 4, propyl 11-(1-cyanopropylidene)-3-fluoro-6,11-dihydrodibenzo[b,e]oxepin-8-carboxylate was obtained. Using the obtained propyl 11-(1-cyanopropylidene)-3-fluoro-6,11-dihydrodibenzo[b,e]oxepin-8-carboxylate (14 g, 38 mmol), and in the same manner as in Reference Example 1, step 5, (E)-2-[3-fluoro-8-(hydroxymethyl)dibenzo[b,e]oxepin-11(6H)-ylidene]butanenitrile (800 mg, 4.5%) was obtained.

$^1$H NMR (270 MHz, $CDCl_3$, δ): 1.20-1.37 (m, 3H), 1.66-1.85 (m, 1H), 2.43-2.68 (m, 2H), 4.68-4.76 (m, 2H), 4.87 (d, J=12.8 Hz, 1H), 5.48 (d, J=12.8 Hz, 1H), 6.54-6.60 (m, 1H), 6.60-6.68 (m, 1H), 6.91-7.06 (m, 1H), 7.36-7.53 (m, 3H).

[step 3] Using (E)-2-[3-fluoro-8-(hydroxymethyl)dibenzo[b,e]oxepin-11(6H)-ylidene]butanenitrile (940 mg, 3.04 mmol) obtained in step 2, and in the same manner as in Reference Example 1, step 6, the title compound (960 mg, 85%) was obtained.

$^1$H NMR (270 MHz, $CDCl_3$, δ): 1.21-1.40 (m, 3H), 2.49-2.71 (m, 2H), 4.49 (s, 2H), 4.86 (d, J=12.8 Hz, 1H), 5.45 (d, J=12.8 Hz, 1H), 6.50-6.75 (m, 2H), 6.94-7.11 (m, 1H), 7.39-7.52 (m, 3H).

Reference Example 9

2-(8-ethynyl-3-fluorodibenzo[b,e]oxepin-11(6H)-ylidene)propanenitrile 2-(8-Bromo-3-fluorodibenzo[b,e]oxepin-11(6H)-ylidene)propanenitrile (5.0 g, 14.5 mmol) obtained in Reference Example 1, step 3 was dissolved in DMF (41 mL), bistriphenylphosphinedichloropalladium (1.02 g, 1.45 mmol), copper iodide (280 mg, 1.45 mmol), triethylamine (8.1 mL, 58.1 mmol) and trimethylsilylacetylene (4.1 mL, 29.1 mmol) were added, and the mixture was stirred at room temperature for 6 hr. Water was added to the mixture, and the mixture was extracted 3 times with ethyl acetate. The combined organic layers were dried over anhydrous magnesium sulfate, and concentrated under reduced pressure. The obtained residue was purified by silica gel column chromatography (hexane/ethyl acetate=1/1 v/v) to give a white amorphous (4.08 g). The obtained amorphous was dissolved in methanol (80 mL), potassium carbonate (1.56 g, 11.3 mmol) was added, and the mixture was stirred at room temperature for 5 hr. Water was added to the mixture, and the mixture was extracted 3 times with ethyl acetate. The combined organic layers were dried over anhydrous magnesium sulfate, and concentrated under reduced pressure. The obtained residue was purified by silica gel column chromatography (hexane/ethyl acetate=5/1 v/v) to give the title compound (2.5 g, 59%).

$^1$H NMR (270 MHz, $CDCl_3$, δ): 2.01 (s, 1.2H), 2.27 (s, 1.8H), 3.06-3.19 (m, 1H), 4.74-4.92 (m, 1H), 5.33-5.52 (m, 1H), 6.47-6.77 (m, 2H), 6.98-7.18 (m, 1H), 7.36-7.60 (m, 3H).

Reference Example 10

2-cyclopropyl-2-(8-ethynyl-3-fluorodibenzo[b,e]oxepin-11(6H)-ylidene)acetonitrile

[step 1]2-(8-Bromo-3-fluorodibenzo[b,e]oxepin-11(6H)-ylidene)-2-cyclopropylacetonitrile (1.0 g, 2.7 mmol) obtained in Reference Example 6, step 2 was dissolved in DMF (7.7 mL), copper (I) iodide (0.051 g, 0.27 mmol), trimethylsilylacetylene (0.76 mL, 5.4 mmol), bis(triphenylphosphine)dichloropalladium (0.19 g, 0.27 mmol) and triethylamine (1.5 mL, 10 mmol) were added, and the mixture was stirred at room temperature for 6 hr. The reaction was discontinued with water, and the mixture was extracted 3 times with ethyl acetate. The combined organic layers were washed with saturated brine, dried over anhydrous magnesium sulfate, and concentrated under reduced pressure. The residue was purified by silica gel column chromatography (hexane/ethyl acetate=10/1 v/v) to give 2-cyclopropyl-2-{3-fluoro-8-[(trimethylsilyl)ethynyl]dibenzo[b,e]oxepin-11(6H)-ylidene}acetonitrile (1.04 g, 99%, E/Z=1/1).

$^1$H NMR (300 MHz, $CDCl_3$, δ): 0.24 (s, 9H), 0.70-1.08 (m, 4H), 1.92-2.05 (m, 1H), 4.82 (d, J=12.5 Hz, 1H), 5.48 (d, J=12.5 Hz, 1H), 6.50-6.68 (m, 2H), 7.30-7.53 (m, 4H).

[step 2] 2-Cyclopropyl-2-{3-fluoro-8-[(trimethylsilyl)ethynyl]dibenzo[b,e]oxepin-11(6H)-ylidene}acetonitrile (1.0 g, 2.6 mmol) obtained in step 1 was dissolved in methanol (10 mL), potassium carbonate (0.35 g, 2.6 mmol) was added, and the mixture was stirred at room temperature for 1 hr. The reaction was discontinued with water, and the mixture was extracted 3 times with ethyl acetate. The combined organic layers were washed with saturated brine, dried over anhydrous magnesium sulfate, and concentrated under reduced pressure. The residue was crystallized from isopropyl ether and collected by filtration to give the title compound (600 mg, 74%, E/Z=1/1).

$^1$H NMR (300 MHz, $CDCl_3$, δ): 0.74-1.16 (m, 4H), 1.97-2.02 (m, 1H), 3.13 (s, 1H), 4.84 (d, J=13.7 Hz, 1H), 5.49 (d, J=13.7 Hz, 1H), 6.52-6.70 (m, 2H), 7.30-7.57 (m, 4H).

Reference Example 11

(E)-2-(8-ethynyl-3-fluorodibenzo[b,e]oxepin-11(6H) ylidene)acetonitrile

[step 1] Using 8-bromo-3-fluorodibenzo[b,e]oxepin-11 (6H)-one (5.00 g, 16.3 mmol) obtained in Reference Example 1, step 2 and diethyl cyanomethylphosphate (5.77 g, 32.6 mmol), and in the same manner as in Reference Example 1, step 3,2-(8-bromo-3-fluorodibenzo[b,e]oxepin-11(6H)-ylidene)acetonitrile (3.39 g, 63%, E/Z=10/1) was obtained.

$^1$H NMR (400 MHz, $CDCl_3$, δ): 5.10 (s, 2H), 5.82 (s, 1H), 6.58-6.62 (m, 1H), 6.69-6.75 (m, 1H), 7.27-7.31 (m, 1H), 7.46 (d, J=8.0 Hz, 1H), 7.57-7.58 (m, 1H), 7.62 (dd, J=8.0, 2.0 Hz, 1H).

[step 2] Using 2-(8-bromo-3-fluorodibenzo[b,e]oxepin-11 (6H)-ylidene)acetonitrile (1.00 g, 3.03 mmol) obtained in step 1, and in the same manner as in Reference Example 10, step 1, (E)-2-{3-fluoro-8-[(trifluoromethylsilyl)ethynyl] dibenzo[b,e]oxepin-11(6H)-ylidene}acetonitrile (799 mg, 76%) was obtained.

$^1$H NMR (400 MHz, $CDCl_3$, δ): 0.26 (s, 9H), 5.10 (s, 2H), 5.80 (s, 1H), 6.59 (dd, J=9.8, 2.9 Hz, 1H), 6.68-6.73 (m, 1H), 7.26-7.31 (m, 1H), 7.49-7.57 (m, 3H)

[step 3] Using (E)-2-{3-fluoro-8-[(trifluoromethylsilyl) ethynyl]dibenzo[b,e]oxepin-11(6H)-ylidene}acetonitrile (799 mg, 2.30 mmol) obtained in step 2, and in the same manner as in Reference Example 10, step 2, the title compound (540 mg, 85%) was obtained.

$^1$H NMR (400 MHz, $CDCl_3$, δ): 3.18 (s, 1H), 5.12 (s, 2H), 5.82 (s, 1H), 6.60 (dd, J=9.8, 2.9 Hz, 1H), 6.68-6.75 (m, 1H), 7.26-7.32 (m, 1H), 7.51-7.61 (m, 3H).

Reference Example 12

2-(8-ethynyl-3-fluorodibenzo[b,e]oxepin-11(6H)-ylidene)-2-fluoroacetonitrile

[step 1] Ethyl 2-(diethoxyphosphoryl)-2-fluoroacetate (315 mg, 1.3 mmol) was dissolved in THF (2 mL), lithium diisopropylamide (2 mol/L THF solution, 0.65 mL, 1.3 mmol) was added, and the mixture was stirred at 0° C. for 30 min. 8-Bromo-3-fluorodibenzo[b,e]oxepin-11(6H)-one (200 mg, 0.651 mmol) obtained in Reference Example 1, step 2 was dissolved in THF (2 mL), added dropwise in the reaction system, and the mixture was stirred at room temperature for 2 hr. To the mixture was added aqueous ammonium chloride solution, and the mixture was extracted 3 times with ethyl acetate. The combined organic layers were dried over anhydrous magnesium sulfate, and concentrated under reduced pressure. The obtained residue was purified by silica gel column chromatography (hexane/ethyl acetate=4/1 v/v) to give ethyl 2-(8-bromo-3-fluorodibenzo[b,e]oxepin-11(6H)-ylidene)-2-fluoroacetate (217 mg, 84%).

$^1$H NMR (270 MHz, $CDCl_3$, δ): 1.10-1.33 (m, 3H), 4.05-4.38 (m, 2H), 4.67-4.95 (m, 1H), 5.43-5.68 (m, 1H), 6.47-6.77 (m, 2H), 6.97-7.61 (m, 4H).

[step 2] Ethyl 2-(8-bromo-3-fluorodibenzo[b,e]oxepin-11 (6H)-ylidene)-2-fluoroacetate (1.6 g, 4.05 mmol) obtained in step 1 was dissolved in THF (14 mL), 2 mol/L ammonia methanol solution (20 mL, 40.5 mmol) was added, and the mixture was stirred at 55° C. overnight. The mixture was concentrated under reduced pressure and the obtained residue was purified by silica gel column chromatography (hexane/ethyl acetate=2/1 v/v) to give 2-(8-bromo-3-fluorodibenzo[b,e]oxepin-11(6H)-ylidene)-2-fluoroacetamide (910 mg, 61%).

$^1$H NMR (270 MHz, $CDCl_3$, δ): 4.59-4.89 (m, 1H), 5.30-5.64 (m, 1H), 6.10-6.72 (m, 4H), 6.98-7.64 (m, 4H).

[step 3]2-(8-Bromo-3-fluorodibenzo[b,e]oxepin-11(6H)-ylidene)-2-fluoroacetamide (910 mg, 2.49 mmol) obtained in step 2 was dissolved in dichloromethane (8 mL), triethylamine (1.04 mL, 7.46 mmol) and trifluoroacetic anhydride (0.70 mL, 4.97 mmol) were added, and the mixture was stirred at room temperature for 2 hr. Water was added to the mixture, and the mixture was extracted 3 times with ethyl acetate. The combined organic layers were dried over anhydrous magnesium sulfate, and concentrated under reduced pressure. The obtained residue was purified by silica gel column chromatography (hexane/ethyl acetate=4/1 v/v) to give 2-(8-bromo-3-fluorodibenzo[b,e]oxepin-11(6H)-ylidene)-2-fluoroacetonitrile (750 mg, 87%).

$^1$H NMR (270 MHz, $CDCl_3$, δ): 5.16 (br s, 2H), 6.54-6.80 (m, 2H), 7.17-7.52 (m, 2H), 7.52-7.71 (m, 2H).

[step 4] Using 2-(8-bromo-3-fluorodibenzo[b,e]oxepin-11 (6H)-ylidene)-2-fluoroacetonitrile (400 mg, 1.15 mmol) obtained in step 3, and in the same manner as in Reference Example 9, the title compound (260 mg, 77%) was obtained.

$^1$H NMR (270 MHz, $CDCl_3$, δ): 3.06-3.24 (m, 1H), 4.94-5.40 (m, 2H), 6.53-6.67 (m, 1H), 6.67-6.81 (m, 1H), 7.17-7.61 (m, 4H).

INDUSTRIAL APPLICABILITY

According to the present invention, a dibenzoxepin derivative having a PPAR γ activating action, which is useful as a therapeutic and/or prophylactic agent for type 2 diabetes, impaired glucose tolerance, insulin resistance syndrome, hypertension, hyperlipidemia, metabolic syndrome, visceral obesity, obesity, hypertriglyceridemia, inflammatory skin diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), inflammatory neuropsychiatric diseases (e.g., multiple sclerosis etc.), neurodegenerative neuropsychiatric diseases (e.g., Alzheimer's disease, Parkinson's disease etc.), cardiovascular diseases such as arteriosclerosis, cardiac disease, cerebral apoplexy, renal diseases, or the like, a pharmaceutically acceptable salt thereof and the like are provided.

The invention claimed is:

1. A compound of formula (I)

(I)

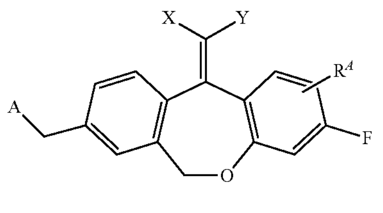

[wherein Y is a hydrogen atom, lower alkyl optionally having substituent(s), lower alkoxy optionally having substituent(s), cycloalkyl optionally having substituent(s) or halogen, $R^A$ is a hydrogen atom, halogen, hydroxy, lower alkoxy, or lower alkyl, X is any one of the formula (b1)-(b16)

(b1)

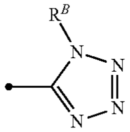

(b2)

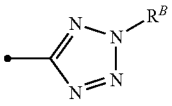

(b3)

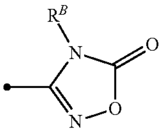

(b4)

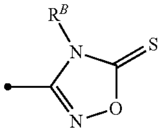

(b5)

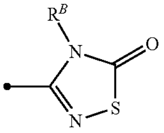

(b6)

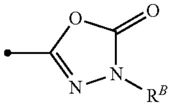

(b7)

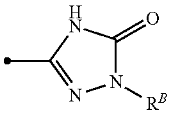

(b8)

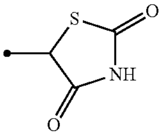

(b9)

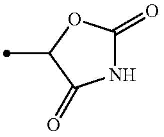

(b10)

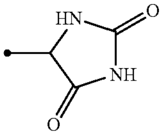

-continued (b11)

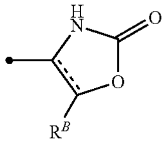

(b12)

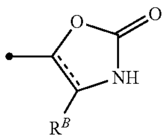

(b13)

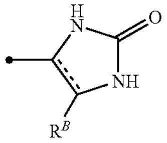

(b14)

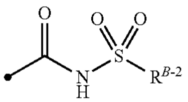

(b15)

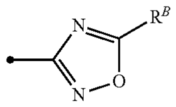

(b16)

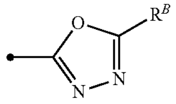

(wherein $R^{B-2}$ is lower alkyl optionally having substituent(s) or cycloalkyl optionally having substituent(s), $R^B$ is a hydrogen atom, lower alkyl optionally having substituent(s) or cycloalkyl optionally having substituent(s), and the broken line shows absent or a single bond), A is any one of the formula (a1)-(a29)

(a1)

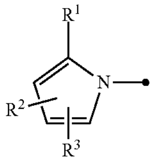

(a2)

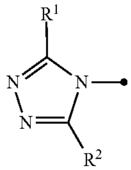

(a3)

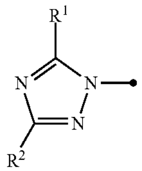

-continued
(a4)
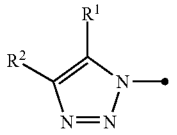
(a5)
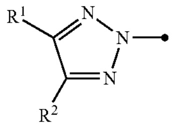
(a6)
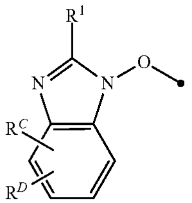
(a7)
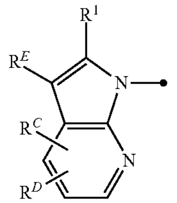
(a8)
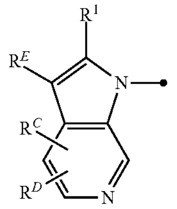
(a9)
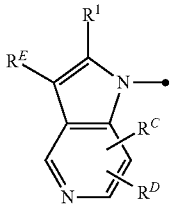
(a10)
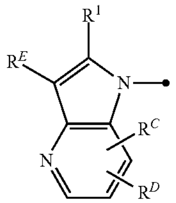
(a11)
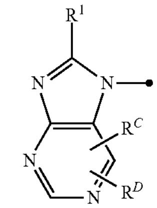
-continued
(a12)
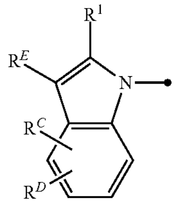
(a13)
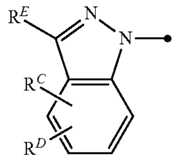
(a14)
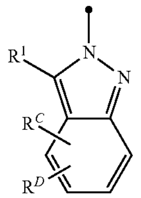
(a15)
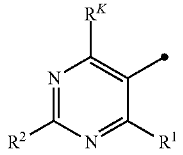
(a16)
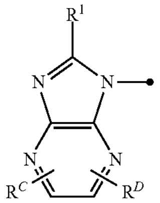
(a17)
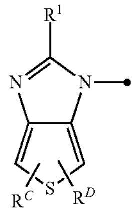
(a18)
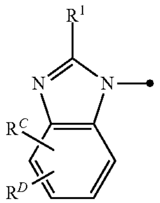
(a19)
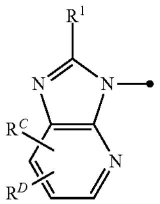

-continued (a20)

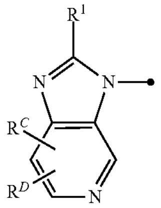

(a21)

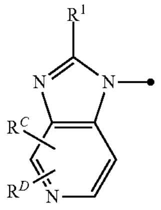

(a22)

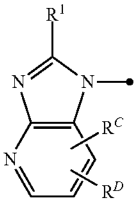

(a23)

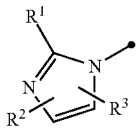

(a24)

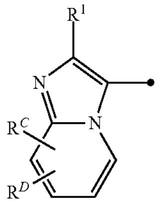

(a25)

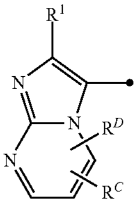

(a26)

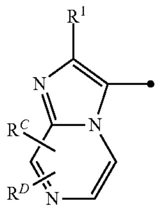

-continued (a27)

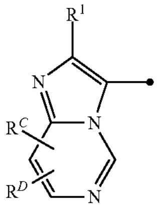

(a28)

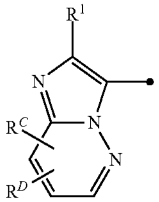

(a29)

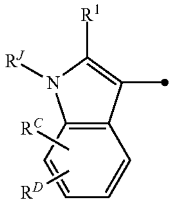

(wherein $R^1$, $R^2$ and $R^3$ are the same or different and each is a hydrogen atom, cyano, lower alkyl optionally having substituent(s), cycloalkyl optionally having substituent(s), halogen, lower alkoxy optionally having substituent(s), —$NR^FR^G$ (wherein $R^F$ and $R^G$ are the same or different and each is a hydrogen atom, lower alkyl optionally having substituent(s), lower alkanoyl optionally having substituent(s), lower alkoxycarbonyl optionally having substituent(s) or aralkyl optionally having substituent(s), or $R^F$ and $R^G$ form, together with the adjacent nitrogen atom, a nitrogen-containing heterocyclic group optionally having substituent(s)), lower alkylsulfanyl optionally having substituent(s), lower alkenyl optionally having substituent(s), lower alkanoyl optionally having substituent(s), lower alkoxycarbonyl optionally having substituent(s), carbamoyl, lower alkylcarbamoyl optionally having substituent(s), di-lower alkylcarbamoyl optionally having substituent(s), aliphatic heterocyclylcarbonyl optionally having substituent(s), aryloxy optionally having substituent(s), aryl optionally having substituent(s), aromatic heterocyclic group optionally having substituent(s), aliphatic heterocyclic group optionally having substituent(s), aralkyl optionally having substituent(s) or aralkyloxy optionally having substituent(s), $R^C$, $R^D$ and $R^E$ are the same or different and each is a hydrogen atom, halogen, nitro, cyano, formyl, oxo, hydroxy, lower alkoxy optionally having substituent(s), —$NR^{Fa}R^{Ga}$ (wherein $R^{Fa}$ and $R^{Ga}$ are as defined for the aforementioned $R^F$ and $R^G$, respectively), lower alkanoyloxy optionally having substituent(s), lower alkyl optionally having substituent(s), lower alkenyl optionally having substituent(s), lower alkynyl optionally having substituent(s), lower alkanoyl optionally having substituent(s), lower alkoxycarbonyl optionally having substituent(s), lower alkylsulfonyl optionally having substituent(s), lower alkylsulfanyl optionally having substituent(s), cycloalkyl optionally having substituent(s) or —$CONR^HR^I$ (wherein $R^H$ and $R^I$ are the same or different and each is a hydrogen atom, lower alkyl optionally having substituent(s), lower alkanoyl optionally having substituent(s), lower alkoxycarbonyl optionally having substituent(s) or aralkyl optionally having substituent(s), or $R^H$ and $R^I$ form, together with the adjacent nitrogen atom, a nitrogen-containing heterocyclic group optionally having substituent(s)), $R^J$ is a hydrogen atom, lower alkyl optionally having substituent(s), lower alkanoyl optionally having substituent(s), lower alkoxycarbonyl optionally having substituent(s), aryl optionally having substituent(s), lower alkylsulfonyl optionally having substituent(s), aralkyl optionally having substituent(s) or cycloalkyl optionally having substituent(s), and $R^K$ is a hydrogen atom, halogen, hydroxy, lower alkoxy, lower alkyl or —$NR^{Fb}R^{Gb}$ (wherein $R^{Fb}$ and $R^{Gb}$ are as defined for the aforementioned $R^F$ and $R^G$, respectively)

wherein the substituents of the lower alkyl optionally having substituent(s), the lower alkylsulfonyl optionally having substituent(s), the lower alkenyl optionally having substituent(s), the lower alkynyl optionally having substituent(s), the lower alkoxy optionally having substituent(s), the lower alkylsulfanyl optionally having substituent(s), the lower alkanoyloxy optionally having substituent(s), the lower alkanoyl optionally having substituent(s), the lower alkoxycarbonyl optionally having substituent(s), the lower alkylcarbamoyl optionally having substituent(s), and the di-lower alkylcarbamoyl optionally having substituent(s) are the same or different and are 1 to 3 substituents selected from the group consisting of halogen, hydroxy, sulfanyl, nitro, cyano, carboxy, carbamoyl, $C_{3-8}$ cycloalkyl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ are the same or different and each represents a hydrogen atom, $C_{1-10}$ alkyl, $C_{3-8}$ cycloalkyl, $C_{6-14}$ aryl, an atomatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl and di-$C_{1-10}$ alkylcarbamoyl, wherein the substituents of the aryl optionally having substituent(s), the aryloxy optionally having substituent(s), the aralkyl optionally having substituent(s), the aralkyloxy optionally having substituent(s) and the aromatic heterocyclic group optionally having substituent(s) are the same or different and are 1 to 3 substituents selected from the group consisting of halogen, hydroxy, sulfanyl, nitro, cyano, carbamoyl, $C_{1-10}$ alkyl, trifluoromethyl, $C_{3-8}$ cycloalkyl, $C_{6-14}$ aryl, aliphatic heterocyclic group, aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^{X1}R^{Y1}$ (wherein $R^{X1}$ and $R^{Y1}$ are the same or different and each as defined above), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, and di-$C_{1-10}$ alkylcarbamoyl, wherein the substituents of the cycloalkyl optionally having substituent(s), the aliphatic heterocyclic group optionally having substituent(s), the aliphatic heterocyclylcarbonyl optionally having substituent(s) and the nitrogen-containing heterocyclic group optionally having substituent(s) are the same or different and are 1 to 3 substituents selected from the group consisting of oxo, halogen, hydroxy, sulfanyl, nitro, cyano, carbamoyl, $C_{1-10}$ alkyl, trifluoromethyl, $C_{3-8}$ cycloalkyl, $C_{6-14}$ aryl, aliphatic heterocyclic group, aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^{X2}R^{Y2}$ (wherein $R^{X2}$ and $R^{Y2}$ are the same or different and each is as defined above), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, and di-$C_{1-10}$ alkylcarbamoyl, wherein the nitrogen-containing heterocyclic group is a 5-membered or 6-membered monocyclic heterocyclic group with 3- to 8-membered rings fused together, containing at least one nitrogen atom (said monocyclic heterocyclic group may contain other nitrogen atom(s), oxygen atom(s) or sulfur atom(s)); or a bicyclic or tricyclic fused heterocyclic group containing at least one nitrogen atom (said fused heterocyclic group may contain other nitrogen atom(s), oxygen atom(s) or sulfur atom(s)), wherein the aliphatic heterocyclic group and the aliphatic heterocyclic group moiety of aliphatic heterocyclylcarbonyl are respectively, a 5-membered or 6-membered monocyclic aliphatic heterocyclic group comprising at least one atom selected from a nitrogen atom, an oxygen atom and a sulfur atom; or a bicyclic or tricyclic condensed aliphatic heterocyclic group with 3- to 8-membered rings fused together containing at least one atom selected from a nitrogen atom, an oxygen atom and a sulfur atom, and wherein the aromatic heterocyclic group is a 5-membered or 6-membered monocyclic aromatic heterocyclic group containing at least one atom selected from a nitrogen atom, an oxygen atom and a sulfur atom; or a bicyclic or tricyclic condensed aromatic heterocyclic group with 3- to 8-membered rings fused together, containing at least one atom selected from a nitrogen atom, an oxygen atom and a sulfur atom], or a pharmaceutically acceptable salt thereof.

2. The compound according to claim 1, wherein Y is halogen, lower alkyl or cycloalkyl, or a pharmaceutically acceptable salt thereof.

3. The compound according to claim 1, wherein Y is lower alkyl, or a pharmaceutically acceptable salt thereof.

4. The compound according to claim 1, wherein Y is cycloalkyl, or a pharmaceutically acceptable salt thereof.

5. The compound according to claim 1, wherein X is the formula (b3-1)

(b3-1)

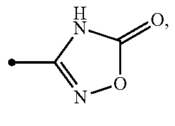

or a pharmaceutically acceptable salt thereof.

6. The compound according to claim 1, wherein A is the formula (a15), (a16), (a17), (a18), (a19), (a21), (a22), (a23), (a24), (a25), (a26), (a28) or (a29)

(a15)

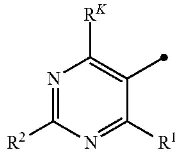

-continued (a16)

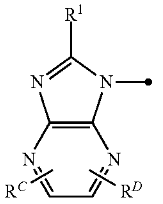

(a17)

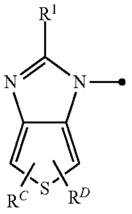

(a18)

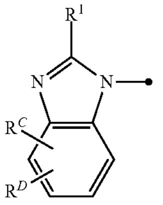

(a19)

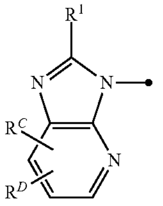

(a21)

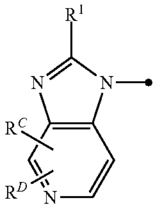

(a22)

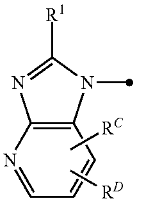

(a23)

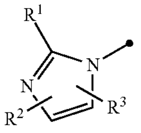

(a24)

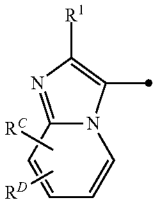

-continued (a25)

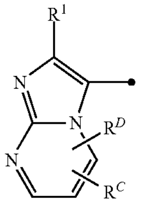

(a26)

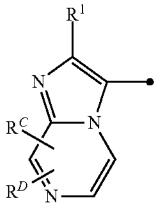

(a28)

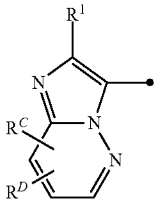

(a29)

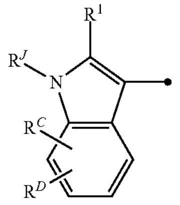

(wherein $R^1$, $R^2$, $R^3$, $R^C$, $R^D$, $R^K$, and $R^J$ are each as defined above), or a pharmaceutically acceptable salt thereof.

7. The compound according to any claim 1, wherein A is the formula (a18)

(a18)

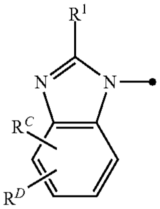

(wherein $R^1$, $R^C$, and $R^D$ are each as defined above), or a pharmaceutically acceptable salt thereof.

8. The compound according to claim 1, wherein A is the formula (a24)

(a24)

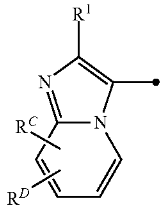

(wherein $R^1$, $R^C$, and $R^D$ are each as defined above), or a pharmaceutically acceptable salt thereof.

9. The compound according to claim 1, wherein A is the formula (a26)

(a26)

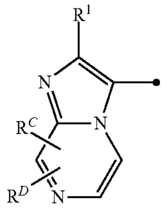

(wherein $R^1$, $R^C$, and $R^D$ are each as defined above), or a pharmaceutically acceptable salt thereof.

10. The compound according to claim 1, wherein $R^1$ is cyano; halogen; lower alkoxy; lower alkyl optionally substituted by 1 to 3 substituents of halogen, lower alkylamino, di-lower alkylamino, cycloalkyl or lower alkoxy; cycloalkyl optionally substituted by 1 to 3 substituents of halogen or lower alkyl; an aromatic heterocyclic group; an aliphatic heterocyclic group; or di-lower alkylamino, wherein the aliphatic heterocyclic group is as defined above, or a pharmaceutically acceptable salt thereof.

11. The compound according to claim 1, wherein $R^1$ is lower alkyl optionally substituted by 1 to 3 substituents of halogen or lower alkoxy, or a pharmaceutically acceptable salt thereof.

12. The compound according to claim 1, wherein $R^1$ is cycloalkyl, or a pharmaceutically acceptable salt thereof.

13. The compound according to claim 1, wherein $R^C$ and $R^D$ are the same or different and each is a hydrogen atom; cyano; lower alkyl optionally substituted by 1 to 3 substituents of halogen, hydroxy or lower alkoxy; lower alkoxy optionally substituted by 1 to 3 halogens; lower alkylsulfanyl; lower alkylsulfonyl; cycloalkyl; lower alkynyl; —CONR$^{H-1}$R$^{I-1}$ (wherein $R^{H-1}$ and $R^{I-1}$ are the same or different and each is a hydrogen atom or lower alkyl, or $R^{H-1}$ and $R^{I-1}$ form, together with the adjacent nitrogen atom, a nitrogen-containing heterocyclic group); —NR$^{Fa-1}$R$^{Ga-1}$ (wherein $R^{Fa-1}$ and $R^{Ga-1}$ are the same or different and each is a hydrogen atom or lower alkyl); or halogen, wherein the nitrogen-containing heterocyclic group is as defined above, or a pharmaceutically acceptable salt thereof.

14. The compound according to claim 1, wherein $R^C$ and $R^D$ are the same or different and each is lower alkyl optionally substituted by 1 to 3 substituents of halogen, hydroxy or lower alkoxy; lower alkoxy optionally substituted by 1 to 3 halogens; or halogen, or a pharmaceutically acceptable salt thereof.

15. The compound according to claim 13, wherein $R^C$ is a hydrogen atom, or a pharmaceutically acceptable salt thereof.

16. The compound according claim 1, wherein $R^A$ is a hydrogen atom or halogen, or a pharmaceutically acceptable salt thereof.

17. A pharmaceutical composition comprising the compound or the pharmaceutically acceptable salt thereof according to claim 1, as an active ingredient.

* * * * *

UNITED STATES PATENT AND TRADEMARK OFFICE

CERTIFICATE OF CORRECTION

PATENT NO. : 8,969,345 B2
APPLICATION NO. : 14/236545
DATED : March 3, 2015
INVENTOR(S) : Yamamoto et al.

It is certified that error appears in the above-identified patent and that said Letters Patent is hereby corrected as shown below:

In the claims:

Claim 1, column 195, line 37, “atomatic” should read “aromatic”

Signed and Sealed this
Eighth Day of December, 2015

Michelle K. Lee
*Director of the United States Patent and Trademark Office*